(12) United States Patent
Marasco et al.

(10) Patent No.: US 9,587,028 B2
(45) Date of Patent: *Mar. 7, 2017

(54) AFFINITY MATURED ANTI-CCR4 HUMANIZED MONOCLONAL ANTIBODIES AND METHODS OF USE

(71) Applicants: DANA-FARBER CANCER INSTITUTE, INC., Boston, MA (US); BRIGHAM AND WOMEN'S HOSPITAL, INC., Boston, MA (US)

(72) Inventors: Wayne A. Marasco, Wellesley, MA (US); Jianhua Sui, Waltham, MA (US); Quan Zhu, Needham, MA (US); De-Kuan Chang, Malden, MA (US); Thomas S. Kupper, Belmont, MA (US)

(73) Assignees: Dana-Farber Cancer Institute, Inc., Boston, MA (US); Brigham and Women's Hospital, Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/820,882

(22) Filed: Aug. 7, 2015

(65) Prior Publication Data
US 2016/0185865 A1    Jun. 30, 2016

Related U.S. Application Data

(63) Continuation of application No. 14/398,910, filed as application No. PCT/US2013/039744 on May 6, 2013, now Pat. No. 9,441,045.

(60) Provisional application No. 61/642,749, filed on May 4, 2012, provisional application No. 61/785,559, filed on Mar. 14, 2013.

(51) Int. Cl.
| | | |
|---|---|---|
| *C07K 16/28* | (2006.01) | |
| *A61K 39/395* | (2006.01) | |
| *C07K 16/40* | (2006.01) | |
| *A61K 47/48* | (2006.01) | |
| *A61K 39/00* | (2006.01) | |

(52) U.S. Cl.
CPC .... *C07K 16/2866* (2013.01); *A61K 47/48546* (2013.01); *C07K 16/40* (2013.01); *A61K 2039/505* (2013.01); *A61K 2039/53* (2013.01); *C07K 2317/24* (2013.01); *C07K 2317/31* (2013.01); *C07K 2317/35* (2013.01); *C07K 2317/56* (2013.01); *C07K 2317/565* (2013.01); *C07K 2317/622* (2013.01); *C07K 2317/64* (2013.01); *C07K 2317/72* (2013.01); *C07K 2317/732* (2013.01); *C07K 2317/734* (2013.01); *C07K 2317/92* (2013.01)

(58) Field of Classification Search
CPC ....................... C07K 16/00–16/468
See application file for complete search history.

(56) References Cited

U.S. PATENT DOCUMENTS

| | | | | |
|---|---|---|---|---|
| 8,962,806 B2* | 2/2015 | Marasco | ............ | C07K 14/7158 424/130.1 |
| 9,441,045 B2* | 9/2016 | Marasco | ............ | C07K 16/2866 |

FOREIGN PATENT DOCUMENTS

| | | |
|---|---|---|
| WO | WO 2009/086514 | 7/2009 |
| WO | WO2009/086514 A1 * | 7/2009 |

OTHER PUBLICATIONS

Wood, K.J. & Sakaguchi, S. "Regulatory T cells in transplantation tolerance." *Nat Rev Immunol* 3 199-210 (2003).
Levings, M.K., Sangregorio, R. & Roncarolo, M.G. "Human cd25(+)cd4(+) t regulatory cells suppress naive and memory T cell proliferation and can be expanded in vitro without loss of function." *J Exp Med* 193, 1295-1302 (2001).
Curiel, T.J., et al. "Specific recruitment of regulatory T cells in ovarian carcinoma fosters immune privilege and predicts reduced survival." *Nat Med* 10, 942-949 (2004).
Iellem, A., et al. "Unique chemotactic response profile and specific expression of chemokine receptors CCR4 and CCR8 by CD4(+)CD25(+) regulatory T cells." *J Exp Med* 194, 847-853.
Imai, T., et al. "Selective recruitment of CCR4-bearing Th2 cells toward antigen-presenting cells by the CC chemokines thymus and activation-regulated chemokine and macrophage-derived chemokine." *Int Immunol* 11, 81-88 (1999).
Wagsater, D., Dienus, O., Lofgren, S., Hugander, A. & Dimberg, J. "Quantification of the chemokines CCL17 and CCL22 in human colorectal adenocarcinomas." *Mol Med Report* 1, 211-217 (2008).
Niens, M., et al. "Serum chemokine levels in Hodgkin lymphoma patients: highly increased levels of CCL17 and CCL22." *Br J Haematol* 140, 527-536 (2008).
Jacobs, J.F., et al. "Prognostic significance and mechanism of Treg infiltration in human brain tumors." *J Neuroimmunol* 225, 195-199 (2010).
Hiraoka, N., Onozato, K., Kosuge, T. & Hirohashi, S. "Prevalence of FOXP3+ regulatory T cells increases during the progression of pancreatic ductal adenocarcinoma and its premalignant lesions." *Clin Cancer Res* 12, 5423-5434 (2006).

(Continued)

*Primary Examiner* — Jessica H Roark
(74) *Attorney, Agent, or Firm* — Cooley LLP; Ivor Elrifi; Cynthia Kozakiewicz

(57) ABSTRACT

The present invention provides affinity matured humanized monoclonal antibodies, bi-specific antibodies, antibody conjugates, and fusion proteins that bind to the chemokine receptor CCR4. This antibody is derived from mAb 1567 and recognizes the same epitope. Binding of the antibodies disclosed herein to CCR4 inhibits ligand-mediated activities and is used to treat symptoms of cancer. Moreover, the antibody is used in combination with vaccines to suppress the activity of regulatory T cells.

6 Claims, 63 Drawing Sheets

(56) References Cited

OTHER PUBLICATIONS

Woo, E.Y., et al. "Regulatory CD4(+)CD25(+) T cells in tumors from patients with early-stage non-small cell lung cancer and late-stage ovarian cancer." *Cancer Res* 61, 4766-4772 (2001).
Zou, W. "Regulatory T cells, tumour immunity and immunotherapy." *Nat Rev Immunol* 6 295-307 (2006).
Yu, P., et al. "Intratumor depletion of CD4+ cells unmasks tumor immunogenicity leading to the rejection of late-stage tumors." *J Exp Med* 201, 779-791 (2005).
Mahnke, K., et al. "Depletion of CD4+CD25+ human regulatory T cells in vivo: kinetics of Treg depletion and alterations in immune functions in vivo and in vitro." *Int J Cancer* 120, 2723-2733 (2007).
Roncarlo, M.G. & Battaglia, M. "Regulatory T-cell immunotherapy for tolerance to self antigens and alloantigens in humans." *Nat Rev Immunol* 7, 585-598 (2007).
Sakaguchi, S., Yamaguchi, T., Nomura, T. & Ono, M. "Regulatory T cells and immune tolerance." *Cell* 133, 775-787 (2008).
Kohm, A.P., et al. "Cutting Edge: Anti-CD25 monoclonal antibody injection results in the functional inactivation, not depletion, of CD4+CD25+ T regulatory cells." *J Immunol* 176, 3301-3305 (2006).
Baatar, D., et al. "Human peripheral blood T regulatory cells (Tregs), functionally primed CCR4+ Tregs and unprimed CCR4- Tregs, regulate effector T cells using FasL." *J Immunol* 178, 4891-4900 (2007).
Mizukami, Y., et al. "CCL17 and CCL22 chemokines within tumor microenvironment are related to accumulation of Foxp3+ regulatory T cells in gastric cancer." *Int J Cancer* 122, 2286-2293 (2008).
Gobert, M., et al. "Regulatory T cells recruited through CCL22/CCR4 are selectively activated in lymphoid infiltrates surrounding primary breast tumors and lead to an adverse clinical outcome." *Cancer Res* 69, 2000-2009 (2009).
Faget, J., et al. "Early detection of tumor cells by innate immune cells leads to T(reg) recruitment through CCL22 production by tumor cells." *Cancer Res* 71, 6143-6152 (2011).
Chang, D.K., et al. Humanization of an anti-CCR4 antibody that kills Cutaneous T Cell Lymphoma cells and abrogates suppression by T regulatory cells. Mol Cancer Ther (2012), vol. 11, pp. 2451-2461.
Han, T., et al. Human Anti-CCR4 Minibody Gene Transfer for the Treatment of Cutaneous T-Cell Lymphoma. PLoS One 7, e44455 (2012).
International Search Report and Written Opinion for International Application No. PCT/US2013/039744, mailed Jul. 17, 2013, 11 pages.

\* cited by examiner

Figure 2D

```
                                                VH-CDR1                         VH-CDR2
Mouse     1567 VH    QVQLQQSGPE  LVRPGASVRL  SCKASGYTFA  SYYLWMQR   PGQGLEWIGW  INPGNVNTKY
Humanized 1567 VH    QVQLVQSGAE  VKKPGASVKV  SCKASGYTFA  SYYLWMRQA  PGQGLEWIGW  INPGNVNTKY VH-CDR3
Mouse     1567 VH    NEKFKGKATL  TADKSSTTAY  MQLSSLTSED  SAVYFCARST YYRPLDYWGQ  GTLVTVSS
Humanized 1567 VH    NEKFKGRATL  TVDTSTSTAY  MELSSLRSED  TAVYFCARST YYRPLDYWGQ  GTLVTVSS VL-CDR1                         VL-CDR2
Mouse     1567 VK    DIELTQSPSS  LAVSAGEKVT  MSCKSSQSIL  YSSNQKNYLA WYQQKPGQSP  KLLIYWASTR
Humanized 1567 VK    DIVMTQSPDS  LAVSLGERAT  INCKSSQSIL  YSSNQKNYLA WYQQKPGQSP  KLLIYWASTR VL-CDR3
Mouse     1567 VK    ESGVPDRFTG  SGSGTDFTLT  ISSVQAEDLA  VYYCQYLSS  YTFGGGTKLE  IK
Humanized 1567 VK    ESGVPDRFSG  SGSGTDFTLT  ISSLQAEDVA  VYYCQYLSS  YTFGQGTKLE  IK
```

Mouse 1567 VH – SEQ ID NO: 43
Mouse 1567 VK – SEQ ID NO: 44
Humanized 1567 VH – SEQ ID NO: 45
Humanized 1567 VK – SEQ ID NO: 4

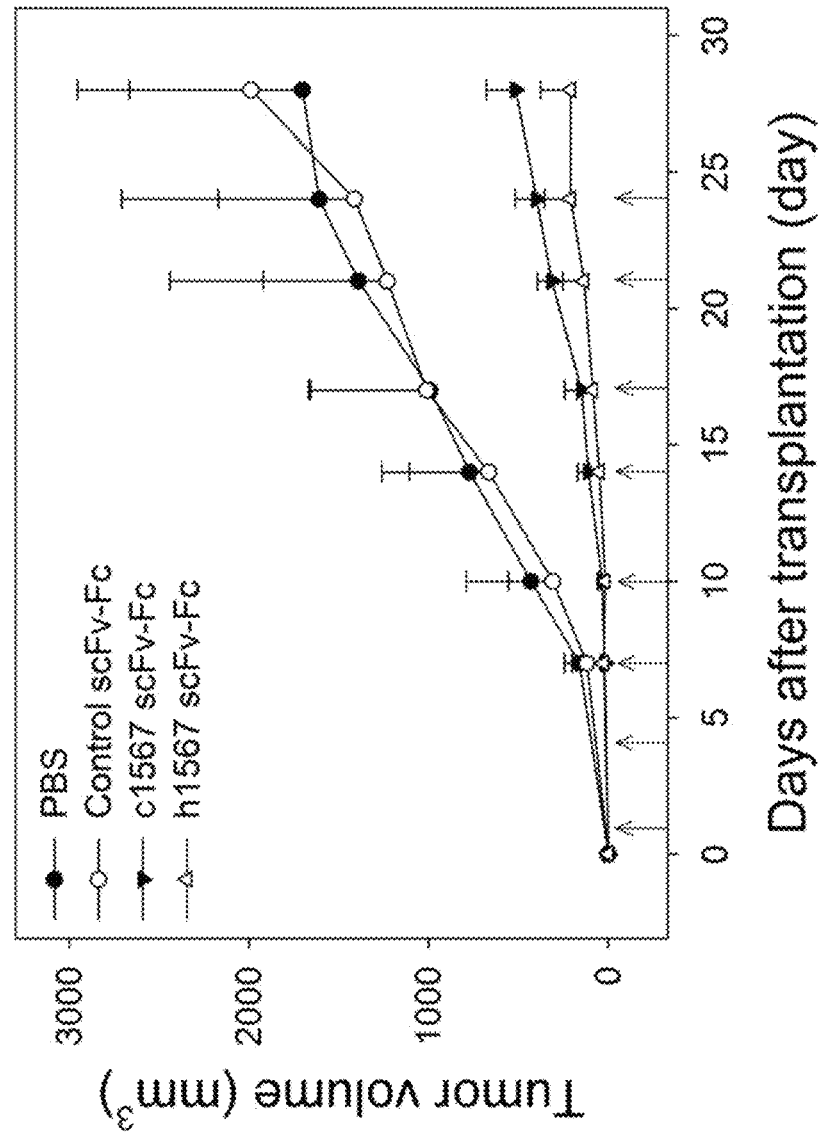

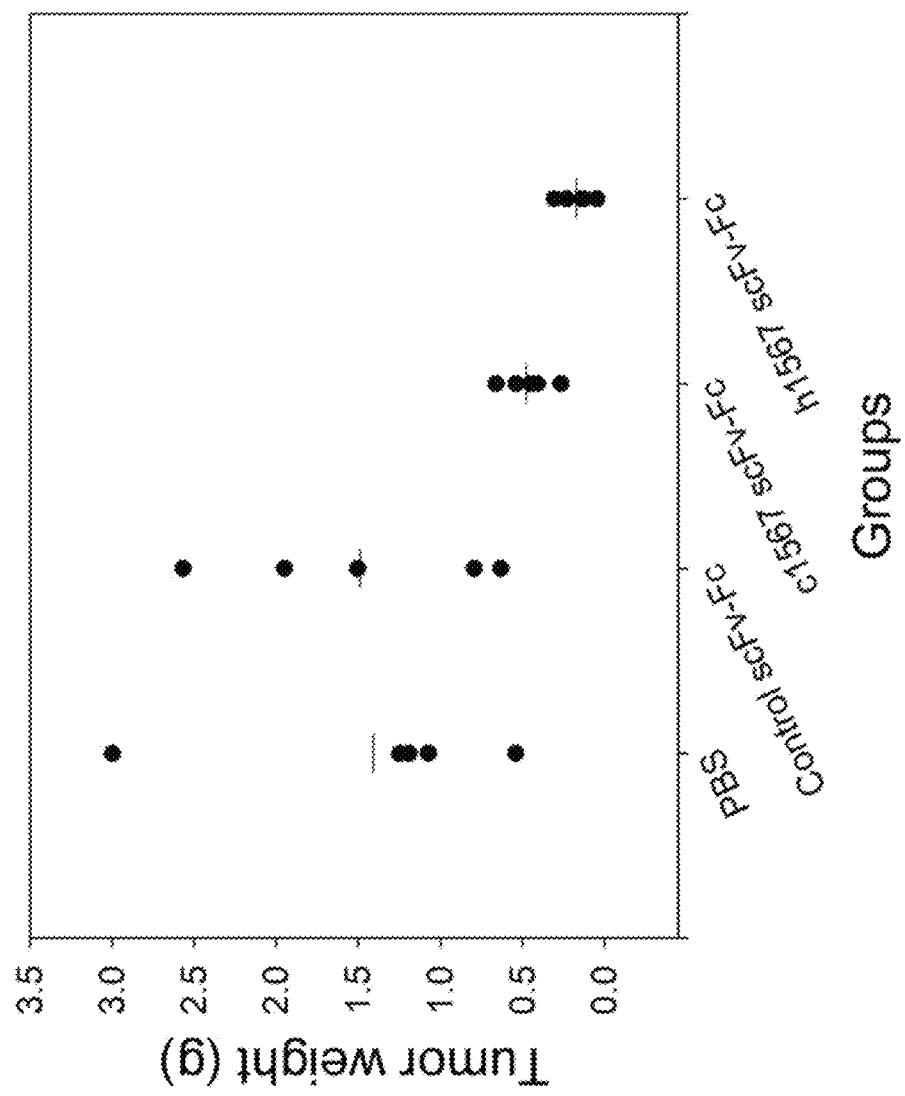

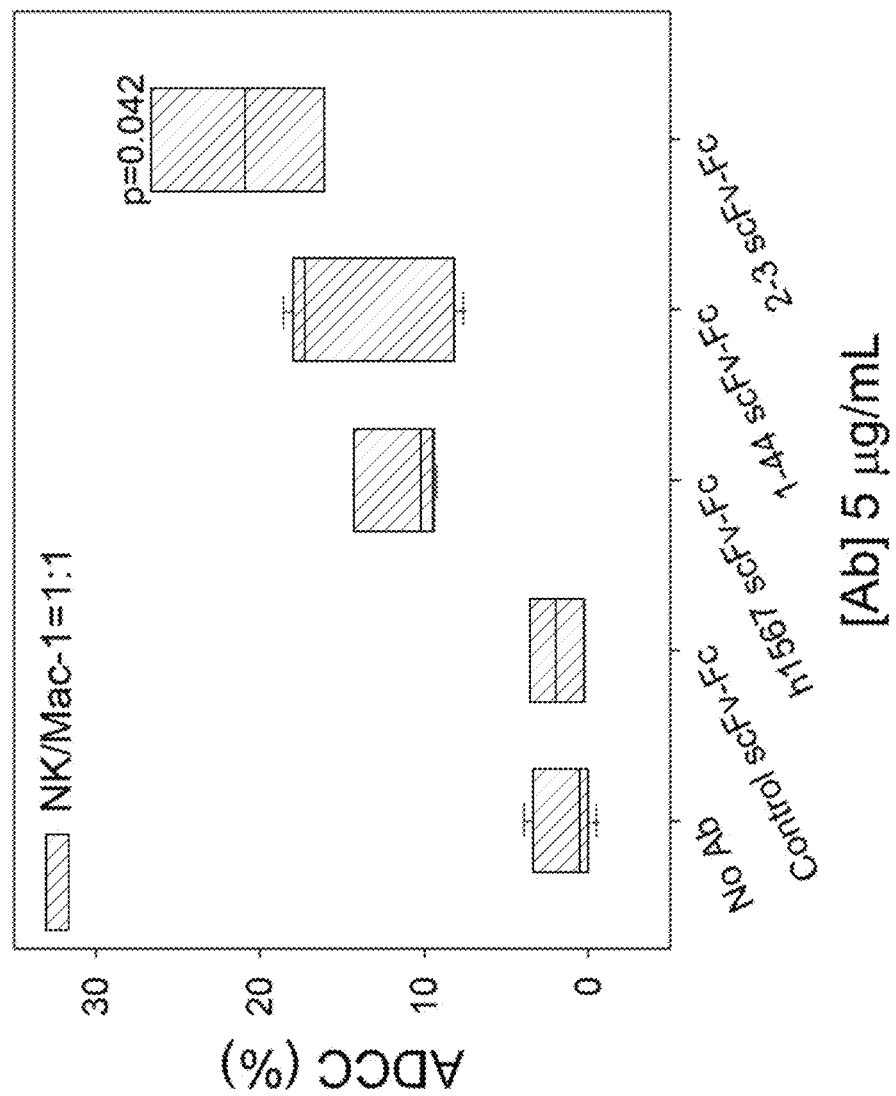

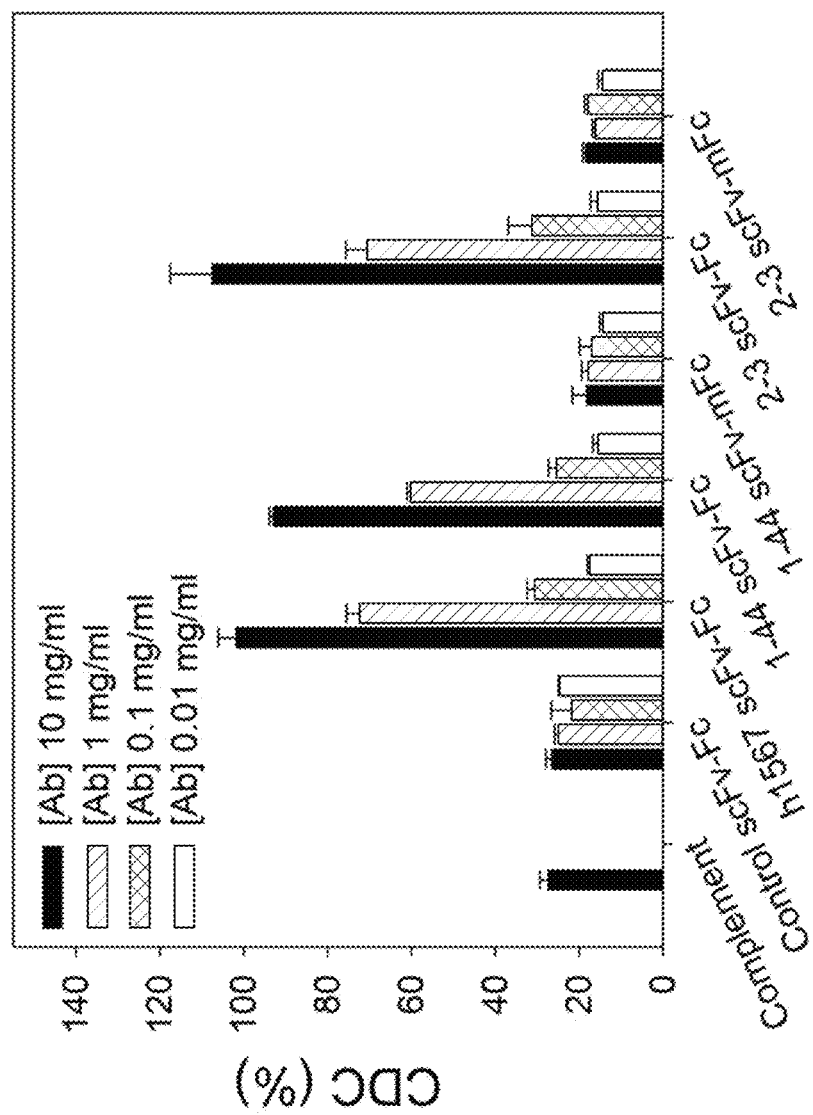

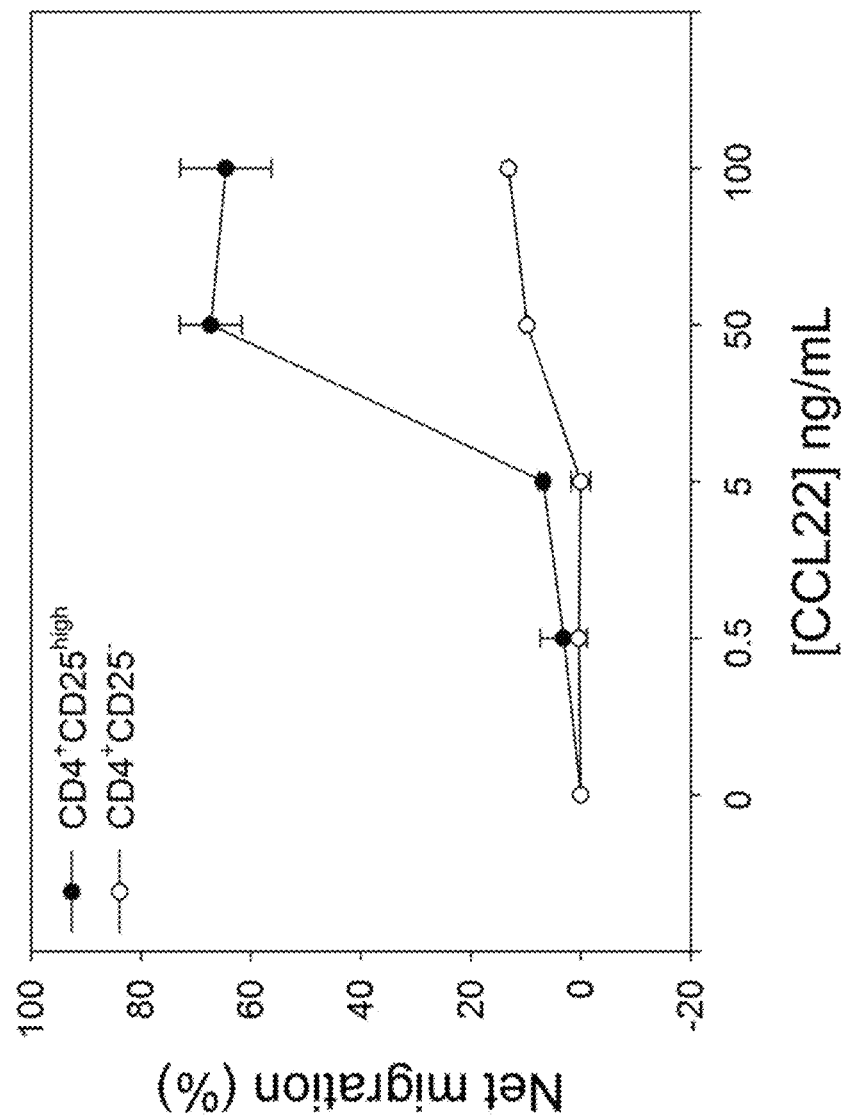

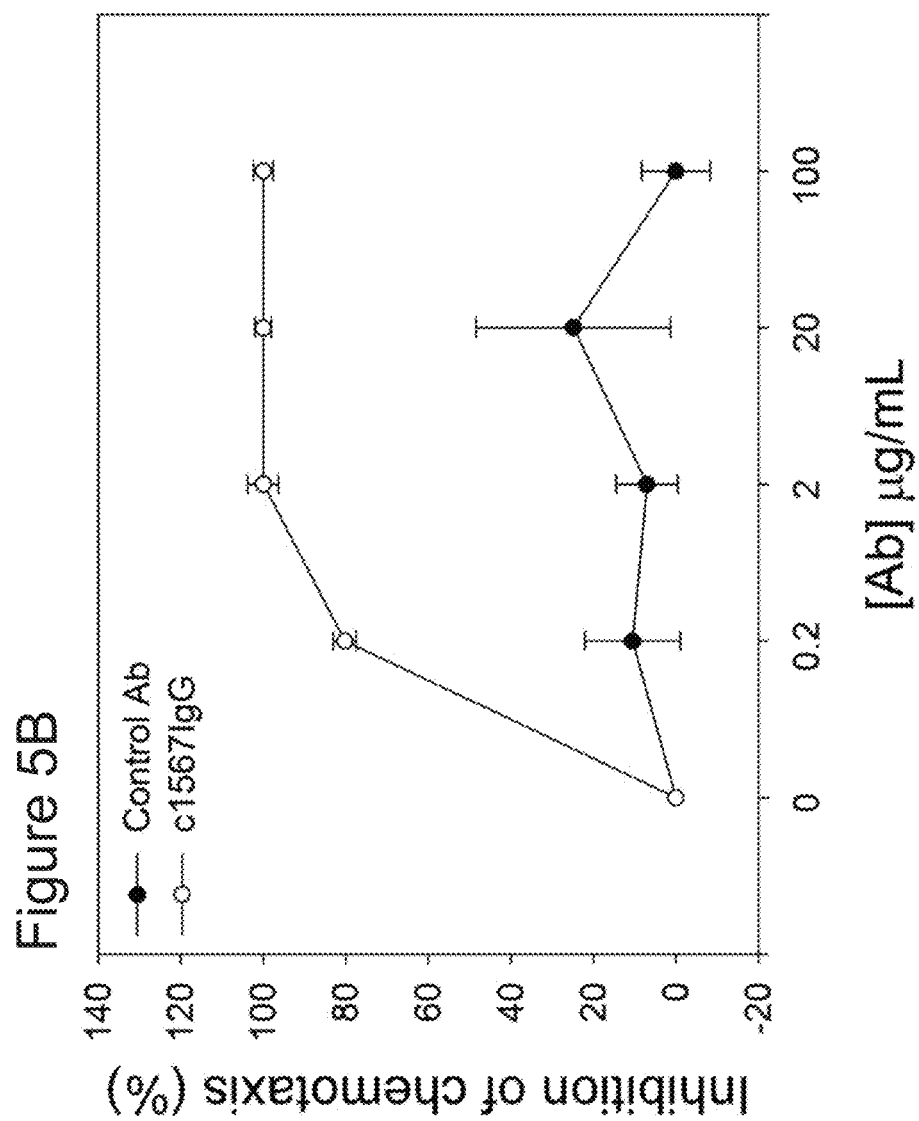

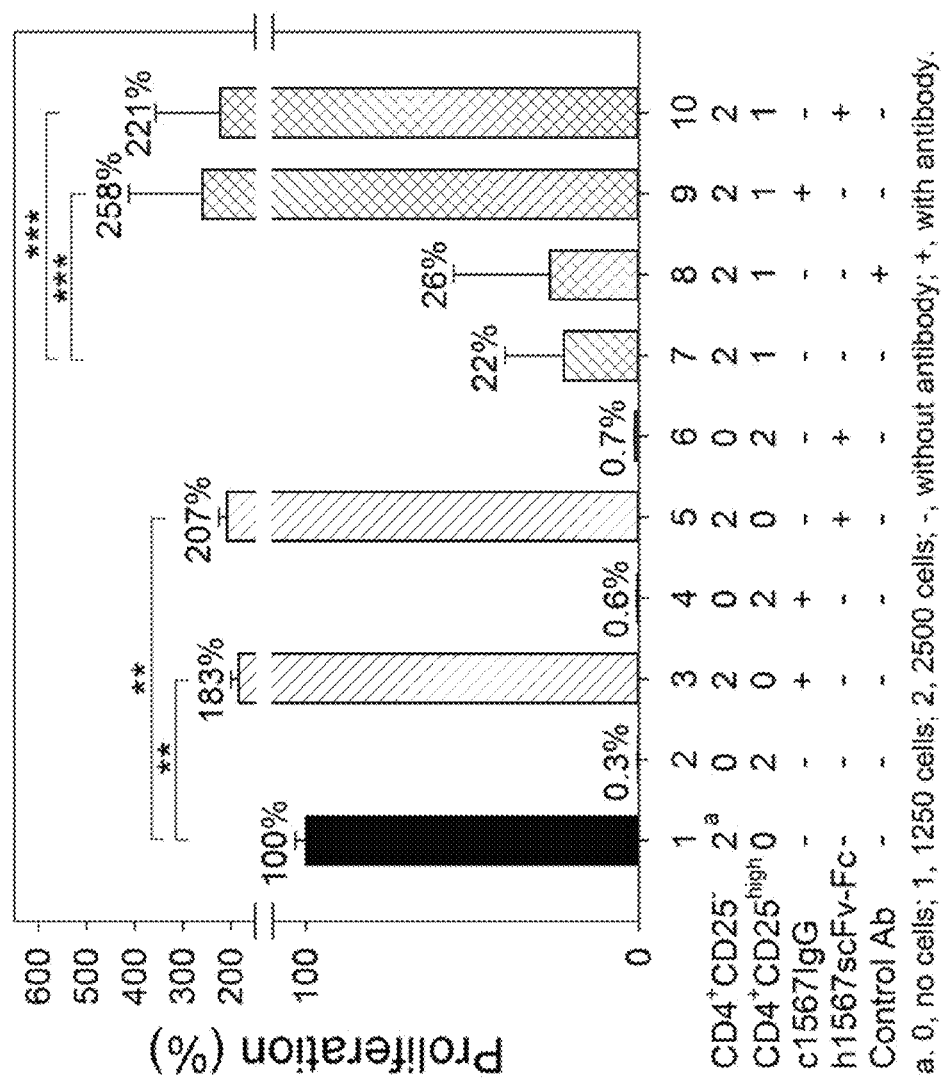

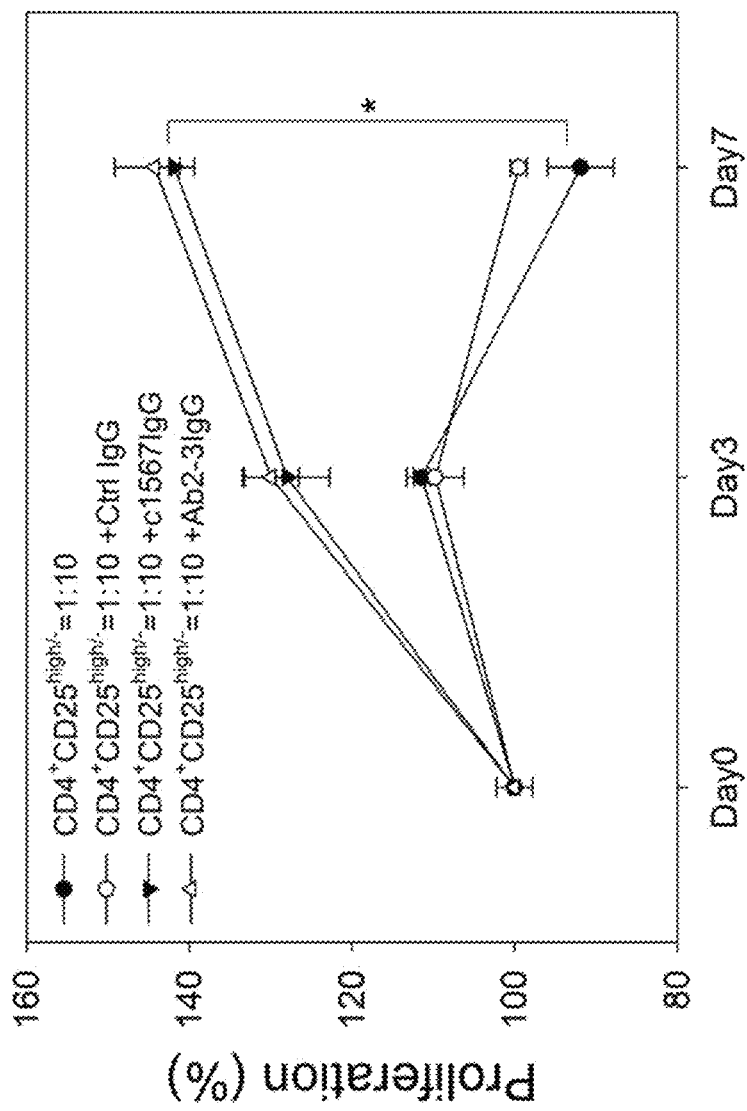

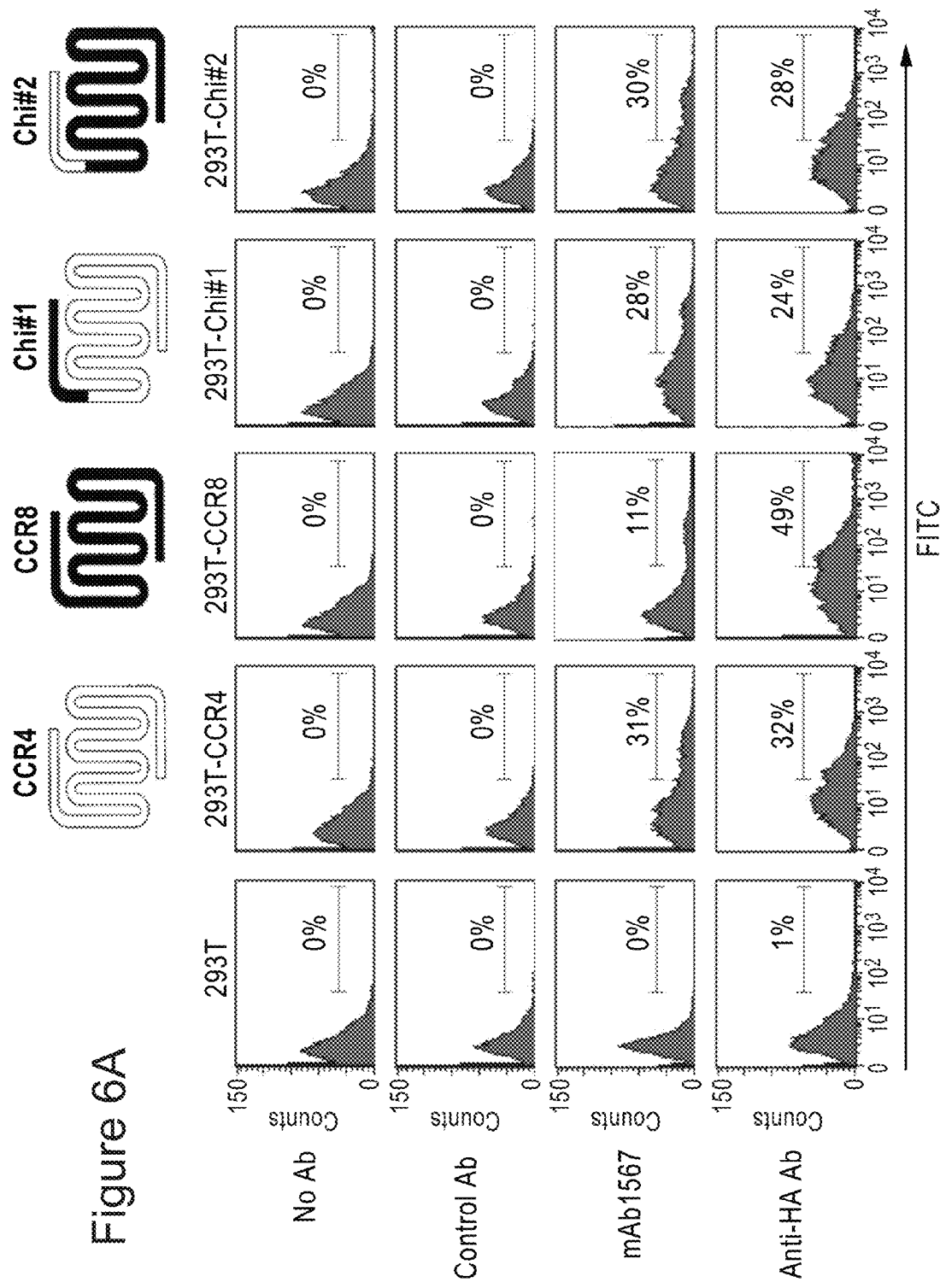

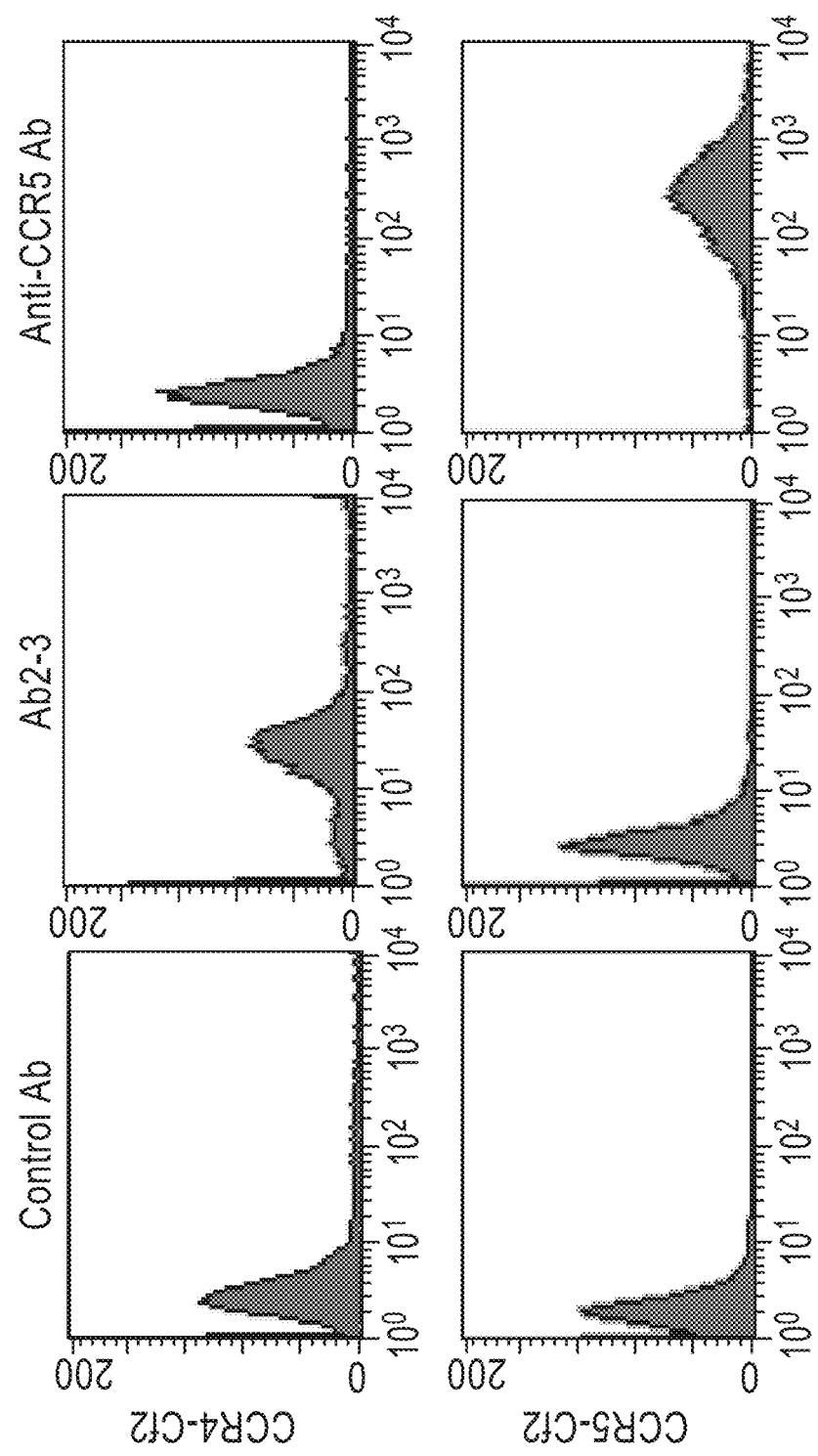

Figure 7A
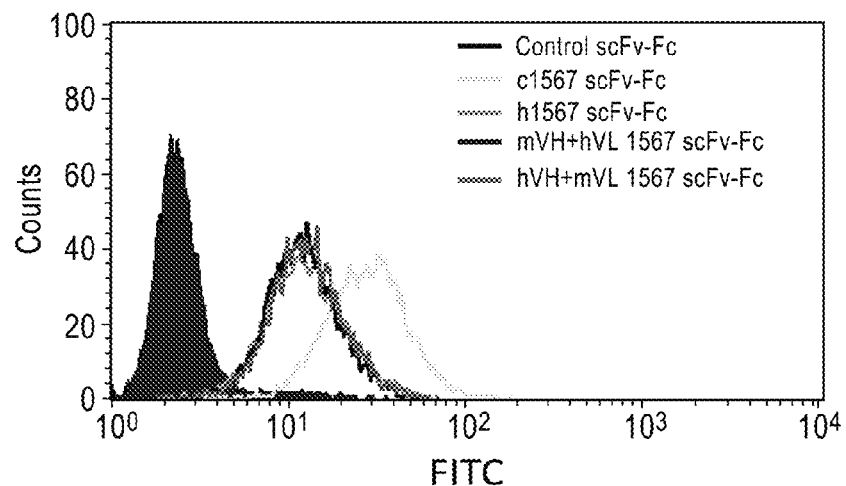
Figure 7B
VL-CDR3
105       112
h1567 scFv-Fc    HQYLSSYT    (SEQ ID NO: 34)
Clone1           QHYYSSPT    (SEQ ID NO: 46)
Clone2           QQYYSTPT    (SEQ ID NO: 47)
Figure 7C
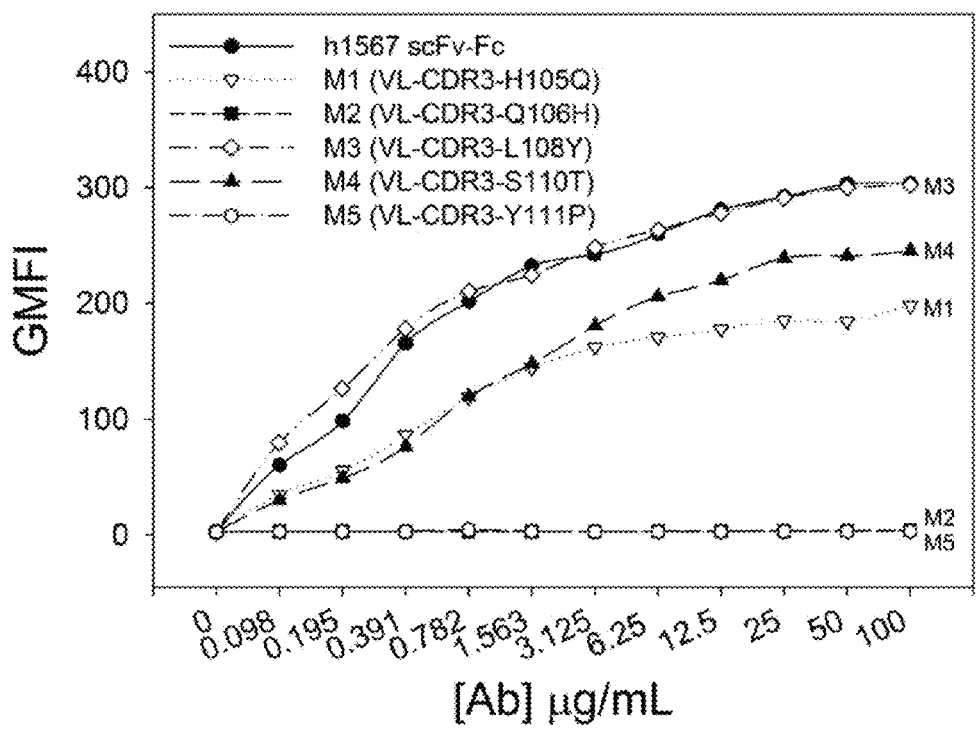

|  | VH-CDR1 | | VH-CDR3 | | VL-CDR3 | |
|---|---|---|---|---|---|---|
| h1567 scFv-Fc | GYTFASYY | SEQ ID NO: 21 | STYYRPLDY | SEQ ID NO: 29 | HQYLSSYT | SEQ ID NO: 34 |
| 1-44 scFv-Fc | ------QW | SEQ ID NO: 22 | --W------ | SEQ ID NO: 30 | ---T--- | SEQ ID NO: 35 |
| 1-49 scFv-Fc | ------SW | SEQ ID NO: 23 | --W---N-- | SEQ ID NO: 31 | ---K--- | SEQ ID NO: 36 |
| 2-1 scFv-Fc | ------SW | SEQ ID NO: 23 | T-R------ | SEQ ID NO: 32 | ---R--- | SEQ ID NO: 37 |
| 2-2 scFv-Fc | ------Q- | SEQ ID NO: 24 | L-----P-- | SEQ ID NO: 33 | ---Y--- | SEQ ID NO: 38 |
| 2-3 scFv-Fc | ------AW | SEQ ID NO: 25 | --------- | SEQ ID NO: 29 | ---M--- | SEQ ID NO: 39 |

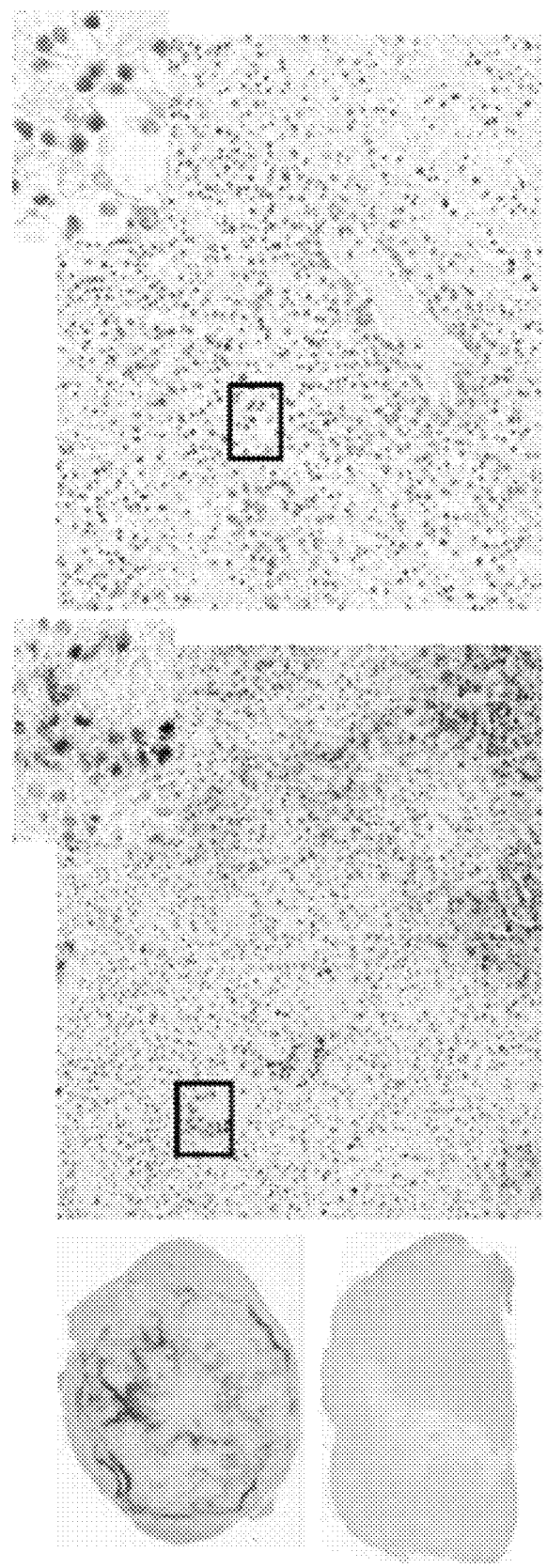

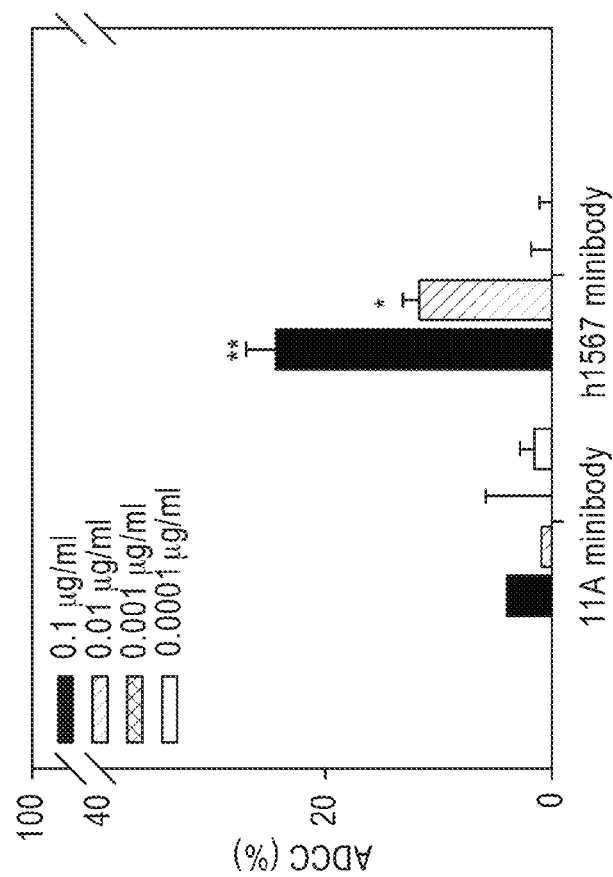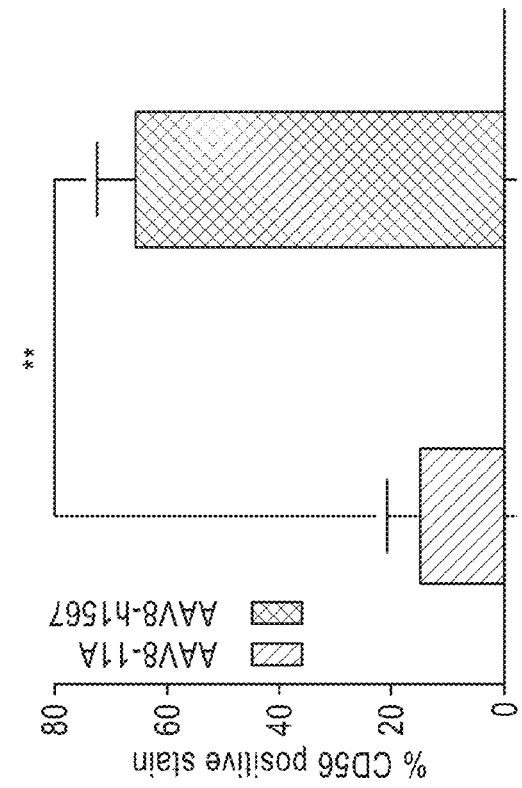
Figure 12B
Figure 12C

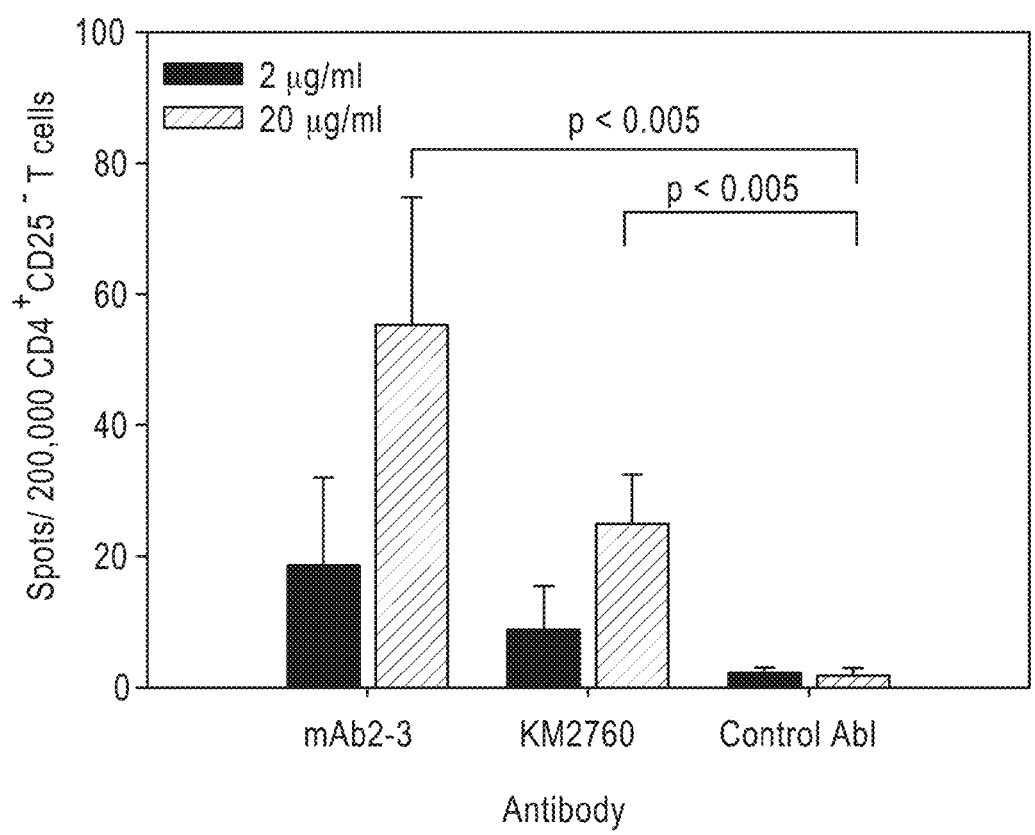

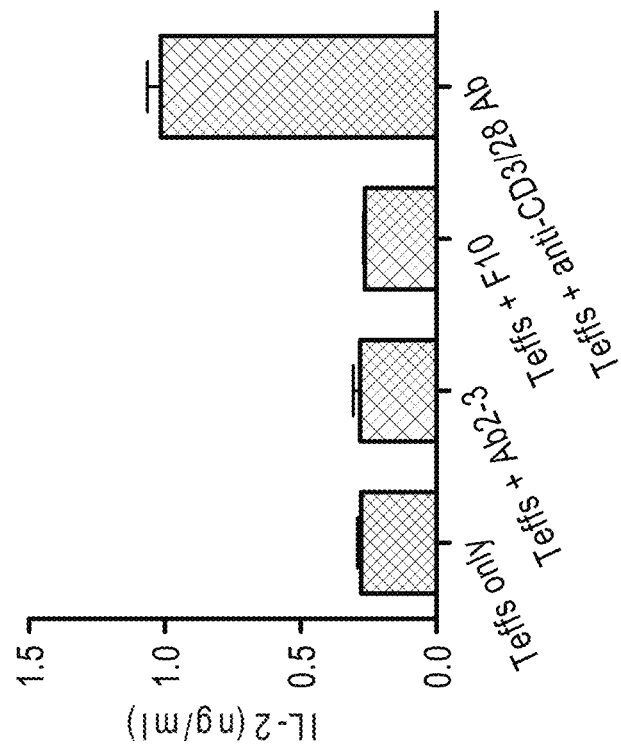
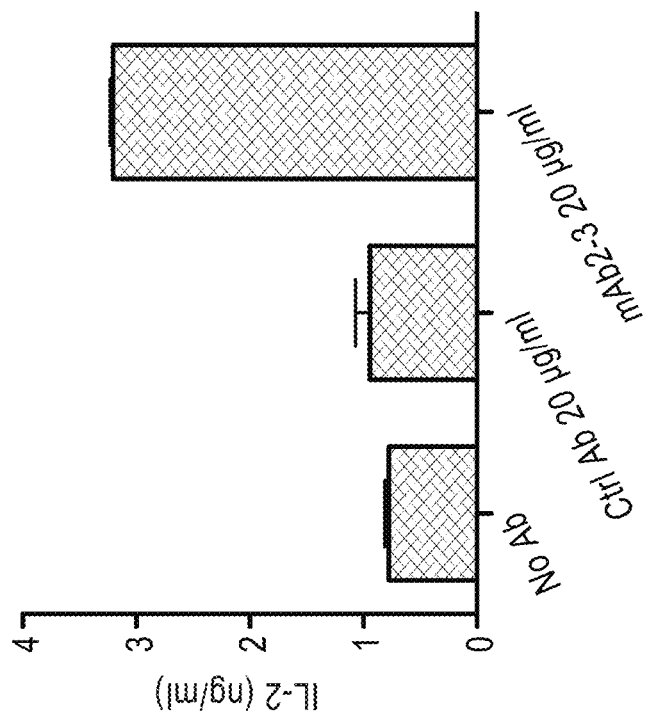
Figure 23A
Figure 23B

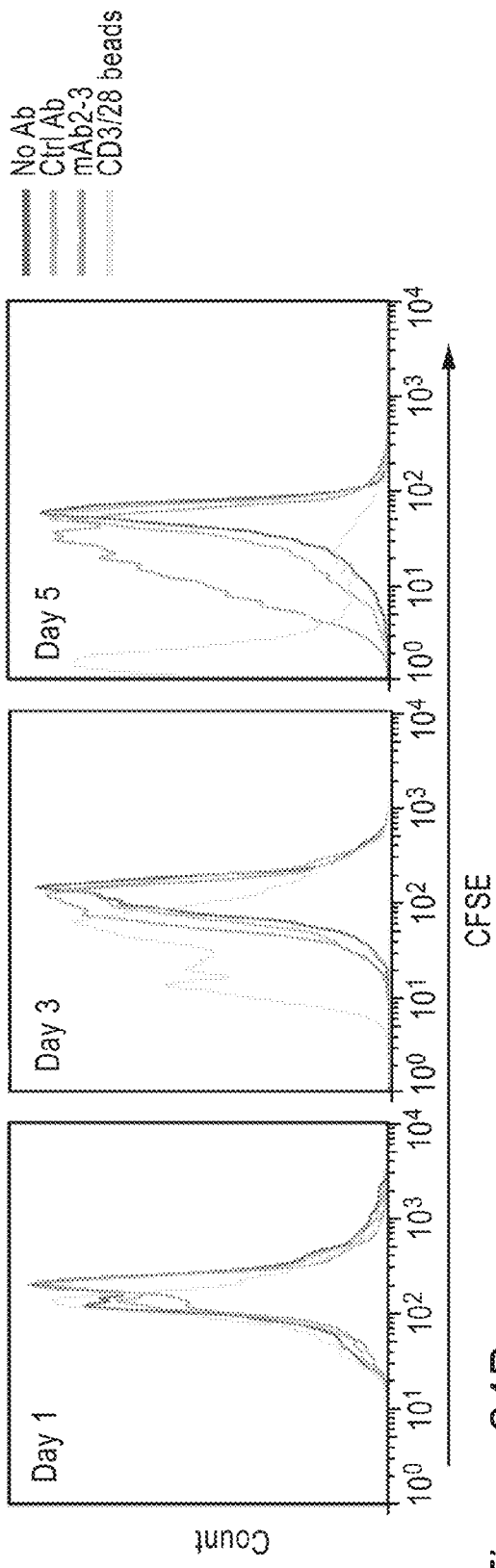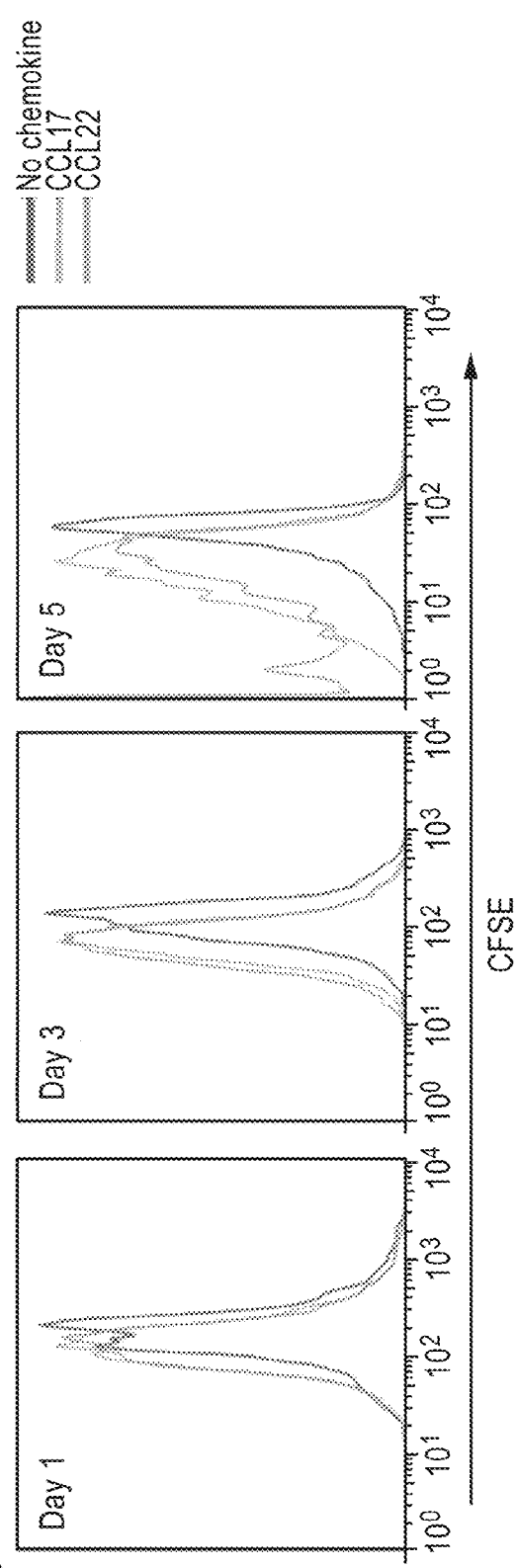

AFFINITY MATURED ANTI-CCR4 HUMANIZED MONOCLONAL ANTIBODIES AND METHODS OF USE

RELATED APPLICATIONS

This application is a continuation of U.S. application Ser. No. 14/398,910 filed on Nov. 4, 2014, which in turn is national stage application, filed under 35 U.S.C §371, of PCT/US2013/039744, filed May 6, 2013, which claims the benefit of U.S. Provisional Patent Application No. 61/642,749, filed May 4, 2012, and U.S. Provisional Patent Application No. 61/785,559, filed Mar. 14, 2013, the contents of each of which are each incorporated herein by reference in their entireties.

GOVERNMENT SUPPORT CLAUSE

This invention was made with government support under grant number CA093683 and AI058804 awarded by The National Institutes of Health. The government has certain rights to the invention.

INCORPORATION-BY-REFERENCE OF SEQUENCE LISTING

The contents of the text file named "DFCI 065 CO1US ST25", which was created on Nov. 3, 2014, and is 24 kilobytes in size, are hereby incorporated by reference in their entirety.

FIELD OF THE INVENTION

This invention relates generally to affinity matured humanized anti-CCR4 antibodies as well as to methods for use thereof.

BACKGROUND OF THE INVENTION

Cutaneous T cell lymphomas (CTCLs) are the most common extranodal non-Hodgkin's T cell lymphomas in adults. A recent WHO-EORTC consensus classification (Willemze R. et al. Blood 2005, 105:3768-3785) indicates that there are thirteen clinically and histologically distinct types of CTCL; however, 90% of CTCLs fall into three classes; mycosis fungoides (MF), primary cutaneous anaplastic large cell lymphoma (ALCL), and Sezary syndrome. The most common type of CTCL, mycosis fungoides, is characterized by erythematous patches and plaques that most commonly contain CD4+ T cells that show an affinity for the epidermis, or epidermotropism (Willemze R. et al. Blood 2005, 105:3768-3785). Staging is based upon a TNM classification; patients with Stage 1A disease have normal life expectancies, while patients with Stage 1B or greater have a diminished life expectancy (Kim, Y. H. et al. Arch Dermatol 2003, 139:857-866). Patients with Stage II-IV disease have a median survival of less than five years, with large cell transformation often leading to accelerated deterioration (Kim, Y. H. et al. Arch Dermatol 2003, 139:857-866). Sezary syndrome is a leukemic variant of CTCL wherein clonal CD4+ T cells accumulate in blood and lymph nodes as well as skin; five year survival is less than 25%. Primary cutaneous ALCL has a much less aggressive course, with a five year survival of 95%; however, cutaneous ALCL with concurrent nodal involvement is more aggressive (Willemze R. et al. Blood 2005, 105:3768-3785; Kadin M E, Carpenter C. Semin Hematol 2003, 40:244-256).

There is significant immune dysfunction in these patients, with global dysregulation of the T cell repertoire of unknown etiology (Yamanaka K. et al. Clin Cancer Res 2005, 11:5748-5755; Yawalkar N. et al. Blood 2003, 102: 4059-4066). The terminal event in most patients is bacterial sepsis. Current therapies for advanced MF and Sezary syndrome are palliative and durable long-term remissions are rare (Querfeld C. et al. Curr Opin Hematol 2005, 12:273-278). Thus, there is an urgent need for more effective therapies.

SUMMARY OF THE INVENTION

The invention is based upon the discovery of monoclonal antibodies which bind the CC-chemokine receptor 4 (CCR4). The monoclonal antibody is fully human. The antibodies bind CCR4. The antibodies are referred to herein as huCCR4 antibodies.

In one aspect, the invention provides an isolated humanized monoclonal antibody having a heavy chain with three CDRs including the amino acid sequences GYTFASQW (SEQ ID NO:22), INPGNVNT (SEQ ID NO:27), and STWYRPLDY (SEQ ID NO:30) respectively and a light chain with three CDRs including the amino acid sequences QSILYSSNQKNY (SEQ ID NO:26), WASTRE (SEQ ID NO:28), and HQYISSYT (SEQ ID NO:35) respectively; or a heavy chain with three CDRs comprising the amino acid sequences GYTFASSW (SEQ ID NO:23), INPGNVNT (SEQ ID NO:27), and STWYRPNDY (SEQ ID NO:31) respectively and a light chain with three CDRs comprising the amino acid sequences QSILYSSNQKNY (SEQ ID NO:26), WASTRE (SEQ ID NO:28), and HQYKSSYT (SEQ ID NO:36) respectively; or a heavy chain with three CDRs including the amino acid sequences GYTFASSW (SEQ ID NO:23), INPGNVNT (SEQ ID NO:27), and TTRYRPLDY (SEQ ID NO:32) respectively and a light chain with three CDRs including the amino acid sequences QSILYSSNQKNY (SEQ ID NO:26), WASTRE (SEQ ID NO:28), and HQYRSSYT (SEQ ID NO:37) respectively; or a heavy chain with three CDRs including the amino acid sequences GYTFASQY (SEQ ID NO:24), INPGNVNT (SEQ ID NO:27), and LTYYRPPDY (SEQ ID NO:33) respectively and a light chain with three CDRs including the amino acid sequences QSILYSSNQKNY (SEQ ID NO:26), WASTRE (SEQ ID NO:28), and HQYYSSYT (SEQ ID NO:38) respectively; or a heavy chain with three CDRs including the amino acid sequences GYTFASAW (SEQ ID NO:25), INPGNVNT (SEQ ID NO:27), and STYYRPLDY (SEQ ID NO:29) respectively and a light chain with three CDRs including the amino acid sequences QSILYSSNQKNY (SEQ ID NO:26), WASTRE (SEQ ID NO:28), and HQYMSSYT (SEQ ID NO:39) respectively. The antibody is monovalent or bivalent. The antibody is a single chain antibody. The antibody may be a bi-specific antibody. The antibody has a binding affinity of about 1 $nM^{-1}$. The antibody has a binding affinity of less than 1.5 $nM^{-1}$.

Additionally, the invention provides a single chain antibody containing a $V_H$ nucleotide sequence having SEQ ID NO: 1 and a $V_L$ nucleotide sequence having SEQ ID NO: 3; a $V_H$ nucleotide sequence having SEQ ID NO: 5 and a $V_L$ nucleotide sequence having SEQ ID NO:7; a $V_H$ nucleotide sequence having SEQ ID NO: 9 and a $V_L$ nucleotide sequence having SEQ ID NO: 11; a $V_H$ nucleotide sequence having SEQ ID NO: 13 and a $V_L$ nucleotide sequence having SEQ ID NO: 15; or a $V_H$ nucleotide sequence having SEQ ID NO: 17 and a $V_L$ nucleotide sequence having SEQ ID NO:19.

The invention further provides a single chain antibody containing a $V_H$ amino acid sequence having SEQ ID NO: 2 and a $V_L$ amino acid sequence having SEQ ID NO: 4; a $V_H$ amino acid sequence having SEQ ID NO: 6 and a $V_L$ amino acid sequence having SEQ ID NO: 8; a $V_H$ amino acid sequence having SEQ ID NO: 10 and a $V_L$ amino acid sequence having SEQ ID NO: 12; a $V_H$ amino acid sequence having SEQ ID NO: 14 and a $V_L$ amino acid sequence having SEQ ID NO: 16; or a $V_H$ amino acid sequence having SEQ ID NO: 18 and a $V_L$ amino acid sequence having SEQ ID NO: 20.

The invention also provides a huCCR4 antibody that is a bi-specific antibody containing the heavy-light chain of a huCCR4 antibody and the heavy-light chain of an antibody that recognizes a second antigen. For example, the second antigen is PD-L1 or CAIX (carbonic anhydrase). The CAIX antibody may be the G119 antibody.

In another aspect, the invention provides a cell producing a huCCR4 antibody.

In a further aspect, the huCCR4 antibody is linked to a therapeutic agent. The therapeutic agent is, for example a toxin, a radiolabel, a siRNA, a small molecule, or a cytokine. The cytokine is, for example, TGF-beta.

The invention further provides fusion proteins containing the antibodies of the invention. A fusion protein is, for example, an anti-CCR4 antibody or a functional fragment thereof, operably linked to a cytokine or growth factor, such as an IL-2 or TGF-beta polypeptide. The invention further provides methods for increasing T cell proliferation by contacting a T cell with a fusion protein containing an anti-CCR4 antibody operably linked to a cytokine.

Additionally, the invention provides a method for selectively killing a tumor cell by contacting the cell with a huCCR4 antibody. For example, the selective killing occurs by any one or more of the following: antibody-dependent cellular toxicity (ADCC), complement-dependent cytotoxicity (CDC), and antibody dependent cellular phagocytosis (ADCP). In one aspect, the tumor cell expresses CCR4. In another aspect, the tumor cell is a T-cell.

In another aspect, the invention provides method for decreasing suppressor T-cell activity by contacting the T-cell with a huCCR4 antibody.

Also included in the invention is a method for augmenting an immune response to an antigen by contacting the antigen with a huCCR4 antibody. In a further aspect, the huCCR4 antibody is administered prior to or after exposure to the antigen. The administration of the antibody of the present invention causes an increase in antigen-specific T-cell activity. For example, the antigen is a viral antigen, a bacterial antigen, or a tumor associated antigen. In one aspect, the viral antigen is, for example, HIV. In another aspect, the administration of the antibody of the present invention causes an increase in T-cell proliferation. For example, the T cell is an effector T-cell.

Additionally, the invention provides a method for increasing T cell proliferation comprising contacting a T cell with a huCCR4 antibody. The invention also provides a method for reversing regulatory T cell-mediated suppression of effector T cell proliferation comprising contacting a T cell with a huCCR4 antibody.

The invention further provides a method for increasing cytokine production or secretion comprising contacting a T cell with a huCCR4 antibody. In one aspect, the cytokine is IFN-gamma. In another aspect, the IFN-gamma secretion is increased and secretion of IL-10, IL-4, or TGF-beta is unchanged or decreased.

In a further aspect, the invention provides a method of increasing vaccine efficiency by administering to a subject a huCCR4 antibody and a vaccine. For example, the huCCR4 antibody and the vaccine are administered sequentially or concurrently. The vaccine is, for example, a tumor vaccine, a bacterial vaccine, or a viral vaccine.

In another aspect, the invention provides a method for treating or alleviating a symptom of cancer by administering to a subject in need thereof a composition including a huCCR4 antibody. The cancer is, for example, a solid cancer or a hematologic cancer. Exemplary hematologic cancers include, but are not limited to: cutaneous T-cell lymphoma (CTCL), mycosis fungoides (MF), primary cutaneous anaplastic large cell lymphoma (cutaneous ALCL), Sezary syndrome, or adult T cell Leukemia/Lymphoma (ATLL). Exemplary solid cancers include, but are not limited to: renal cell carcinoma, breast cancer, lung cancer, ovarian cancer, prostate cancer, colon cancer, cervical cancer, brain cancer, liver cancer, pancreatic cancer, kidney or stomach cancer. In another aspect, the cancer is a cancer that secretes CCL22. In some aspects, a bi-specific antibody of the present invention that also binds CAIX can be used for treatment of cancers that overexpress CAIX. In other aspects, a bi-specific antibody of the present invention that also binds PD-L1 can be used for treatment of cancers that overexpress PD-L1.

In another aspect, the invention provides a method of treating or alleviating a symptom of an autoimmune disease by administering to a subject in need thereof a composition containing a huCCR4 antibody linked to a regulatory T-cell expansion agent. The regulatory T-cell expansion agent is, for example, a cytokine. The cytokine is, for example, TGF-beta.

In another aspect, the invention provides a method for decreasing regulatory T-cell activity by contacting a regulatory T-cell with an antibody of the present invention linked to a toxin.

The invention further provides a nucleic acid sequence containing the nucleic acid sequence of SEQ ID NO: 1, 3, 5, 7, 9, 11, 13, 115, 17, or 19.

The invention further provides a nucleic acid sequence encoding the polypeptide of SEQ ID NO: 2, 4, 6, 8, 10, 12, 14, 16, 18, or 20. The invention further provides a polypeptide comprising the amino acid sequence of SEQ ID NO: 2, 4, 6, 8, 10, 12, 14, 16, 18, or 20.

The invention further provides a vector containing the nucleic acid sequence containing SEQ ID NO: 1, 3, 5, 7, 9, 11, 13, 115, 17, or 19 or encoding the polypeptide of SEQ ID NO: 2, 4, 6, 8, 10, 12, 14, 16, 18, or 20.

Additionally, the invention provides a cell containing a vector containing the nucleic acid sequence containing SEQ ID NO: 1, 3, 5, 7, 9, 11, 13, 115, 17, or 19 or encoding the polypeptide of SEQ ID NO: 2, 4, 6, 8, 10, 12, 14, 16, 18, or 20.

The administration routes, in any methods of this disclosure, include, but are not limited to parenteral, (e.g., intravenous), intradermal, subcutaneous, oral (e.g., inhalation), transdermal (i.e., topical), transmucosal, and rectal administration.

The subject in any methods of this disclosure is, for example, a mammal. The mammal is, for example, a human.

Other features and advantages of the invention will be apparent from and are encompassed by the following detailed description and claims.

BRIEF DESCRIPTION OF THE DRAWINGS

FIG. 5. Anti-CCR4 antibody abrogates suppression by T regulatory cells. A, CD4+CD25$^{high}$ T cells showed demonstrable chemotactic responses toward CCL22. The percentage of cells was calculated relative to T cells expressing CD4±CD25, as determined by flow cytometry. The data represent the mean±S.D. B, Chimeric mAb1567 effectively inhibited chemotaxis of Tregs to CCR4 ligand CCRL22. C, The effect of c1567-IgG1 antibody on proliferation of T effector cells and the abrogation of the suppressive function of Tregs. Tregs and T effector cells were co-cultured at 2500 (1:1 ratio) 1250 (0.5:1) cells each per well and cell proliferation was measured on day 5 by $^3$H-labelled thymidine incorporation using a scintillation counter. The percent proliferation was normalized to CD4+CD25− T effector cells without antibody treatment. Bars represent mean±S.D. from triplicate samples of one representative of three experiments. D, CD4+CD25− T cells were CFSE-labeled, incubated with Tregs at 10:1 ratio, and then stimulated with anti-CCR4 antibodies and control antibody in the presence of anti-CD3/28 co-stimulation. After 3 and 7 days cells were harvested and analyzed by flow cytometry. The percentage of cells was calculated among the fluorescence positive CD4+CD25− T and counting beads. The percent proliferation was normalized to CD4+CD25− T effector cells at Day 0. The data shown were calculated from two independent experiments. Bars represent mean±S.D. "*" indicates p<0.05.

FIG. 7. Affinity maturation of humanized anti-CCR4 mAb1567. A, Binding activity comparison among chimeric, humanized and mouse/human VH and VK hybrid 1567 antibodies. Both mouse heavy chain-human light chain (mVH+hVL 1567 scFv-Fc) and human heavy chain-mouse light chain (hVH+mVL 1567 scFv-Fc) showed similar affinity as h1567 scFv-Fc but weaker than parental c1567 at 0.1 µg/ml, an Ab concentration that can discriminate binding affinities. The VL of Ab1567 played an equally important role as the VH in recognizing CCR4. B, By sequencing 48 randomly picked non-binding Ab clones from the unselected VL shuffled library, two sequences was found to have the same VL sequence as h1567 except for five residues in the CDR3. Amino acid number based on the IMGT database numbering scheme is shown on the top. C, Mutations in VL-CDR3 effecting 1567's binding to CCR4. Further mutagenesis on these singly selected residues showed that mutant M3 (L108Y) retained full binding activity whereas M1 (H105Q) and M4 (S110T) had moderate loss of binding activity and mutants M2 (Q106H) and M5 (Y111P) had complete loss of binding. The VL and in particular the four residues (H105, Q106, S110 and Y111) in the VL-CDR3 are critically important for binding to CCR4. D, Alanine-scanning analysis of residues in the CDRs of h1567 for binding to CCR4 on Mac-1 cells. As the VL played an equally important role as VH in CCR4 binding, all the CDRs in both VH and VL were included in the mutagenesis study (total of 31 residues) to assess the specific contribution of each CDR residue to CCR4 binding. A few non-alanine mutants in VL-CDR3 were also included in the analysis. Binding percentage of each mutant was normalized against wild type humanized mAb1567 scFv-Fc (100%) and mutant Abs were all tested at concentration of 3.7 µg/ml. Total 13 residues in four CDRs (VH-CDR1 (HCDR1), VL-CDR1 (LCDR1), HCDR3 and LCDR3) reduced more than 50% binding activity. Further analysis of the 13 residues in their possible roles for maintaining CDR3 loop canonical structures showed that seven residues might act as "scaffolding" residues (HCDR3-P112, HCDR3-D114, LCDR1-Y38, LCDR3-H105, LCDR3-Q106, LCDR3-Y107 and LCDR3-Y111). To maintain the structural integrity of the antigen-binding site, these seven amino acids were kept as wild type. The other six amino acids were chosen to be randomized (asterisks) and a mutant h1567-Ab phage-display library with a diversity of $4.1\times10^7$ was constructed for affinity optimization. E, Amino acid sequence alignment of humanized mAb1567 and mAb binding variants with associated VH-CDR1, VH-CDR3 and VL-CDR3 amino acid differences among them. After panning against Mac-1 cells, five unique h1567 phage-scFv variants that bound strongly were identified. F, Dose dependent binding curve of humanized 1567 and it's variants to $CCR4^+$ Mac-1 cells by FACS analysis. Binding percentage shown on Y-axis of each variant was normalized against h1567 scFv-Fc (100%). Three out of the five, 2-2, 1-44 and 2-3, showed higher binding activity to Mac-1 cells than parental h1567 with $EC_{50}$ of 1.73, 1.47, and 1.39 nM, respectively.

FIG. 8. Human mAb1567 variants mediated ADCC activity against Cf2-CCR4 cells via human NK cells. Antibodies were tested at concentration of 5 μg/mL, NK cell to target cells ratio was at 1:1. Data are shown in a box and whiskers graph and represent three independent experiments and each was performed with NK cells from a different health donor; the box extends from lowest percentile to the highest percentile, with a line at the median. The whiskers above and below the box indicate the 95th and 5th percentiles. A, Cf2-CCR4 cells; B, control Cf2 cells.

FIG. 9. AAV vector construction and the expression of human mAbs in AAV-transduced mice. (a) Schematic representation of AAV-single chain variable region antibody (scFv)—human IgG1 Fc fusion (scFvFc) or "minibody" construct. Human mAb 11A (control) and "humanized" h1567 genes encoding the V domains of heavy (VH) and light (VL) chains were cloned between the AAV internal terminal repeats (ITRs) contained in vector pTRUF and expressed as a minibody protein. (b) In vivo transduction with AAV8-h1567-scFvFc and AAV8-11A-scFvFc in SCID-BEIGE mice after administering $2\times10^{11}$ vg (viral genome) units per mouse by a single intravenous (i.v.) tail vein injection and in a final volume of 150 ul PBS. Serum levels were measured over time by human IgG ELISA. (c) SDS-PAGE confirming the molecular weight and disulfide-bond integrity of the 11A and h1567 minibodies. (d) Western blotting analysis of the monomer and dimer forms of the 11A and h1567 minibodies using an anti-human IgG1-Fc antibody and processed under reducing and non-reducing conditions. (c & d) minibody proteins recovered from in vitro culture (left) and serum following in vivo transduction (right) are shown. (e) Binding specificity of the AAV8-derived h1567 minibody. The specific binding of h1567 scFv-Fc in serum was shown using CCR4-positive cell lines, Mac-1 and 293T-CCR4 by flow cytometry. An equivalent concentration of the control 11A minibody did not show any binding. 293T cells serve as CCR4 negative control cells.

FIG. 10. Anti-tumor effect of AAV8-derived h1567 minibody. (a) The tumor volume of each individual tumor plotted as a function of times (days post inoculation). AAV vectors were delivered intravenously by tail vein injection 7 days after the inoculation of $2.5\times10^6$ Mac-1 tumor cells. $P<0.01$, $*P<0.0005$ when comparing tumor mass in AAV8-h1567-treated and control vector AAV8-11A-treated group on Day 18 and Day 21, respectively. (b) Survival analysis of AAV8-h1567 or control AAV8-11A-treated tumor-bearing mice (engrafted with $2.5\times10^6$ Mac-1 tumor cells). Tumor-bearing PBS-treated mice were used as background controls. Statistically significant difference was observed between 1567 minibody-treated group and control groups ($P<0.01$). (c) Immunohistochemical analysis of a representative tumor sections with anti-Ly-6G, a specific mAb recognizing murine neutrophils. The immunostaining shows tumor-infiltrating neutrophils (brown stain) in tumor from the SCID-BEIGE mice 21 days after administration of AAV8-h1567 encoding anti-CCR4 minibody (upper-left for entire tumor section and center-panel for magnified section). No staining was seen in the tumor from the mice treated with control vector AAV8-11A (lower-left and right panel). (d) Quantification of neutrophil infiltration from panel C. Entire tumor sections were captured using the Aperio ImageScope instrument, and the percentage of positively stained cells were quantitated by using a color deconvolution algorithm. $*P<0.05$. (e) In vitro ADCC activity against Mac-1 cells in the presence of h1567 minibody. The ADCC activity was assessed using purified SCID-BEIGE neutrophils as effector cells and CCR4+ Mac-1 cells as target cells. Neutrophil-mediated lysis of target cells was induced at an E:T ratio of 80:1 in the presence of 50 ug/ml purified h1567 minobodies. The figure shown is representative of three independent experiments. $*P<0.05$, $P<0.01$, $*P<0.0005$. All data are represented as the mean±SD.

FIG. 11. PBMC-mediated antitumor activity of the AAV8-derived h1567 minibody in a xenograft SCID-BEIGE mouse model. (a) Growth in tumor volume was quantified by caliper measurements. Tumor progression was significantly inhibited in the AAV8-h1567-treated group compared with the AAV8-11A control group. Mice were given a single intravenous injection of AAV vectors 11 days after inoculation of the tumor cells, which was followed by a single injection of PBMC on day 18. *P<0.05; **P<0.01. (b) Tumor growth was monitored in vivo by optical imaging and quantified weekly by bioluminescent imaging. *P<0.05; **P<0.01. (c) Sequential in vivo imaging of tumor growth over time in the tumor mouse model. Panels depict a representative mouse from each group. (d) Micro-CT/PET fusion images of representative mice 28 days after tumor inoculation. Representative coronal (left), sagittal (right), and transverse sections (below) are shown for both controls and treated mice. Arrows indicate tumor location. FDG PET revealed a decrease in glucose metabolism in AAV8-h1567-treated mice. Data shown are mean values±SD.

FIG. 12. ADCC activity of h1567 minibody in a xenograft human PBMC-SCID/BEIGE mouse model. (a) Immunohistochemical staining of a representative tumor section with mAb directed against human NK cell surface marker CD56. The immunostaining shows highly positive CD56 tumor-infiltrating human NK cells in tumor from the SCID/BEIGE mice treated with AAV8-h1567 and human PBMCs (upper panel). Negative CD56 staining was seen in the tumor treated with control vector AAV8-11A (lower panel). Images are shown from whole tumor cut sections (left panels) and tumor sections at 20× magnifications (right panels). (b) The percentage of immunohistochemically detected tumor-infiltrating natural killer cells was plotted. A significantly higher percentage of tumor-infiltrating human CD56-positive cells were detected in the AAV8-h1567-treated mice group. **, p<0.01. (c) NK cell-mediated cytotoxicity was observed in a dose-dependent manner. Minibody concentrations from 0.0001 to 0.1 ug/ml were tested at an E:T ratio of 2:1. The average and error bars (mean+SD) shown were calculated from triplicate wells of one experiment. The figures shown are representative of three independent experiments. *P<0.05, **P<0.01 when comparing h1567 minibody-treated and 11A control minibody-treated group. All data is shown as the mean±SD.

Figure 13:
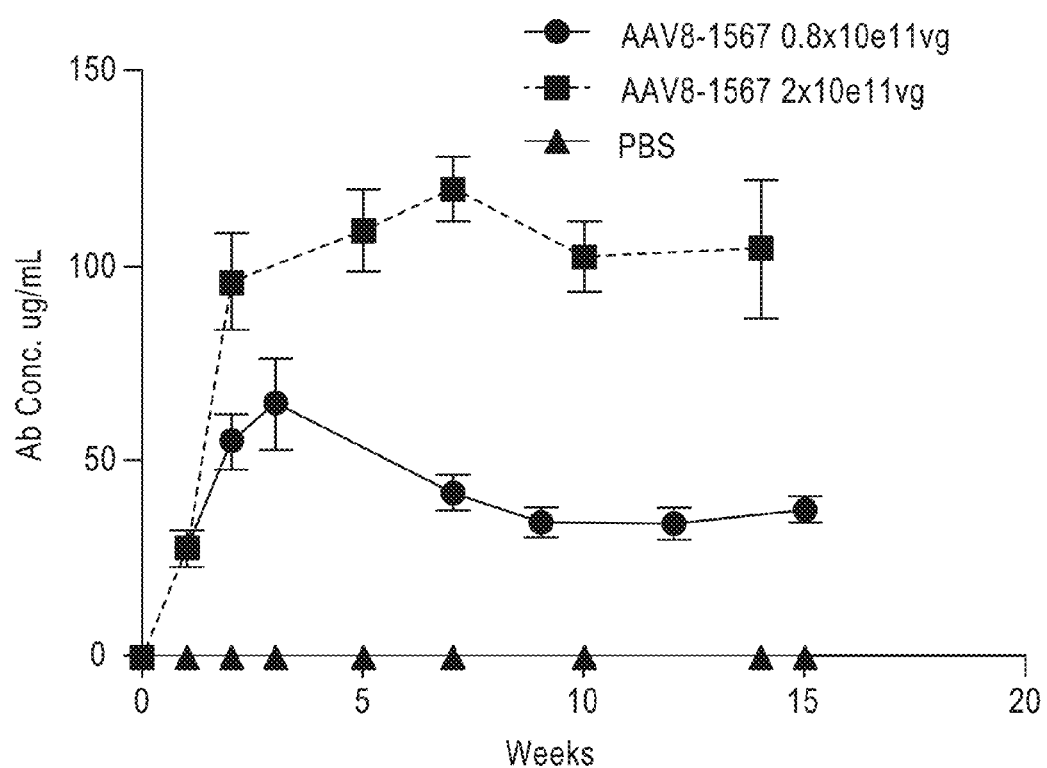

FIG. 13. Dosing study of mAb 1567 in vivo. Nude mice received a single intravenous injection of vector AAV8-h1567 at either a high ($2.0\times10^{11}$ vg/mouse) or low ($0.8\times10^{11}$ vg/mouse) concentration. Control mice were injected with PBS. Serum levels were measured over a period of 15 weeks by human IgG ELISA.

Figure 14:
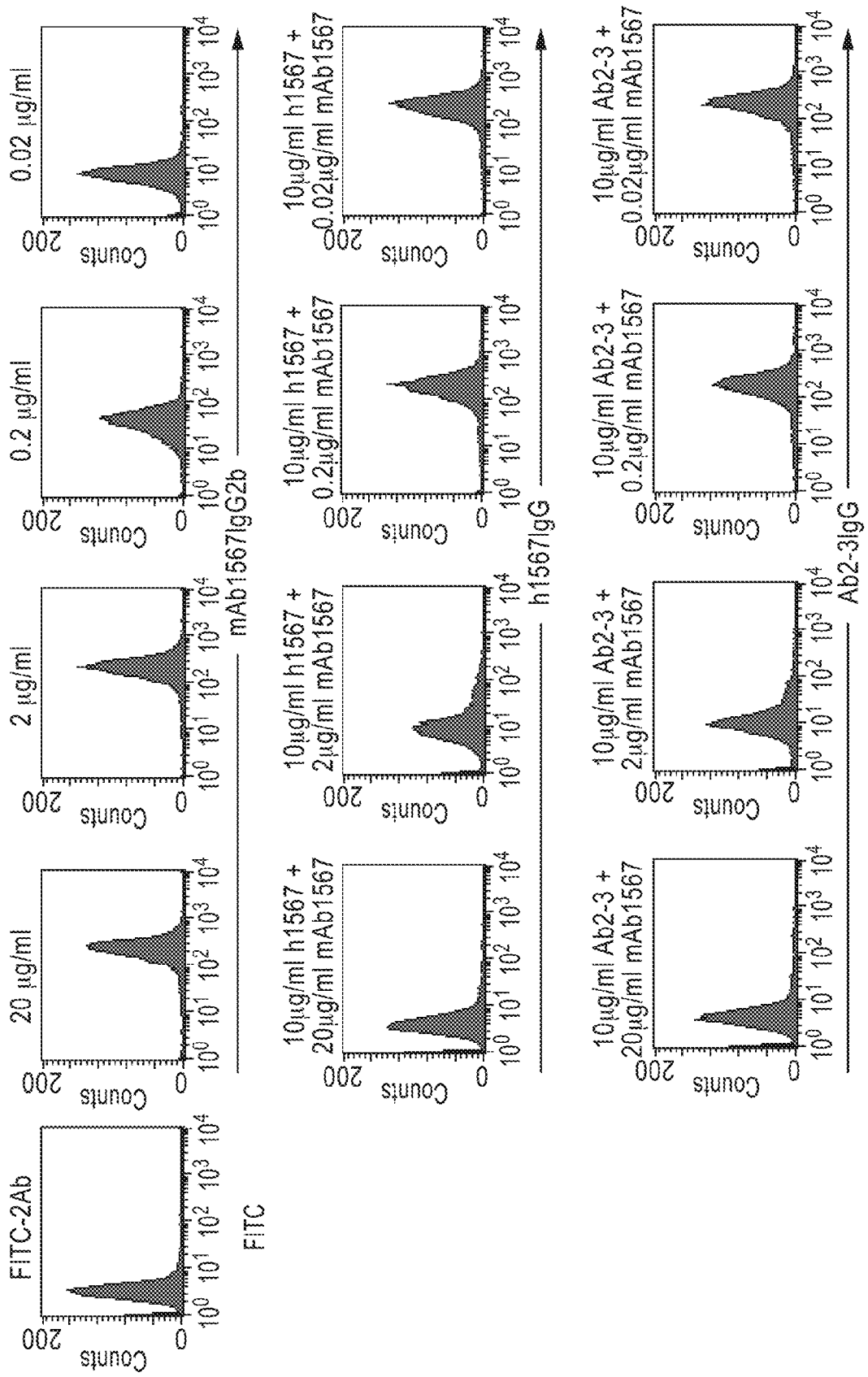
Figure 15A:
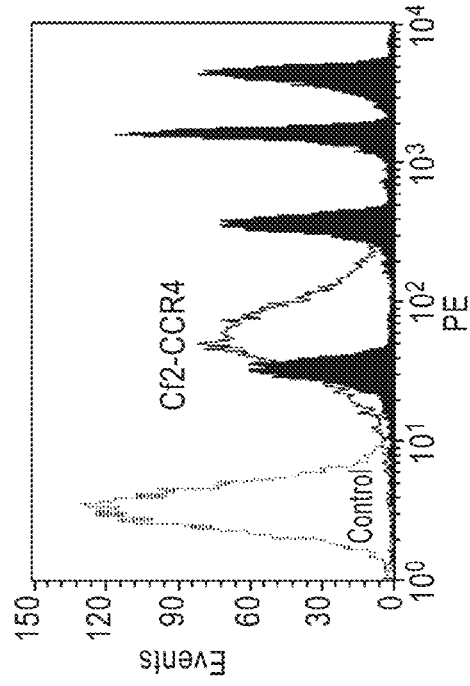
Figure 15B:
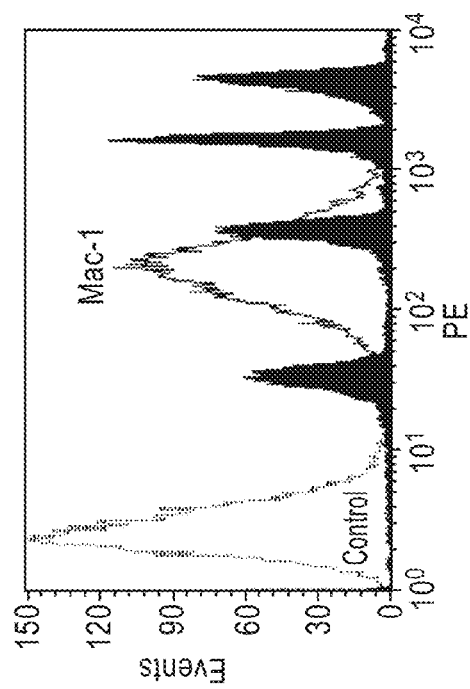
Figure 15C:
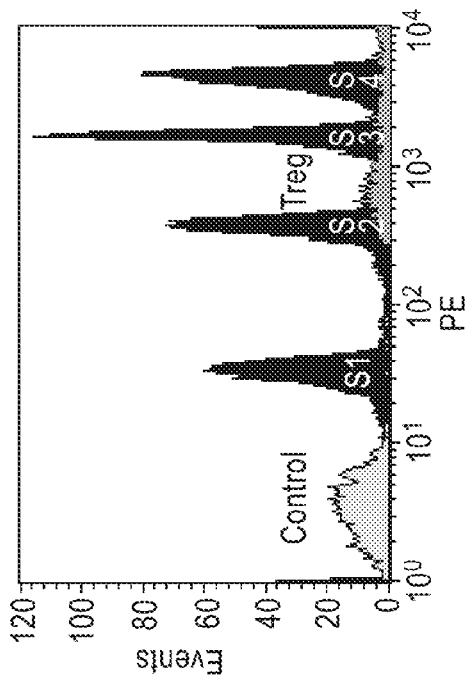
Figure 15D:
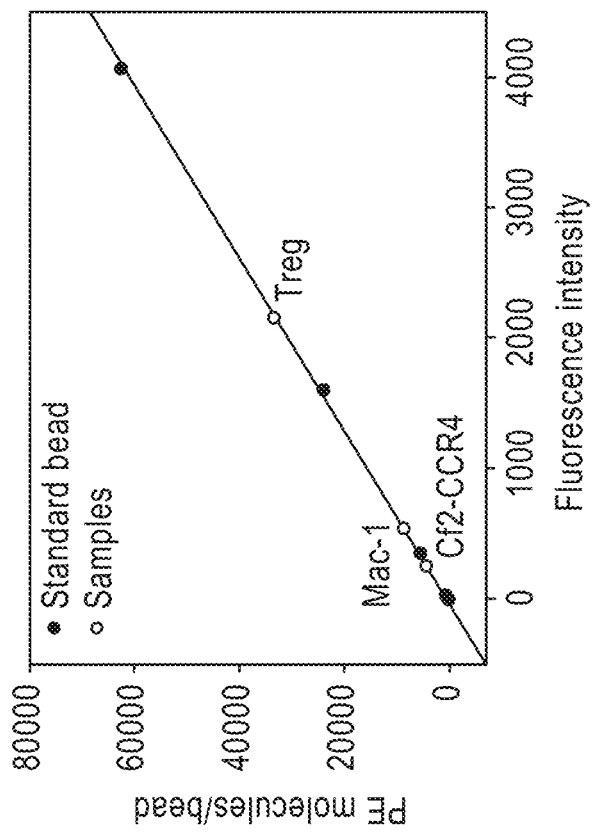

FIG. 14. Competition of mAb1567 monoclonal antibodies (IgG2b) with h1567IgG and Ab2-3IgG. Competition assays were performed by FACS using Mac-1 cells. Cells were incubated with different concentration of mAb1567 plus neither fixed concentration of h1567 or Ab2-3 for 1 hr at 4° C. Data were analyzed by flow cytometry using FITC-labeled anti-Fc domain antibody.

FIG. 15. Representative histograms for the quantitation of CCR4. Mac-1 (A), CCR4 expressed Cf2 cells (B), and T regulatory cell (C) were analyzed as described in Materials and Methods. Cells staining with directly PE-conjugated mAb to CCR4 and isotype-matched control Ab (dashed line). QuantiBRITE beads with four different levels of PE molecules, detailed in text, are shown in filled profiles. D, The average number of molecules of CCR4 on cell surface.

Figure 16A:
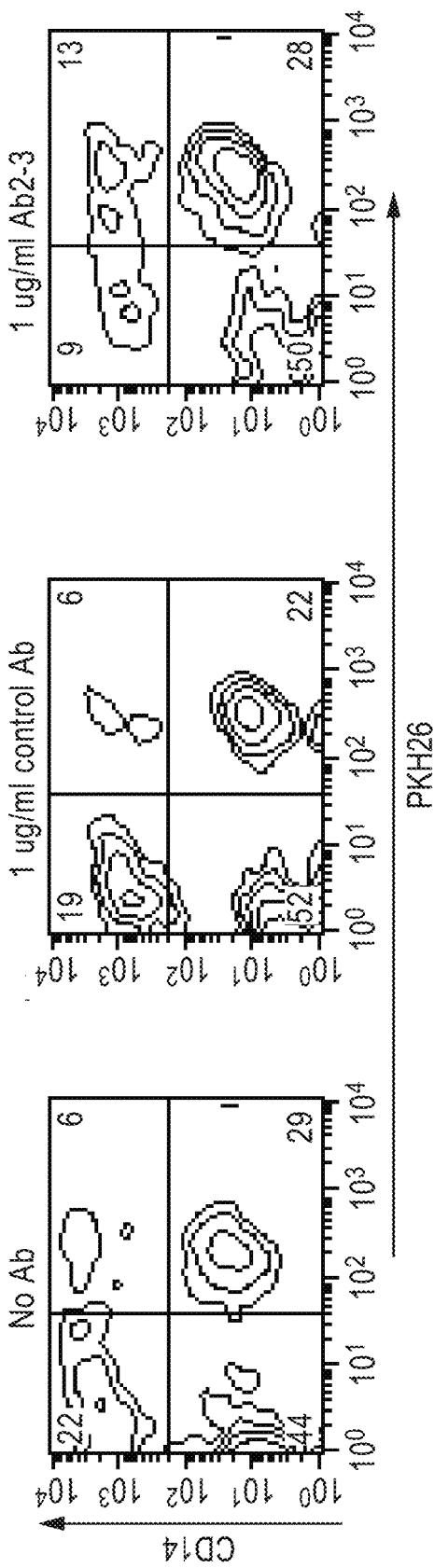
Figure 16B:
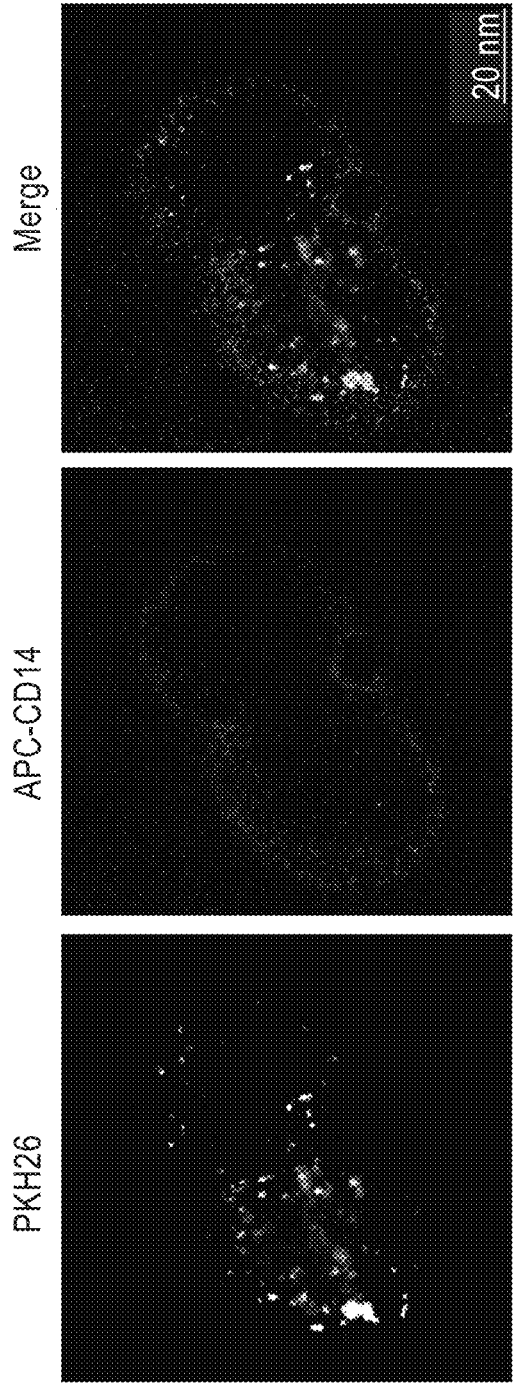

FIG. 16. Anti-CCR4 antibodies mediate macrophage phagocytosis. A, Flow cytometric analysis of ADCP. Mac-1 target cells were stained red with PKH26 and are present in the right lower quadrant of the dot plots. Macrophages were stained with anti-CD14 conjugated with APC. They appear in the left upper quadrant of the dot plots. The left hand dot plot is from a representative 4-h culture of macrophages and target cells (Mac-1) only. The middle plot are from representative 4-h cultures of macrophages and target cells in the presence of scFv-Fc isotype control. The right plot are from representative 4-h cultures of macrophages and target cells in the presence of Ab2-3 scFv-Fc. The effector: target ratio used was 8:1. B, Fluorescent images of macrophages phagocytosing Mac-1 using the confocal microscope. The macrophages have been stained with anti-CD14 conjugated with APC. The target cell line (Mac-1) was stained with PKH26 (Celltracker probe).

Figure 17A:
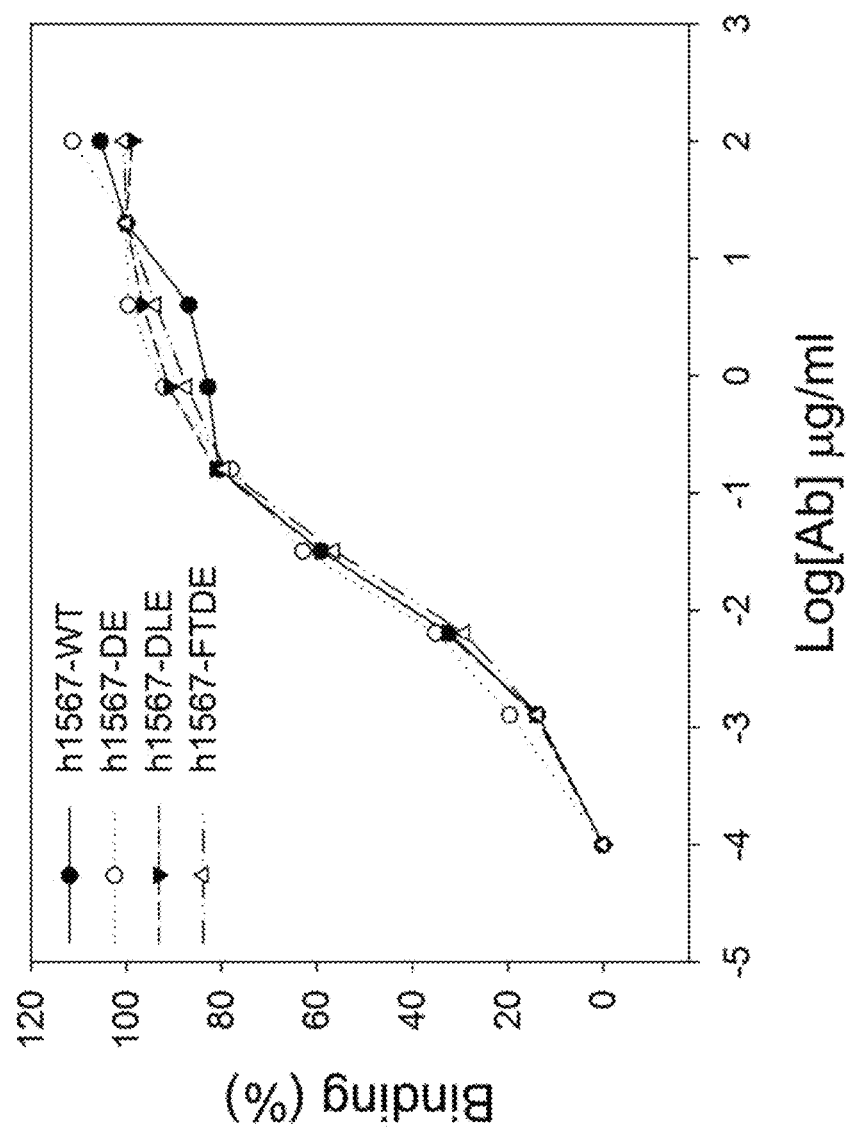
Figure 17B:
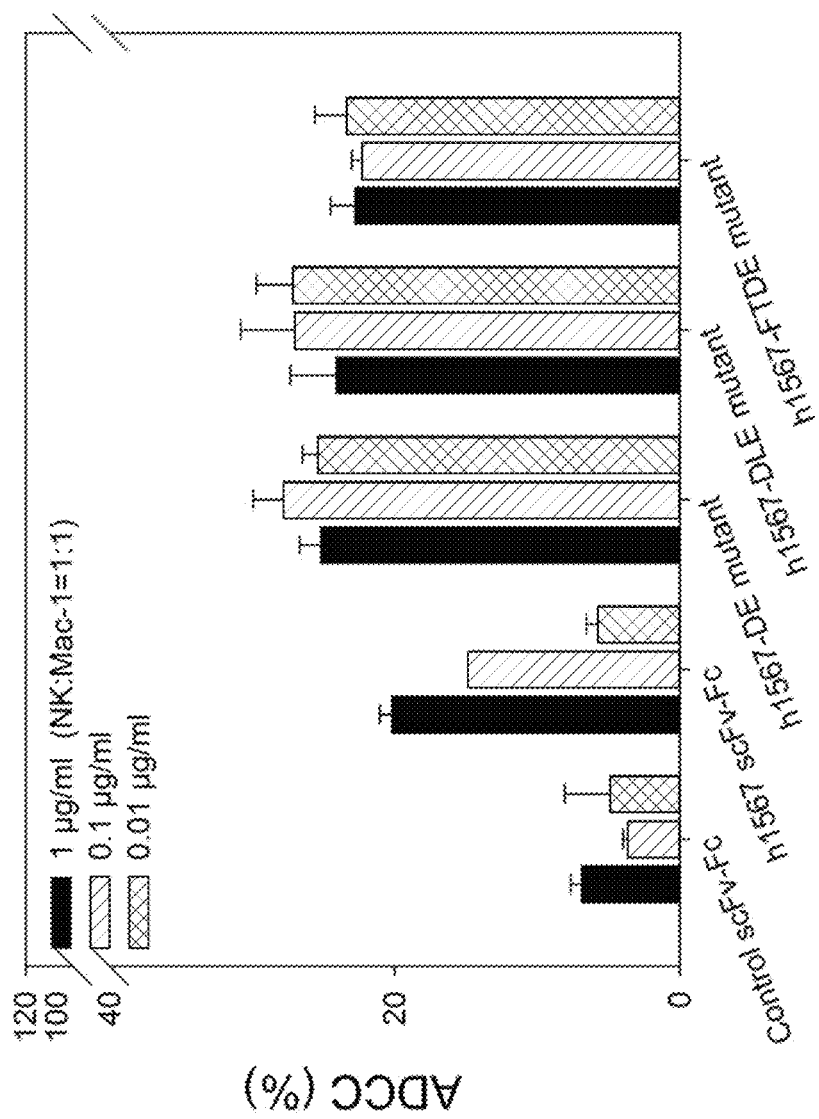
Figure 17C:
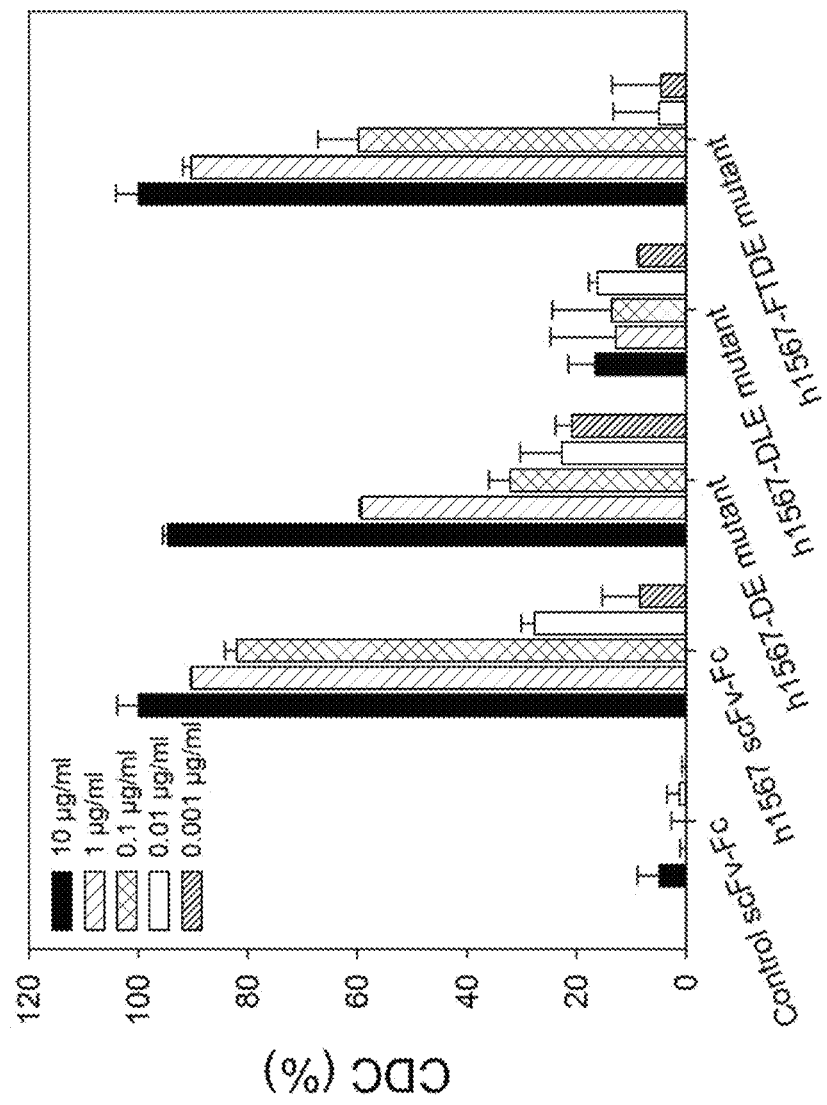

FIG. 17. Functions of h1567 with Fc mutants. A, Binding activity of h1567 and its Fc mutants. B and C, ADCC (B) and CDC (C) (rabbit complement) activity of h1567 and its Fc mutants. Error bars represent mean±S.D.

Figure 18:
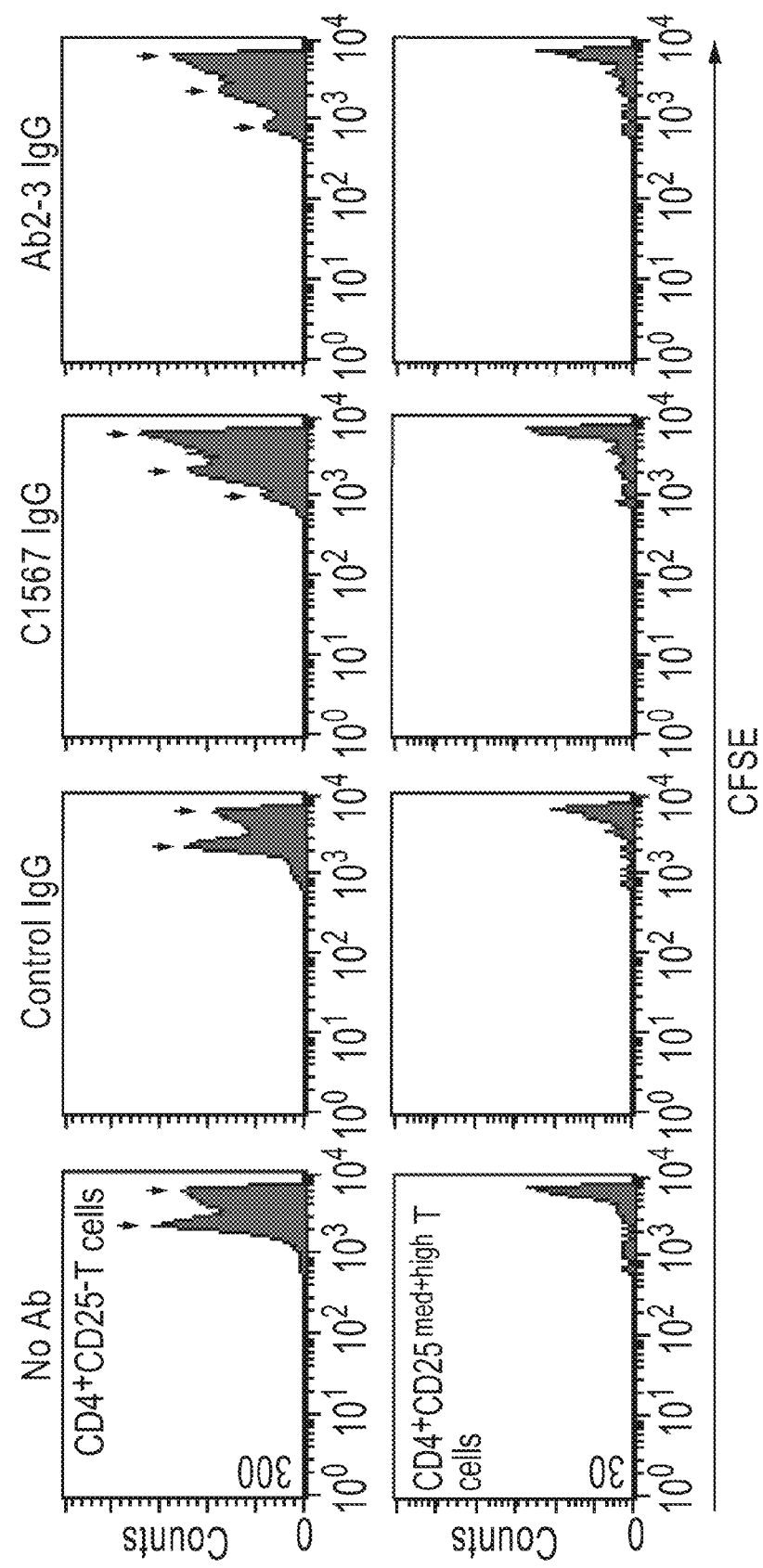

FIG. 18. Anti-CCR4 antibodies modulate the proliferation of CD4$^+$CD25$^-$ T cells. The proliferation assay of CD4$^+$CD25$^-$ T cell (upper panel) and CD4$^+$CD25$^{med-high}$ T cell (lower panel) proliferation assay showing CFSE proliferation profiles of CD4$^+$CD25$^-$ T cells (treated in vitro with PBS, control antibody or anti-CCR4 variants for 2 days).

FIG. 19. Biodistribution of mAb2-3 of T lymphocytes. FACS analysis of cell populations from human donor PBMC (huPBMC) or spleens from humanized mice (hNSG-spleen). A, CD3$^+$CD4$^+$ gated PBMCs were further gated using CCR7 and CD45RA to identify different populations of T cells: differentiated T cells (T-diff), naïve T cells (T-Naïve), effector memory T cells (T-EM) and central memory T cells (T-CM) (left plot). The set of 4 plots on the right shows CCR4 expression as detected by mAb2-3 on each T cell population, T-diff, T-Naïve, T-EM and T-CM. B, CD3$^+$CD4$^+$ gated PBMCs were gated using CD25 and FoxP3 to identify Treg population (left plot). CCR4 expression in CD3$^+$CD4$^+$CD25$^+$FoxP3$^+$ cells was detected by mAb2-3 (right plot). C, CD3$^+$CD4$^+$ gated spleen cells from humanized mice further gated using CCR7 and CD45RA. D, CCR4 expression in CD3$^+$CD4$^+$CD25$^+$FoxP3$^+$ cells was detected by mAb2-3 (right plot).

FIG. 20. Comparison of two different anti-CCR4 antibodies on effector T cell proliferation. A, CCR4-Cf2 cells were all incubated with KM2760 (another anti-CCR4 chimeric antibody) with different concentration and then stained by APC-labeled mAb2-3. Competition assay showed mAb2-3 has different binding motif than KM2760. B, Binding affinity of mAb2-3, KM2760, and KW0761 (humanized KM2760 antibody) showed mAb2-3 has high affinity than the others. C, Anti-CCR4 antibodies stimulate CD4$^+$ Teff proliferation. CD4$^+$CD25$^-$ T cells were CFSE-labeled, incubated with anti-CCR4 antibodies and control antibody in 10 unit IL-2/ml RPMI medium. Cells were harvested at Day3, 5 and 7, and then analyzed by flow cytometry. The percentage of cells was calculated among the fluorescence positive CD4$^+$CD25$^-$ T and counting beads. The percent proliferation was normalized to CD4$^+$CD25$^-$ T effector cells at Day 3. The data shown were calculated in triplicate samples. Bars represent mean±S.D.

FIG. 21. IFN-γ secretion in response to anti-CCR4 antibodies. A, IFN-gamma ELISpot of human CD4$^+$CD25$^-$ T cells in response to mAb2-3 and KM2760. ELISpot results for anti-CCR4 mAbs (mAb2-3 and KM2760), control antibody and anti-CD3 antibody in CD4$^+$CD25$^-$ T cells are depicted. Data result from three separate experiments using three individual donor bloods. B, Quantification of IFN-gamma ELISpot. p<0.005.

FIG. 22. Cytokine expression from CD4$^+$CD25$^-$ T cells. A, Expression of cytokines from CD4$^+$CD25$^-$ T cells in the absence of CD4$^+$CD25$^+$ Tregs. B, Expression of cytokines from CD4$^+$CD25$^-$ T cells in the presence of CD4$^+$CD25$^+$ Tregs. Use of ELISA measured the temporal production of various cytokines including Th1 associated (INF-γ), Th2 associated (IL-4), and Treg associated (TGF-beta and IL-10)

cytokines in response to anti-CCR4 antibody stimulation. Simultaneous measurement of cytokines was conducted with the Sandwich ELISA assay in triplicate using supernatant mixtures from replicate wells following exposure to anti-CCR4 antibody (20 µg/ml) for 48 h of stimulation. IL-4 and IL-10 were expressed at almost the same level, but TGF-beta was slightly changed. Upon exposure to anti-CCR4, IFN-γ was upregulated both in two different anti-CCR4 antibodies.

FIG. 23. ELISA analysis of cytokine levels in $CD4^+CD25^-$ and $CD4^+CD25^+$ T cell culture supernatants after incubation with mAb2-3. A, Tregs were isolated using negative selection of CD4+CD127dimCD49d-EasySep kit. Tregs (3000/reaction) were incubated in the absence of exogenous 6 ng/ml (10 IU) IL-2, IL-2 concentration of incubated Tregs treated with 20 µg/ml of control mAb F10 and mAb2-3 and 0.5/1 µg/ml of plate-bound anti-CD3/28 antibodies. B and C, In the absence of exogenous IL-2, endogenous IL-2 concentration from $1 \times 10^4$ Teffs alone (B) or co-incubated with Tregs (C) and treated with 20 µg/ml of control mAb F10 and mAb2-3 and 1 µg/ml of anti-CD3/28 antibodies. D, the concentrations of IL-2 in supernatants from Teffs and Tregs coculture treated with mAb2-3 in the presence of 50 ng/ml of exogenously added IL-2.

FIG. 24. $CD4^+$ T cells were stained with CFSE and cultured for 5 d with 10 IU/ml IL-2 plus different antibodies and chemokines and analyzed by FACS. A, overlay CFSE histograms of T cells immediately after CFSE staining and after 5 d of stimulation are shown sequentially. B, overlay CFSE histograms of chemokines-treated T cells are shown.

Figure 25:
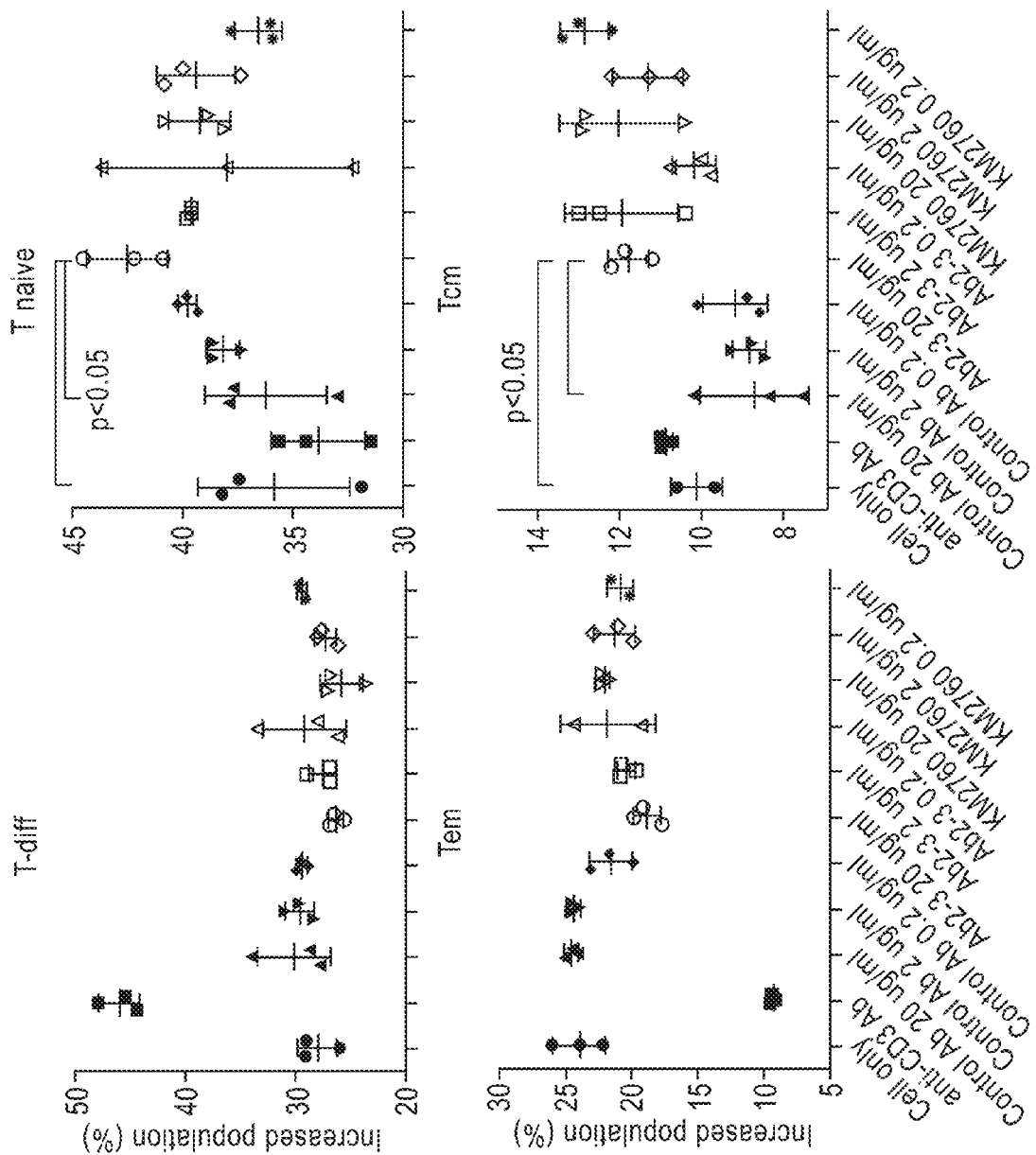

FIG. 25. Effect of Anti-CCR4 antibody, mAb2-3 on Teffs cells. The percentage increase in the four subpopulations of $CD4^+CD25^-$ Teff cells were separately measured after three-day incubation with mAb2-3, a negative control antibody, and KM2760 (another anti-CCR4 monoclonal antibody). T-diff, T-naive, Tem, and Tcm cells were identified by $CD45RA^+CCR7^-$, $CD45RA^+CCR7^+$, $CD45RA^-CCR7^-$ and $CD45RA^-CCR7^+$, respectively. The proliferation was observed on mAb2-3-treated T-naive and Tcm cells with statistical significance, p value<0.05.

FIG. 26. Chemoattraction of human lymphocytes by CCL22-secreting ovarian cancer cells is inhibited by mAb2-3. A, In vitro chemotaxis of $CD4^+CD25^+$ T cells induced by CCL22-expressing ovarian cancer cell supernatant was inhibited by mAb2-3, but not by control antibody. Results were expressed as means±SD and student's t-test. B, The in vivo bioluminescence images of ovarian cancer xenograft mouse model at 48 h post-injection of luciferized $CD4^+$ T cells. Tumor tissues had strong bioluminescence accumulation after injection $CD4^+$ T cells in the presence of control antibody as shown in the circle. However, the intensity of luminescence signal was dramatically reduced by co-injection with mAb2-3. C, Quantification of bioluminescence intensity of tumor-infiltrating $CD4^+$ T cells and Tregs by the region of interest [ROI as specified by the circle in B] analysis using IVIS imaging system.

Figure 27B:
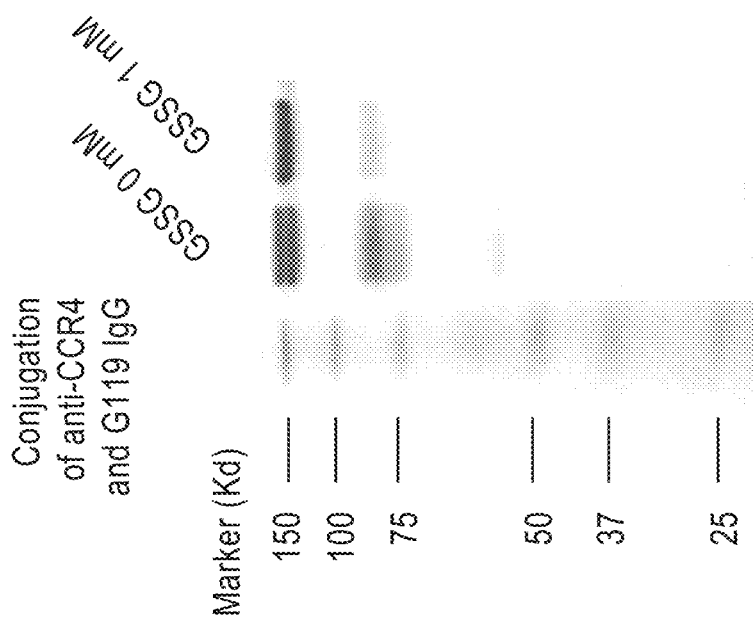
Figure 27A:
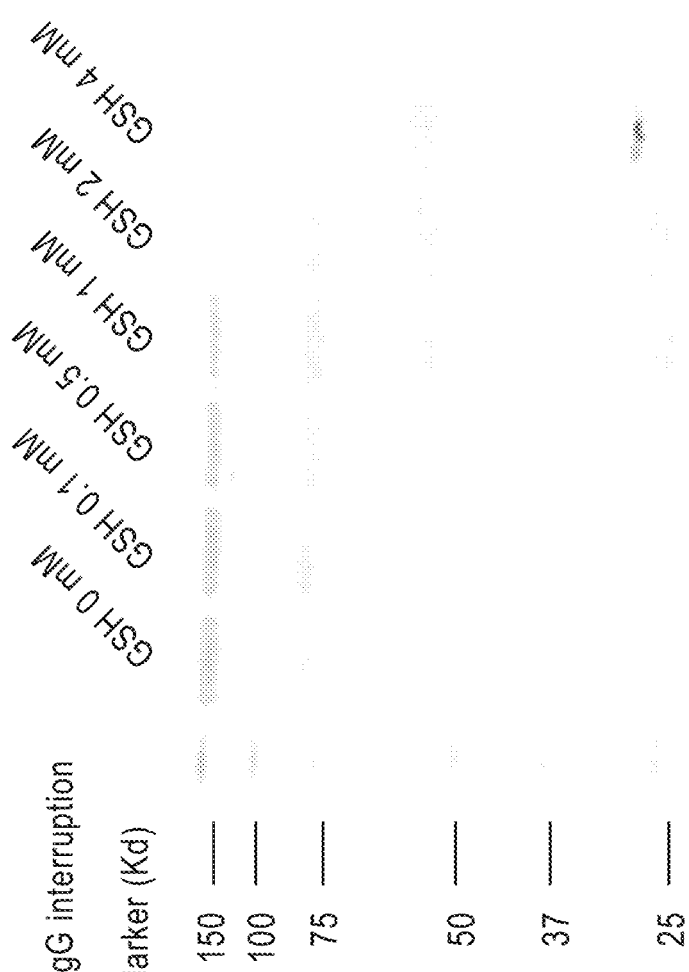
Figure 27C:
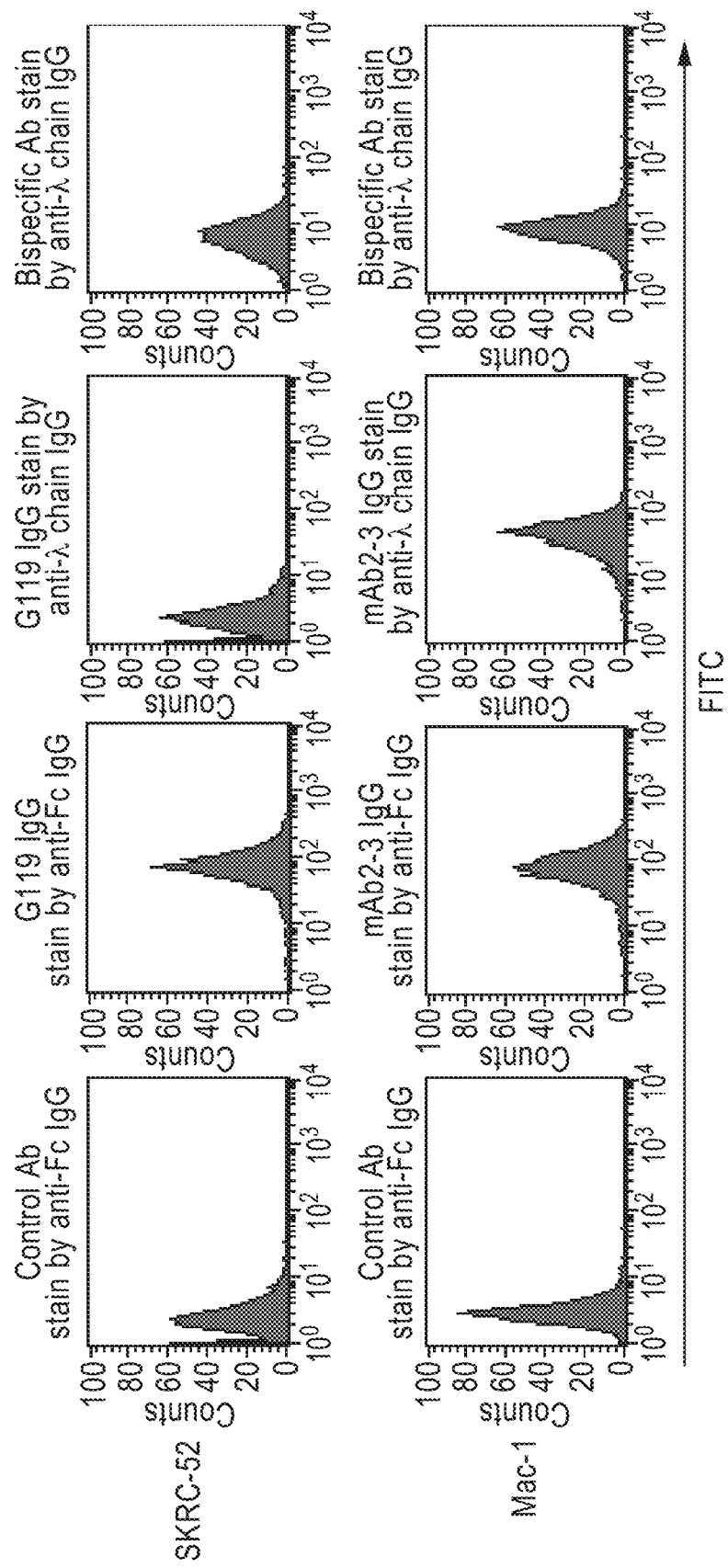

FIG. 27. Generation of bispecific antibody and its function. A, G119, an antibody recognizing carbonic anhydrase IX (CAIX), and anti-CCR4 antibodies were constructed into two independent vectors and produced. Antibodies were interrupted to form antibody monomer by glutathione (GSH). B, G119 and anti-CCR4 monomer were conjugated to form bispecific antibody by glutathione disulfide (GSSG). C, Test the function of bispecific antibody using flow cytometry.

Figure 28:
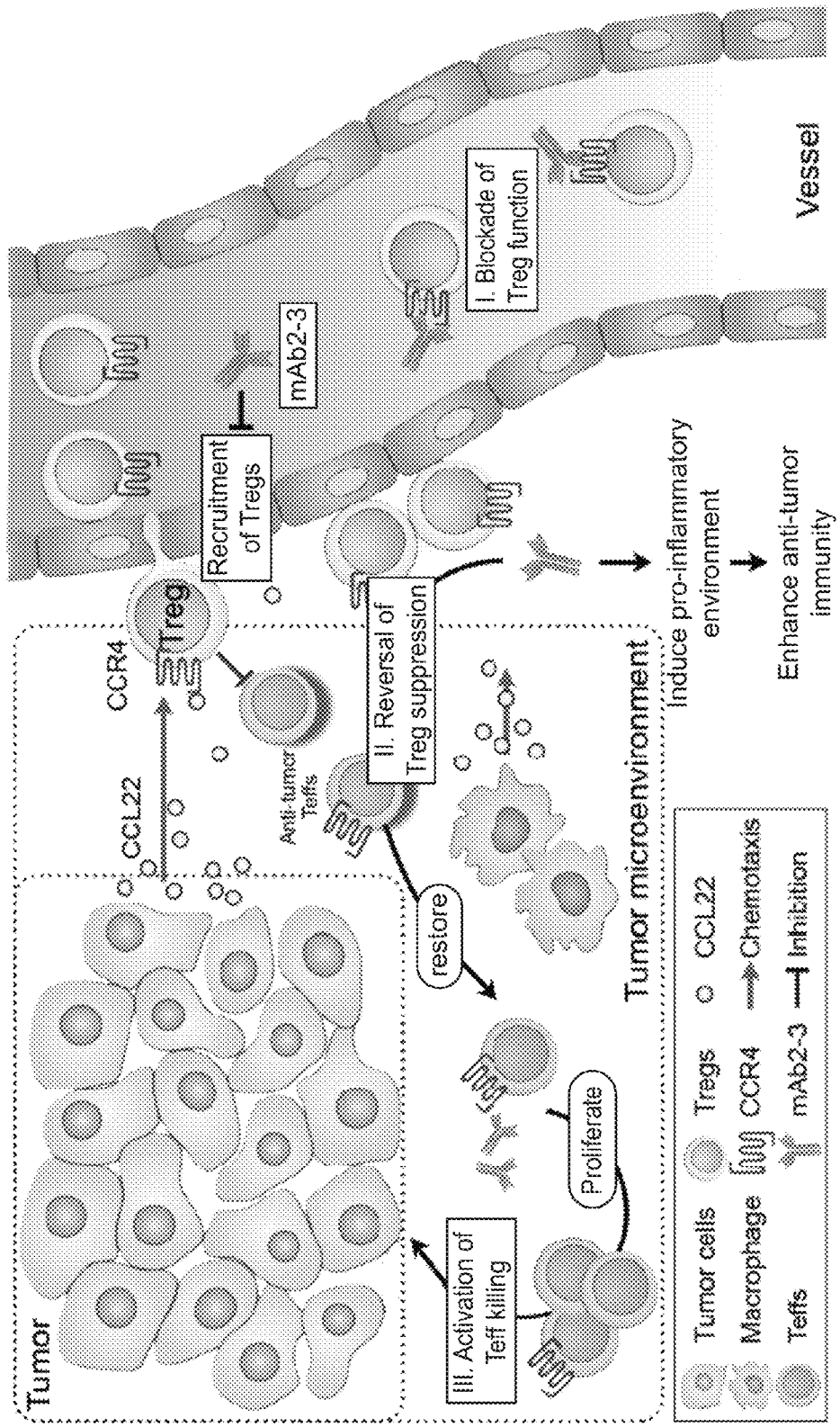

FIG. 28. Schematic of mAb2-3-mediated immunotherapy. MAb 2-3 may form a barrier preventing CCL22 chemotactic recruitment to $CCR4^+$ Tregs, resulting in tumor immune surveillance through tumor infiltrating effector T cells due to the blockade of Tregs accumulation in tumor microenvironment. MAb2-3 may also specifically bind to $CCR4^+$ T cells, including naïve and Tcm cells, resulting in restoration of Teff activity through releasing pro-inflammatory cytokines.

DETAILED DESCRIPTION

Chemokines are a family of secreted proteins known primarily for their roles in leukocyte activation and chemotaxis. Their specific interaction with chemokine receptors on target cells trigger signaling cascades that result in inflammatory mediator release, changes in cell shape, and cellular migration. The CC chemokine receptor 4 (CCR4) is the cognate receptor for the CC chemokines CCL17 and CCL22, and is expressed on functionally distinct subsets of T cells, including T helper type 2 cells (Th2), and the majority of regulatory T cells (Tregs) (Iellem et al., 2001; and Imai et al., 1999). Growing evidence indicate that CCL17/22 secretion promotes increased numbers of tumor-infiltrating Tregs by malignant entities such as colorectal, ovarian, Hodgkin's lymphoma and glioblastoma (Curiel et al., 2004; Wagsater et al., 2008; Niens et al., 2008; Jacobs et al., 2010; Hiraoka et al., 2006). Increased levels of Treg in tumors hinder efficient antitumor immune responses (Wood et al., 2003; and Levings et al., 2001) and are often associated with poor clinical outcome and tumor progression (Hiraoka et al., 2006; and Woo et al., 2001). Accordingly, one major obstacle of successful cancer therapies might be caused by migration of Treg into tumors and their suppression of antitumor immune responses in the tumor microenvironment (Zou et al, 2006; and Yu et al, 2005). In an effort to abrogate Treg suppressive function and consequently promote antitumor immunity, monoclonal antibodies (mAbs) as immunotherapeutics against Tregs have been evaluated in preclinical and clinical studies in recent years (Mahnke et al., 2007; Roncarolo et al., 2007). However, a caveat to systemic Treg depletion with mAb immunotherapy is its highly anticipated association with autoimmunity (Sakaguchi et al., 2008; and Kohm et al., 2006). An alternative strategy to avoid Treg induced cancer immune evasion is to develop a tumor-associated Treg targeting therapy that directly hinders Treg attraction and accumulation in tumor tissue.

One potential of mAbs in cancer immunotherapy lies in their capacity to block or modulate immunological axes which promote immune evasion by tumors. The chemokine receptor CCR4 is highly expressed on the majority of $FOXP3^+$ Tregs, immune cells which are considered the most potent inhibitors of anti-tumor immunity and the greatest barrier to successful immunotherapy (Baatar et al., 2007). Moreover, the tumor-associated chemokines of CCR4 have been detected in patients with different types of cancer (Mizukami et al., 2008; Gobert et al., 2009; and Faget et al., 2011). Thus, the targeted approach of human anti-CCR4 mAb immunotherapy described herein offers significant advantages in improving cancer immunotherapeutic efficacy while simultaneously reducing its side effects.

The present invention provides affinity optimized humanized monoclonal antibodies specific against chemokine (C-C motif) receptor 4 (CCR4). The initial humanization of the anti-CCR4 antibodies is described in WO 2009/086514, the contents of which are incorporated by reference in its entirety. The antibodies were produced by humanizing a mouse anti-CCR4 monoclonal antibody, mAb1567 that recognizes the N-terminal and extracellular domains of CCR4.

Unlike affinity maturation of antibodies against antigens for which pure protein is readily available, affinity maturation of ant-CCR4 antibodies was particular challenging due to 7-transmembrane structure of the protein. This complex structure of CCR4 made screening and selection affinity matured antibodies less efficient and less predictable.

The humanized mAb1567 is referred to herein as "h1567". The affinity optimized variants of h1567antibodies are referred to herein as "huCCR4 antibodies". A preferred variant of the h1567 antibody is the Ab2-3 antibody. The affinity optimized huCCR4 antibodies have affinities that are at least 1-fold, 1.5-fold, 2-fold higher that then h1567.

In addition to greater affinity, the huCCR4 antibodies of the invention have stronger CDC and ADCC activities against CCR4$^+$ tumor cells than h1567. In addition, the affinity optimized anti-CCR4 antibodies also effectively inhibit the chemotaxis of CD4$^+$CD25$^{high}$ Tregs. Surprisingly, the affinity optimized anti-CCR4 antibodies also stimulated CD4$^+$CD25$^-$ cell proliferation and inhibited Treg immunosuppressive activity. Accordingly, the affinity optimized anti-CCR4 antibodies are useful in treating CCR4-expressing tumors such as cutaneous T-cell lymphoma. Additionally, the affinity optimized anti-CCR4 antibodies are also useful in the treatment of other tumors by enhancing the anti-tumor immune response, by suppressing Treg trafficking.

Cutaneous T-cell lymphomas (CTCLs) are a heterogenous group of lymphoproliferative disorders causes by clonally derived skin homing T cells. CTCL cells uniformly express CCR4. Specifically, CCR4 is a prominent feature of malignant T cells in MF, cutaneous ALCL, and roughly 50% of nodal ALCL. Unlike CLA, it is reliably expressed in Sezary syndrome and during large cell transformation of MF and is also expressed by other T lymphoid malignancies that can involve skin, such as Adult T Cell Leukemia/Lymphoma (ATLL). Expression of CCR4 is limited amongst non-malignant cells and absent on neutrophils, monocytes, or B cells. Importantly, CCR4 is absent on naïve T cells, and present on fewer than half of all memory T cells. The reliable expression of CCR4 on CTCL cells, and its limited expression on other immune cells, makes targeted therapy of CCR4 an attractive goal for these malignancies.

While some progress has been made in identifying small molecule inhibitors that are relatively selective for CCR4, specific monoclonal antibodies against CCR4 are an attractive target for immunotherapy of CTCL because of their exquisite binding specificity. In addition, the in vivo effector functions that are mediated through Fc binding to Fcγ receptors can be exploited to kill tumor cells. The precise properties of Mabs that are required for optimal in vivo immunodepleting activity are not known, but antibodies can be selected to act as either as receptor agonists or antagonists, and/or to promote or inhibit receptor dimerization and/or internalization. Different immune mechanisms of antibody-mediated tumor clearance have also been identified. For example, Mab-mediated recruitment of natural killer cells to tumors can occur through the Fc-γ activation of receptors on these immune effector cells, a process known as antibody-dependent cellular cytoxicity (ADCC). Other immune mechanisms include complement dependent cytotoxicity (CDC) and antibody dependent cellular phagocytosis (ADCP). Additional mechanisms related to intrinsic Mab activities include: blockade of ligand binding or heterodimerization, inhibition of downstream signaling of Akt, and acceleration of receptor internalization. The latter mechanism is particularly effective because ligand-induced endocytosis and degradation of active receptor tyrosine kinases (RTKs) is considered a major physiological process underlying attenuation of growth-promoting signals.

Leukocyte trafficking, which is critically regulated by chemokines and their receptors, share many of the characteristics of tumor cell infiltration and metastasis. While expression of the chemokine receptor CCR4 by tumor cells is associated with skin involvement, CCR4 also has an important role in both normal and tumor immunity. In a subset of CTCL patients with HTLV-1 associated Adult T-cell leukemia/lymphoma (ATLL), the tumor cells themselves function as regulatory T (Treg) cells, contributing to tumor survival in the face of host anti-tumor immune responses. In other types of cancers, the chemokines TARC/CCL17 and MDC/CCL22, specific ligands for CCR4 that are produced by tumor cells and the tumor microenvironment, attract CCR4$^+$ Treg cells to the tumor, where they create a favorable enrivonment for tumor escape from host immune responses. Thus, a therapeutic anti-CCR4 Mab is the ideal treatment modality for many different cancers, not only to directly kill the CCR4$^+$ tumor cells, but also to overcome the suppressive effect of CCR4 Treg cells on the host immune response to tumor cells.

In one aspect the present invention provides a high affinity humanized monoclonal antibody that specifically binds CCR4 proteins. Binding of this antibody to the CCR4 receptor, interrupts ligand or agonist binding of CCR4. Exemplary ligands or agonists that compete for binding to the CCR4, and which are blocked in the presence of the invented antibody, include, but are not limited to, CCL17, CCL22, and vMIP-III. By a variety of mechanisms, the antibody may decrease ligand-induced chemotaxis of CCR4-expressing cells, such as cutaneous T cell lymphoma cells (CTCL cells) or ovarian cancer cells. The huCCR4 antibody is monovalent or bivalent and comprise a single or double chain. The huCCR4 antibody may also be a bi-specific antibody, wherein at least one of the heavy-light chain heterodimers recognizes CCR4. Functionally, the binding affinity of the huCCR4 antibody is about 1.5 nM$^{-1}$ or less. The glycosylation of the Fc region of the antibody is modified to alter CCR4 binding or CCR4 ligand-blocking characteristics. For instance, the fucose content of the Fc region is decreased compared to wild type. Furthermore, the antibody comprises a therapeutic agent including, but not limited to, a toxin, a radiolabel, a siRNA, or a cytokine.

The huCCR4 antibody modulates T cell activity. Specifically, the huCCR4 antibody can block, inhibit or decrease the suppressor activity of T cells, for example, regulatory T cell-mediated suppression of T cell activity. In another aspect, the huCCR4 antibody can augment an immune response to an antigen. For example, the huCCR4 antibody increases antigen-specific T cell activity. In other aspects, the huCCR4 antibody restores or increases T cell proliferation, for example, effector T cell proliferation. In a further aspect, the huCCR4 antibody activates T cells to secrete cytokines, such as IFN-γ.

The huCCR4 antibody is capable of inducing cell death. Cell death is induced by either direct or indirect mechanisms. For example, the huCCR4 antibody binds CCR4 expressed on the surface of the target cell and leads to the death of that CCR4-expressing cell via intracellular signaling pathways. For instance, CCR4 binding by the huCCR4 antibody can lead to complement-dependent cytotoxicity (CDC). Alternatively, the huCCR4 antibody binds CCR4, and leads to the recruitment of a second cell type that will kill the CCR4-expressing target cell. Exemplary mechanisms by which the huCCR4 antibody mediates cell death by recruitment of a second cell type include, but are not limited to, antibody-dependent cellular toxicity (ADCC) and antibody dependent cellular phagocytosis (ADCP). Target CCR4-expressing cell types comprise tumor and regulatory, or supplementary, T cells (also referred to as Treg cells).

Five unique affinity matured huCCR4 antibodies were identified. These include Ab1-44, Ab1-49, Ab2-1, Ab2-2, and Ab2-3.

The nucleic acid and amino acid sequence of the affinity matured huCCR4 antibodies are provided below:

TABLE 1A

Antibody 1-44 Variable
Region nucleic acid sequences $V_H$ chain of 1-44
(SEQ ID NO: 1)
CAGGTGCAGCTGGTGCAGAGCGGAGCCGAGGTGAAGAAGCCTGGAGC

TTCCGTCAAGGTGTCCTGCAAGGCCAGCGGCTACACCTTCGCCAGCC

AATGGATGCACTGGATGCGGCAGGCACCTGGACAGGGCCTCGAATGG

ATCGGCTGGATCAACCCCGGCAACGTGAACACCAAGTACAACGAGAA

GTTCAAGGGCAGGGCCACCCTGACCGTGGACACCAGCACCAACACCG

CCTACATGGAACTGAGCAGCCTGCGGAGCGAGGACACCGCCGTGTAC

TACTGCGCCAGAAGCACCTGGTACCGGCCGCTGGACTACTGGGGCCA

GGGCACCCTGGTGACCGTGAGCAGC $V_L$ chain of 1-44
(SEQ ID NO: 3)
GACATCGTGATGACCCAGAGCCCCGACAGCCTGGCCGTGAGCCTGGG

CGAGCGGGCCACCATCAACTGCAAGAGCAGCCAGAGCATCCTGTACA

GCAGCAACCAGAAGAACTACCTGGCCTGGTATCAGCAGAAGCCCGGC

CAGAGCCCCAAGCTGCTGATCTACTGGGCCAGCACCCGGGAGAGCGG

CGTGCCCGACCGGTTTAGCGGCAGCGGCTCCGGCACCGACTTCACCC

TGACCATCAGCAGCCTGCAGGCCGAGGACGTGGCCGTGTACTACTGC

CACCAGTACATCAGCAGCTACACCTTCGGCCAGGGCACAAAGCTGGA

AATCAAG

TABLE 1B

Antibody 1-44 Variable
Region amino acid sequences $V_H$ chain of 2A
(SEQ ID NO: 2)
QVQLVQSGAEVKKPGASVKVSCKASGYTFASQWMHWMRQAPGQGLEW

IGWINPGNVNTKYNEKFKGRATLTVDTSTNTAYMELSSLRSEDTAVY

YCARSTWYRPLDYWGQGTLVTVSS $V_L$ chain of 2A
(SEQ ID NO: 4)
DIVMTQSPDSLAVSLGERATINCKSSQSILYSSNQKNYLAWYQQKPG

QSPKLLIYWASTRESGVPDRFSGSGSGTDFTLTISSLQAEDVAVYYC

HQYISSYTFGQGTKLEIK

TABLE 2A

Antibody 1-49 Variable
Region nucleic acid sequences $V_H$ chain of 1-44
(SEQ ID NO: 5)
CAGGTGCAGCTGGTGCAGAGCGGAGCCGAGGTGAAGAAGCCTGGAGC

TTCCGTCAAGGTGTCCTGCAAGGCCAGCGGCTACACCTTCGCCAGCA

GCTGGATGCACTGGATGCGGCAGGCACCTGGACAGGGCCTCGAATGG

ATCGGCTGGATCAACCCCGGCAACGTGAACACCAAGTACAACGAGAA

GTTCAAGGGCAGGGCCACCCTGACCGTGGACACCAGCACCAACACCG

CCTACATGGAACTGAGCAGCCTGCGGAGCGAGGACACCGCCGTGTAC

TACTGCGCCAGAAGCACGTGGTATCGGCCGAATGACTACTGGGGCCA

GGGCACCCTGGTGACCGTGAGCAGC $V_L$ chain of 1-44
(SEQ ID NO: 7)
GACATCGTGATGACCCAGAGCCCCGACAGCCTGGCCGTGAGCCTGGG

CGAGCGGGCCACCATCAACTGCAAGAGCAGCCAGAGCATCCTGTACA

GCAGCAACCAGAAGAACTACCTGGCCTGGTATCAGCAGAAGCCCGGC

CAGAGCCCCAAGCTGCTGATCTACTGGGCCAGCACCCGGGAGAGCGG

CGTGCCCGACCGGTTTAGCGGCAGCGGCTCCGGCACCGACTTCACCC

TGACCATCAGCAGCCTGCAGGCCGAGGACGTGGCCGTGTACTACTGC

CACCAGTACAAAAGCAGCTACACCTTCGGCCAGGGCACAAAGCTGGA

AATCAAG

TABLE 2B

Antibody 1-49 Variable
Region amino acid sequences $V_H$ chain of 2A
(SEQ ID NO: 6)
QVQLVQSGAEVKKPGASVKVSCKASGYTFASSWMHWMRQAPGQGLEW

IGWINPGNVNTKYNEKFKGRATLTVDTSTNTAYMELSSLRSEDTAVY

YCARSTWYRPNDYWGQGTLVTVSS $V_L$ chain of 2A
(SEQ ID NO: 8)
DIVMTQSPDSLAVSLGERATINCKSSQSILYSSNQKNYLAWYQQKPG

QSPKLLIYWASTRESGVPDRFSGSGSGTDFTLTISSLQAEDVAVYYC

HQYKSSYTFGQGTKLEIK

TABLE 3A

Antibody 2-1 Variable
Region nucleic acid sequences $V_H$ chain of 1-44
(SEQ ID NO: 9)
CAGGTGCAGCTGGTGCAGAGCGGAGCCGAGGTGAAGAAGCCTGGAGC

TTCCGTCAAGGTGTCCTGCAAGGCCAGCGGCTACACCTTCGCCAGCA

GCTGGATGCACTGGATGCGGCAGGCACCTGGACAGGGCCTCGAATGG

ATCGGCTGGATCAACCCCGGCAACGTGAACACCAAGTACAACGAGAA

TABLE 3A-continued

Antibody 2-1 Variable
Region nucleic acid sequences

GTTCAAGGGCAGGGCCACCCTGACCGTGGACACCAGCACCAACACCG

CCTACATGGAACTGAGCAGCCTGCGGAGCGAGGACACCGCCGTGTAC

TACTGCGCCAGAACCACCCGTTATCGGCCCCTGGACTACTGGGGCCA

GGGCACCCTGGTGACCGTGAGCAGC

V_L chain of 1-44
(SEQ ID NO: 11)
GACATCGTGATGACCCAGAGCCCCGACAGCCTGGCCGTGAGCCTGGG

CGAGCGGGCCACCATCAACTGCAAGAGCAGCCAGAGCATCCTGTACA

GCAGCAACCAGAAGAACTACCTGGCCTGGTATCAGCAGAAGCCCGGC

CAGAGCCCCAAGCTGCTGATCTACTGGGCCAGCACCCGGGAGAGCGG

CGTGCCCGACCGGTTTAGCGGCAGCGGCTCCGGCACCGACTTCACCC

TGACCATCAGCAGCCTGCAGGCCGAGGACGTGGCCGTGTACTACTGC

CACCAGTACCGTAGCAGCTACACCTTCGGCCAGGGCACAAAGCTGGA

AATCAAG

TABLE 3B

Antibody 2-1 Variable
Region amino acid sequences

V_H chain of 2A
(SEQ ID NO: 10)
QVQLVQSGAEVKKPGASVKVSCKASGYTFASSWMHWMRQAPGQGLEW

IGWINPGNVNTKYNEKFKGRATLTVDTSTNTAYMELSSLRSEDTAVY

YCARTTRYRPLDYWGQGTLVTVSS

V_L chain of 2A
(SEQ ID NO: 12)
DIVMTQSPDSLAVSLGERATINCKSSQSILYSSNQKNYLAWYQQKPG

QSPKLLIYWASTRESGVPDRFSGSGSGTDFTLTISSLQAEDVAVYYC

HQYRSSYTFGQGTKLEIK

TABLE 4A

Antibody 2-2 Variable
Region nucleic acid sequences

V_H chain of 1-44
(SEQ ID NO: 13)
CAGGTGCAGCTGGTGCAGAGCGGAGCCGAGGTGAAGAAGCCTGGAGC

TTCCGTCAAGGTGTCCTGCAAGGCCAGCGGCTACACCTTCGCCAGCC

AATATATGCACTGGATGCGGCAGGCACCTGGACAGGGCCTCGAATGG

ATCGGCTGGATCAACCCCGGCAACGTGAACACCAAGTACAACGAGAA

GTTCAAGGGCAGGGCCACCCTGACCGTGGACACCAGCACCAACACCG

CCTACATGGAACTGAGCAGCCTGCGGAGCGAGGACACCGCCGTGTAC

TACTGCGCCAGACTGACCTATTATCGGCCGCCGGACTACTGGGGCCA

GGGCACCCTGGTGACCGTGAGCAGC

TABLE 4A-continued

Antibody 2-2 Variable
Region nucleic acid sequences

V_L chain of 1-44
(SEQ ID NO: 15)
GACATCGTGATGACCCAGAGCCCCGACAGCCTGGCCGTGAGCCTGGG

CGAGCGGGCCACCATCAACTGCAAGAGCAGCCAGAGCATCCTGTACA

GCAGCAACCAGAAGAACTACCTGGCCTGGTATCAGCAGAAGCCCGGC

CAGAGCCCCAAGCTGCTGATCTACTGGGCCAGCACCCGGGAGAGCGG

CGTGCCCGACCGGTTTAGCGGCAGCGGCTCCGGCACCGACTTCACCC

TGACCATCAGCAGCCTGCAGGCCGAGGACGTGGCCGTGTACTACTGC

CACCAGTACTATAGCAGCTACACCTTCGGCCAGGGCACAAAGCTGGA

AATCAAG

TABLE 4B

Antibody 2-2 Variable
Region amino acid sequences

V_H chain of 2A
(SEQ ID NO: 14)
QVQLVQSGAEVKKPGASVKVSCKASGYTFASQYMHWMRQAPGQGLEW

IGWINPGNVNTKYNEKFKGRATLTVDTSTNTAYMELSSLRSEDTAVY

YCARLTYYRPPDYWGQGTLVTVSS

V_L chain of 2A
(SEQ ID NO: 16)
DIVMTQSPDSLAVSLGERATINCKSSQSILYSSNQKNYLAWYQQKPG

QSPKLLIYWASTRESGVPDRFSGSGSGTDFTLTISSLQAEDVAVYYC

HQYYSSYTFGQGTKLEIK

TABLE 5A

Antibody 2-3 Variable
Region nucleic acid sequences

V_H chain of 1-44
(SEQ ID NO: 17)
CAGGTGCAGCTGGTGCAGAGCGGAGCCGAGGTGAAGAAGCCTGGAGC

TTCCGTCAAGGTGTCCTGCAAGGCCAGCGGCTACACCTTCGCCAGCG

CGTGGATGCACTGGATGCGGCAGGCACCTGGACAGGGCCTCGAATGG

ATCGGCTGGATCAACCCCGGCAACGTGAACACCAAGTACAACGAGAA

GTTCAAGGGCAGGGCCACCCTGACCGTGGACACCAGCACCAACACCG

CCTACATGGAACTGAGCAGCCTGCGGAGCGAGGACACCGCCGTGTAC

TACTGCGCCAGAAGCACGTATTACCGGCCGCTGGACTACTGGGGCCA

GGGCACCCTGGTGACCGTGAGCAGC

V_L chain of 1-44
(SEQ ID NO: 19)
GACATCGTGATGACCCAGAGCCCCGACAGCCTGGCCGTGAGCCTGGG

CGAGCGGGCCACCATCAACTGCAAGAGCAGCCAGAGCATCCTGTACA

TABLE 5A-continued

Antibody 2-3 Variable
Region nucleic acid sequences

GCAGCAACCAGAAGAACTACCTGGCCTGGTATCAGCAGAAGCCCGGC

CAGAGCCCCAAGCTGCTGATCTACTGGGCCAGCACCCGGGAGAGCGG

CGTGCCCGACCGGTTTAGCGGCAGCGGCTCCGGCACCGACTTCACCC

TGACCATCAGCAGCCTGCAGGCCGAGGACGTGGCCGTGTACTACTGC

CACCAGTACATGAGCAGCTACACCTTCGGCCAGGGCACAAAGCTGGA

AATCAAG

TABLE 5B

Antibody 2-3 Variable
Region amino acid sequences $V_H$ chain of 2A
(SEQ ID NO: 18)
QVQLVQSGAEVKKPGASVKVSCKASGYTFASAWMHWMRQAPGQGLEW

IGWINPGNVNTKYNEKFKGRATLTVDTSTNTAYMELSSLRSEDTAVY

YCARSTYYRPLDYWGQGTLVTVSS $V_L$ chain of 2A
(SEQ ID NO: 20)
DIVMTQSPDSLAVSLGERATINCKSSQSILYSSNQKNYLAWYQQKPG

QSPKLLIYWASTRESGVPDRFSGSGSGTDFTLTISSLQAEDVAVYYC

HQYMSSYTFGQGTKLEIK

The amino acid sequences of the heavy and light chain complementary determining regions of the neutralizing influenza antibodies are shown in Table 6 below.

TABLE 6

Amino Acid Sequences of Heavy and Light Chains.

| Antibody | Variable region | CDR1 | CDR2 | CDR3 |
|---|---|---|---|---|
| Mouse 1567 | VH | GYTFASYY (SEQ ID NO: 21) | INPGNVNT (SEQ ID NO: 27) | STYYRPLDY (SEQ ID NO: 29) |
| Humanized 1567 | VH | GYTFASYY (SEQ ID NO: 21) | INPGNVNT (SEQ ID NO: 27) | STYYRPLDY (SEQ ID NO: 29) |
| Ab1-44 | VH | GYTFASQW (SEQ ID NO: 22) | INPGNVNT (SEQ ID NO: 27) | STWYRPLDY (SEQ ID NO: 30) |
| Ab1-49 | VH | GYTFASSW (SEQ ID NO: 23) | INPGNVNT (SEQ ID NO: 27) | STWYRPNDY (SEQ ID NO: 31) |
| Ab2-1 | VH | GYTFASSW (SEQ ID NO: 23) | INPGNVNT (SEQ ID NO: 27) | TTRYRPLDY (SEQ ID NO: 32) |
| Ab2-2 | VH | GYTFASQY (SEQ ID NO: 24) | INPGNVNT (SEQ ID NO: 27) | LTYYRPPDY (SEQ ID NO: 33) |
| Ab2-3 | VH | GYTFASAW (SEQ ID NO: 25) | INPGNVNT (SEQ ID NO: 27) | STYYRPLDY (SEQ ID NO: 29) |
| Mouse 1567 | VL | QSILYSSNQKNY (SEQ ID NO: 26) | WASTRE (SEQ ID NO: 28) | HQYLSSYT (SEQ ID NO: 34) |
| Humanized 1567 | VL | QSILYSSNQKNY (SEQ ID NO: 26) | WASTRE (SEQ ID NO: 28) | HQYLSSYT (SEQ ID NO: 34) |
| Ab1-44 | VL | QSILYSSNQKNY (SEQ ID NO: 26) | WASTRE (SEQ ID NO: 28) | HQYISSYT (SEQ ID NO: 35) |
| Ab1-49 | VL | QSILYSSNQKNY (SEQ ID NO: 26) | WASTRE (SEQ ID NO: 28) | HQYKSSYT (SEQ ID NO: 36) |
| Ab2-1 | VL | QSILYSSNQKNY (SEQ ID NO: 26) | WASTRE (SEQ ID NO: 28) | HQYRSSYT (SEQ ID NO: 37) |
| Ab2-2 | VL | QSILYSSNQKNY (SEQ ID NO: 26) | WASTRE (SEQ ID NO: 28) | HQYYSSYT (SEQ ID NO: 38) |
| Ab2-3 | VL | QSILYSSNQKNY (SEQ ID NO: 26) | WASTRE (SEQ ID NO: 28) | HQYMSSYT (SEQ ID NO: 39) |

As described supra, huCCR4 antibodies of the present invention modulates T cell activity. In some aspects, administration of Ab2-3 reverses regulatory T-cell-mediated suppression of effector T cell proliferation. Specifically, treatment with Ab2-3 stimulates or increases proliferation of effector T cells (Teff), without stimulating the proliferation of regulatory T cells (Treg). Effector T cells consists of four distinct populations, as classified by CD45RA and CCR7 expression profiles: T-different types (Tdiff), naïve T cells (Tnaive), central memory T cells (Tcm) and effector memory T cells (Tem). The Ab2-3 of the present invention can stimulate or increase the proliferation of any of the Teff populations. In some aspects, increasing proliferation of effector T cells increases antigen-specific T cell activity to augment an immune response to an antigen. In some aspects, augmenting effector T-cell-mediated immune response may contribute to inhibition of tumorigenesis or reduction in tumor size.

In other aspects, Ab2-3 modulates T cell cytokine production and secretion. For example, administration of Ab2-3 specifically increases IFN-gamma (IFNγ) production and release from T cells. In other aspects, administration of Ab2-3 may not affect IL-10 or IL-4 release. In another aspect, administration of Ab2-3 may not affect, or may slightly reduce TGF-beta release. Cytokine release profiles may indicate the specific T cell population activated by treatment with Ab2-3, as IFNγ secretion is a characteristic of Th1 cells (T-helper type 1 cells), while TGF-beta and IL-10 secretion is characteristic of regulatory T cells and IL-4 is released by Th2 (T helper type 2 cells). In some aspects, Ab2-3 stimulates T cell activity, wherein the T cells are Th1 cells. In some embodiments, Ab2-3 stimulates secretion of IFNγ and decreases or does not change secretion of TGF-β, IL-10 or IL-4.

Antibodies

As used herein, the term "antibody" refers to immunoglobulin molecules and immunologically active portions of immunoglobulin (Ig) molecules, i.e., molecules that contain an antigen binding site that specifically binds (immunoreacts with) an antigen. By "specifically binds" or "immunoreacts with" is meant that the antibody reacts with one or more antigenic determinants of the desired antigen and does not react with other polypeptides. Antibodies include, but are not limited to, polyclonal, monoclonal, chimeric, dAb (domain antibody), single chain, $F_{ab}$, $F_{ab'}$ and $F_{(ab')2}$ fragments, scFvs, and $F_{ab}$ expression libraries.

A single chain Fv ("scFv") polypeptide molecule is a covalently linked $V_H$:$V_L$ heterodimer, which can be expressed from a gene fusion including $V_H$- and $V_L$-encoding genes linked by a peptide-encoding linker. (See Huston et al. (1988) Proc Nat Acad Sci USA 85(16):5879-5883). A number of methods have been described to discern chemical structures for converting the naturally aggregated, but chemically separated, light and heavy polypeptide chains from an antibody V region into an scFv molecule, which will fold into a three dimensional structure substantially similar to the structure of an antigen-binding site. See, e.g., U.S. Pat. Nos. 5,091,513; 5,132,405; and 4,946,778.

Very large naïve human scFv libraries have been and can be created to offer a large source of rearranged antibody genes against a plethora of target molecules. Smaller libraries can be constructed from individuals with infectious diseases in order to isolate disease-specific antibodies. (See Barbas et al., Proc. Natl. Acad. Sci. USA 89:9339-43 (1992); Zebedee et al., Proc. Natl. Acad. Sci. USA 89:3175-79 (1992)).

In general, antibody molecules obtained from humans relate to any of the classes IgG, IgM, IgA, IgE and IgD, which differ from one another by the nature of the heavy chain present in the molecule. Certain classes have subclasses as well, such as $IgG_1$, $IgG_2$, and others. Furthermore, in humans, the light chain may be a kappa chain or a lambda chain. The term "antigen-binding site," or "binding portion" refers to the part of the immunoglobulin molecule that participates in antigen binding. The antigen binding site is formed by amino acid residues of the N-terminal variable ("V") regions of the heavy ("H") and light ("L") chains. Three highly divergent stretches within the V regions of the heavy and light chains, referred to as "hypervariable regions," are interposed between more conserved flanking stretches known as "framework regions," or "FRs". Thus, the term "FR" refers to amino acid sequences which are naturally found between, and adjacent to, hypervariable regions in immunoglobulins. In an antibody molecule, the three hypervariable regions of a light chain and the three hypervariable regions of a heavy chain are disposed relative to each other in three dimensional space to form an antigen-binding surface. The antigen-binding surface is complementary to the three-dimensional surface of a bound antigen, and the three hypervariable regions of each of the heavy and light chains are referred to as "complementarity-determining regions," or "CDRs." CDRs for the VH and VL regions of the antibodies of the present invention are listed in Table 6.

As used herein, the term "epitope" includes any protein determinant capable of specific binding to an immunoglobulin, a scFv, or a T-cell receptor. Epitopic determinants usually consist of chemically active surface groupings of molecules such as amino acids or sugar side chains and usually have specific three dimensional structural characteristics, as well as specific charge characteristics. For example, antibodies may be raised against N-terminal or C-terminal peptides of a polypeptide.

As used herein, the terms "immunological binding," and "immunological binding properties" refer to the non-covalent interactions of the type which occur between an immunoglobulin molecule and an antigen for which the immunoglobulin is specific. The strength, or affinity of immunological binding interactions can be expressed in terms of the dissociation constant ($K_d$) of the interaction, wherein a smaller $K_d$ represents a greater affinity. Immunological binding properties of selected polypeptides can be quantified using methods well known in the art. One such method entails measuring the rates of antigen-binding site/antigen complex formation and dissociation, wherein those rates depend on the concentrations of the complex partners, the affinity of the interaction, and geometric parameters that equally influence the rate in both directions. Thus, both the "on rate constant" ($K_{on}$) and the "off rate constant" ($K_{off}$) can be determined by calculation of the concentrations and the actual rates of association and dissociation. (See Nature 361:186-87 (1993)). The ratio of $K_{off}/K_{on}$ enables the cancellation of all parameters not related to affinity, and is equal to the dissociation constant $K_d$. (See, generally, Davies et al. (1990) Annual Rev Biochem 59:439-473). An antibody of the present invention is said to specifically bind to a CCR4 epitope when the equilibrium binding constant ($K_d$) is ≤1 µM, preferably 100 nM, more preferably ≤10 nM, and most preferably ≤100 pM to about 1 pM, as measured by assays such as radioligand binding assays or similar assays known to those skilled in the art.

A CCR4 protein of the invention, or a derivative, fragment, analog, homolog or ortholog thereof, may be utilized as an immunogen in the generation of antibodies that immunospecifically bind these protein components.

Those skilled in the art will recognize that it is possible to determine, without undue experimentation, if a human monoclonal antibody has the same specificity as a human monoclonal antibody of the invention by ascertaining whether the former prevents the latter from binding to CCR4. If the human monoclonal antibody being tested competes with the human monoclonal antibody of the invention, as shown by a decrease in binding by the human monoclonal antibody of the invention, then it is likely that the two monoclonal antibodies bind to the same, or to a closely related, epitope.

Another way to determine whether a human monoclonal antibody has the specificity of a human monoclonal antibody of the invention is to pre-incubate the human monoclonal antibody of the invention with the CCR4 protein, with which it is normally reactive, and then add the human monoclonal antibody being tested to determine if the human monoclonal antibody being tested is inhibited in its ability to bind CCR4. If the human monoclonal antibody being tested is inhibited then, in all likelihood, it has the same, or functionally equivalent, epitope specificity as the monoclonal antibody of the invention. Screening of human monoclonal antibodies of the invention, can be also carried out by utilizing CCR4 and determining whether the test monoclonal antibody is able to neutralize CCR4.

Various procedures known within the art may be used for the production of polyclonal or monoclonal antibodies directed against a protein of the invention, or against derivatives, fragments, analogs homologs or orthologs thereof (See, for example, Antibodies: A Laboratory Manual, Harlow E, and Lane D, 1988, Cold Spring Harbor Laboratory Press, Cold Spring Harbor, N.Y., incorporated herein by reference).

Antibodies can be purified by well-known techniques, such as affinity chromatography using protein A or protein G, which provide primarily the IgG fraction of immune serum. Subsequently, or alternatively, the specific antigen which is the target of the immunoglobulin sought, or an epitope thereof, may be immobilized on a column to purify the immune specific antibody by immunoaffinity chromatography. Purification of immunoglobulins is discussed, for example, by D. Wilkinson (The Scientist, published by The Scientist, Inc., Philadelphia Pa., Vol. 14, No. 8 (Apr. 17, 2000), pp. 25-28).

The term "monoclonal antibody" or "MAb" or "monoclonal antibody composition", as used herein, refers to a population of antibody molecules that contain only one molecular species of antibody molecule consisting of a unique light chain gene product and a unique heavy chain gene product. In particular, the complementarity determining regions (CDRs) of the monoclonal antibody are identical in all the molecules of the population. MAbs contain an antigen binding site capable of immunoreacting with a particular epitope of the antigen characterized by a unique binding affinity for it.

Monoclonal antibodies can be prepared using hybridoma methods, such as those described by Kohler and Milstein, Nature, 256:495 (1975). In a hybridoma method, a mouse, hamster, or other appropriate host animal, is typically immunized with an immunizing agent to elicit lymphocytes that produce or are capable of producing antibodies that will specifically bind to the immunizing agent. Alternatively, the lymphocytes can be immunized in vitro.

The immunizing agent will typically include the protein antigen, a fragment thereof or a fusion protein thereof. Generally, either peripheral blood lymphocytes are used if cells of human origin are desired, or spleen cells or lymph node cells are used if non-human mammalian sources are desired. The lymphocytes are then fused with an immortalized cell line using a suitable fusing agent, such as polyethylene glycol, to form a hybridoma cell (Goding, *Monoclonal Antibodies: Principles and Practice*, Academic Press, (1986) pp. 59-103). Immortalized cell lines are usually transformed mammalian cells, particularly myeloma cells of rodent, bovine and human origin. Usually, rat or mouse myeloma cell lines are employed. The hybridoma cells can be cultured in a suitable culture medium that preferably contains one or more substances that inhibit the growth or survival of the unfused, immortalized cells. For example, if the parental cells lack the enzyme hypoxanthine guanine phosphoribosyl transferase (HGPRT or HPRT), the culture medium for the hybridomas typically will include hypoxanthine, aminopterin, and thymidine ("HAT medium"), which substances prevent the growth of HGPRT-deficient cells.

Preferred immortalized cell lines are those that fuse efficiently, support stable high level expression of antibody by the selected antibody-producing cells, and are sensitive to a medium such as HAT medium. More preferred immortalized cell lines are murine myeloma lines, which can be obtained, for instance, from the Salk Institute Cell Distribution Center, San Diego, Calif. and the American Type Culture Collection, Manassas, Va. Human myeloma and mouse-human heteromyeloma cell lines also have been described for the production of human monoclonal antibodies. (See Kozbor, J. Immunol., 133:3001 (1984); Brodeur et al., Monoclonal Antibody Production Techniques and Applications, Marcel Dekker, Inc., New York, (1987) pp. 51-63)).

The culture medium in which the hybridoma cells are cultured can then be assayed for the presence of monoclonal antibodies directed against the antigen. Preferably, the binding specificity of monoclonal antibodies produced by the hybridoma cells is determined by immunoprecipitation or by an in vitro binding assay, such as radioimmunoassay (RIA) or enzyme-linked immunoabsorbent assay (ELISA). Such techniques and assays are known in the art. The binding affinity of the monoclonal antibody can, for example, be determined by the Scatchard analysis of Munson and Pollard, Anal. Biochem., 107:220 (1980). Moreover, in therapeutic applications of monoclonal antibodies, it is important to identify antibodies having a high degree of specificity and a high binding affinity for the target antigen.

After the desired hybridoma cells are identified, the clones can be subcloned by limiting dilution procedures and grown by standard methods. (See Goding, Monoclonal Antibodies: Principles and Practice, Academic Press, (1986) pp. 59-103). Suitable culture media for this purpose include, for example, Dulbecco's Modified Eagle's Medium and RPMI-1640 medium. Alternatively, the hybridoma cells can be grown in vivo as ascites in a mammal.

The monoclonal antibodies secreted by the subclones can be isolated or purified from the culture medium or ascites fluid by conventional immunoglobulin purification procedures such as, for example, protein A-Sepharose, hydroxylapatite chromatography, gel electrophoresis, dialysis, or affinity chromatography.

Monoclonal antibodies can also be made by recombinant DNA methods, such as those described in U.S. Pat. No. 4,816,567. DNA encoding the monoclonal antibodies of the invention can be readily isolated and sequenced using conventional procedures (e.g., by using oligonucleotide probes that are capable of binding specifically to genes encoding the heavy and light chains of murine antibodies). The hybridoma cells of the invention serve as a preferred source of such DNA. Once isolated, the DNA can be placed into expression vectors, which are then transfected into host cells such as simian COS cells, Chinese hamster ovary (CHO) cells, or myeloma cells that do not otherwise produce immunoglobulin protein, to obtain the synthesis of monoclonal antibodies in the recombinant host cells. The DNA also can be modified, for example, by substituting the coding sequence for human heavy and light chain constant domains in place of the homologous murine sequences (see U.S. Pat. No. 4,816,567; Morrison, Nature 368, 812-13 (1994)) or by covalently joining to the immunoglobulin coding sequence all or part of the coding sequence for a non-immunoglobulin polypeptide. Such a non-immunoglobulin polypeptide can be substituted for the constant domains of an antibody of the invention, or can be substituted for the variable domains of one antigen-combining site of an antibody of the invention to create a chimeric bivalent antibody.

Fully human antibodies are antibody molecules in which the entire sequence of both the light chain and the heavy chain, including the CDRs, arise from human genes. Such antibodies are termed "humanized antibodies", "human antibodies", or "fully human antibodies" herein. Human monoclonal antibodies can be prepared by using trioma technique; the human B-cell hybridoma technique (see Kozbor, et al., 1983 Immunol Today 4: 72); and the EBV hybridoma technique to produce human monoclonal antibodies (see Cole, et al., 1985 In: MONOCLONAL ANTIBODIES AND CANCER THERAPY, Alan R. Liss, Inc., pp. 77-96). Human monoclonal antibodies may be utilized and may be produced by using human hybridomas (see Cote, et al., 1983. Proc Natl Acad Sci USA 80: 2026-2030) or by transforming human B-cells with Epstein Barr Virus in vitro (see Cole, et al., 1985 In: MONOCLONAL ANTIBODIES AND CANCER THERAPY, Alan R. Liss, Inc., pp. 77-96).

In addition, human antibodies can also be produced using additional techniques, including phage display libraries. (See Hoogenboom and Winter, J. Mol. Biol., 227:381 (1991); Marks et al., J. Mol. Biol., 222:581 (1991)). Similarly, human antibodies can be made by introducing human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545,807; 5,545,806; 5,569,825; 5,625,126; 5,633,425; 5,661,016, and in Marks et al., Bio/Technology 10, 779-783 (1992); Lonberg et al., Nature 368 856-859 (1994); Morrison, Nature 368, 812-13 (1994); Fishwild et al, Nature Biotechnology 14, 845-51 (1996); Neuberger, Nature Biotechnology 14, 826 (1996); and Lonberg and Huszar, Intern. Rev. Immunol. 13 65-93 (1995).

Human antibodies may additionally be produced using transgenic nonhuman animals which are modified so as to produce fully human antibodies rather than the animal's endogenous antibodies in response to challenge by an antigen. (See PCT publication WO94/02602). The endogenous genes encoding the heavy and light immunoglobulin chains in the nonhuman host have been incapacitated, and active loci encoding human heavy and light chain immunoglobulins are inserted into the host's genome. The human genes are incorporated, for example, using yeast artificial chromosomes containing the requisite human DNA segments. An animal which provides all the desired modifications is then obtained as progeny by crossbreeding intermediate transgenic animals containing fewer than the full complement of the modifications. The preferred embodiment of such a nonhuman animal is a mouse, and is termed the Xenomouse™ as disclosed in PCT publications WO 96/33735 and WO 96/34096. This animal produces B cells which secrete fully human immunoglobulins. The antibodies can be obtained directly from the animal after immunization with an immunogen of interest, as, for example, a preparation of a polyclonal antibody, or alternatively from immortalized B cells derived from the animal, such as hybridomas producing monoclonal antibodies. Additionally, the genes encoding the immunoglobulins with human variable regions can be recovered and expressed to obtain the antibodies directly, or can be further modified to obtain analogs of antibodies such as, for example, single chain FAT (scFv) molecules.

An example of a method of producing a nonhuman host, exemplified as a mouse, lacking expression of an endogenous immunoglobulin heavy chain is disclosed in U.S. Pat. No. 5,939,598. It can be obtained by a method, which includes deleting the J segment genes from at least one endogenous heavy chain locus in an embryonic stem cell to prevent rearrangement of the locus and to prevent formation of a transcript of a rearranged immunoglobulin heavy chain locus, the deletion being effected by a targeting vector containing a gene encoding a selectable marker; and producing from the embryonic stem cell a transgenic mouse whose somatic and germ cells contain the gene encoding the selectable marker.

One method for producing an antibody of interest, such as a human antibody, is disclosed in U.S. Pat. No. 5,916,771. This method includes introducing an expression vector that contains a nucleotide sequence encoding a heavy chain into one mammalian host cell in culture, introducing an expression vector containing a nucleotide sequence encoding a light chain into another mammalian host cell, and fusing the two cells to form a hybrid cell. The hybrid cell expresses an antibody containing the heavy chain and the light chain.

In a further improvement on this procedure, a method for identifying a clinically relevant epitope on an immunogen and a correlative method for selecting an antibody that binds immunospecifically to the relevant epitope with high affinity, are disclosed in PCT publication WO 99/53049.

The antibody can be expressed by a vector containing a DNA segment encoding the single chain antibody described above.

These can include vectors, liposomes, naked DNA, adjuvant-assisted DNA, gene gun, catheters, etc. Vectors include chemical conjugates such as described in WO 93/64701, which has targeting moiety (e.g. a ligand to a cellular surface receptor), and a nucleic acid binding moiety (e.g. polylysine), viral vector (e.g. a DNA or RNA viral vector), fusion proteins such as described in PCT/US 95/02140 (WO 95/22618) which is a fusion protein containing a target moiety (e.g. an antibody specific for a target cell) and a nucleic acid binding moiety (e.g. a protamine), plasmids, phage, etc. The vectors can be chromosomal, non-chromosomal or synthetic.

Preferred vectors include viral vectors, fusion proteins and chemical conjugates. Retroviral vectors include moloney murine leukemia viruses. DNA viral vectors are preferred. These vectors include pox vectors such as orthopox or avipox vectors, herpesvirus vectors such as a herpes simplex I virus (HSV) vector (see Geller, A. I. et al., J. Neurochem, 64:487 (1995); Lim, F., et al., in DNA Cloning: Mammalian Systems, D. Glover, Ed. (Oxford Univ. Press, Oxford England) (1995); Geller, A. I. et al., Proc Natl. Acad.

Sci.: U.S.A. 90:7603 (1993); Geller, A. I., et al., Proc Natl. Acad. Sci USA 87:1149 (1990), Adenovirus Vectors (see LeGal LaSalle et al., Science, 259:988 (1993); Davidson, et al., Nat. Genet 3:219 (1993); Yang, et al., J. Virol. 69:2004 (1995) and Adeno-associated Virus Vectors (see Kaplitt, M. G. et al., Nat. Genet. 8:148 (1994).

Pox viral vectors introduce the gene into the cells cytoplasm. Avipox virus vectors result in only a short term expression of the nucleic acid. Adenovirus vectors, adeno-associated virus vectors and herpes simplex virus (HSV) vectors are preferred for introducing the nucleic acid into neural cells. The adenovirus vector results in a shorter term expression (about 2 months) than adeno-associated virus (about 4 months), which in turn is shorter than HSV vectors. The particular vector chosen will depend upon the target cell and the condition being treated. The introduction can be by standard techniques, e.g. infection, transfection, transduction or transformation. Examples of modes of gene transfer include e.g., naked DNA, $CaPO_4$ precipitation, DEAE dextran, electroporation, protoplast fusion, lipofection, cell microinjection, and viral vectors.

The vector can be employed to target essentially any desired target cell. For example, stereotaxic injection can be used to direct the vectors (e.g. adenovirus, HSV) to a desired location. Additionally, the particles can be delivered by intracerebroventricular (icv) infusion using a minipump infusion system, such as a SynchroMed Infusion System. A method based on bulk flow, termed convection, has also proven effective at delivering large molecules to extended areas of the brain and may be useful in delivering the vector to the target cell. (See Bobo et al., Proc. Natl. Acad. Sci. USA 91:2076-2080 (1994); Morrison et al., Am. J. Physiol. 266:292-305 (1994)). Other methods that can be used include catheters, intravenous, parenteral, intraperitoneal and subcutaneous injection, and oral or other known routes of administration.

These vectors can be used to express large quantities of antibodies that can be used in a variety of ways. For example, to detect the presence of CCR4 in a sample. The antibody can also be used to try to bind to and disrupt a CCR4 activity.

Techniques can be adapted for the production of single-chain antibodies specific to an antigenic protein of the invention (see e.g., U.S. Pat. No. 4,946,778). In addition, methods can be adapted for the construction of $F_{ab}$ expression libraries (see e.g., Huse, et al., 1989 Science 246: 1275-1281) to allow rapid and effective identification of monoclonal $F_{ab}$ fragments with the desired specificity for a protein or derivatives, fragments, analogs or homologs thereof. Antibody fragments that contain the idiotypes to a protein antigen may be produced by techniques known in the art including, but not limited to: (i) an $F_{(ab')2}$ fragment produced by pepsin digestion of an antibody molecule; (ii) an $F_{ab}$ fragment generated by reducing the disulfide bridges of an $F_{(ab')2}$ fragment; (iii) an $F_{ab}$ fragment generated by the treatment of the antibody molecule with papain and a reducing agent and (iv) $F_v$ fragments.

Heteroconjugate antibodies are also within the scope of the present invention. Heteroconjugate antibodies are composed of two covalently joined antibodies. Such antibodies have, for example, been proposed to target immune system cells to unwanted cells (see U.S. Pat. No. 4,676,980), and for treatment of HIV infection (see WO 91/00360; WO 92/200373; EP 03089). It is contemplated that the antibodies can be prepared in vitro using known methods in synthetic protein chemistry, including those involving crosslinking agents. For example, immunotoxins can be constructed using a disulfide exchange reaction or by forming a thioether bond. Examples of suitable reagents for this purpose include iminothiolate and methyl-4-mercaptobutyrimidate and those disclosed, for example, in U.S. Pat. No. 4,676,980. Heteroconjugate antibodies may also refer to bi-specific antibodies, wherein a bi-specific antibody is composed of, for example, two covalently joined single chain antibodies, or scFvs, or two covalently joined variable heavy chain-variable light chain dimers from two antibodies that recognize different antigens.

It can be desirable to modify the antibody of the invention with respect to effector function, so as to enhance, e.g., the effectiveness of the antibody in treating cancer. For example, cysteine residue(s) can be introduced into the Fc region, thereby allowing interchain disulfide bond formation in this region. The homodimeric antibody thus generated can have improved internalization capability and/or increased complement-mediated cell killing and antibody-dependent cellular cytotoxicity (ADCC). (See Caron et al., J. Exp Med., 176: 1191-1195 (1992) and Shopes, J. Immunol., 148: 2918-2922 (1992)). Alternatively, an antibody can be engineered that has dual Fc regions and can thereby have enhanced complement lysis and ADCC capabilities. (See Stevenson et al., Anti-Cancer Drug Design, 3: 219-230 (1989)).

The invention also pertains to immunoconjugates comprising an antibody conjugated to a cytotoxic agent such as a toxin (e.g., an enzymatically active toxin of bacterial, fungal, plant, or animal origin, or fragments thereof), or a radioactive isotope (i.e., a radioconjugate).

Enzymatically active toxins and fragments thereof that can be used include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *momordica charantia* inhibitor, curcin, crotin, *sapaonaria officinalis* inhibitor, gelonin, mitogellin, restrictocin, phenomycin, enomycin, and the tricothecenes. A variety of radionuclides are available for the production of radioconjugated antibodies. Examples include $^{212}Bi$, $^{131}I$, $^{131}In$, $^{90}Y$, and $^{186}Re$.

Conjugates of the antibody and cytotoxic agent are made using a variety of bifunctional protein-coupling agents such as N-succinimidyl-3-(2-pyridyldithiol) propionate (SPDP), iminothiolane (IT), bifunctional derivatives of imidoesters (such as dimethyl adipimidate HCL), active esters (such as disuccinimidyl suberate), aldehydes (such as glutaredehyde), bis-azido compounds (such as bis (p-azidobenzoyl) hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene). For example, a ricin immunotoxin can be prepared as described in Vitetta et al., Science 238: 1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. (See WO94/11026).

Those of ordinary skill in the art will recognize that a large variety of possible moieties can be coupled to the resultant antibodies or to other molecules of the invention. (See, for example, "Conjugate Vaccines", Contributions to Microbiology and Immunology, J. M. Cruse and R. E. Lewis, Jr (eds), Carger Press, New York, (1989), the entire contents of which are incorporated herein by reference).

Coupling may be accomplished by any chemical reaction that will bind the two molecules so long as the antibody and the other moiety retain their respective activities. This linkage can include many chemical mechanisms, for instance covalent binding, affinity binding, intercalation, coordinate binding and complexation. The preferred binding is, however, covalent binding. Covalent binding can be achieved either by direct condensation of existing side chains or by the incorporation of external bridging molecules. Many bivalent or polyvalent linking agents are useful in coupling protein molecules, such as the antibodies of the present invention, to other molecules. For example, representative coupling agents can include organic compounds such as thioesters, carbodiimides, succinimide esters, diisocyanates, glutaraldehyde, diazobenzenes and hexamethylene diamines. This listing is not intended to be exhaustive of the various classes of coupling agents known in the art but, rather, is exemplary of the more common coupling agents. (See Killen and Lindstrom, Jour. Immun. 133:1335-2549 (1984); Jansen et al., Immunological Reviews 62:185-216 (1982); and Vitetta et al., Science 238:1098 (1987)). Preferred linkers are described in the literature. (See, for example, Ramakrishnan, S. et al., Cancer Res. 44:201-208 (1984) describing use of MBS (M-maleimidobenzoyl-N-hydroxysuccinimide ester). See also, U.S. Pat. No. 5,030,719, describing use of halogenated acetyl hydrazide derivative coupled to an antibody by way of an oligopeptide linker. Particularly preferred linkers include: (i) EDC (1-ethyl-3-(3-dimethylamino-propyl) carbodiimide hydrochloride; (ii) SMPT (4-succinimidyloxycarbonyl-alpha-methyl-alpha-(2-pridyl-dithio)-toluene (Pierce Chem. Co., Cat. (21558G); (iii) SPDP (succinimidyl-6 [3-(2-pyridyldithio) propionamido]hexanoate (Pierce Chem. Co., Cat #21651G); (iv) Sulfo-LC-SPDP (sulfosuccinimidyl 6 [3-(2-pyridyldithio)-propianamide] hexanoate (Pierce Chem. Co. Cat. #2165-G); and (v) sulfo-NHS (N-hydroxy-sulfo-succinimide: Pierce Chem. Co., Cat. #24510) conjugated to EDC.

The linkers described above contain components that have different attributes, thus leading to conjugates with differing physio-chemical properties. For example, sulfo-NHS esters of alkyl carboxylates are more stable than sulfo-NHS esters of aromatic carboxylates. NHS-ester containing linkers are less soluble than sulfo-NHS esters. Further, the linker SMPT contains a sterically hindered disulfide bond, and can form conjugates with increased stability. Disulfide linkages, are in general, less stable than other linkages because the disulfide linkage is cleaved in vitro, resulting in less conjugate available. Sulfo-NHS, in particular, can enhance the stability of carbodimide couplings. Carbodimide couplings (such as EDC) when used in conjunction with sulfo-NHS, forms esters that are more resistant to hydrolysis than the carbodimide coupling reaction alone.

The antibodies disclosed herein can also be formulated as immunoliposomes. Liposomes containing the antibody are prepared by methods known in the art, such as described in Epstein et al., Proc. Natl. Acad. Sci. USA, 82: 3688 (1985); Hwang et al., Proc. Natl Acad. Sci. USA, 77: 4030 (1980); and U.S. Pat. Nos. 4,485,045 and 4,544,545. Liposomes with enhanced circulation time are disclosed in U.S. Pat. No. 5,013,556.

Particularly useful liposomes can be generated by the reverse-phase evaporation method with a lipid composition comprising phosphatidylcholine, cholesterol, and PEG-derivatized phosphatidylethanolamine (PEG-PE). Liposomes are extruded through filters of defined pore size to yield liposomes with the desired diameter. Fab' fragments of the antibody of the present invention can be conjugated to the liposomes as described in Martin et al., J. Biol. Chem., 257: 286-288 (1982) via a disulfide-interchange reaction.

Use of Antibodies Against CCR4

Methods for the screening of antibodies that possess the desired specificity include, but are not limited to, enzyme linked immunosorbent assay (ELISA) and other immunologically mediated techniques known within the art.

Antibodies directed against a CCR4 protein (or a fragment thereof) may be used in methods known within the art relating to the localization and/or quantitation of a CCR4 protein (e.g., for use in measuring levels of the CCR4 protein within appropriate physiological samples, for use in diagnostic methods, for use in imaging the protein, and the like). In a given embodiment, antibodies specific to a CCR4 protein, or derivative, fragment, analog or homolog thereof, that contain the antibody derived antigen binding domain, are utilized as pharmacologically active compounds (referred to hereinafter as "Therapeutics").

An antibody specific for a CCR4 protein of the invention can be used to isolate a CCR4 polypeptide by standard techniques, such as immunoaffinity, chromatography or immunoprecipitation. Antibodies directed against a CCR4 protein (or a fragment thereof) can be used diagnostically to monitor protein levels in tissue as part of a clinical testing procedure, e.g., to, for example, determine the efficacy of a given treatment regimen. Detection can be facilitated by coupling (i.e., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}$I, $^{131}$I, $^{35}$S or $^{3}$H.

Antibodies of the invention, including polyclonal, monoclonal, humanized and fully human antibodies, may used as therapeutic agents. Such agents will generally be employed to treat or prevent cancer in a subject, increase vaccine efficiency or augment a natural immune response. An antibody preparation, preferably one having high specificity and high affinity for its target antigen, is administered to the subject and will generally have an effect due to its binding with the target. Administration of the antibody may abrogate or inhibit or interfere with an activity of the CCR4 protein.

A therapeutically effective amount of an antibody of the invention relates generally to the amount needed to achieve a therapeutic objective. As noted above, this may be a binding interaction between the antibody and its target antigen that, in certain cases, interferes with the functioning of the target. The amount required to be administered will furthermore depend on the binding affinity of the antibody for its specific antigen, and will also depend on the rate at which an administered antibody is depleted from the free volume other subject to which it is administered. Common ranges for therapeutically effective dosing of an antibody or antibody fragment of the invention may be, by way of nonlimiting example, from about 0.1 mg/kg body weight to about 50 mg/kg body weight. Common dosing frequencies may range, for example, from twice daily to once a week.

Antibodies specifically binding a CCR4 protein or a fragment thereof of the invention, as well as other molecules identified by the screening assays disclosed herein, can be administered for the treatment of cancer or other proliferative disorders in the form of pharmaceutical compositions. Principles and considerations involved in preparing such compositions, as well as guidance in the choice of components are provided, for example, in Remington: The Science And Practice Of Pharmacy 19th ed. (Alfonso R. Gennaro, et al., editors) Mack Pub. Co., Easton, Pa., 1995; Drug Absorption Enhancement: Concepts, Possibilities, Limitations, And Trends, Harwood Academic Publishers, Langhorne, Pa., 1994; and Peptide And Protein Drug Delivery (Advances In Parenteral Sciences, Vol. 4), 1991, M. Dekker, New York.

Where antibody fragments are used, the smallest inhibitory fragment that specifically binds to the binding domain of the target protein is preferred. For example, based upon the variable-region sequences of an antibody, peptide molecules can be designed that retain the ability to bind the target protein sequence. Such peptides can be synthesized chemically and/or produced by recombinant DNA technology. (See, e.g., Marasco et al., Proc. Natl. Acad. Sci. USA, 90: 7889-7893 (1993)). The formulation can also contain more than one active compound as necessary for the particular indication being treated, preferably those with complementary activities that do not adversely affect each other. Alternatively, or in addition, the composition can comprise an agent that enhances its function, such as, for example, a cytotoxic agent, cytokine, chemotherapeutic agent, or growth-inhibitory agent. Such molecules are suitably present in combination in amounts that are effective for the purpose intended.

The active ingredients can also be entrapped in microcapsules prepared, for example, by coacervation techniques or by interfacial polymerization, for example, hydroxymethylcellulose or gelatin-microcapsules and poly-(methylmethacrylate) microcapsules, respectively, in colloidal drug delivery systems (for example, liposomes, albumin microspheres, microemulsions, nano-particles, and nanocapsules) or in macroemulsions.

The formulations to be used for in vivo administration must be sterile. This is readily accomplished by filtration through sterile filtration membranes.

Sustained-release preparations can be prepared. Suitable examples of sustained-release preparations include semipermeable matrices of solid hydrophobic polymers containing the antibody, which matrices are in the form of shaped articles, e.g., films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and γ ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid. While polymers such as ethylene-vinyl acetate and lactic acid-glycolic acid enable release of molecules for over 100 days, certain hydrogels release proteins for shorter time periods.

An antibody according to the invention can be used as an agent for detecting the presence of CCR4 (or a protein or a protein fragment thereof) in a sample. Preferably, the antibody contains a detectable label. Antibodies can be polyclonal, or more preferably, monoclonal. An intact antibody, or a fragment thereof (e.g., $F_{ab}$, scFv, or $F_{(ab)2}$) can be used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently-labeled secondary antibody and end-labeling of a DNA probe with biotin such that it can be detected with fluorescently-labeled streptavidin. The term "biological sample" is intended to include tissues, cells and biological fluids isolated from a subject, as well as tissues, cells and fluids present within a subject. Included within the usage of the term "biological sample", therefore, is blood and a fraction or component of blood including blood serum, blood plasma, or lymph. That is, the detection method of the invention can be used to detect an analyte mRNA, protein, or genomic DNA in a biological sample in vitro as well as in vivo. For example, in vitro techniques for detection of an analyte mRNA includes Northern hybridizations and in situ hybridizations. In vitro techniques for detection of an analyte protein include enzyme linked immunosorbent assays (ELISAs), Western blots, immunoprecipitations, and immunofluorescence. In vitro techniques for detection of an analyte genomic DNA include Southern hybridizations. Procedures for conducting immunoassays are described, for example in "ELISA: Theory and Practice: Methods in Molecular Biology", Vol. 42, J. R. Crowther (Ed.) Human Press, Totowa, N.J., 1995; "Immunoassay", E. Diamandis and T. Christopoulus, Academic Press, Inc., San Diego, Calif., 1996; and "Practice and Theory of Enzyme Immunoassays", P. Tijssen, Elsevier Science Publishers, Amsterdam, 1985. Furthermore, in vivo techniques for detection of an analyte protein include introducing into a subject a labeled anti-analyte protein antibody. For example, the antibody can be labeled with a radioactive marker whose presence and location in a subject can be detected by standard imaging techniques.

Pharmaceutical Compositions

The antibodies or agents of the invention (also referred to herein as "active compounds"), and derivatives, fragments, analogs and homologs thereof, can be incorporated into pharmaceutical compositions suitable for administration. Such compositions typically comprise the antibody or agent and a pharmaceutically acceptable carrier. As used herein, the term "pharmaceutically acceptable carrier" is intended to include any and all solvents, dispersion media, coatings, antibacterial and antifungal agents, isotonic and absorption delaying agents, and the like, compatible with pharmaceutical administration. Suitable carriers are described in the most recent edition of Remington's Pharmaceutical Sciences, a standard reference text in the field, which is incorporated herein by reference. Preferred examples of such carriers or diluents include, but are not limited to, water, saline, ringer's solutions, dextrose solution, and 5% human serum albumin. Liposomes and non-aqueous vehicles such as fixed oils may also be used. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

A pharmaceutical composition of the invention is formulated to be compatible with its intended route of administration. Examples of routes of administration include parenteral, e.g., intravenous, intradermal, subcutaneous, oral (e.g., inhalation), transdermal (i.e., topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfate; chelating agents such as ethylenediaminetetraacetic acid (EDTA); buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

The pharmaceutical compositions can be included in a container, pack, or dispenser together with instructions for administration.

Screening Methods

The invention provides methods (also referred to herein as "screening assays") for identifying modulators, i.e., candidate or test compounds or agents (e.g., peptides, peptidomimetics, small molecules or other drugs) that modulate or otherwise interfere with a CCR4 activity. Also provided are methods of identifying compounds useful to treat cancer. The invention also encompasses compounds identified using the screening assays described herein.

For example, the invention provides assays for screening candidate or test compounds which modulate the CCR4 carbonic anhydrase activity. The test compounds of the invention can be obtained using any of the numerous approaches in combinatorial library methods known in the art, including: biological libraries; spatially addressable parallel solid phase or solution phase libraries; synthetic library methods requiring deconvolution; the "one-bead one-compound" library method; and synthetic library methods using affinity chromatography selection. The biological library approach is limited to peptide libraries, while the other four approaches are applicable to peptide, non-peptide oligomer or small molecule libraries of compounds. (See, e.g., Lam, 1997. Anticancer Drug Design 12: 145).

A "small molecule" as used herein, is meant to refer to a composition that has a molecular weight of less than about 5 kD and most preferably less than about 4 kD. Small molecules can be, e.g., nucleic acids, peptides, polypeptides, peptidomimetics, carbohydrates, lipids or other organic or inorganic molecules. Libraries of chemical and/or biological mixtures, such as fungal, bacterial, or algal extracts, are known in the art and can be screened with any of the assays of the invention.

Examples of methods for the synthesis of molecular libraries can be found in the art, for example in: DeWitt, et al., 1993. Proc. Natl. Acad. Sci. U.S.A. 90: 6909; Erb, et al., 1994. Proc. Natl. Acad. Sci. U.S.A. 91: 11422; Zuckermann, et al., 1994. J. Med. Chem. 37: 2678; Cho, et al., 1993. Science 261: 1303; Carrell, et al., 1994. Angew. Chem. Int. Ed. Engl. 33: 2059; Carell, et al., 1994. Angew. Chem. Int. Ed. Engl. 33: 2061; and Gallop, et al., 1994. J. Med. Chem. 37: 1233.

Libraries of compounds may be presented in solution (see e.g., Houghten, 1992. Biotechniques 13: 412-421), or on beads (see Lam, 1991. Nature 354: 82-84), on chips (see Fodor, 1993. Nature 364: 555-556), bacteria (see U.S. Pat. No. 5,223,409), spores (see U.S. Pat. No. 5,233,409), plasmids (see Cull, et al., 1992. Proc. Natl. Acad. Sci. USA 89: 1865-1869) or on phage (see Scott and Smith, 1990. Science 249: 386-390; Devlin, 1990. Science 249: 404-406; Cwirla, et al., 1990. Proc. Natl. Acad. Sci. U.S.A. 87: 6378-6382; Felici, 1991. J. Mol. Biol. 222: 301-310; and U.S. Pat. No. 5,233,409.).

In one embodiment, a candidate compound is introduced to an antibody-antigen complex and determining whether the candidate compound disrupts the antibody-antigen complex, wherein a disruption of this complex indicates that the candidate compound modulates an CCR4 activity.

In another embodiment, at least one CCR4 protein is provided, which is exposed to at least one neutralizing monoclonal antibody. Formation of an antibody-antigen complex is detected, and one or more candidate compounds are introduced to the complex. If the antibody-antigen complex is disrupted following introduction of the one or more candidate compounds, the candidate compounds is useful to treat cancer or a proliferative disease or disorder, particularly a renal proliferative disorder.

Determining the ability of the test compound to interfere with or disrupt the antibody-antigen complex can be accomplished, for example, by coupling the test compound with a radioisotope or enzymatic label such that binding of the test compound to the antigen or biologically-active portion thereof can be determined by detecting the labeled compound in a complex. For example, test compounds can be labeled with $^{125}$I, $^{35}$S, $^{14}$C, or $^{3}$H, either directly or indirectly, and the radioisotope detected by direct counting of radioemission or by scintillation counting. Alternatively, test compounds can be enzymatically-labeled with, for example, horseradish peroxidase, alkaline phosphatase, or luciferase, and the enzymatic label detected by determination of conversion of an appropriate substrate to product.

In one embodiment, the assay comprises contacting an antibody-antigen complex with a test compound, and determining the ability of the test compound to interact with the antigen or otherwise disrupt the existing antibody-antigen complex. In this embodiment, determining the ability of the test compound to interact with the antigen and/or disrupt the antibody-antigen complex comprises determining the ability of the test compound to preferentially bind to the antigen or a biologically-active portion thereof, as compared to the antibody.

In another embodiment, the assay comprises contacting an antibody-antigen complex with a test compound and determining the ability of the test compound to modulate the antibody-antigen complex. Determining the ability of the test compound to modulate the antibody-antigen complex can be accomplished, for example, by determining the ability of the antigen to bind to or interact with the antibody, in the presence of the test compound.

Those skilled in the art will recognize that, in any of the screening methods disclosed herein, the antibody may be a CCR4 neutralizing antibody. Additionally, the antigen may be a CCR4 protein or a portion thereof (e.g., the CA domain).

The screening methods disclosed herein may be performed as a cell-based assay or as a cell-free assay. In the case of cell-free assays comprising the membrane-bound forms of the CCR4 proteins, it may be desirable to utilize a solubilizing agent such that the membrane-bound form of the proteins is maintained in solution. Examples of such solubilizing agents include non-ionic detergents such as n-octylglucoside, n-dodecylglucoside, n-dodecylmaltoside, octanoyl-N-methylglucamide, decanoyl-N-methylglucamide, Triton® X-100, Triton® X-114, Thesit®, Isotridecypoly(ethylene glycol ether)$_n$, N-dodecyl-N,N-dimethyl-3-ammonio-1-propane sulfonate, 3-(3-cholamidopropyl) dimethylamminiol-1-propane sulfonate (CHAPS), or 3-(3-cholamidopropyl)dimethylamminiol-2-hydroxy-1-propane sulfonate (CHAPSO).

In more than one embodiment, it may be desirable to immobilize either the antibody or the antigen to facilitate separation of complexed from uncomplexed forms of one or both following introduction of the candidate compound, as well as to accommodate automation of the assay. Observation of the antibody-antigen complex in the presence and absence of a candidate compound can be accomplished in any vessel suitable for containing the reactants. Examples of such vessels include microtiter plates, test tubes, and microcentrifuge tubes. In one embodiment, a fusion protein can be provided that adds a domain that allows one or both of the proteins to be bound to a matrix. For example, GST-antibody fusion proteins or GST-antigen fusion proteins can be adsorbed onto glutathione sepharose beads (Sigma Chemical, St. Louis, Mo.) or glutathione derivatized microtiter plates, that are then combined with the test compound, and the mixture is incubated under conditions conducive to complex formation (e.g., at physiological conditions for salt and pH). Following incubation, the beads or microtiter plate wells are washed to remove any unbound components, the matrix immobilized in the case of beads, complex determined either directly or indirectly. Alternatively, the complexes can be dissociated from the matrix, and the level of antibody-antigen complex formation can be determined using standard techniques.

Other techniques for immobilizing proteins on matrices can also be used in the screening assays of the invention. For example, either the antibody or the antigen (e.g. the CCR4 protein or the CA domain thereof) can be immobilized utilizing conjugation of biotin and streptavidin. Biotinylated antibody or antigen molecules can be prepared from biotin-NHS (N-hydroxy-succinimide) using techniques well-known within the art (e.g., biotinylation kit, Pierce Chemicals, Rockford, Ill.), and immobilized in the wells of streptavidin-coated 96 well plates (Pierce Chemical). Alternatively, other antibodies reactive with the antibody or antigen of interest, but which do not interfere with the formation of the antibody-antigen complex of interest, can be derivatized to the wells of the plate, and unbound antibody or antigen trapped in the wells by antibody conjugation. Methods for detecting such complexes, in addition to those described above for the GST-immobilized complexes, include immunodetection of complexes using such other antibodies reactive with the antibody or antigen.

The invention further pertains to novel agents identified by any of the aforementioned screening assays and uses thereof for treatments as described herein.

Diagnostic Assays

Antibodies of the present invention can be detected by appropriate assays, e.g., conventional types of immunoassays. For example, a sandwich assay can be performed in which a CCR4 protein or fragment thereof (e.g., the CA domain) is affixed to a solid phase. Incubation is maintained for a sufficient period of time to allow the antibody in the sample to bind to the immobilized polypeptide on the solid phase. After this first incubation, the solid phase is separated from the sample. The solid phase is washed to remove unbound materials and interfering substances such as non-specific proteins which may also be present in the sample. The solid phase containing the antibody of interest bound to the immobilized polypeptide is subsequently incubated with a second, labeled antibody or antibody bound to a coupling agent such as biotin or avidin. This second antibody may be another anti-CCR4 antibody or another antibody. Labels for antibodies are well-known in the art and include radionuclides, enzymes (e.g. maleate dehydrogenase, horseradish peroxidase, glucose oxidase, catalase), fluors (fluorescein isothiocyanate, rhodamine, phycocyanin, fluorescarmine), biotin, and the like. The labeled antibodies are incubated with the solid and the label bound to the solid phase is measured. These and other immunoassays can be easily performed by those of ordinary skill in the art.

The anti-CCR4 antibodies and scFv antibodies of the invention, when joined to a detectable moiety, provides a way for detecting "cancerous tissue" or tissue subject to aberrant cell proliferation and therefore at risk for cancer. In addition to tissue that becomes cancerous due to an in situ neoplasm, for example, the antibody-detectable moiety conjugates also provides a method of detecting cancerous metastatic tissue present in distal organs and/or tissues. Thus such tissue may be detected by contacting tissue suspected of being cancerous with the antibody-detectable moiety under appropriate conditions to cause the detectable moiety to be detected in cancerous tissue, thereby detecting the presence of cancerous tissue.

The detectable moieties can be conjugated directly to the antibodies or fragments, or indirectly by using, for example, a fluorescent secondary antibody. Direct conjugation can be accomplished by standard chemical coupling of, for example, a fluorophore to the antibody or antibody fragment, or through genetic engineering. Chimeras, or fusion proteins can be constructed which contain an antibody or antibody fragment coupled to a fluorescent or bioluminescent protein. For example, Casadei, et al., describe a method of making a vector construct capable of expressing a fusion protein of aequorin and an antibody gene in mammalian cells.

As used herein, the term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently-labeled secondary antibody and end-labeling of a DNA probe with biotin such that it can be detected with fluorescently-labeled streptavidin. The term "biological sample" is intended to include tissues, cells and biological fluids isolated from a subject (such as a biopsy), as well as tissues, cells and fluids present within a subject. That is, the detection method of the invention can be used to detect cancer, a cancer cell, or a cancer-associated cell (such as a stromal cell associated with a tumor or cancer cell) in a biological sample in vitro as well as in vivo. For example, in vitro techniques for detection of CCR4 include enzyme linked immunosorbent assays (ELISAs), Western blots, immunoprecipitations, and immunofluorescence. Furthermore, in vivo techniques for detection of CCR4 include introducing into a subject a labeled anti-CCR4 antibody. For example, the antibody can be labeled with a radioactive marker whose presence and location in a subject can be detected by standard imaging techniques. In embodiments, the invention provides a non-invasive method of detecting a tumor or cancer cell in a subject. The subject is administered an antibody or scFv antibody of the invention, where the antibody is linked to a detectable moiety (i.e., any moiety capable of being detected by, e.g., fluorescent, chemical, chemiluminescent, radioactive, or other means known in the art), the antibody is allowed to localize to the tumor then is detected by observation of the detectable moiety.

In the case of "targeted" conjugates, that is, conjugates which contain a targeting moiety—a molecule or feature designed to localize the conjugate within a subject or animal at a particular site or sites, localization refers to a state when an equilibrium between bound, "localized", and unbound, "free" entities within a subject has been essentially achieved. The rate at which such equilibrium is achieved depends upon the route of administration. For example, a conjugate administered by intravenous injection to localize thrombi may achieve localization, or accumulation at the thrombi, within minutes of injection. On the other hand, a conjugate administered orally to localize an infection in the intestine may take hours to achieve localization. Alternatively, localization may simply refer to the location of the entity within the subject or animal at selected time periods after the entity is administered. By way of another example, localization is achieved when a moiety becomes distributed following administration.

In all of the above cases, a reasonable estimate of the time to achieve localization may be made by one skilled in the art. Furthermore, the state of localization as a function of time may be followed by imaging the detectable moiety (e.g., a light-emitting conjugate) according to the methods of the invention, such as with a photodetector device. The "photodetector device" used should have a high enough sensitivity to enable the imaging of faint light from within a mammal in a reasonable amount of time, and to use the signal from such a device to construct an image.

In cases where it is possible to use light-generating moieties which are extremely bright, and/or to detect light-generating fusion proteins localized near the surface of the subject or animal being imaged, a pair of "night-vision" goggles or a standard high-sensitivity video camera, such as a Silicon Intensified Tube (SIT) camera (e.g., from Hammamatsu Photonic Systems, Bridgewater, N.J.), may be used. More typically, however, a more sensitive method of light detection is required.

In extremely low light levels the photon flux per unit area becomes so low that the scene being imaged no longer appears continuous. Instead, it is represented by individual photons which are both temporally and spatially distinct form one another. Viewed on a monitor, such an image appears as scintillating points of light, each representing a single detected photon. By accumulating these detected photons in a digital image processor over time, an image can be acquired and constructed. In contrast to conventional cameras where the signal at each image point is assigned an intensity value, in photon counting imaging the amplitude of the signal carries no significance. The objective is to simply detect the presence of a signal (photon) and to count the occurrence of the signal with respect to its position over time.

At least two types of photodetector devices, described below, can detect individual photons and generate a signal which can be analyzed by an image processor. Reduced-Noise Photodetection devices achieve sensitivity by reducing the background noise in the photon detector, as opposed to amplifying the photon signal. Noise is reduced primarily by cooling the detector array. The devices include charge coupled device (CCD) cameras referred to as "backthinned", cooled CCD cameras. In the more sensitive instruments, the cooling is achieved using, for example, liquid nitrogen, which brings the temperature of the CCD array to approximately −120° C. "Backthinned" refers to an ultra-thin backplate that reduces the path length that a photon follows to be detected, thereby increasing the quantum efficiency. A particularly sensitive backthinned cryogenic CCD camera is the "TECH 512", a series 200 camera available from Photometrics, Ltd. (Tucson, Ariz.).

"Photon amplification devices" amplify photons before they hit the detection screen. This class includes CCD cameras with intensifiers, such as microchannel intensifiers. A microchannel intensifier typically contains a metal array of channels perpendicular to and co-extensive with the detection screen of the camera. The microchannel array is placed between the sample, subject, or animal to be imaged, and the camera. Most of the photons entering the channels of the array contact a side of a channel before exiting. A voltage applied across the array results in the release of many electrons from each photon collision. The electrons from such a collision exit their channel of origin in a "shotgun" pattern, and are detected by the camera.

Even greater sensitivity can be achieved by placing intensifying microchannel arrays in series, so that electrons generated in the first stage in turn result in an amplified signal of electrons at the second stage. Increases in sensitivity, however, are achieved at the expense of spatial resolution, which decreases with each additional stage of amplification. An exemplary microchannel intensifier-based single-photon detection device is the C2400 series, available from Hamamatsu.

Image processors process signals generated by photodetector devices which count photons in order to construct an image which can be, for example, displayed on a monitor or printed on a video printer. Such image processors are typically sold as part of systems which include the sensitive photon-counting cameras described above, and accordingly, are available from the same sources. The image processors are usually connected to a personal computer, such as an IBM-compatible PC or an Apple Macintosh (Apple Computer, Cupertino, Calif.), which may or may not be included as part of a purchased imaging system. Once the images are in the form of digital files, they can be manipulated by a variety of image processing programs (such as "ADOBE PHOTOSHOP", Adobe Systems, Adobe Systems, Mt. View, Calif.) and printed.

In one embodiment, the biological sample contains protein molecules from the test subject. One preferred biological sample is a peripheral blood leukocyte sample isolated by conventional means from a subject.

The invention also encompasses kits for detecting the presence of CCR4 or a CCR4-expressing cell in a biological sample. For example, the kit can comprise: a labeled compound or agent capable of detecting a cancer or tumor cell (e.g., an anti-CCR4 scFv or monoclonal antibody) in a biological sample; means for determining the amount of CCR4 in the sample; and means for comparing the amount of CCR4 in the sample with a standard. The standard is, in some embodiments, a non-cancer cell or cell extract thereof. The compound or agent can be packaged in a suitable container. The kit can further comprise instructions for using the kit to detect cancer in a sample.

Bi-Specific Antibodies

A bi-specific antibody (bsAb) is an antibody comprising two variable domains or scFv units such that the resulting antibody recognizes two different antigens. The present invention provides for bi-specific antibodies that recognize CCR4 and a second antigen. Exemplary second antigens include tumor associated antigens, cytokines and cell surface receptors. In some embodiments, the second antigen can be CAIX (carbonic anhydrase IX, or G250 or PD-L1.

A bi-specific antibody of the present invention comprises a heavy chain and a light chain combination or scFv of the huCCR4 antibodies disclosed herein.

Bi-specific antibodies of the present invention can be constructed using methods known art. In some embodiments, the bi-specific antibody is a single polypeptide wherein two different heavy-light chain heterodimers or two different scFv antibodies, or fragments thereof, that each recognize a different antigen are joined by a long linker polypeptide, of sufficient length to allow intramolecular association between the two scFv molecules to form a bi-specific antibody, with two heavy chains and two light chains. In one embodiment, one of the scFv molecules recognizes CCR4, for example, any of the scFv antibodies described herein. In other embodiments, the bi-specific antibody consists of more than one polypeptide, for example, two separate scFv antibodies, or fragments thereof, linked by covalent or non-covalent bonds, wherein one of the scFv antibodies recognizes CCR4.

In one embodiment, the bi-specific antibody is constructed using the "knob into hole" method (Ridgway et al., Protein Eng 7:617-621 (1996)). In this method, the Ig heavy chains of the two different variable domains are reduced to selectively break the heavy chain pairing while retaining the heavy-light chain pairing. The two heavy-light chain heterodimers that recognize two different antigens are mixed to promote heteroligation pairing, which is mediated through the engineered "knob into holes" of the CH3 domains.

In another embodiment, the bi-specific antibody can be constructed through exchange of heavy-light chain heterodimers from two or more different antibodies to generate a hybrid antibody where the first heavy-light chain heterodimer recognizes CCR4 and the second heavy-light chain heterodimer recognizes a second antigen. The mechanism for generating a bi-specific antibody consisting of two heavy-light chain heterodimers from two different antibodies is similar to the formation of human IgG4, which also functions as a bispecific molecule. Dimerization of IgG heavy chains is driven by intramolecular force, such as the pairing the CH3 domain of each heavy chain and disulfide bridges. Presence of a specific amino acid in the CH3 domain (R409) has been shown to promote dimer exchange and construction of the IgG4 molecules. Heavy chain pairing is also stabilized further by interheavy chain disulfide bridges in the hinge region of the antibody. Specifically, in IgG4, the hinge region contains the amino acid sequence Cys-Pro-Ser-Cys (in comparison to the stable IgG1 hinge region which contains the sequence Cys-Pro-Pro-Cys) at amino acids 226-230. This sequence difference of Serine at position 229 has been linked to the tendency of IgG4 to form novel intrachain disulfides in the hinge region (Van der Neut Kolfschoten, M. et al., 2007, *Science* 317:1554-1557 and Labrijn, A. F. et al, 2011, *Journal of immunol* 187:3238-3246).

In another embodiment, the use of glutathione and glutathione disulfide can be used in the production of bi-specific antibodies from two distinct full antibodies. For example, the full antibodies, each which recognize different antigens, are incubated with reducing glutathione to separate the antibodies into heavy-light chain heterodimers, or molecules. The heavy-light chain heterodimers may be mixed with oxidized glutathione (GSSG) which allows reassembly and reoxidation to form highly pure bi-specific antibodies.

Therefore, bi-specific antibodies of the present invention can be created through introduction of the R409 residue in the CH3 domain and the Cys-Pro-Ser-Cys sequence in the hinge region of antibodies that recognize CCR4 or a second antigen, so that the heavy-light chain dimers exchange to produce an antibody molecule with one heavy-light chain dimer recognizing CCR4 and the second heavy-light chain dimer recognizing a second antigen, wherein the second antigen is any antigen disclosed herein. Heavy-light chain heterodimer exchange can also be enhanced with addition of a reducing agent, such as reduced glutathione, to promote the exchange. Known IgG4 molecules may also be altered such that the heavy and light chains recognize CCR4 or a second antigen, as disclosed herein. Use of this method for constructing the bi-specific antibodies of the present invention may be beneficial due to the intrinsic characteristic of IgG4 molecules wherein the Fc region differs from other IgG subtypes in that it interacts poorly with effector systems of the immune response, such as complement and Fc receptors expressed by certain white blood cells. This specific property makes these IgG4-based bi-specific antibodies attractive for therapeutic applications, in which the antibody is required to bind the target(s) and functionally alter the signaling pathways associated with the target(s), however not trigger effector activities.

In some embodiments, mutations are introduced to the constant regions of the bsAb such that the antibody dependent cell-mediated cytotoxicity (ADCC) activity of the bsAb is altered. For example, the mutation is an LALA mutation in the CH2 domain, wherein the leucines at positions 234 and 235 of the Fc region is mutated to alanine, and abrogates binding by specific Fc receptors. In one aspect, the bsAb contains mutations on one scFv molecule of the heterodimeric bsAb, which reduces the ADCC activity. In another aspect, the bsAb contains mutations on both chains of the heterodimeric bsAb, which completely ablates the ADCC activity. For example, the mutations introduced one or both scFv molecules of the bsAb are LALA mutations in the CH2 domain. These bsAbs with variable ADCC activity can be optimized such that the bsAbs exhibits maximal selective killing towards cells that express one antigen that is recognized by the bsAb, however exhibits minimal killing towards the second antigen that is recognized by the bsAb.

The present invention provides for bi-specific antibodies that recognize CCR and a second antigen. In one embodiment, the second antigen is PD-L1. In another embodiment, the second antigen is CAIX.

The bi-specific antibodies disclosed herein may be useful in treatment of diseases or medical conditions, for example, cancer. The cancer is, for example, a solid cancer, such as renal cell carcinoma, breast cancer or prostate cancer. In other embodiments, the cancer is a cancer in which CAIX or PD-L1 is overexpressed when compared to tissue or a subject that does not have cancer. The bi-specific antibodies of the present invention may be used to treat, prevent, or alleviate a symptom of the cancer.

The bi-specific antibodies of the present invention may be used to increase T cell proliferation, in which the T cell is a regulatory T cell. The bi-specific antibodies of the present invention may be particularly useful for promoting or augmenting a T cell response, such as an antigen-specific T cell response. The bi-specific antibodies of the present invention can also be useful for reversing regulatory T cell-mediated suppression of effector T cell proliferation.

Fusion Proteins

The invention provides a fusion protein containing a huCCR4 antibodies disclosed herein, or a functional fragment thereof, operably linked to a second protein. The second protein can be, for example, a cytokine or a growth factor. In particularly preferred embodiments, the cytokine is IL-2 or TGF-beta. In some other embodiments, the second protein may be a therapeutic agent, such as a toxin, or a detectable moiety, such as a fluorescent protein for detection. In some embodiments, the huCCR4 antibodies of the present invention may be operably linked to more than one additional protein or peptide, for example 2, 3, 4, 5, 6, 7, 8, 9, or 10 additional proteins or peptide sequences.

In some embodiments, the huCCR4 antibody disclosed herein, or functional fragment thereof, is joined directly to the second protein. In other embodiments, the huCCR4 antibody, or functional fragment thereof, is joined to the second protein via a linker, such as a flexible polypeptide chain. The linker can be any suitable linker of any length, but can be at least 1, 2, 3, 4, 5, 10, 15, 20, 25, or 30 amino acids in length. In one embodiment, the linker is an amino acid sequence that is naturally present in immunoglobulin molecules of the host, such that the presence of the linker would not result in an immune response against the linker sequence by the mammal. Fusion proteins of the present invention that include more than one additional protein to the huCCR4 antibody may have multiple linker sequences that join each additional protein or peptide sequence.

The fusion proteins of the present invention may be constructed by recombinant methods known to the skilled artisan. For example, an expression vector containing the nucleic acid sequence encoding a huCCR4 antibody of the present invention can be operably linked to the nucleic acid sequence encoding the second protein and can be introduced to an expression system to translate and produce the fusion protein. Alternatively, one skilled in the art could readily utilize de novo protein synthesis techniques to produce the fusion proteins described herein.

Methods of Treatment

The invention provides for both prophylactic and therapeutic methods of treating a subject at risk of (or susceptible to) a cancer, or other cell proliferation-related diseases or disorders. Such diseases or disorders include but are not limited to, e.g., those diseases or disorders associated with aberrant expression of CCR4. For example, the methods are used to treat, prevent or alleviate a symptom of a hematologic cancer such cutaneous T-cell Lymphoma (CTCL), mycosis fungoides (MF), primary cutaneous anaplastic large cell Lymphoma (cutaneous ALCL), Sezary syndrome, or adult T cell Leukemia/Lymphoma (ATLL). Alternatively, the methods are used to treat, prevent or alleviate a symptom of a solid tumor such as renal cell carcinoma, breast cancer, lung cancer, ovarian cancer, prostate cancer, colon cancer, cervical cancer, brain cancer, liver cancer, pancreatic cancer or stomach cancer. In other embodiments, the antibodies of the present invention, such as bi-specific antibodies of the present invention, can be used for the treatment of cancers that are characterized by CAIX or PD-L1-overexpressing tumors. For example, the bi-specific antibody that recognizes CAIX and CCR4 may be used for treatment of a cancer with tumors that overexpress CAIX. For example, the bi-specific antibody that recognizes PD-L1 and CCR4 may be used for treatment of a cancer with tumors that overexpress PD-L1.

Accordingly, in one aspect, the invention provides methods for preventing, treating or alleviating a symptom cancer or a cell proliferative disease or disorder in a subject by administering to the subject a monoclonal antibody or scFv antibody of the invention. For example, a huCCR4 antibody may be administered in therapeutically effective amounts.

Subjects at risk for cancer or cell proliferation-related diseases or disorders include patients who have a family history of cancer or a subject exposed to a known or suspected cancer-causing agent. Administration of a prophylactic agent can occur prior to the manifestation of cancer such that the disease is prevented or, alternatively, delayed in its progression.

In another aspect, tumor cell growth is inhibited or suppressor T-cell activity is decreased by contacting a cell with a CCR4 antibody of the invention. The cell is any cell that expresses CCR4. For example the cell is T-cell.

Also included in the invention are methods of increasing or enhancing an immune response to an antigen. An immune response is increased or enhanced by administering to the subject a monoclonal antibody or scFv antibody of the invention. The antigen is a viral (e.g. HIV), bacterial, fungal or tumor antigen. The immune response is a natural immune response. By natural immune response is meant an immune response that is a result of an infection. The infection is a chronic infection.

Alternatively, the immune response is a response induced due to a vaccination. Accordingly, in another aspect the invention provides a method of increasing vaccine efficiency by administering to the subject a monoclonal antibody or scFv antibody of the invention and a vaccine. The antibody and the vaccine are administered sequentially or concurrently. The vaccine is a tumor vaccine a bacterial vaccine or a viral vaccine.

The immune response is augmented for example by augmenting antigen specific T effector function.

Combinatory Methods

The invention provides treating cancer in a patient by administering two antibodies that bind to the same epitope of the CCR4 protein or, alternatively, two different epitopes of the CCR4 protein. Also, the cancer is treated by administering a first antibody that binds to CCR4 and a second antibody that binds to a protein other than CCR4.

Additionally, the invention provides administration of an antibody that binds to the CCR4 protein and an anti-neoplastic agent, such a small molecule, a growth factor, a cytokine or other therapeutics including biomolecules such as peptides, peptidomimetics, peptoids, polynucleotides, lipid-derived mediators, small biogenic amines, hormones, neuropeptides, and proteases. Small molecules include, but are not limited to, inorganic molecules and small organic molecules. Suitable growth factors or cytokines include an IL-2, GM-CSF, IL-12, and TNF-alpha. Small molecule libraries are known in the art. (See, Lam, Anticancer Drug Des., 12:145, 1997.)

The invention will be further described in the following examples, which do not limit the scope of the invention described in the claims.

EXAMPLES

Example 1

General Methods

Cells

Primary cutaneous CD30+ lymphoproliferative disorders (LPDs) are the second most common group of CTCLs, accounting for approximately 30% of CTCLs. This group includes primary cutaneous anaplastic large cell lymphoma (C-ALCL) (1). Mac-1 cell line was isolated from a patient with C-ALCL (22). Luciferase-expressed Mac-1 cells were stably transduced with a luciferase reporter retrovirus and both cell lines were cultured in RPMI-1640 (Invitrogen Life Technologies, MD) supplemented with 10% (v/v) heat-inactivated FBS, 100 IU/ml penicillin, and 100 µg/ml streptomycin at 37° C. with 5% CO2. 293F cell line (Invitrogen) was cultured in FreeStyle medium (Invitrogen) at 37° C. with 5% CO2. 293T (ATCC: CRL-11268) and Cf2Th (ATCC: CRL-1430) cell lines were cultured in DMEM (Invitrogen) supplemented with 10% (v/v) heat-inactivated FBS, 100 IU/ml penicillin, and 100 µg/ml streptomycin at 37° C. with 5% CO2. Both 293T and Cf2Th were established by transfection with full-length CCR4 expressing plasmid (pcDNA3.1-CCR4) and followed by 800 µg/ml and 500 µg/ml G418 selection, respectively, and FACS sorting for CCR4+ cell population.

The human skin-tropic Anaplastic large-cell lymphoma (ALCL) cell line Mac-1, which was originally isolated in the laboratory of Marshall E. Kadin at Harvard Medical School (Wasik, M A et al. Am J Pathol 2011, 144:1089-1097), was cultured in RPMI medium supplemented with 10% fetal bovine serum (FBS), 0.06 mM 2-mercaptoethanol, and 500 µg/ml G418. Immunophenotyping of the Mac-1 cell line showed the expression of all known tumor-specific chemokine receptors, including high levels of CCR4, CCR7, and CXCR4. This MAC-1 cell line was stably transduced with a luciferase encoding retrovirus. HEK 293 cells were cultured in Dulbecco's modified Eagle's medium supplemented with 10% FBS and 1% penicillin/streptomycin (Invitrogen). All cells and cultures were maintained at 37° C. in a 5% $CO_2$ humidified incubator. Human PBMCs obtained from the Dana-Farber Blood Center were purified by a Ficoll-Hypaque density gradient centrifugation as described in the general protocol of Miltenyi Biotec Inc. (Auburn, Calif.). Mouse neutrophils were isolated from SCID-BEIGE mouse blood by Percoll density gradient centrifugation, as described (Luo, Y et al. Curr Protoc Immunol. 2001, Chapter 3:Unit 3 20). Human NK cells were isolated from human PBMC using the NK cell isolation kit, according to the manufacturer's protocol (Miltenyi Biotec, CA).

Antibodies and Flow Cytometry Analysis

MAb 1567 was purchased from R&D systems and the other 1567 variants, including scFv-Fcs and whole human IgG1, were produced as described previously (Sui, J et al. Proc Natl Acad Sci 2004, 101:2536-41). In brief, chimeric (c1567)-scFv-Fc, humanized (h1567)-scFv-Fc and h1567 variants were constructed by cloning the corresponding single-chain variable region (scFv) fragment into pcDNA3.1-Hinge expression vector in frame with the C-terminal human IgG1 Fc region. The scFv-Fc proteins were produced in 293T cells or 293F cells by transient transfection and purified by proteinA-Sepharose (Amersham, N.J.) affinity chromatography. The full-length c1567 IgG1 was generated by cloning the VH and VL separately into a human IgG1 expression vector, TCAE5.3 (Reff, M E et al. Blood 1994, 83:435-45). For cell staining, Mac-1 were stained with antibodies at 4° C. for 1 hour and then washed with cold PBS three times. Next, FITC-conjugated goat anti-human IgG or anti-mouse IgG antibodies were added with 1:200 dilution. Data were collected with FACSCalibur (BD Biosciences, CA) and analyzed with CellQuest cytometry software.

IgG and scFv-Fcs format of mAb2-3 and KM2760 were constructed by cloning the single-chain variable region (scFv) into pcDNA3.1-Hinge vector in frame with human IgG1 Fc region and by cloning heavy-chain variable region (VH) and light-chain variable region (VL) into TCAE5.3 vector. Antibodies were produced in 293T or 293F cells and purified by proteinA-Sepharose (Amersham) affinity chromatography.

Chemotaxis

Mac-1 cells (1×106 per well) were placed in Transwell-migration wells (5 μM pore; Corning) with or without mAb1567 for 3 h at 37° C., and migrated cells harvested from the bottom chamber containing 50 ng/ml human CCL17 or CCL22 (R&D Systems, MN) were enumerated by FACS. Percentages of migrated cells were calculated by dividing the number of transmigrated Mac-1 by the number of input cells. Human CD4+ T cells were isolated by CD4+ T cell isolation kit (Miltenyi Biotech) and placed in Transwell-migration assays with c1567IgG for 3 h at 37° C., and migrated cells (CD4+CD25high) were enumerated as above in response to 100 ng/ml human CCL22. Percentages of migrated cells were calculated by dividing the number of transmigrated CD4+CD25high cells by the number of input cells with comparable CD4+ and CD25+ levels.

Antibody-Dependent Cell Cytotoxicity Assay

ADCC assays were performed using the LDH release assay method. Briefly, SCID/Beige mouse neutrophils, human PBMCs, or purified human NK cells and neutrophils were used as effector cells and Mac-1, Cf2Th-CCR4, or Cf2Th cells were used as target cells. Target cells were plated at a density of 1×104 cells/well into 96-well plates and then antibodies were added at an appropriate concentration. After one-hour incubation, freshly effector cells were added to achieve an appropriate E/T ratio. After incubation at 37° C. (PBMCs for 4 hours, NK cells for 16 hours and neutrophils for 6 hours), the supernatants from each well were recovered by centrifugation at 300×g for 5 min. The supernatant were measured using a nonradioactive cytotoxicity assay kit (Promega, WI). The absorbance at 490 nm of the plates was determined using an ELISA reader. For 51Cr release assay, 1×106 Mac-1 cells were labeled with 100 μCi (3.7 MBq) of Na51Cr (Amersham International) for 1 h at 37° C., washed extensively, and used as targets. 51Cr-labeled target cells (5000 per well) were seeded into 96-well plates. Experiments were conducted in triplicates at various PBMC (effector) to Mac-1 (target) ratios of 12.5:1, 25:1, and 50:1, incubated at 37° C. for 4 hours, and then the release of 51Cr into supernatants was determined. The cytotoxicity was calculated by the following formula:

% Cytotoxicity=100×(E−SE−ST)/(M−ST) where E is the experimental release of the LDH form the target cells incubated with effector cells and antibody, SE the spontaneous release of the LDH from the effector cells, ST the spontaneous release of the LDH from the target cells and M is the maximum release of the LDH from the target cells incubated with 10% triton-X.

Complement Dependent Cytotoxicity Assay

Mac-1 cells were used as the target cell. Briefly, 5×104 cells resuspended with serum free culture medium containing baby rabbit serum (1:16, Cedarlane Laboratories) or mouse complement serum (1:10, Innovative Research, pooled from BALB/c and C57BL/6 mice that are the background mouse strains of the SCID/Beige mice) were plated per well in a 96-well plate with dose-dependent anti-CCR4 antibodies. After two-hour incubation at 37° C., the supernatants were recovered by centrifugation at 300×g for 5 min. The detection of cytotoxicity was measured using a nonradioactive cytotoxicity assay kit (Promega). The formula of cytotoxicity is: % Cytotoxicity=100×(E−ST)/(M−ST).

Regulatory T Cell Suppression Assay

CD4+CD25high and CD4+CD25− T cells were sorted by FACSCanto II flow cytometer using anti-CD4 and anti-CD25 antibodies (Biolegend). CD4+CD25-Teffs (2500 cells) were cultured with or without CD4+CD25high Tregs (2500 or 1250 cells) in round-bottom 96-well plates coated with bound anti-CD3 (0.05 μg/ml) and soluble anti-CD28 (1 μg/ml) antibodies (Biolegend, CA). 25,000 irradiated (300 rad) CD3-depleted PBMCs with or without c1567IgG were added into the cocultured wells. Proliferation of T cells was measured by incorporation of 3H-thymidine on day 5 using a scintillation counter. The percent proliferation of Teffs in Tregs cocultures in all analyses was normalized to the proliferation of Teffs in mono-Teffs culture; the proliferation of mono-Teffs culture was considered 100% for this normalization. For activation, plates were coated with anti-CD3 at 37° C. for 2 hours and washed twice with PBS.

CCR4+ CTCL Tumor-Bearing Mouse Model

Human cancer xenografts were established in SCID/Beige mice (Charles River). 2×106 Mac-1-luciferase cells or 1×107 Mac-1 cells were injected subcutaneously into the dorsolateral flank in 6-week mice. After 24 hours of injection, mice were randomly assigned to different treatment groups and treated with 3 mg/kg of mAb1567 and mouse IgG2b (twice a week for three weeks) or 5 mg/kg of control-scFv-Fc, c1567-scFv-Fc, h1567-scFv-Fc, and equivalent volumes of saline by i.p. injection (twice a week for four weeks). Mouse body weight and tumor size were measured and monitored twice a week using digital caliper or Xenogen imaging. The tumor volumes were calculated using the equation, length×(width)2×0.52. Animal care was carried out in accordance with the guidelines of Animal Care and Use Committee of Dana-Farber Cancer Institute.

Statistical Analyses

Data was analyzed using two-sided unpaired Student's t-test. We considered a P value below 0.05 as significant for all analyses. All values are represented as mean±standard deviation (S.D)

Statistical analyses were performed using 2-way ANOVA with Bonferroni post hoc tests and unpaired 2-tailed t-tests using GraphPad Prism 5 (GraphPad Software, Inc., La Jolla, Calif.). P values less than 0.05 were considered statistically significant.

Transfections and Biosynthetic Analyses of Human CCR-Fc Fusion Proteins

Transfections were done with 293 cells and a F105-L3-Nt-hCCR-Fc fusion protein vector using the same method described above. Two days post-transfection, the cells were washed and then incubated for various times with either 250 µCi/ml [35S]Met/Cys or 400 µCi/ml Na2 35SO4 (PerkinElmer Life Sciences, MA). After two days, culture supernatant was collected and prepared for immunoprecipitation using Protein A sepharose beads. The purified hCCR-Fc fusion proteins, i.e. hCCR4Nt-Fc, hCCR5Nt-Fc and mutant hCCR5Nt-Fc (with four N-terminal tyrosine residues mutated to aspartic acid, DDDD mutant version), were further analyzd by SDS-PAGE and silver staining.

Sandwich Enzyme-Linked Immunosorbent Assay (ELISA)

The 96-well plates were coated with mAb1567 antibody in 50 mM carbonate buffer (pH 9.6) at 4° C. overnight, and the wells were washed five times with PBST (PBS containing 0.2% Tween-20), followed by incubation with 200 µl of blocking buffer (PBS, pH 7.4, containing 5% sucrose and 1% BSA) at 37° C. for 2 h. Human CCRNt-Fc fusion proteins were added at concentration of 0.25, 0.5 or 1 µg per well and then incubated at 4° C. for 1 h. After washing PBST, the horseradish peroxidase (HRP) labeled goat anti-human IgG (Thermo scientific, IL) was added into wells and then incubated for 1 h at 4° C. The plates were then washed and incubated with TMB substrate solution (KPL, MD) at room temperature in the dark. The reaction was stopped by the addition of 0.6N sulfuric acid and the absorbance determined at 450 nm with a microplate reader.

Construction of Humanized 1567 Light-Chain Shuffling Phage Display Library

VH (Variable region of heavy chain) gene of humanized 1567, in particular HCDR3, was cloned as a NcoI/BspEI fragment into the vector pFarber-Vκ-rep which contains a repertoire of 1.2×108 non-immune Vκ genes derived from 57 healthy donors. Ligated DNA was transformed into eclectroporation-competent E. Coli. TG1 cells following manufacturer's instructions (Stratagene, CA). Multiple transformations were performed to generate the h1567-Vk chain shuffled library at desired size close to that of the Vκ repertoire.

Cloning and Construction of MAB1567 Gene from Hybridoma Cell Line

Briefly, total RNA was extracted from hybridoma cells MAB1567 (R&D systems) using Total RNA Purification Kit (Ambio Inc., TX) and then reverse transcribed to cDNAs using manufacturer's protocol (Promega) and AMV reverse transcriptase (Promega). The cDNAs of VH and VL antibody fragments were subsequently amplified by PCR with degenerative primers specific for mouse antibody V regions and the full length scFvs (VH-(G4S)3 linker-VL) was assembled by PCR according the manufacture's protocol (GE-Pharmacia Biotech). For antibody production, the constructed scFv-Fc in pcDNA3.1-Hinge vector (murine scFv in frame with the C-terminal human IgG1 Fc) and IgG1 in TCAE5.3 vector were transiently transfected into 293T or 293F cells, and the secreted antibodies in the cell culture supernatants were purified by Protein A affinity chromatography.

Construction of h1567 Phage Display Random Mutagenesis Library

At the selected six CDR positions, all 20 amino acids except proline, cysteine or methionine were allowed at each position to be totally randomized at equal frequency. The full scFv fragments were de novo synthesized to carry these mutations at the designated positions by Sloning Biotech. The synthesized scFv fragment library was sample sequenced to confirm the mutation frequency and accuracy. The library was constructed by subcloning the synthesized scFv library into phage display vector pFarber by electroporation of E. Coli. TG1 cells following manufacturer's instructions (Stratagene, CA).

Library Selection and Screening

CCR4-PMPL preparation for phage antibody library selection, library selection with CCR4-PMPLs or CCR4+ Mac-1 cells, FACS screening for positive binder, DNA sequencing and sequence analysis were performed following the procedure described previously (Willemze, R et al. Blood 2005, 105:3768-85; Clark, R A et al. Sci Transl Med 2012, 4:117ra7; Bekkenk, M W et al. Blood 2009, 95:3653-61).

Construction of AAV8 Vector Encoding Anti-CCR4 Humanized scFvFc h1567 mAb

Figure 1A:
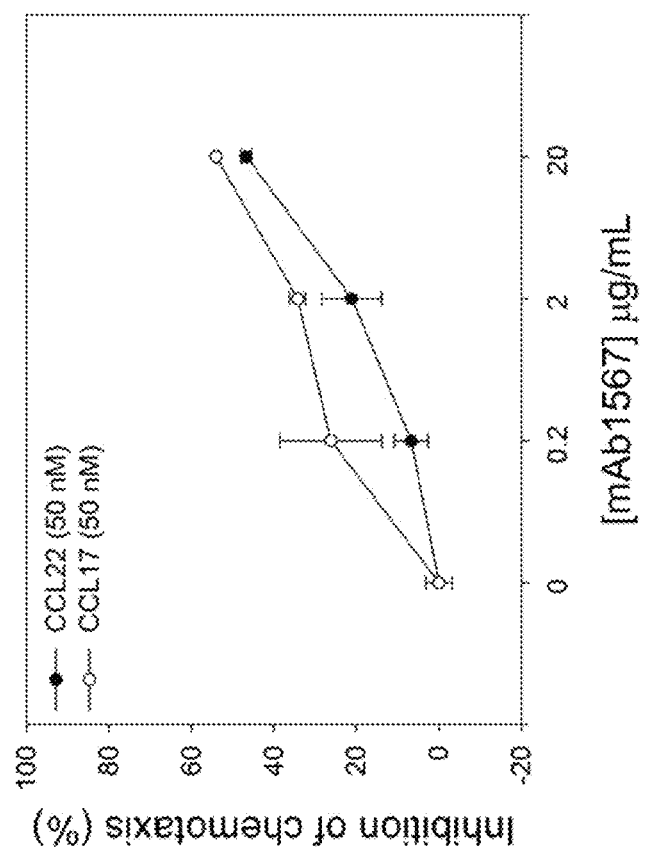
FIG. 1. Overexpression of functional CCR4 on cutaneous T cell lymphoma and mouse anti-CCR4 mAb1567 inhibits tumor formation. A, Dose dependent binding curve of mAb1567 and isotype control mAb to CCR4+ Mac-1 cells by FACS analysis. The half maximal effective concentrations ($EC_{50}$) was generated using Sigma Plot software. B, MAb1567 effectively inhibited chemotaxis of Mac-1 cells to CCR4 ligands, CCRL22 and CCL17. C, The antitumor effect of mAb1567 in SCID/Beige mice bearing Mac-1 xenografts. Antibody was injected intraperitoneal with 3 mg/kg twice a week for three weeks beginning on day 0. D, MAb1567 mediated CDC activity via mouse complement. The complement source was from sera pooled from BALB/c and C57BL/6 mice and Mac-1 cells were target cells. Abs were tested at four different concentrations. Figure shown is one experiment that is representative of at least three independent experiments, bars represent mean±S.D. E, MAb1567 mediated CDC activity with rabbit complement. Similar experimental procedure except the complement source was baby rabbit serum. F, Neutrophils from SCID-Beige mice mediated-mAb1567-dependent ADCC. Bars represent mean±S.D.

To construct the scFvFc h1567 minibody expression cassette, the scFvFc h1567 gene was PCR-amplified from a plasmid coding for the humanized anti-human CCR4 antibody that is derived from heavy and light antibody chains of mAb 1567 (R&D Systems, Inc) previously cloned in our laboratory (DK. Chang et al., manuscript submitted) and inserted into the AAV-cloning vector pTRUF (obtained from the University of Iowa Viral Vector Core) at the restriction sites of Sfi1 and Not1. Consequently, to efficiently direct the expression and secretion of the single chain mAb, the pTRUF vector was modified by inserting the human IgG VH4 leader sequence and the Fc sequence (hinge, CH2 and CH3 domains) of the human IgG1 flanked by 145-bp and AAV2-inverted terminal repeats (ITRs) (FIG. 1a).

Viral Vector Production

Recombinant AAV8 viral vectors were produced using a helper virus-free system with some modifications (Collaco, R F et al. Gene 1999, 238:397-405). Low-passage human HEK 293 cells were cotransfected by linear polyethylenimine (Polysciences) with three plasmids: the AAV cis-plasmid pTRUF encoding the human mAb gene expression cassette flanked with ITRs; the AAV-packaging plasmid p5e18 (2/8) containing AAV2 rep and AV8 cap genes; and the Ad helper plasmid pXX6-80 containing the VA RNA, E2, and E4 genes required for AAV propagation (obtained from Dr. Jim Wilson, University of Pennsylvania)(Michelfelder S. et al. Exp Hematol 2007, 35:1766-1776). At 48 h post-transfection, the cells were harvested, and the AAV virus extracted by freezing and thawing the cells. Subsequently, AAV was purified by two sequential iodixanol density gradients, concentrated, then desalted by centrifugation through Biomax 100-K filters (Millipore) according to the manufacturer's instructions. Viral titers were determined as genome copy titers (vg), by quantitative real-time PCR using primers and probe speicific for AAV vector pTRUF (Veldwijk M R, et al. Mol Ther 2002, 6:272-278). Forward primer (5'-TCTGAGTAGGTGTCATTCTAT-TCTGGG-3', SEQ ID NO: 40) is located at the end of the 3'-poly(A), and reverse primer (5'-CACTAGGGGTTCCTA- GATCTCTCCC-3', SEQ ID NO: 41) is at the beginning of the 3' inverted terminal repeat (ITR). The probe (5'-TCT-TCCCAATCCTCCCCCTTGCTGTC-3; FAM/TAMRA; SEQ ID NO: 42) is located in between.

Larger quantity of the AAV serotype 8 vectors encoding scFvFc 11A, control minibody specific for SARS (Sui J, et al. PLoS Pathog, 4:e1000197), and scFvFc h1567 were produced at Harvard Gene Therapy Initiative (Harvard Institute of Medicine, Boston, Mass.) and used in the animal studies.

Therapeutic Animal Models

SCID-BEIGE female mice aged 6-8 weeks were purchased from Charles River Laboratories and maintained in the animal facilities of Harvard Medical School. For therapeutic minibody gene transfer studies (Mouse model 1), mice were inoculated subcutaneously into the left flank using a 13-gauge trocar with $2.5 \times 10^6$ cells CCR4$^+$ Mac-1 cells in 200 uL PBS. At one-week post-tumor inoculation, mice were injected intravenously through the tail vein in a single treatment of AAV8 vector encoding the anti-CCR4 h1567 minibody or the irrelevant control 11A minibody at a dose of $2 \times 10^{11}$ v.g. (viral genomes) in 150 uL of PBS. For a human PBMC-engrafted mice model (Mouse model 2), mice were inoculated with $1 \times 10^6$ luciferase-expressing CCR4$^+$ Mac-1 cells. Eleven days after tumor cell inoculation, the tumor-bearing mice were injected intravenously via the tail vein with AAV8 vectors. Human PBMC were injected intravenously through a tail vein, to a final concentration of $1 \times 10^6$ cells per mouse at 7 days post-AAV8 injection. Subcutaneous tumors were measured using calipers, and tumor volumes were recorded according to the formula V=d×D×π/2, where d is the smaller diameter and D is the larger diameter. Treated and control mice were euthanized when the tumor diameter reached 1.5 cm or when the mice were moribund. The mice underwent necropsy and the tumors were evaluated by histology and immunohistochemistry (IHC).

Optical Imaging

Mice were monitored for tumor development and progression by both caliber measurement and Xenogen BLI. The latter was initiated for the monitoring of tumor growth 7 days after tumor implantation, which was repeated once a week. Mice were anesthetized with 3.5% isoflurane in an induction chamber, which was followed by the intraperitoneal administration of 50 mg/ml D-luciferin. For imaging, mice were maintained under 1.5% isoflurane anesthesia that was delivered through a nose cone. Whole body images were repeatedly acquired until the maximum peak of photon number was confirmed during various exposure times (10 s-1 min). Data were quantified using the time point that gave the highest photon number during the scanning time and analyzed using the Living Imaging software (Caliper Life Sciences, Hopkinton, Mass.).

CT/PET Imaging

PET/CT scans were performed at the Harvard Medical School Imaging Core Facility. Mice were fasted for 12 h before the $^{18}$F-FDG injections, but provided water ad libitum. For $^{18}$F-FDG injection and imaging, mice were anesthetized using 2% isoflurane. The animals were then intraperitoneally injected with 7.4 MBq (200 µCi) of $^{18}$F-FDG, allowed to regain consciousness, and then kept at 37° C. until imaging. Imaging was started 30 min after the intraperitoneal injection. Mice were imaged in a chamber that minimized positioning errors between PET and CT to less than 1 mm. Image acquisition time was 10 min. Images were analyzed using AMIDE software (Loening A M, et al. Mol Imaging 2003, 2:131-137). All regions of interest were defined on fused PET/CT images to ensure reproducible positioning.

Protein Expression and Purification

HEK 293T cells (ATCC, Manassas, Va.) were transfected with the AAV-coding plasmid containing the minibody-expressing constructs using Lipofectamine 2000 (Invitrogen, Carlsbad, Calif.). Three days after transfection, the minibodies were purified from the supernatants with protein A sepharose affinity chromatography. The in vivo production of AAV8-minibodies was generated by i.v. injections into SCID-BEIGE mice as described above. Levels of minibodies in the serum were measured in duplicate using a human IgG ELISA quantitation kit according to the manufacturer's protocol (Bethyl Laboratories, Inc., Montgomery, Tex.).

Western Blot Analysis

Western immunoblotting was performed on protein A column purified samples containing in vitro synthesized minibodies and in vivo AAV8-derived minibodies. The proteins were separated by SDS-PAGE under reducing or nonreducing conditions and electrophoretically transferred onto a nitrocellulose membrane using the iBLot dry blotting system (Invitrogen). After blocking with 5% skim milk overnight, the blot was probed with an AP-conjugated human IgG-Fc antibody that was diluted 1:30,000 in blocking buffer for 1 h at room temperature. Excess conjugate was removed by five washes with Phosphate buffered saline containing 0.1% Tween 20 (PBS-T). The detection of protein was performed by incubating the membrane with BCIP/NBT alkaline phosphatase substrate (KPL).

Flow Cytometry Analysis

The biological activity of the in vivo AAV8-derived h1567 minbodies was analyzed by fluorescence-activated cell sorting (FACS) for binding activity. Mac-1 cells or 293T-CCR4 cells were washed with PBS supplemented with 0.5% bovine serum albumin (PBS-B) and then incubated with in vivo produced h1567 for 1 h at room temperature, which was followed by incubation with anti-human IgG-Fc conjugated to fluorescein isothiocyanate (FITC). Flow cytometric analysis was performed using BD FacsCalibur (BD Biosciences, San Jose, Calif.) and FlowJo data analysis software (Tree Star, Inc., Ashland, Oreg.).

Immunohistochemistry and Quantification of Cell Staining

Immunohistochemical staining was performed at DFCI/Harvard Cancer Center Research Pathology Core. For qualitative and quantitative immunohistochemical analysis, formalin-fixed and paraffin-embedded tissue sections were stained with antibodies directed against Ly-6G on the surface of mouse neutrophils and human CD56 antigen on human NK cells. The stained slides were then scanned using the Aperio ImageScope (Aperio Technologies, Inc., Vista, Calif.), and full tumor sections were selected for quantitative analyses. The percentage of positively stained cells in the entire tumor sections was calculated using a color deconvolution algorithm (Ruifrok and Johnston, 2001).

In Vitro Antibody-Dependent Cell Cytotoxicity Assay

ADCC was performed using the lactate dehydrogenase (LDH) release assay method, according to the CytoTox96 non-radioactive cytotoxicity assay procedure specified by the manufacturer (Promega, Madison, Wis.). Mouse neutrophils purified from SCID-BEIGE mouse or purified human NK cells from PBMC was used as effector cells and CCR4+ Mac1 tumor cells were used as target cells. Briefly, purified SCID-BEIGE mouse neutrophils or NK cells were plated at a density of $1 \times 10^4$ cells per well in a round-bottom 96-well plate in the presence of h1567 or 11A minibodies. After 1-hour of incubation, freshly prepared effector cells were added at an effector-target cell ratio (E:T) of 80:1 (mouse neutrophils) or 2:1 (human NK cells). After 2 h incubation at 37° C., supernatants of each well were recovered by centrifugation at 300×g for 5 min. LDH activity in the supernatant was determined by measuring absorbance at a wavelength of 490 nm. The cytotoxicity (%) was calculated according to the following formula:

% Cytotoxicity=100×(E−SE−ST)/(M−ST) where E is the LDH release by effector-target coculture, SE the spontaneous release of the LDH from the effector cells, ST the spontaneous release of the LDH from the target cells and M the maximum release of the LDH from the target cells incubated with lysis solution (10% Triton-X). All measurements were done in triplicate.

Example 2

Characterization of a Mouse Anti-CCR4 mAb, mAb1567, In Vitro and In Vivo

CCR4 has four regions exposed at the cell surface: the NT (~30-50 aa) and three extracellular domains loops (ECLs, each of ~10-30 aa), which are important for ligand binding, intracellular signaling and other biological functions. In this study, two commercially available murine anti-CCR4 mAbs, mAb1567 (R&D systems) and 1G1 (BD Pharmingen), both generated by immunizing mouse with full-length human CCR4 (hCCR4) expressing cells (Campbell J J et al. Nature 1999, 400:776-800; www.rndsystems.com/pdf/fab1567a.pdf), were initially selected for evaluation. Both mAb1567 and 1G1 showed specific binding activity in FACS analysis to hCCR4 expressing Cf2Th-CCR4 cells but not to the parental Cf2Th cells. By comparison, mAb1567 had relatively higher affinity than 1G1 under the same antibody concentrations tested (data not shown). Therefore, we selected only mAb1567 for further characterization.

Figure 1B:
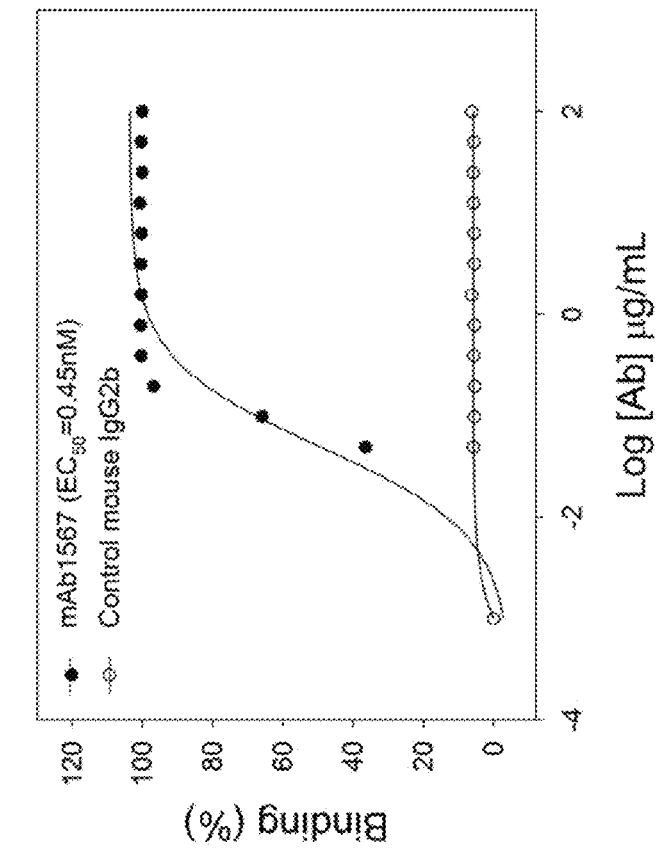

Binding of mAb1567 was further tested using the CCR4$^+$ Mac-1 cell line by FACS analysis and the half maximal effective binding concentration (EC$_{50}$) is about 0.45 nM (FIG. 1A). Chemotaxis inhibition assay showed that mAb1567 effectively inhibited chemotaxis of Mac-1 cells in a dose dependent manner toward both CCR4 ligands, CCL17 and CCL22 (FIG. 1B). We next examined the epitope recognized by mAb1567, in particular whether it recognizes solely the NT or a non-linear conformational dependent epitope comprising of both NT and ECL, by using hCCR4 and hCCR8 NT swapping chimeras that either contained CCR8-NT/CCR4-ECLs (Chi#1) or CCR4-NT/CCR8-ECLs (Chi#2)(Jopling L A et al. Journal of Biological Chemistry 2002, 277:6864-73). As shown in FIG. S1A, all the constructs encoding wild type or chimeras CCR4 and CCR8 expressed to the similar level on the cell surface as validated by antibody staining against the HA tag at NT of these constructs. mAb1567 specifically recognized cell surface full-length hCCR4 but not hCCR8. It bound to Chi#1 and Chi#2 to similar level as wild type CCR4 indicating that the epitope of mAb1567 is not solely a linear epitope on NT of CCR4, rather both ECLs and NT contribute to the binding of mAb1567 with CCR4. However, the CCR4-Nt alone is also sufficient for some degree of mAb1567 binding to CCR4-Nt-Fc as determined in Elisa studies to plate bound mAb1567.

Figure 1D:
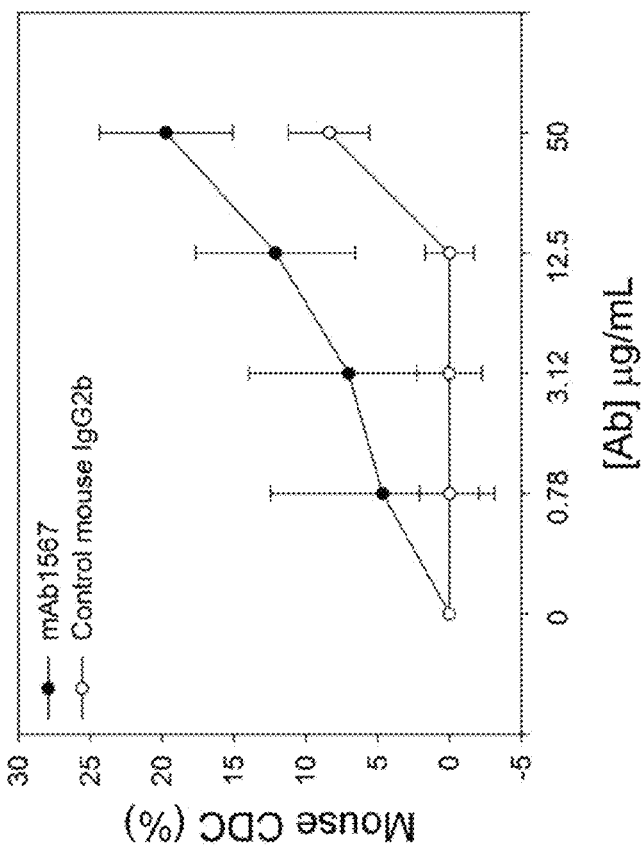
Figure 1C:
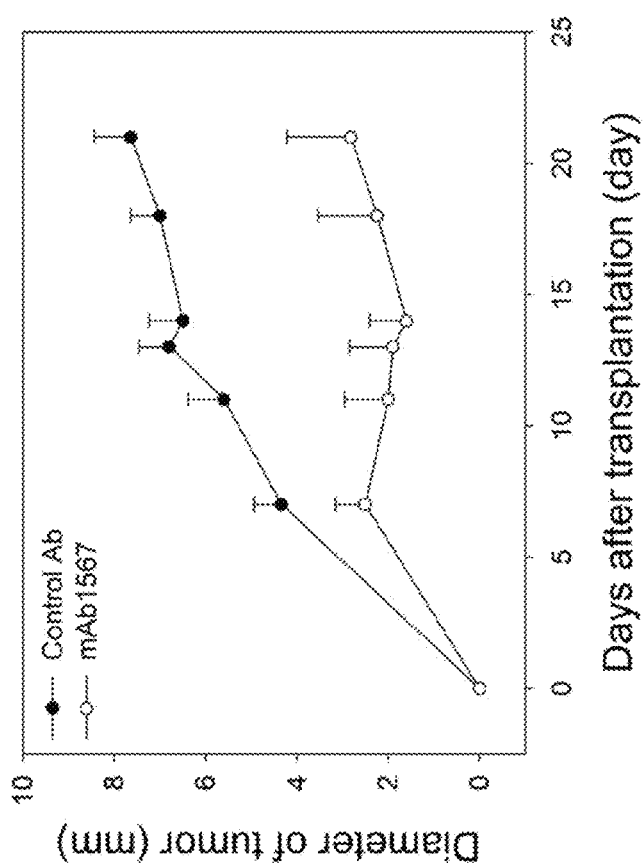

We then tested the antitumor effect of mAb1567 in vivo in a CTCL model using immunodeficient SCID/Beige mice that lack T- and B-cells and have defective NK function. SCID/Beige mice implanted with Mac-1 cells can efficiently form subcutaneous tumors (Pfeifer W et al. Am J Pathol 1999, 155:1353-9). As shown in FIG. 1C, the tumor size in the mAb1567 treated group was about 3 to 4-fold smaller than that in the control group. None of the mice showed mAb1567 treatment related toxicity.

Figures 1E, 1F:
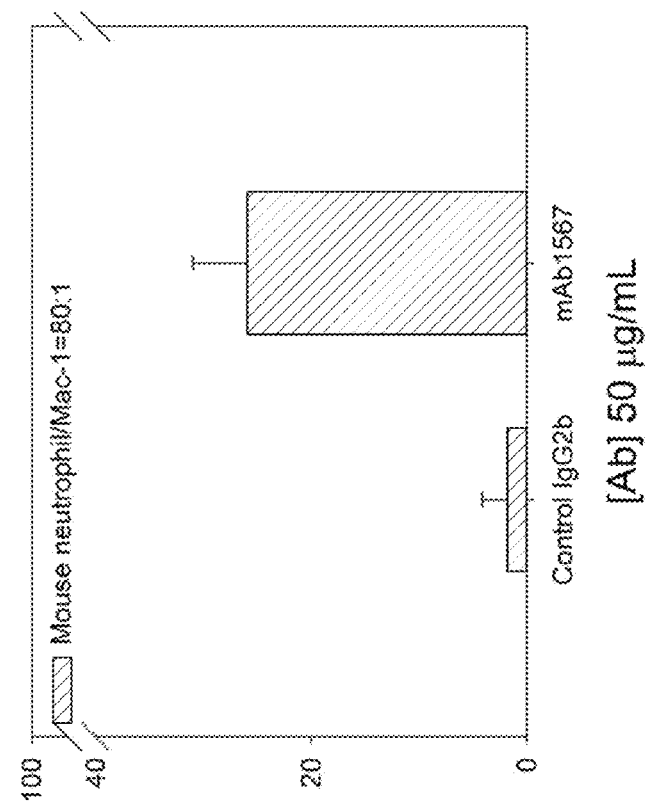

Example 3 mAb1567 Mediates Against Mac-1 Cells Both CDC in the Presence of Mouse and Rabbit Complement and Neutrophil-ADCC To further understand the mechanism underlying the anti-tumor effect of mAb1567 seen in the SCID/Beige mice, we tested if mAb1567 can mediate CDC and/or neutrophil-mediated ADCC effects against CCR4$^+$ tumor cells in vitro. MAb1567 induced a significant lysis of Mac-1 cells in a dose-dependent manner in the presence of mouse complement as compared to the mouse IgG2b isotype control antibody (FIG. 1D). Rabbit complement was also tested and mAb1567 mediated a much more potent CDC activity, reached 80% of target cell lysis (FIG. 1E). Next, neutrophils isolated from the SCID/Beige mice were tested in an in vitro ADCC assay. As shown in FIG. 1F, mAb1567 specifically mediated ~20% lysis via mouse neutrophils as compared to control at effectors/target cells (E/T, neutrophils/Mac-1) ratio of 80:1. These results show that mAb1567 can directly mediate not only CDC but also mouse neutrophil-induced ADCC activities.

Example 4

Cloning, Expression and Activity of Chimeric mAb1567

To humanize mAb1567 for further pre-clinical studies, the cDNAs encoding the heavy chain variable region (VH) and light chain variable region (VL) genes from the hybridoma cell line were individually recovered by RT-PCR using primers specific for mouse antibody variable genes. The VH and VL of mAb1567 belong to mouse V$_H$1 (IGHV1S56*01) and V$_K$8 (IGKV8-27*01) families and were rearranged with the J$_H$1 (IGHJ1*01) and J$_K$2 (IGKJ2*01) segments, respectively. The cloned rearranged VH and VL genes were then assembled as a single chain antibody variable region fragment (scFv) using a (G4S)$_3$ linker. Binding of the recombinant mAb1567 to CCR4 was verified in both scFv-Fc IgG1 minibody (c1567-scFv-Fc) (FIG. 2A) and full-length chimeric IgG1 form (c1567-IgG) (data not shown).

As NK cell-mediated ADCC is one of the most important mechanisms of action for immunotherapy with human IgG1 Abs, we further tested if recombinant mAb1567 can mediate ADCC via NK cells. Chimeric 1567 in both scFv-Fc or IgG1 forms were highly effective in killing Mac-1 cells in an in vitro ADCC assay using human peripheral blood mononucleated cells (PBMCs, FIG. 2B) or purified NK (CD56$^+$ CD16$^+$) cells (FIG. 2C) from healthy donors as effector cells at different E/T ratios.

Example 5

Humanization of mAb1567 and Related Biological Studies

Next, the structure-guided complementarity-determining region (CDR) grafting approach was employed to humanize mAb1567. Homology three-dimensional modeling of the VH and VL chains of mAb1567 using Web Antibody Modeling program (WAM) (Whitelegg N R et al. Protein Eng. 2000, 13:819-24) was generated to known antibody structures in the PDB database. For selecting the human acceptor framework template for CDR-grafting, the VH and VL amino acid sequences of mAb1567 were separately compared to human Ab sequences in the IGBLAST database to identify the most similar human Ab and Ig germline VH and VL sequences (FIG. 2D). The human VH (McAb Ctm01, PDB:lae6H) and VL (Genebank #ABG38372) share 82% and 84% amino acid sequence homology to the VH and VL of mAb1567, respectively; the best matched human Ig germline V sequences are IGHV1-3*01 (67% homology to mAb1567-VH) and IGKV4-1*01 (83% homology to mAb1567-VL). The framework residues of mAb1567 were manually changed to the selected human framework residues to generate the humanized mAb1567 (h1567). GROMOS force field energy minimization parameter was then applied to homology model h1567 using DeepView program (Daura X et al, Proteins 1996, 25:89-103). Examination of this energy minimized homology model of h1567 was performed to ensure no residues that had distorted geometry or steric clashes with other residues.

Figure 2A:
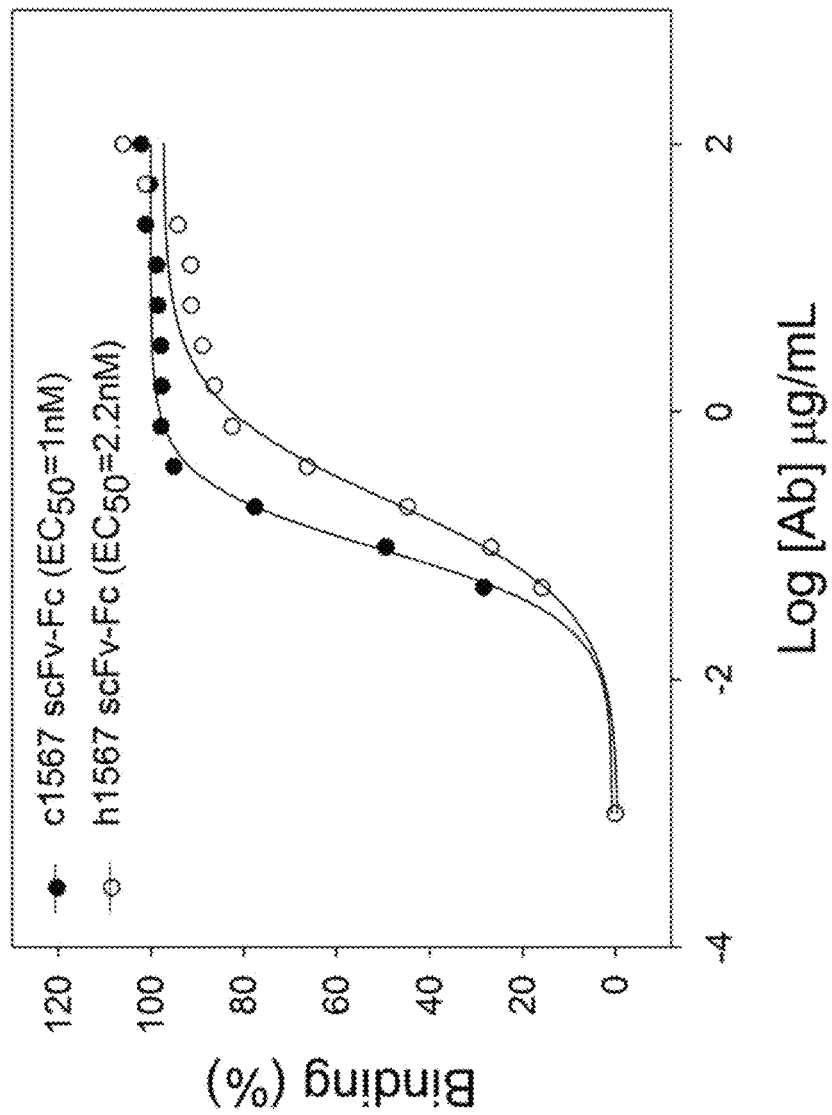
FIG. 2. Humanization of mAb 1567 and function analysis. A, Comparative binding analysis of c1567 and h1567 scFv-Fcs. The $EC_{50}$ of chimeric 1567 (c1567) and h1567 scFv-Fc are 1 nM and 2.2 nM, respectively. B and C, ADCC activity mediated by c1567 scFv-Fc. Either peripheral blood mononuclear cells (B) or NK cells (C) from healthy donors were used as effector cells and Mac-1 cells were used as target cells in the presence or absence of 1 or 5 µg/ml c1567 or control F10 scFv-Fc (50). Target cell lysis was measured either by Cr51 release (B) or LDH cytotoxicity kit (C). The data shown were calculated from triplicate wells of one experiment and are representative of three independent experiments. Bars represent mean±S.D. D, Amino acid sequence alignment of the rearranged mouse and humanized variable heavy (VH) and variable light kappa (VK) domains. The complementarity determining regions (CDRs) were boxed. Light gray scale residues indicate framework residues that were changed for humanization.
Figure 2B:
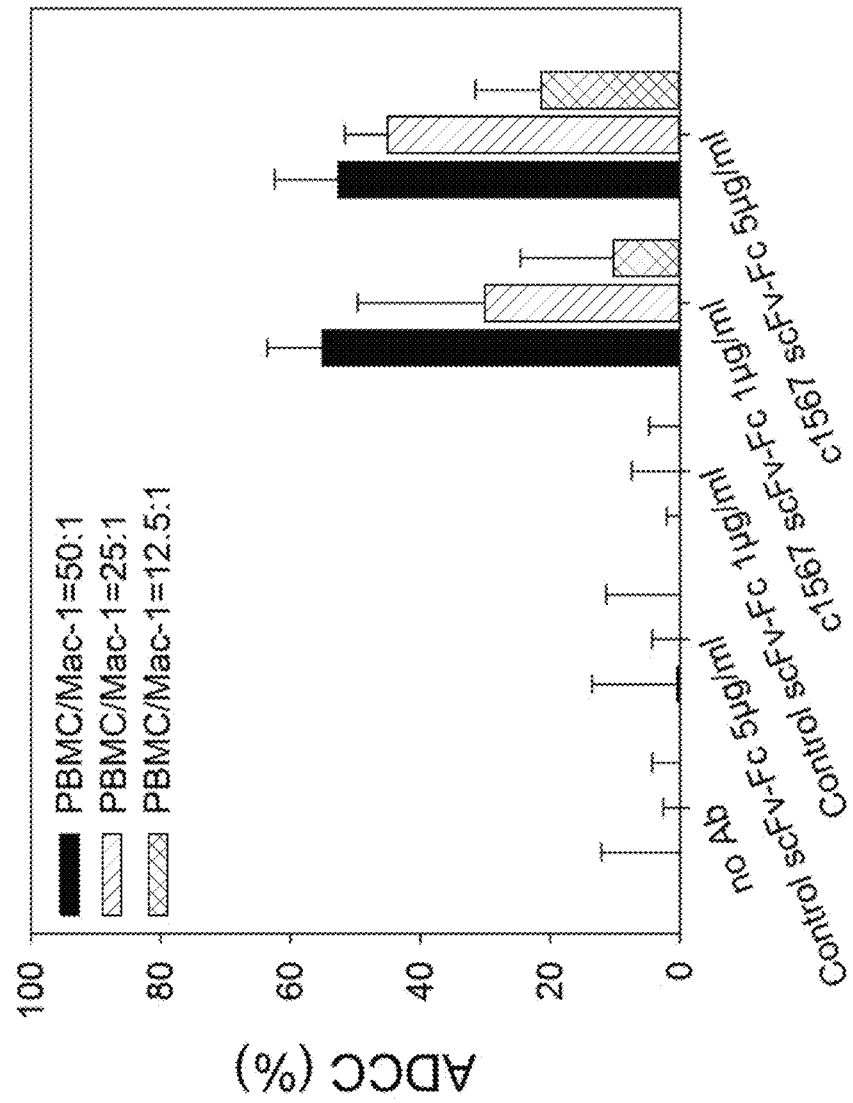
Figure 2C:
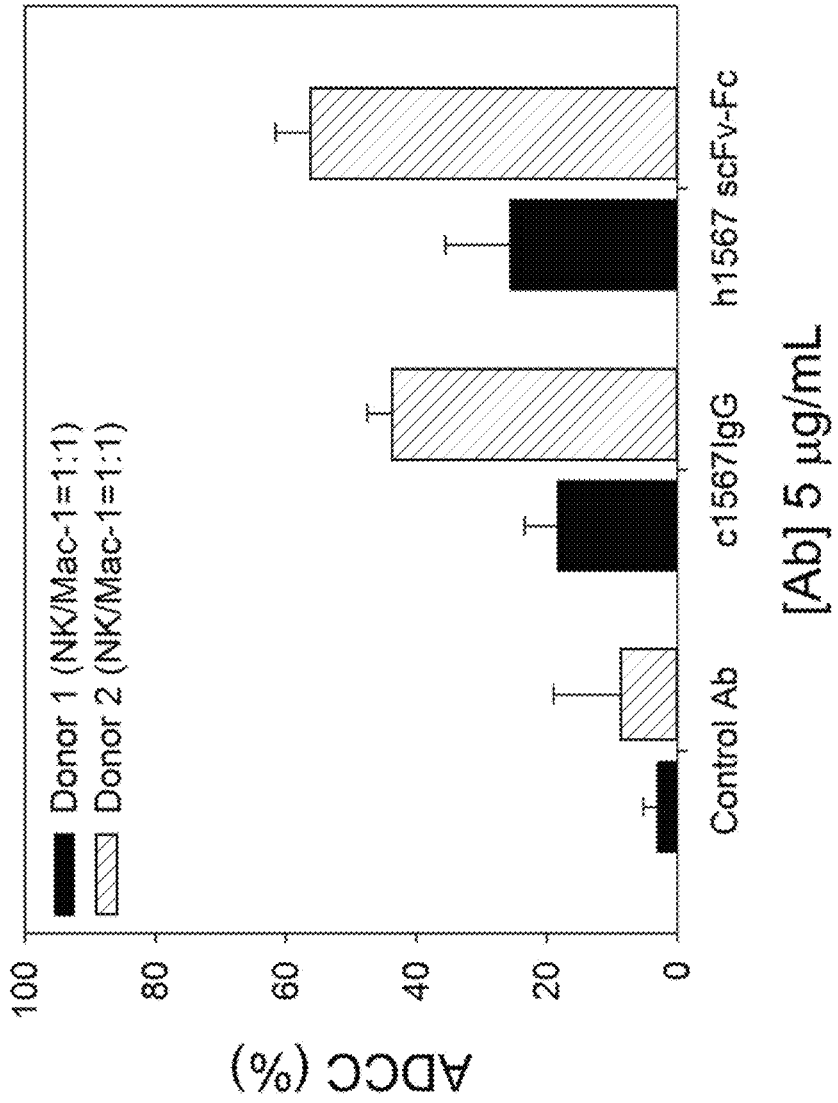

The h1567 sequence shown in FIG. 2D has 21 and 11 amino acid differences in the framework regions compared to the mouse VH and VL, respectively. The humanized VH and VL gene were de novo synthesized and codon-optimized for mammalian cell expression. The binding affinity of h1567 and c1567 scFv-Fcs to CCR4 was then compared by FACS with Mac-1 cells. The h1567 had ~2-fold decrease in binding as compared to c1567 but both are in the nanomolar range, with $EC_{50}$ of 2.2 nM and 1 nM, respectively (FIG. 2A). The humanized h1567 scFv-Fc maintained potent NK-mediated ADCC killing of Mac-1 cells compared to c1567 (FIG. 2C).

Figure 3A:
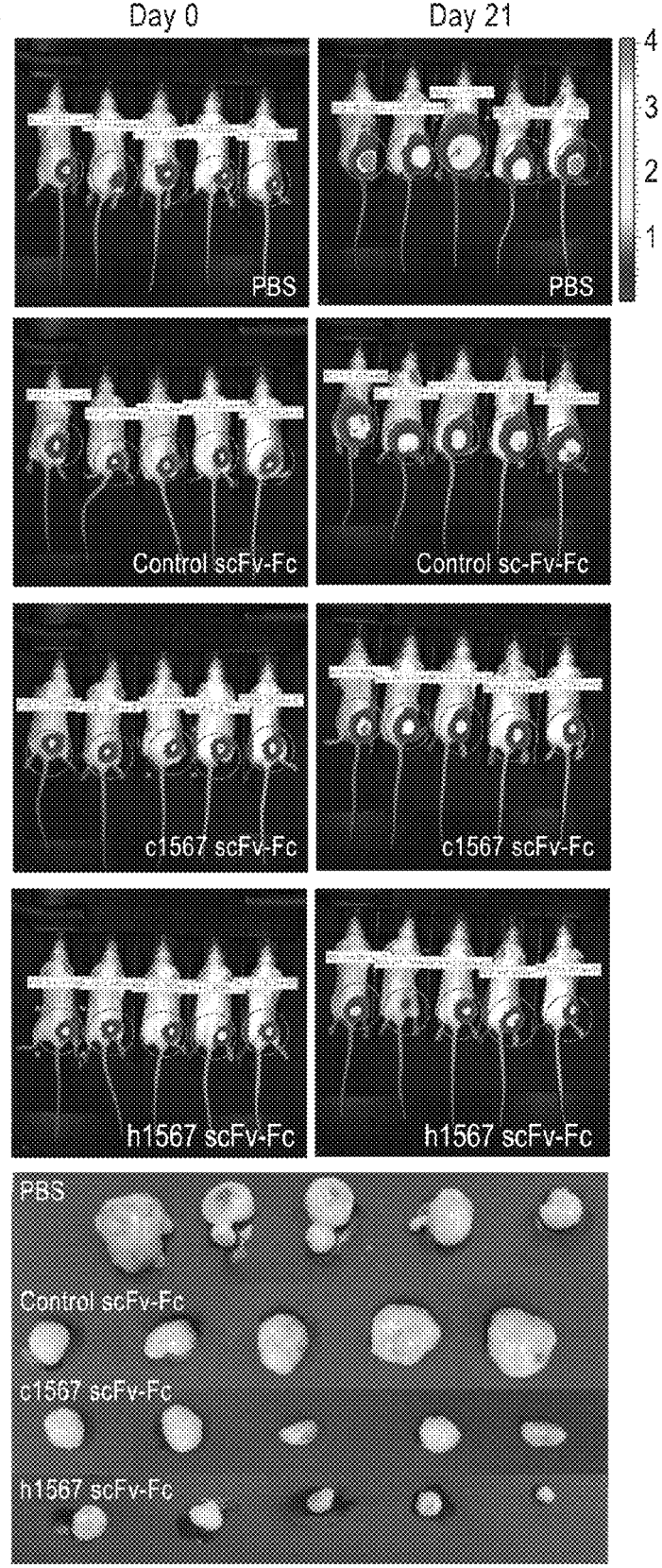
FIG. 3. Humanized 1567 in tumor treatment. A, Mac-1 cells were implanted subcutaneously (s.c.) in the dorsolateral flank of mice and imaged using an IVIS imaging system. Luciferase signal (top) and tumor size (bottom) in mice treated with anti-CCR4 antibodies. Bar scale, 1 cm. B, At selected time points after injection, tumor sizes and image intensity (C) were measured twice a week. Results are presented as mean±S.D. for each group of 5 animals. D, At the end point, the tumors were collected and weighed.
Figure 3C:
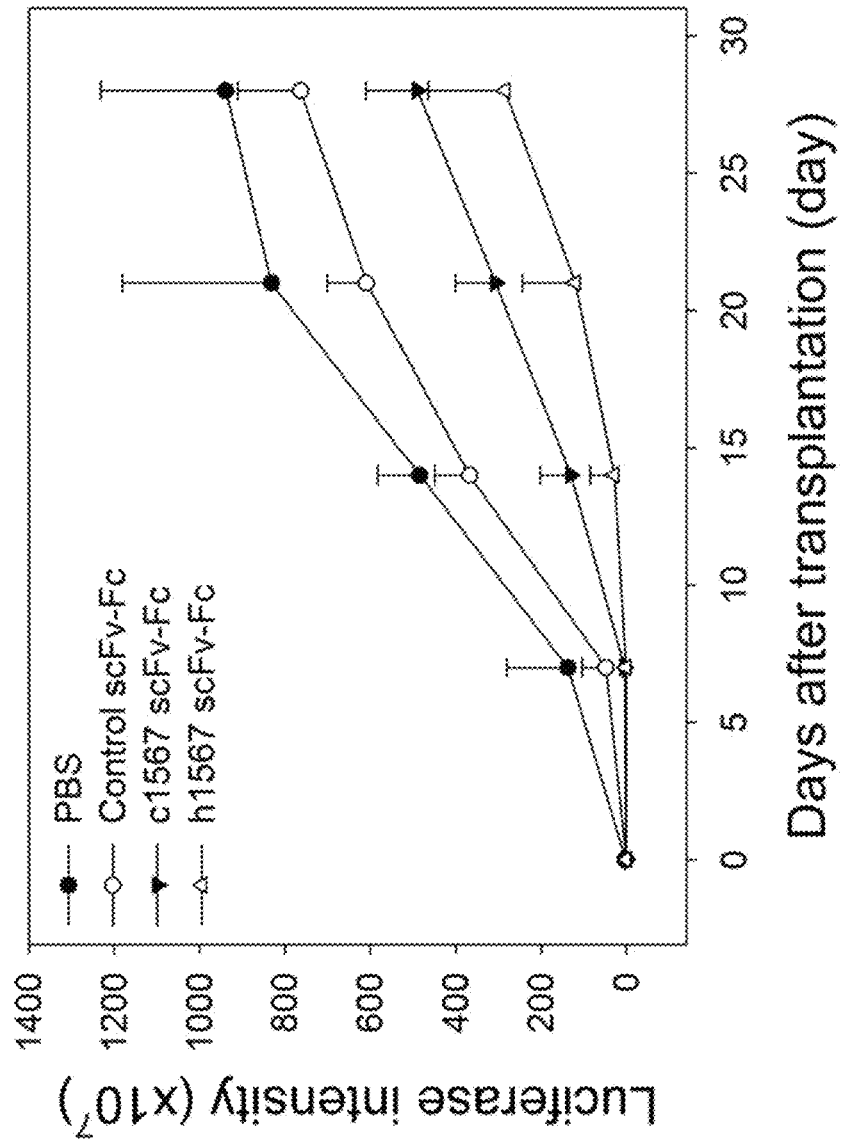

To test the in vivo anti-tumor effect of the h1567, the luciferase expressing Mac-1 cells were subcutaneously implanted into the dorsolateral flank of SCID/Beige mice, and mice were treated with 5 mg/kg of control-scFv-Fc, c1567-scFv-Fc, h1567-scFv-Fc or equivalent volumes of saline by intraperitoneal (i.p.) injection. Tumor growth in mice was monitored for luciferase intensity by IVIS imaging. All mice were sacrificed on day 28 and tumors were excised for photographing and measuring tumor weight. As shown in FIG. 3, tumors were significantly reduced in size at day 21 in the c1567 and h1567 treated groups but not in the control-scFv-Fc or PBS treated groups as measured by IVIS imaging (FIGS. 3A-top and C), size of the excised tumors (FIG. 3A-bottom), tumor volume (FIG. 3B) and tumor weight (FIG. 3D).

Example 6

ADCC and CDC Activities of Higher-Affinity H1567 Variants

Figure 7D:
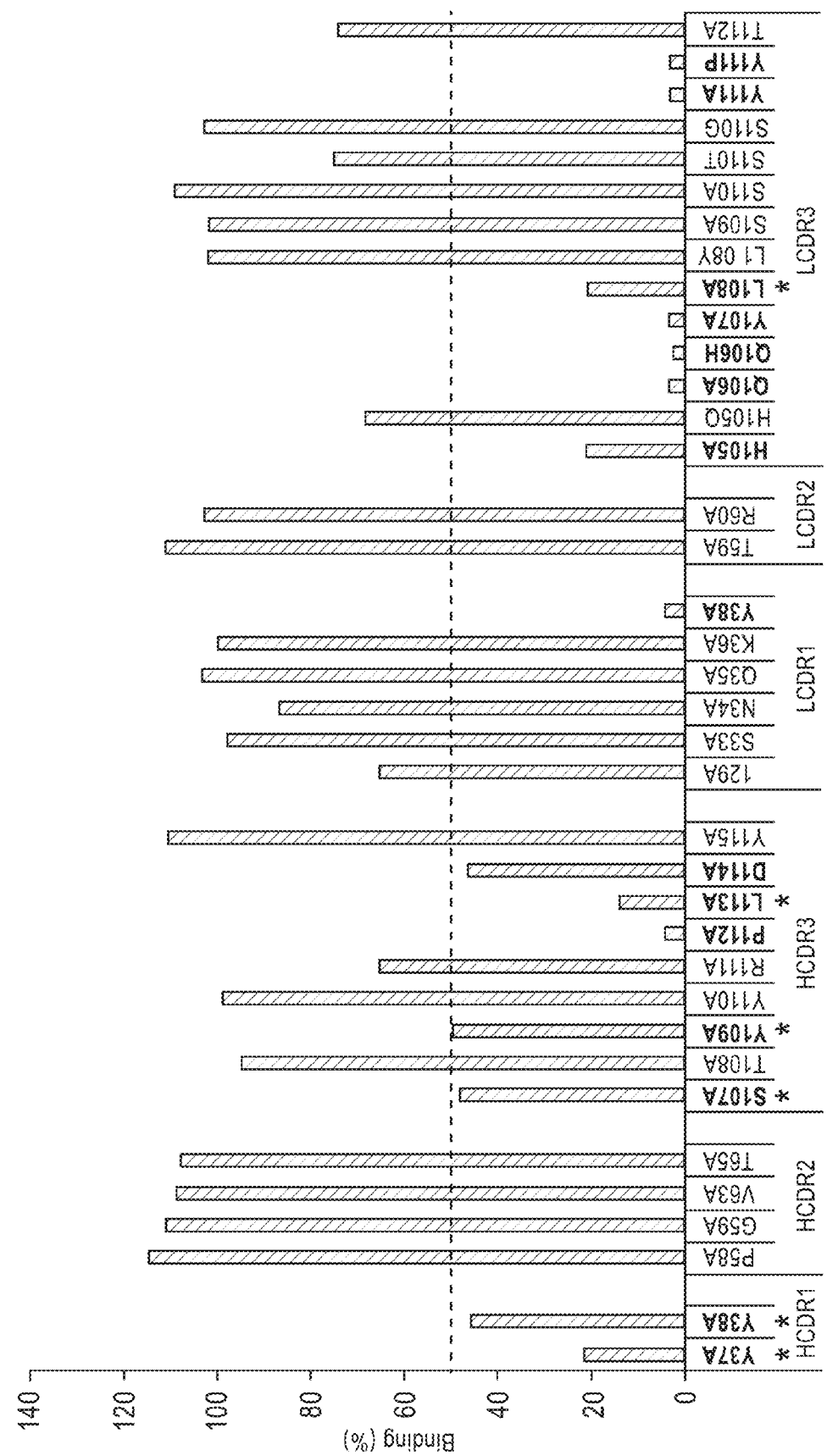
Figures 7E, 7F:
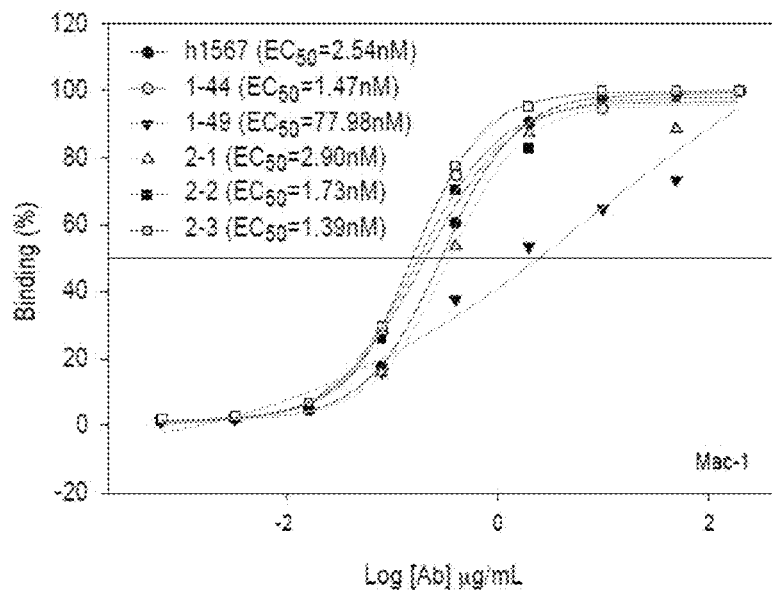

Although the h1567 exhibited similar biological activity as its murine counterpart in both in vitro and in vivo, the relative apparent binding affinity of h1567 is 2-fold lower than c1567 (FIG. 2A). In order to further affinity mature the h1567 mAb, we performed VL-chain shuffling and alanine scanning to identify key residues in CDRs, followed by selection and screening of phage display library constructed by random mutagenesis of key residues in the CDRs (FIG. 7 for details).

Figure 4B:
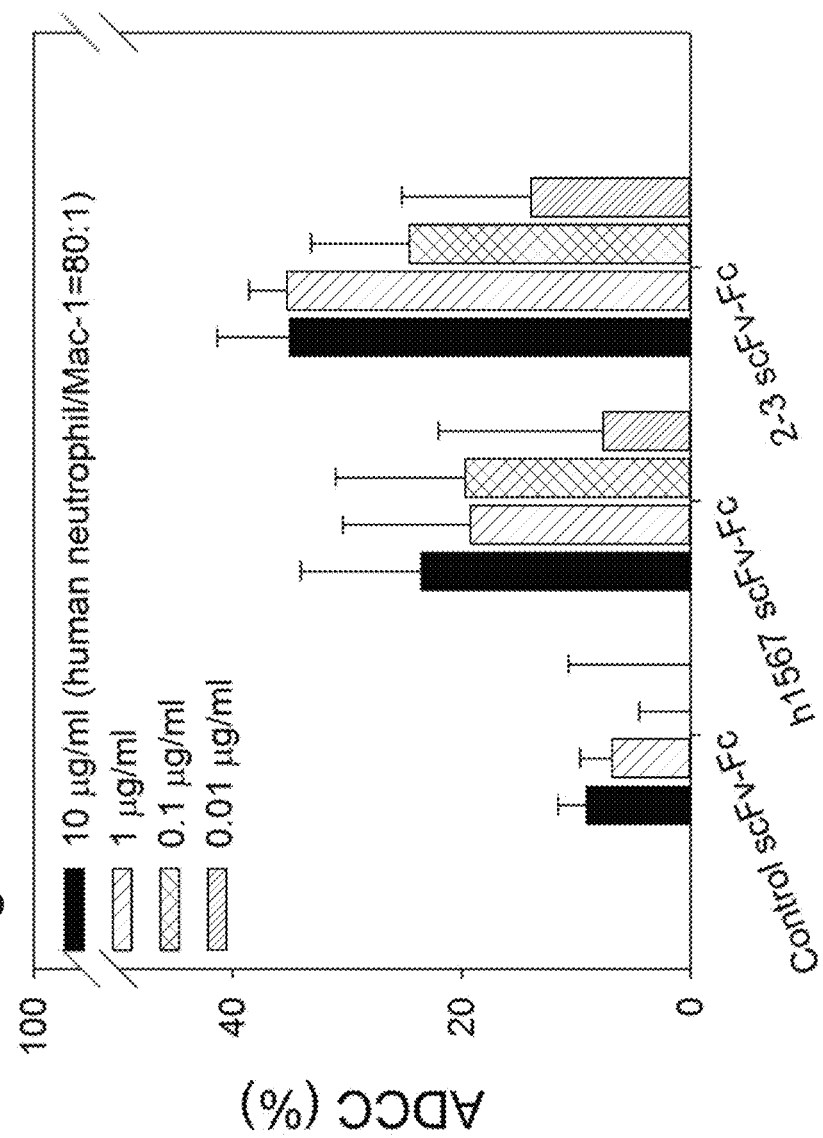
FIG. 4. Humanized 1567 variants with improved binding affinity, ADCC and CDC activity. A, ADCC activity on Mac-1 cells. h1567 and its variants 1-44 and 2.3 were tested at concentration of 5 µg/mL. Human NK cell to target cell ratio was at 1:1. Data shown in the box and whiskers graph represent three independent experiments and each was performed with NK cells from a different healthy donor; the box extends from lowest percentile to the highest percentile, with a line at the median. The whiskers above and below the box indicate the 95th and 5th percentiles. B, ADCC activities on Mac-1 cells with human neutrophil to target cell ratio of 80:1. C, CDC activity of h1567, 1-44 and 2-3 variants against Mac-1 cells. D, Similar to panel B except antibodies were tested at different concentrations using human NK cells purified from a single donor. ScFv-mFc are Abs with engineered triple mutations in the Fc to improve ADCC activity. "*" and "**" indicate p<0.05 and p<0.01, respectively using Student's t test to compare differences between h1567 wild type and it's variants (lower symbols) and between 1567 variants and their mFc mutants [upper bracketed symbols]. E, CDC of wild-type Fc antibodies (h1567, 1-44, and 2-3 scFv-Fcs) and mutant Fc antibodies (1-44 and 2-3 scFv-mFcs) against Mac-1 cells. For panel A-E, results shown are from one of three representative experiments, data are derived from triplicates samples in each experiment. Bars represent mean±S.D.
Figure 4C:
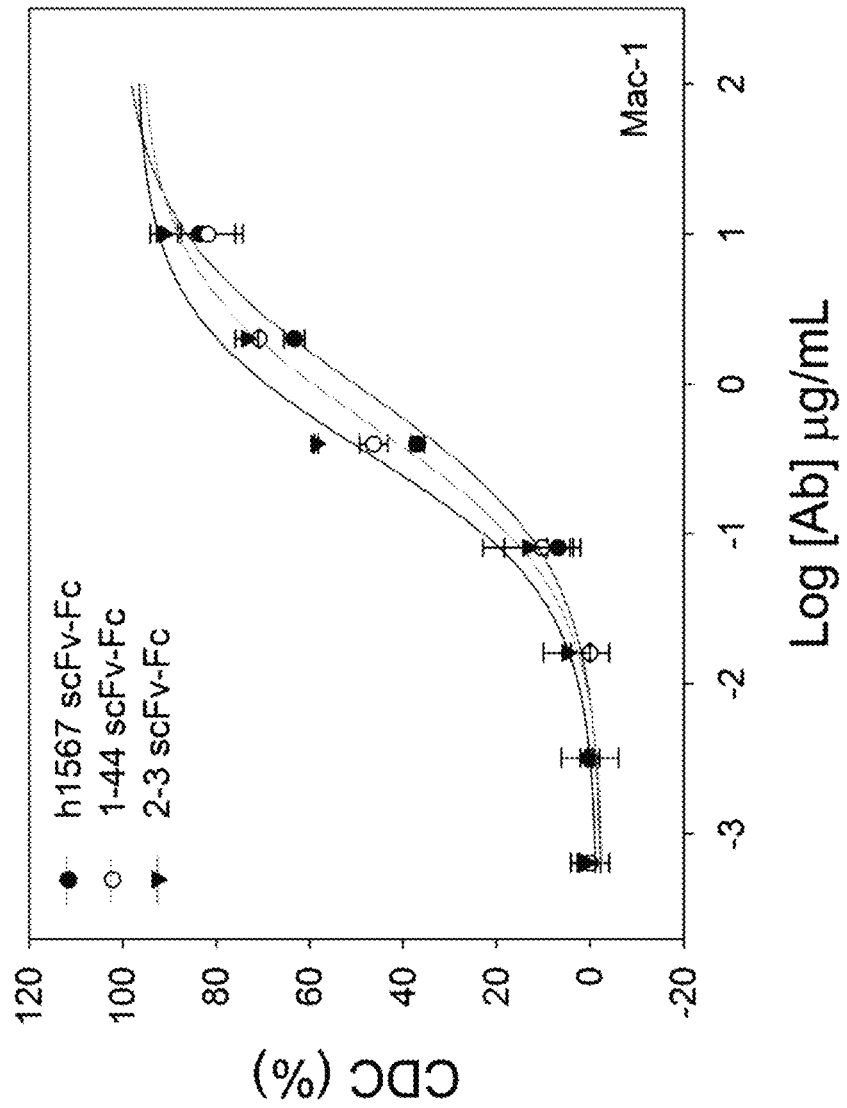
Figure 8B:
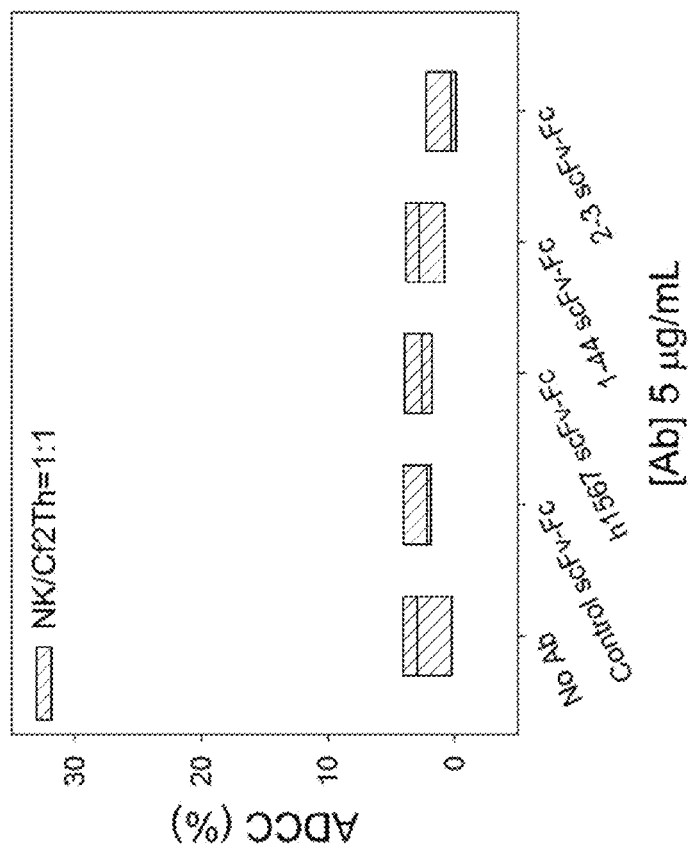
Figure 8A:
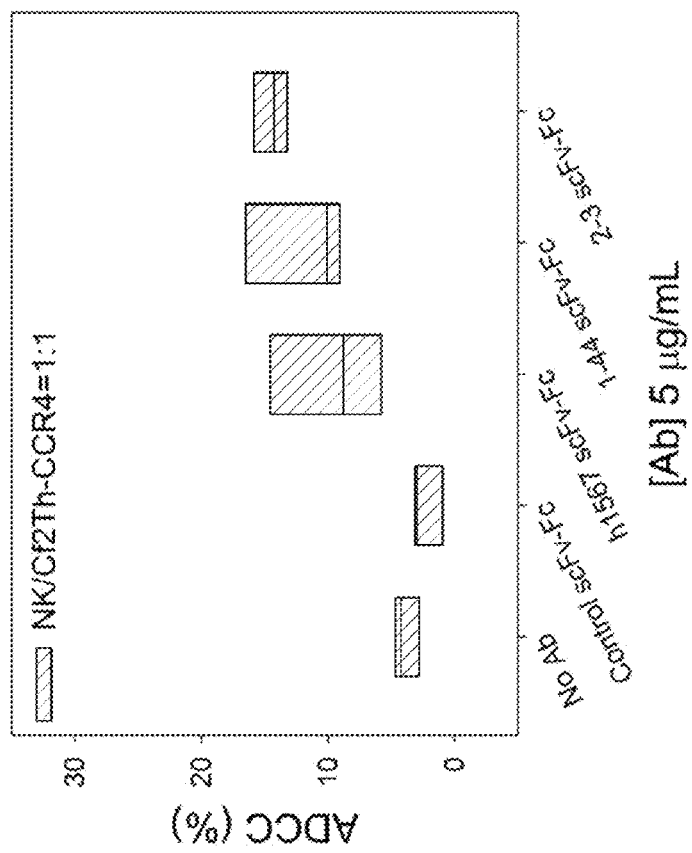

The two affinity improved h1567 variants, mAb 1-4 and 2-3 that showed higher binding affinity to Mac-1 cells that parental h1567 with $EC_{50}$ of 1.47 and 1.39 nM, respectively (FIG. 7F), were further evaluated for their capacity to mediate ADCC activity using human NK cells as effector cells. The result showed that the improvement in ADCC activity of the h1567 variants is correlated with their binding affinity, 2-3-scFv-Fc exhibited the best human NK-mediated ADCC activity for both Mac-1 cells (FIG. 4A) and Cf2Th-CCR4 cells but not to negative control Cf2Th (FIG. 8). Moreover, since parental mAb1567 could induce mouse neutrophil-mediated ADCC, h1567 and 2-3 were tested for human neutrophil-mediated ADCC assay and mAb2-3 showed enhanced cytotoxic activity (FIG. 4B) compared with h1567. Furthermore, slightly improved CDC activity against Mac-1 cells was also observed for both 1-44 and 2-3 variants, but more for the 2-3-scFv-Fc (FIG. 4C).

Figure 4D:
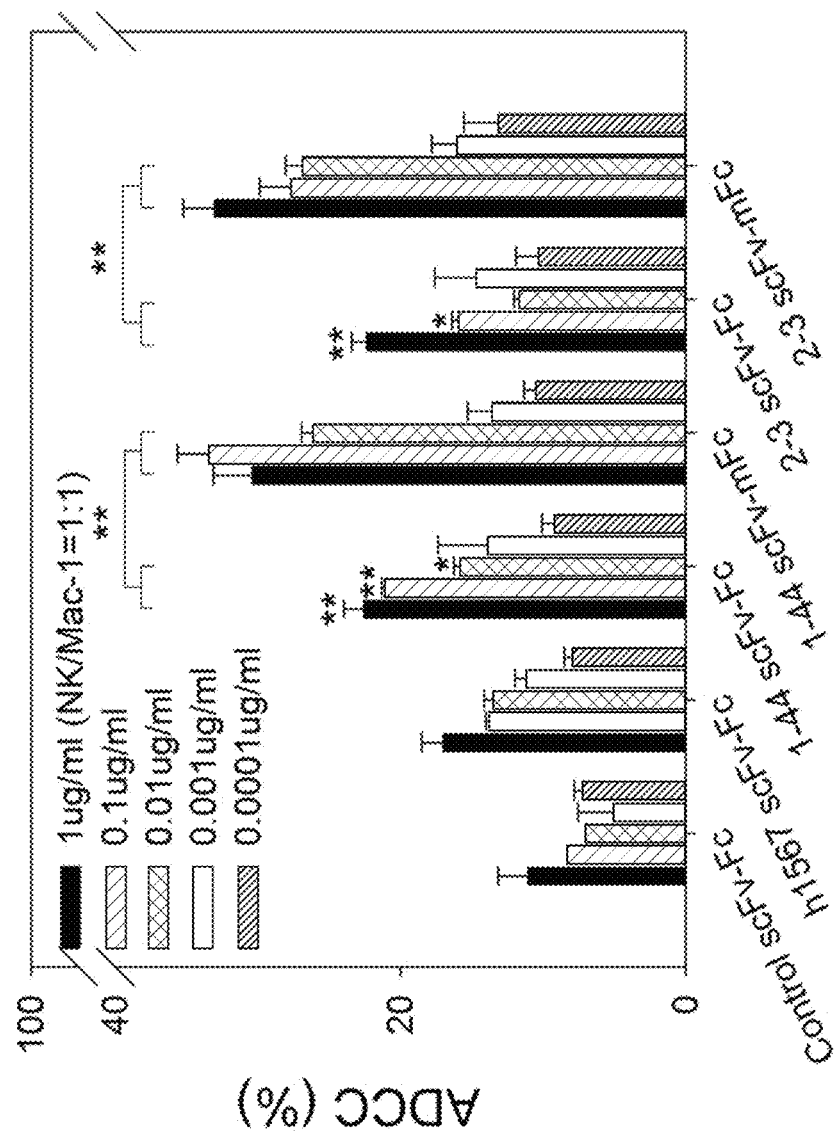
Figure 6B:
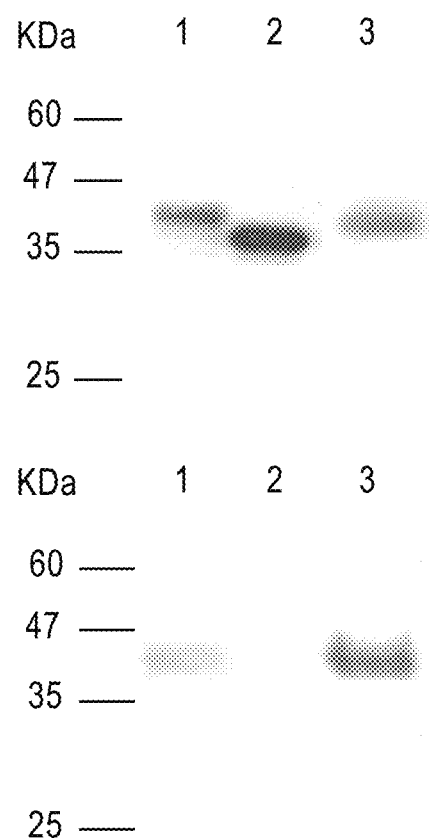
FIG. 6. Epitope mapping of mAb1567. A, The $NH_2$-terminal extracellular domains of human CCR4 and CCR8 were swapped as indicated and designated as Chimera #1 and #2 (Chi#1 and Chi#2). The chimeras as well wild type human CCR4 and CCR8 were transiently transfected into 293T cells and tested for binding with murine mAb1567. Similar level of surface expression of these receptors was validated by detecting the N-terminal haemagglutinin (HA) tag using anti-HA antibody. B, Expression of human CCR4 N-terminal with Fc domain fusion protein (CCR4Nt-Fc). 293T cells expressing hCCR4Nt-Fc fusion protein were labeled with [$^{35}$S]-cysteine and [$^{35}$S]-methionine (upper panel) or [$^{35}$S]-sulfate (lower panel). Culture supernatant containing secreted proteins were immunoprecipitated with protein A sepharose beads and applied to SDS-PAGE reducing gel for analysis. Lane 1 and 2, wt or DDDD mutant version of CCRSNt-Fc where 4Y's at positions 3, 10, 14 and 15 which undergo tyrosine sulfation are changed to D; lane 3, wt CCR4Nt-Fc. The lower panel shows tyrosine sulfation of Nt-tyrosine residues in CCR5-Nt (lane 1) and CCR4-Nt (lane 3) but not the CCR5-Nt DDDD mutant (lane 2). C, Silver staining of secreted CCR4Nt-Fc on non-reducing and reducing gel showed the presence of dimeric and monomeric protein, respectively. D, Three different fusion proteins, control protein-Fc (CtrlP-Fc), CCR5Nt-Fc and CCR4Nt-Fc, and Bovine serum albumin (BSA) were tested the binding ability to mAb1567 at three different concentrations (0.25, 0.5 or 1 µg per well) and detected by HRP-anti-human Fc IgG using an ELISA reader. E, Flow cytometry graphs that indicate the binding of Ab2-3 and anti-CCR5 antibodies to CCR4-Cf2 and CCR5-Cf2 cells.
Figure 6C:
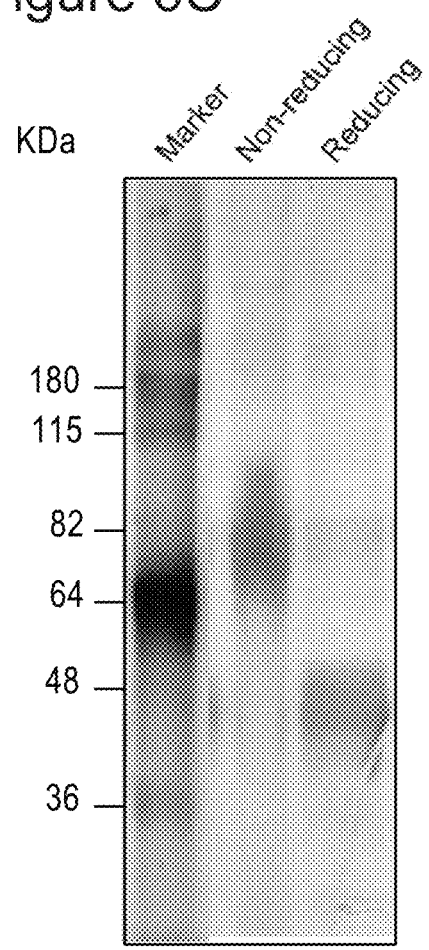
Figure 6D:
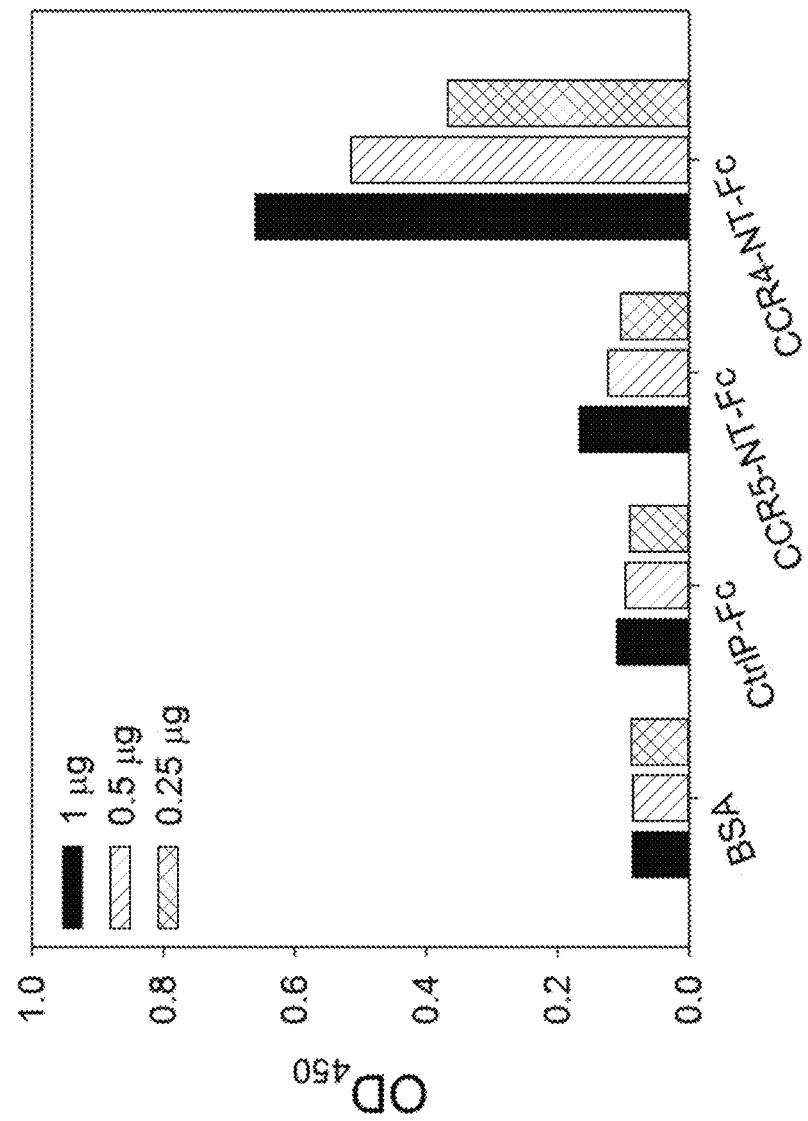

Fc engineering was also performed on mutant Abs 1-44 and 2-3 to further enhance ADCC activity by mutating three residues (S239D, A330L and I332E) in CH2 domain, which have been shown to increase human IgG1 antibody's ADCC effect (Carter PJ. Nat Rev Immunol 2006, 6:343-57). As shown in FIG. 4D, ADCC mediated by 1-44- and 2-3-scFv-mFcs was significantly enhanced as compared to their wild type Fc counterparts or the wild type h1567. However as the A330L mutation in the Fc domain can ablate CDC function (Lazar G A et al. Proc Natl Acad Sci USA 2006, 103:4005-10), we also tested and confirmed that CDC activity for the scFv-mFcs forms of 1-44 and 2-3 scFv-mFcs was completely abolished (FIG. 4E). Taken together, the affinity optimized variants of humanized 1567, in particular the 2-3 variant, demonstrated improved ADCC and CDC effector functions, and NK cell-mediated ADCC activity can be further enhanced through Fc engineering.

Example 7

1567 Inhibits Tregs Chemotaxis and Partially Abrogates Tregs' Suppressive Activity In Vitro Finally, as the majority (94%) of freshly isolated $CD4^+$ $CD25^{high}$ Tregs from peripheral blood express high level of surface CCR4 (Hirahara K et al. J Immunol 2006, 177:4488-94; Baatar D et al. J Immunol 2007, 178:4891-900) and they have been reported to migrate to tumors secreting CCL22 (34), we investigated whether Ab1567 could have an anti-tumor role by modulating the chemotactic recruitment and suppressive activity of human CD4+ Tregs. First, we confirmed that $CD4^+CD25^{high}$ Tregs migrated toward CCL22 much more effectively than $CD4^+CD25^-$ T cells (FIG. 5A). Next, using peripheral blood $CD4^+$ T cells in combination with examining the Treg phenotype of the migrated cells, we confirmed that c1567 completely inhibited the migration of $CD4^+CD25^{high}$ Tregs in a transwell chemotaxis assay at concentrations greater than 2 μg/mL (FIG. 5B).

Analysis of chemotaxis after treatment with mAb2-3 or other anti-CCR4 antibodies of the present invention can be determined as described above.

In addition, as we are unaware of any published data on the role of CCR4 in $T_{reg}$ function, we also examined whether 1567 engagement of CCR4 could result in modulation of Treg suppression activity in an in vitro $T_{reg}$ suppression assay. As shown in FIG. 5C, the proliferation of $CD4^+$ T effector cells ($T_{eff}$ alone, lane 1) was inhibited by highly purified $CD4^+CD25^{high}$Tregs (1:1 ratio) by 81% (lane 3), which is a typical $T_{reg}$ suppression effect on $T_{eff}$ cells. Surprisingly, in the presence of c1567IgG, the proliferation of $T_{\mathit{eff}}$ was stimulated to 142% (lane 4) but there was no stimulatory effect on $T_{reg}$ (lane 5). In the $T_{reg}/T_{\mathit{eff}}$ co-culture (1:1 ratio), the proliferation of $T_{\mathit{eff}}$ was partially restored to 72% in the presence of c1567 (lane 7) but not by control mAb (lane 6). Moreover, in the $T_{reg}/T_{\mathit{eff}}$ coculture (0.5:1 ratio) (lane 8) T cell proliferation was restored with a net positive response to 187% (lane 9). These results suggest that restoration of $T_{\mathit{eff}}$ proliferation by c1567 may in part be due to a direct effect on $T_{\mathit{eff}}$ proliferation, however, it is likely that c1567 can also abrogate the suppressive activity of $T_{reg}$ by a mechanism that is presently unknown.

Example 8

In Vitro and In Vivo Expression of AAV8-Encoding Anti-CCR4 H1567

A modified scFvFc minibody format was used as the antibody moiety in the AAV8 vector, in which the V domains of heavy (VH) and light (VL) chains of the humanized scFv h1567 were fused to the coding region of the hinge and constant domains 2 and 3 (CH2 and CH3) of the human IgG1 heavy chain, to yield bivalent binding to the target molecule hCCR4 (FIG. 9a) The resulting recombinant AAV8 vector was used for both in vitro protein synthesis and virus production for in vivo antibody gene delivery. In a pilot dosing study, nude mice received a single injection of two different concentrations of AAV8-h1567 via intravenous tail vein injection. Serum h1567 minibody levels were followed for 15 weeks. H1567 minibody levels rose for the first 2-3 weeks, reaching levels of circa 65 and 96 ug/ml for the low ($0.8 \times 10^{11}$ vg/mouse) and high ($2.0 \times 10^{11}$ vg/mouse) vector doses, respectively and then through the remaining weeks of the study leveled off at near peak levels for the high dosed vector and circa ⅓rd that level (~35 ug/ml) for the low dosed vector (FIG. 13). Because $2 \times 10^{11}$ vg per mouse gave higher serum levels of h1567, this vector concentration was used in the subsequent in vivo studies.

Figure 9B:
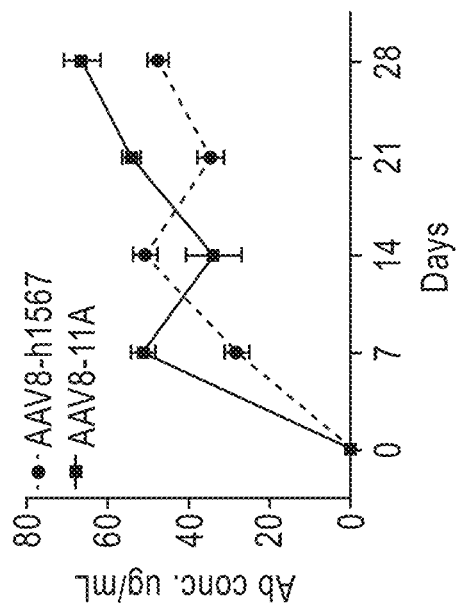
Figure 9A:
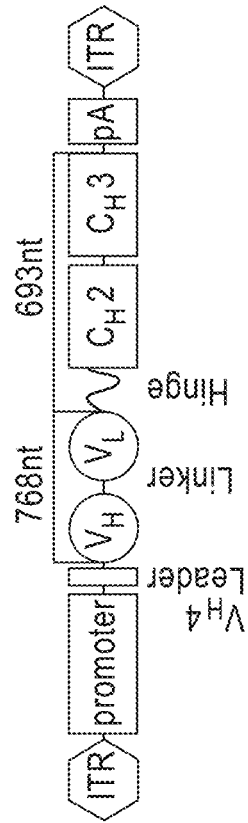
Figure 9C:
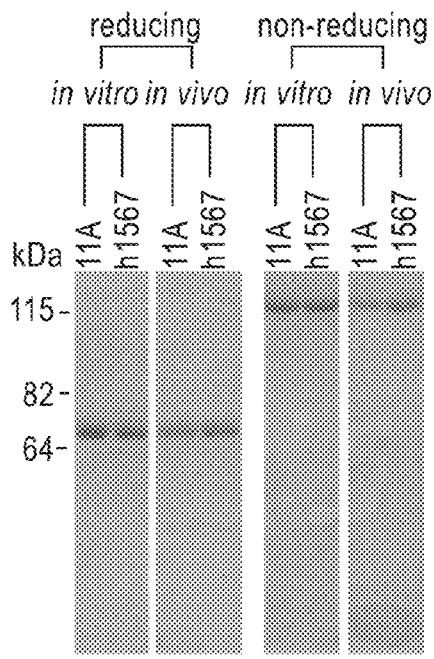
Figure 9D:
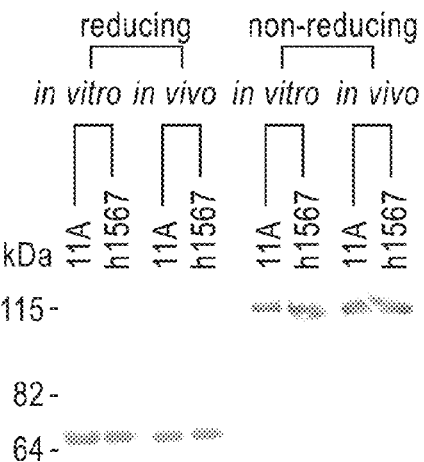

CCR4+ Mac-1 tumor cells grow well in SCID-BEIGE mice and therefore we established a SCID-BEIGE/Mac-1 xenograft tumor model to evaluate the efficacy of AAV8-h1567 therapeutic minibody gene transfer. In SCID-BEIGE mice treated with a single intravenous tail vein injection of the AAV8 vectors, a time-dependent increase in serum concentrations of the control 11A and h1567 minibodies, reaching steady state levels of circa 50 ug/ml after 7-14 days and remaining at those peak levels through day 28, the last day of the study (FIG. 9b). To determine whether the AAV8-minibody transduction in vivo could result in production of properly folded scFvFc, protein A-purified minibodies recovered from serum of SCID-BEIGE mice three weeks following intravenous delivery of AAV8 vectors were analyzed by sodium dodecyl sulfate polyacrylamide gel electrophoresis (SDS-PAGE) and Western blotting. As shown in FIG. 9c, when examined under reducing conditions, the 11A and h1567 minibodies recovered from both in vitro and in vivo sources showed bands at the expected size for scFvFc, circa 60 kD. Analysis under non-reducing conditions showed dimer formation (mol wt circa 120 kD), thereby confirming that the minibodies were divalent in vitro and in vivo (FIG. 9c). In addition, the ease of recovery of the AAV8-derived minibodies from serum using affinity purification on protein A, their reactivity on Western blot with the anti-human Fc antibody, and their stable dimer formation confirms the proper folding and structural integrity of their CH2-CH3 domains (FIGS. 9c and 9d).

Example 9

Figure 9E:
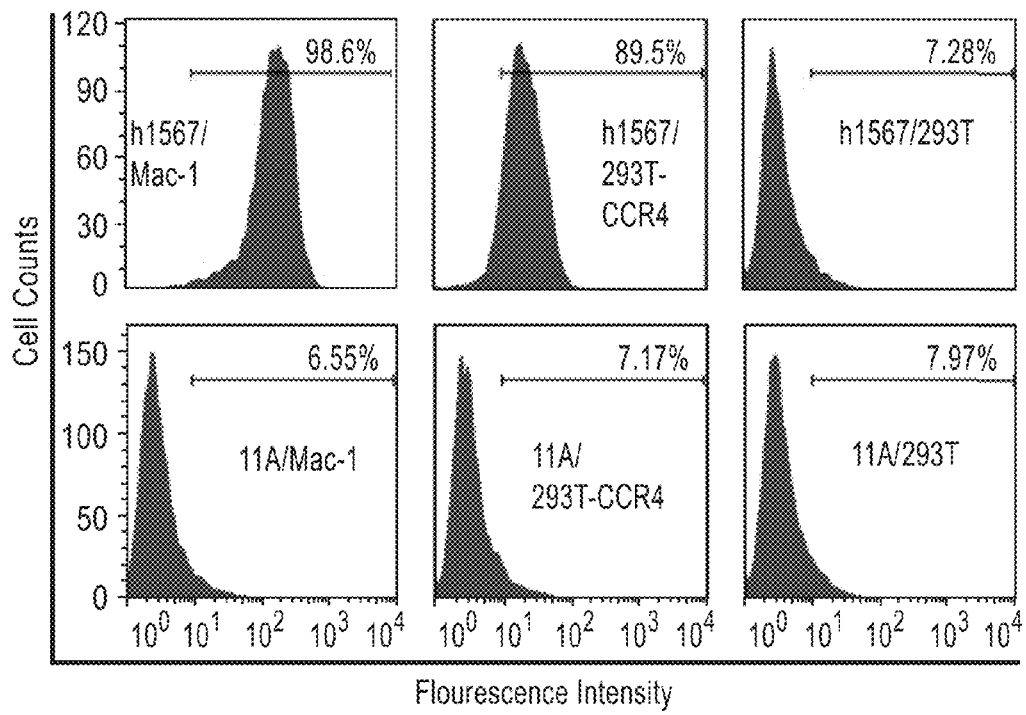

Binding Activity of H1567 Minibody in Serum Following AAV8-Mediated Gene Transfer To determine the functional integrity of the AAV8-derived scFvFc minibodies, sera obtained from mice 14 days after in vivo AAV8 transduction were examined for the level of binding to CCR4 by flow cytometry. As shown in FIG. 9e, the secreted h1567 minibody in the mouse serum could specifically bind to the CCR4$^+$ Mac-1 cells and CCR4$^+$293T cells but not to parental 293T cells, indicating that the scFv domain was correctly folded and that it retained full antigen-binding activity. Irrelevant 11A minibody (directed against SARS Spike protein), which served as a negative control, did not bind to CCR4-expressing cells (Sui J et al. PLoS pathog 2008, 4:e1000197).

Example 10

Treatment of Pre-Established Tumor-Bearing Mice with AAV8-H1567

Figure 10B:
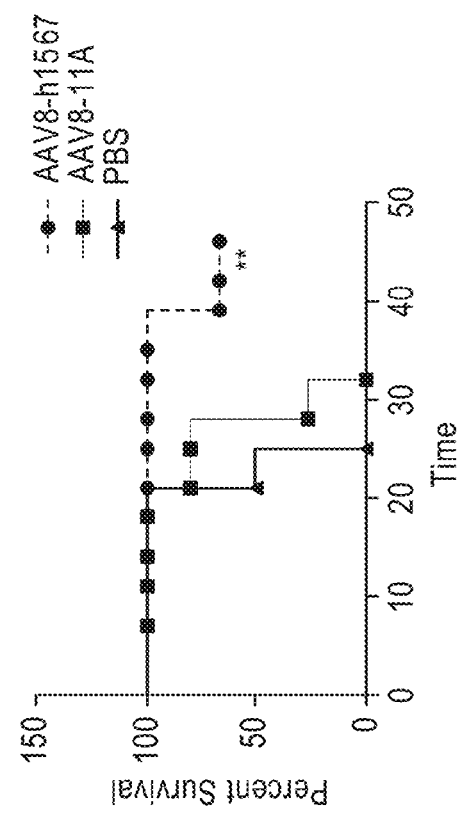
Figure 10A:
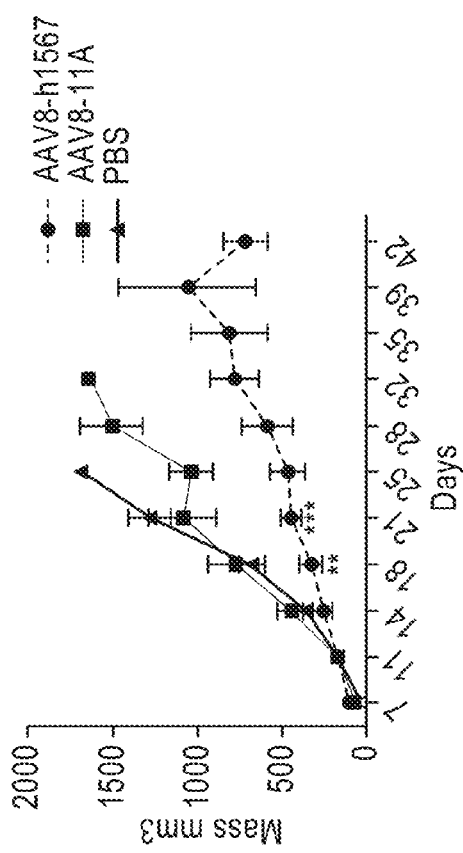

The therapeutic effects of AAV8-h1567 gene transfer were next evaluated in vivo in SCID-BEIGE mice that carried subcutaneously implanted Mac-1 tumor xenografts. Groups of 4 mice were given a single intravenous injection of AAV8-h1567 or control AAV8-11A vector on day 7 after tumor inoculation and tumor volume was assessed twice weekly. As shown in FIG. 10a, a single injection of AAV8-h1567 resulted in significantly reduced tumor growth compared with AAV8-11A treated mice or PBS control treated mice ($P<0.01$ at day 18, $P<0.0005$ at day 21). Mouse survival was monitored for up to 2 months. Tumor-bearing mice treated with AAV8-h1567 significantly outlived ($P<0.005$) mice treated with AAV8-11A or untreated mice (FIG. 10b).

Example 11

Mechanisms of Tumor Cell Killing by H1567 in SCID-Beige Mice

Figure 10E:
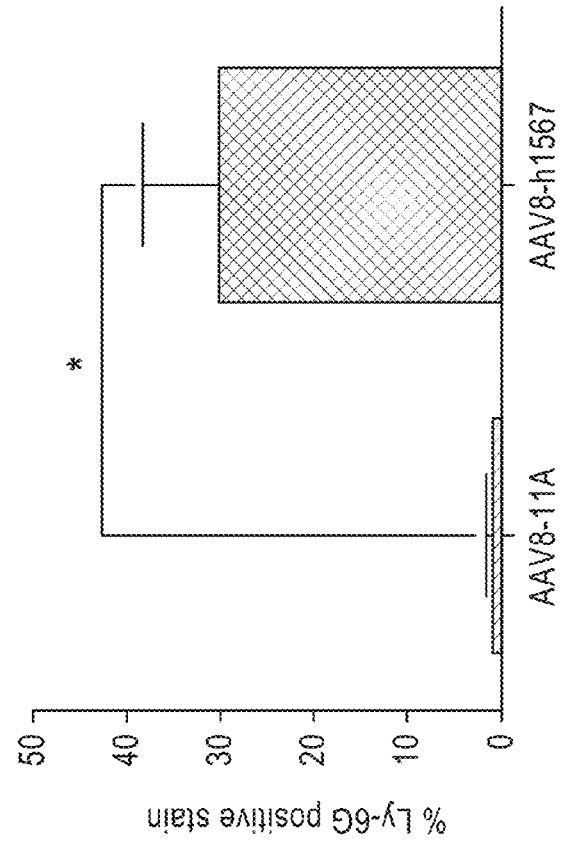
Figure 10D:
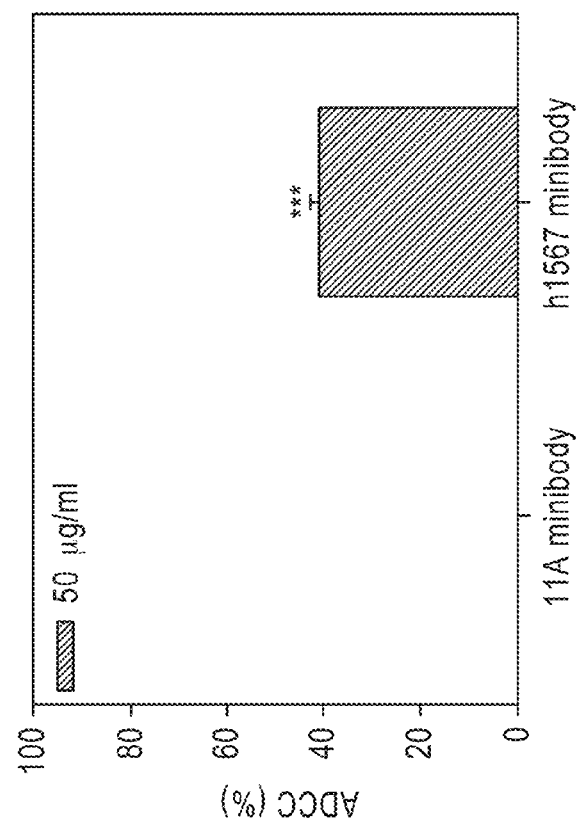

Since SCID-BEIGE mice lack T and B lymphocytes as well as functional natural killer (NK) cells, it is possible that the CCR4$^+$ Mac-1 tumor cells were eliminated by h1567 through neutrophil-dependent ADCC as neutrophils are intact in SCID-BEIGE mice and they express FcγRIIIA receptors which have been shown to mediated ADCC (Selvaraj P et al. Immunol Res 2004, 29:219-230; Siders W M et al. Leuk Lymphoma 2010, 51:1293-1304). Tumor sections were excised 21 days after AAV8 gene transfer and analyzed histologically for expression of Ly6G, a member of the Ly-6 family of glycosyl-phosphatidylinositol (GPI)-anchored proteins expressed on murine neutrophils (Fleming T J et al. J Immunol 1993, 150:5379-5390). Immunostaining of tumors sections with neutrophil-specific Ly-6G mAb confirmed infiltration of neutrophils into tumors treated with AAV8-h1567 (FIG. 10c, upper-left and middle panels) but not with AAV8-11A (FIG. 10c, lower-left and right panels). Quantification of the neutrophil infiltration demonstrated a marked accumulation of Ly-6G+ staining cells only in the 1567 treated mice (FIG. 10d).

To further assess the h1567-mediated, mouse neutrophil-dependent tumor cell killing, in vitro ADCC assay was carried out using purified SCID-BEIGE mouse neutrophils and h1567 minibody. Coculturing Mac-1 cells with mouse neutrophils in the presence of h1567 at the effector to target ration of 80:1 resulted in significant neutrophil-mediated ADCC as measured by lactate dehydrogenase (LDH) release from Mac-1 cell (FIG. 10e). Control 11A minibody was not able to induce neutrophil-mediated cytotoxicity. These in vitro results correlate with the observed anti-tumor activity in vivo and suggest that the antitumor activity of the h1567 minibody in this CTCL murine model is mediated, at least in part, through Fcγ receptor IIIA (CD16A) engagement on mouse neutrophils to induce ADCC effector functions.

Example 12

Figure 11B:
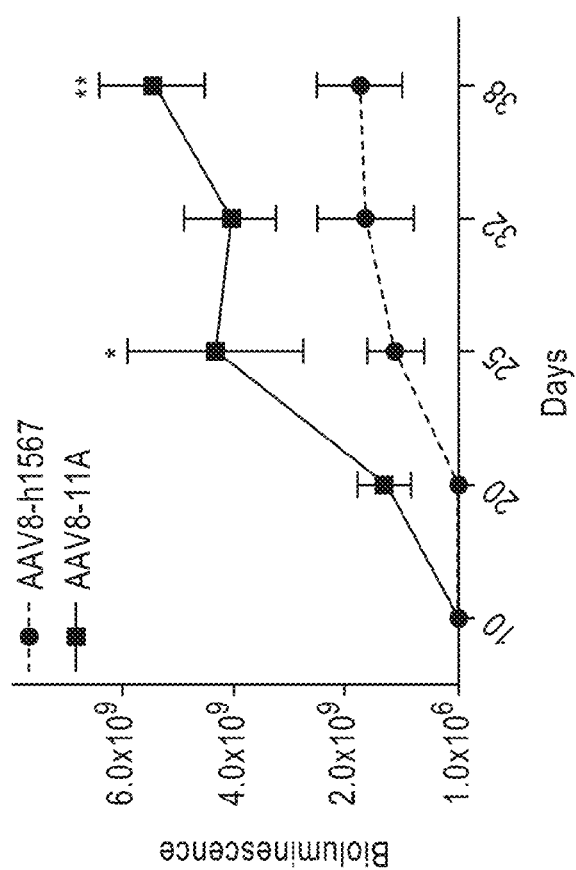
Figure 11A:
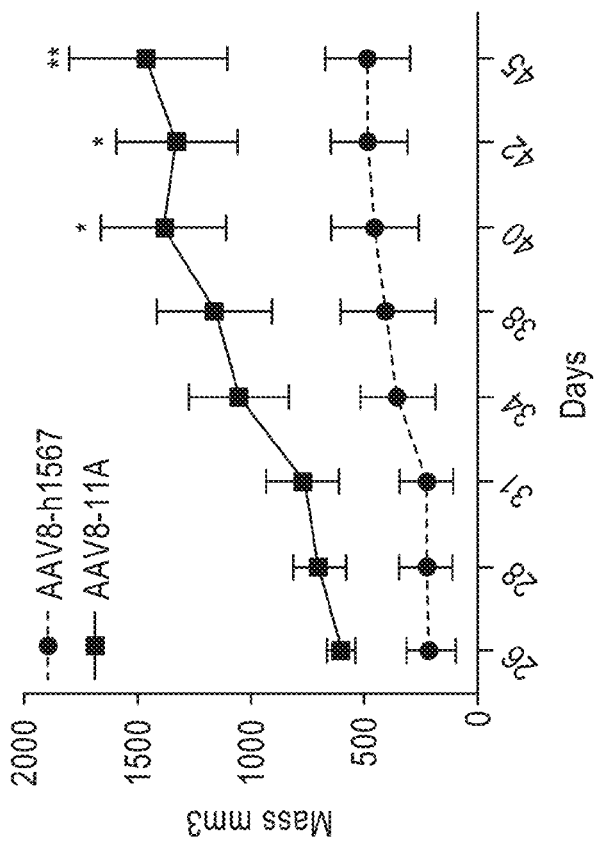
Figure 11D:
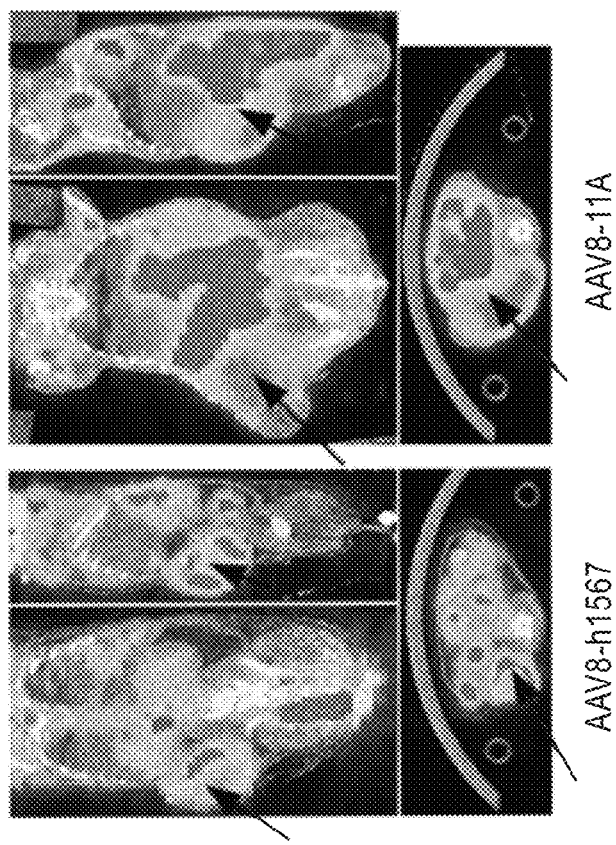
Figure 11C:
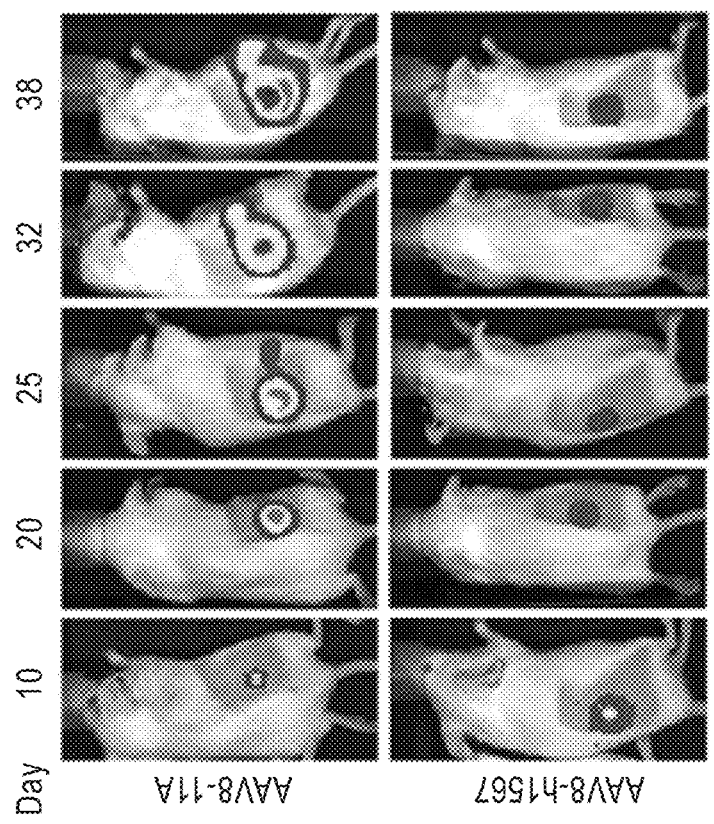

Mechanism(s) of H1567 In Vivo Tumor Killing in Human Peripheral Blood Mononuclear Cell (PBMC)-Engrafted Mice Bearing Pre-Established CCR4-Positive Tumor The therapeutic CTCL model was further extended to evaluate the role of human effector cells in tumor cell killing using bioluminescence imaging (BLI) of luciferase expressing $CCR4^+$ Mac-1 cells established by retroviral transduction. Ten SCID-BEIGE mice that were grafted with $1 \times 10^6$ $CCR4^+$ Mac-1 cells and developed equivalent sized tumors as detected on day 7 by BLI were divided into two groups. Eleven days after initial tumor cell inoculation, the AAV8-minibody vectors were administered intravenously. Next, human PMBCs (hPBMCs) were given by intraperitoneal injection 7 days after AAV vector administration. As shown in FIG. 11a, treatment with AAV8-h1567 and hPBMCs resulted in substantial tumor growth inhibition compared to AAV8-11A plus hPBMC treated mice. Quantitative monitoring of tumor growth by in vivo BLI correlated with visible tumor growth, further confirming the tumor growth inhibition effect of AAV8-h1567 compared with control group (FIG. 11b). A significant difference was observed between the control AAV8-11A and therapeutic AAV8-h1567 groups on days 40, 42, and 45 after tumor inoculation by caliper measurement and by days 25 and 38 by BLI (FIGS. 11a and b). Real-time whole-body BLI of a representative mouse showed that tumor growth was considerably inhibited in mice treated with AAV8-h1567 compared with control mice over the treatment period (FIG. 11c). Analysis of micro-computed tomography/positron emission tomography (mCT/PET) images also revealed tumor growth inhibition with AAV8-h1567 treatment compared with the control group. While both AAV8-h1567 and AAV8-11A showed primary tumor growth 28 days after tumor inoculation, and the tumor cells became much more locally invasive in the AAV8-11A treated group and showed increased metabolic activity as indicated by the accumulation of the PET tracer $^{18}$F-fluorodeoxyglucose (FDG) in whole-body images of mice (FIG. 11d).

Figure 12A:
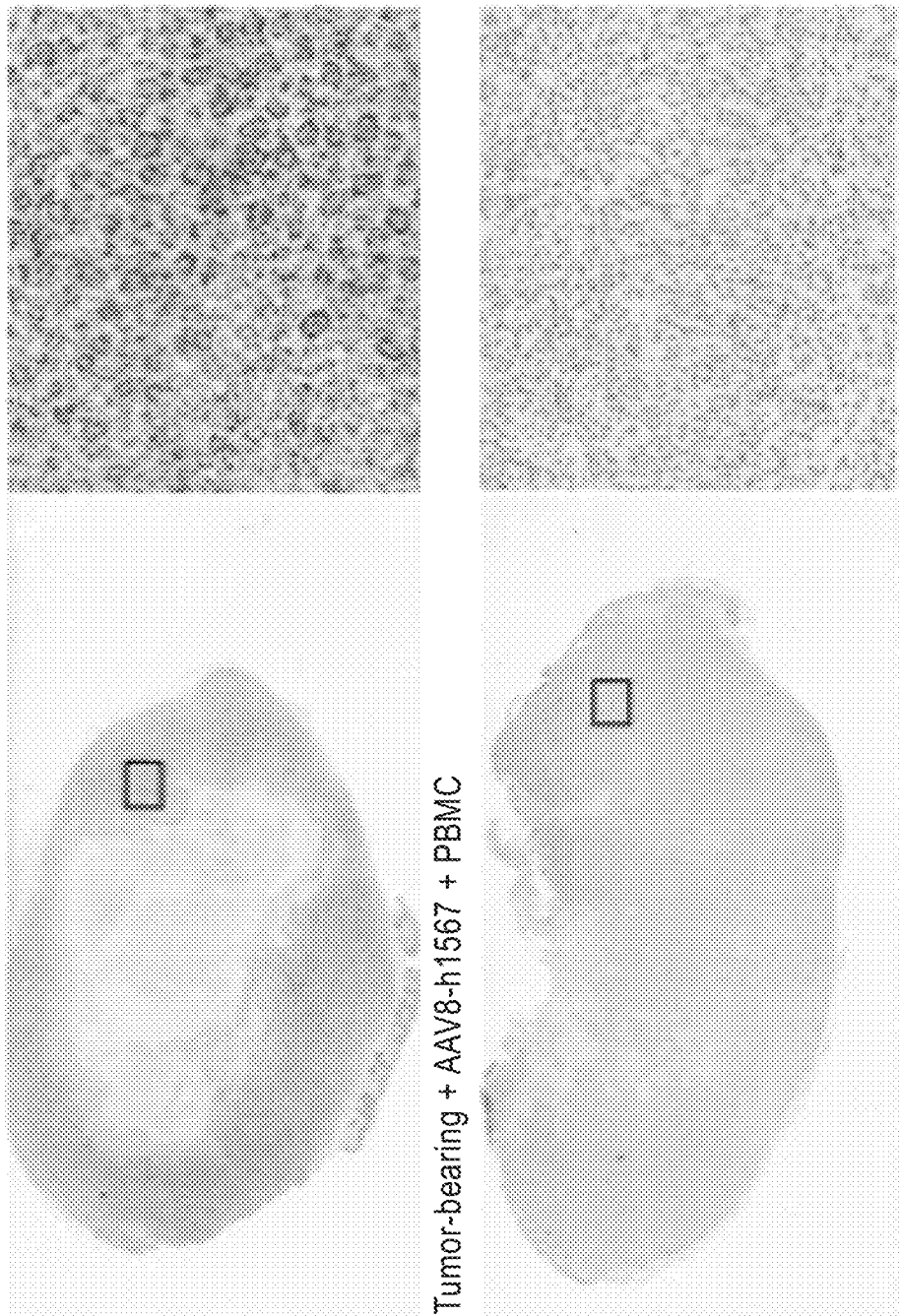

To further assess the in vivo mechanisms of tumor cell killing in the AAV8-h1567 plus human PBMC treated group, the role of human NK cells, which also express FcγRIIIA receptors, was evaluated. In the AAV8-h1567 treatment group, a substantial increase in tumor-infiltrating human NK cells was observed, as shown by the intense CD56 immunostaining compared with control 11A treated mice (FIG. 12a). Quantitative color deconvolution analysis showed a significantly increased staining in the mouse group treated with AAV8-h1567 compared with the control group treated with AAV8-11A (P<0.01; FIG. 12b). Human NK cell-mediated ADCC activity was also evaluated in vitro using purified human NK cells as effector cells. As shown in FIG. 4c, human NK cells were able to kill Mac-1 target cells in the presence of h1567 in a dose dependent fashion. Control 11A minibody showed only very low levels of killing. As both mouse neutrophils and human NK cells express FcγRIIIA receptors (CD16A) on their surface that can bind h1567, these in vitro and in vivo data strongly support that h1567 mediated killing occurs, at least in part, through FcγRIIIA engagement and activation of immune cell effector functions.

Example 13

Binding Affinities of the CCR4 Antibodies

The binding affinities of the CCR4 antibodies were determined by flow cytometry. The affinities were as follows:
h1567: 2.54 $nM^{-1}$
Mab 1-44: 1.47 $nM^{-1}$
Mab 1-49: 77.98 $nM^{-1}$
Mab 2-1: 2.90 $nM^{-1}$
Mab 2-2: 1.73 $nM^{-1}$
Mab 2-3: 1.39 $nM^{-1}$ Example 14

General Methods Used for Characterization of mAb2-3

MAb2-3 is a humanized, affinity matured derivative of the murine anti-CCR4 monoclonal antibody 1567 (mAb1567). This mAb was developed as a cytotoxic agent for treatment of $CCR4^+$ cutaneous T cell lymphoma (CTCL), a T-cell malignancy of $CCR4^+$ skin-homing T cells, where it has been shown to have potent anti-tumor activity in vivo against $CCR4^+$ CTCL cells through the processes of complement-dependent cytotoxicity (CDC) and antibody dependent cellular cytotoxicity (ADCC). The following examples describe the unique characteristics and properties of mAb2-3. MAb2-3 blocks chemotaxis of $CCR4^+$ CTCL and Tregs to the CCR4 ligands CCL17/CCL22. In addition, unexpected observations were made that mAb2-3 can both reverse the Treg-mediated suppression of $CD4^+CD25^-$ Teff proliferation and simultaneously activate the Teffs to secrete the potent cytokine IFN-γ. These antagonistic and agonist activities delineate a unique role for mAb2-3. Therefore, not only does mAb2-3 bind CCR4 with high affinity, but it is also capable of triggering specific signaling.

Cells

Mac-1 cell line was isolated from a patient with PC-ALCL and cultured in 10% FBS RPMI-1640. Cf2Th (CRL-1430) cell lines were purchased from American Type Culture Collection and incubated in 10% FBS Dulbecco's Modified Eagle's Medium. Human peripheral blood mononuclear cells were obtained from healthy donors and cultured in 10% FBS RPMI-1640.

Antibodies and Flow Cytometry Analysis

IgG and scFv-Fcs format of mAb2-3 and KM2760 were constructed by cloning the single-chain variable region (scFv) into pcDNA3.1-Hinge vector in frame with human IgG1 Fc region and by cloning heavy-chain variable region (VH) and light-chain variable region (VL) into TCAE5.3 vector. Antibodies were produced in 293T or 293F cells and purified by proteinA-Sepharose (Amersham) affinity chromatography.

Flow Cytometric Analysis

Four color fluorescence staining was performed using anti-CD3 (PerCP, APC), anti-CD4 (FITC, PE), anti-CD25 (APC), anti-FOXP3 (FITC), anti-CD45RA (PE-Cy5.5), and anti-CCR7 (APC) (all from eBioscience and BioLegend) and a FITC or PE-Cy5 anti-human Fc domain antibody (BD) were used according to the manufacturer's instructions. To define dividing cells, purified cell fractions were stained with carboxyfluorescein diacetate succinimidyl ester (CFSE, Sigma-Aldrich). Human peripheral blood mononuclear cells isolated CD4$^+$CD25$^+$ and CD4$^+$CD25 cells were isolated with the Treg isolation kit (Miltenyi Biotec) stained with CFSE according to the manufacturer's protocol. CD4$^+$CD25$^+$ cells alone and CD4$^+$CD25$^-$ cells alone as well as a combination of CD4$^+$CD25$^+$ and CD4$^+$CD25 where always only one population was CFSE stained, was incubated at 37° C. in a $CO_2$ incubator. All cytometric measurements were performed with a FACSCalibur and evaluated with CellQuest software (Becton Dickinson).

Chemotaxis

Human CD4$^+$CD25$^-$ and CD4$^+$CD25$^+$ T cells were isolated by CD4$^+$CD25$^+$ T cell isolation kit (Miltenyi Biotech) and placed in Transwell migration assays with c1567IgG. Migrated cells (CD4$^+$CD25$^{high}$) were in response to 100 ng/mL CCL22. Percentages of migrated cells were calculated by dividing the number of transmigrated CD4$^+$CD25$^{high}$ cells by the number of input cells.

Regulatory T Cell Suppression Assay

CD4$^+$CD25$^{high}$ and CD4$^+$CD25 T cells were sorted by Beckman CoulterMoFlo sorter using mouse-anti-human CD4-PE-Cy5 (RPA-T4) and antihuman CD25-PE (M-A251) antibodies (BD Pharmigen). CD4$^+$CD25 Teffs (2,500) were cultured with or without CD4$^+$CD25$^{high}$ Tregs (1,250) in 96-well plates with 25,000 irradiated (3,000 rad) CD3-depleted PBMCs. Cells were stimulated with 0.05 μg/mL plate-bound anti-CD3 (UCHT1) and 1 μg/mL soluble anti-CD28 (CD28.2) antibodies (BD Pharmigen). Anti-CCR4 antibodies were included in the appropriate cultures. The cultures were pulsed on day 5 after culture initiation with 1 μCi 3H-labeled thymidine/well (Perkin Elmer). Proliferation of cultures was measured in terms of incorporation of 3H-thymidine by reading counts in a scintillation counter (Perkin Elmer). For CFSE experiment, CD4$^+$CD25$^-$ Teffs (1×10$^4$ cells) were stained by CFSE (Invitrogen) and then cultured with CD4$^+$CD25$^{high}$ Tregs (1×10$^3$ cells) in round-bottom 96-well Costar plates coated with 0.05 μg/ml plate-bound anti-CD3 and 1 μg/ml soluble anti-CD28 antibodies (BD Pharmigen). Anti-CCR4 antibodies, c1567IgG and Ab2-3IgG, and control IgG were added and incubated for 3 and 7 days and then analyzed by counting beads and flow cytometry.

ELISpot Assay

The secretion of Interferon-gamma (IFN-γ) following stimulation with anti-CCR4 antibodies was analyzed in an IFN-γ ELISpot assay according to manufacturer's recommendations (Mabtech). Negative controls were incubated with medium with 10 unit/ml IL-2, and positive controls were incubated with anti-CD3 antibody. Spots were counted by computer-assisted image analysis (Immunospot 5.0; Cellular Technology Limited). Each assay was performed in triplicate.

Cytokine ELISA

CD4$^+$ T cells were seeded into 96-well plates in 10/0 FBS RPMI medium with 10 unit/ml IL-2. The cells were treated with antibodies (20 μg/mL) for 48 h. After the incubation period, supernatants were collected and used for further investigation. The results of selected cytokine measurements were then expressed as picograms per milliliter per 10$^5$ cells. Human cytokine ELISA (eBioscience) assay was performed according to the manufacturer's instructions.

Statistical Analyses

Data were analyzed using 2-sided unpaired Student t test. *, , and * indicate P<0.05, 0.01, and 0.001, respectively. All values and bars are represented as mean±SD.

Example 15 mAb2-3 Abrogates Treg Suppression of Teff Proliferation

It was also examined whether mAb1567 and/or mAb 2-3 engagement of CCR4 could result in modulation of Treg suppressive activity in an in vitro Treg suppression assay. Proliferation of CD4$^+$CD25$^-$ Teffs was monitored by analyzing the fluorescence intensity of 5,6-carboxyfluorescein diacetate succinimidyl ester (CFSE) labeled Teffs in the Treg/Teff (1:10) co-culture. The analysis revealed that compared to those in the control IgG or no IgG treated cultures, CD4$^+$CD25$^-$ T cell proliferated only in the presence of anti-CCR4 antibodies (c1567IgG and its humanized, affinity maturated derivative mAb2-3) in a time-dependent manner (FIG. 5D). The reversal of Treg mediated suppression of Teff proliferation by the anti-CCR4 antibodies is independent of the co-stimulation by anti-CD3/CD28 or IL-2 (FIG. 5D—NO anti-CD3/CD28 but with IL-2; FIG. 5C with anti-CD3/CD28). To further examine the effect of mAb2-3 on the immune suppressive function of Tregs, the Treg suppression assay was performed in a higher Treg/Teff ratio (1:2) co-culture. As shown in FIG. 5C, proliferation of CD4$^+$ Teffs (lane 1) was inhibited by highly purified Tregs (78%, lane 7), which is a typical Treg suppression effect on Teffs. The Teff proliferation was restored with a net positive response to 258% and 221% (lane 9 and 10) in the presence of c1567IgG or humanized mAb1567 (h1567scFv-Fc), respectively. In order to further understand the results from the Treg/Teff co-culture study, the effect of anti-CCR4 antibodies (c1567IgG or h1567scFv-Fc) was tested on the proliferation of Teff or Treg when cultured individually. Surprisingly, proliferation of Teffs were stimulated to 183% and 207%, respectively, (FIG. 5C, lanes 3 and 5) but there was little effect on Treg proliferation (lanes 4 and 6). The same phenomena was observed in a flow cytometry assay where Teffs and Tregs are each labeled with CFSE and cultured alone for 2 days in the absence or presence of anti-CCR4 mAbs (data not shown). These results indicate that mAb1567 and mAb2-3 appears to abrogate the immune suppressive function of Tregs AND have a direct effect on the proliferation of Teffs.

Example 16 mAb2-3 Promotes IFN-Gamma Secretion

Figure 19A:
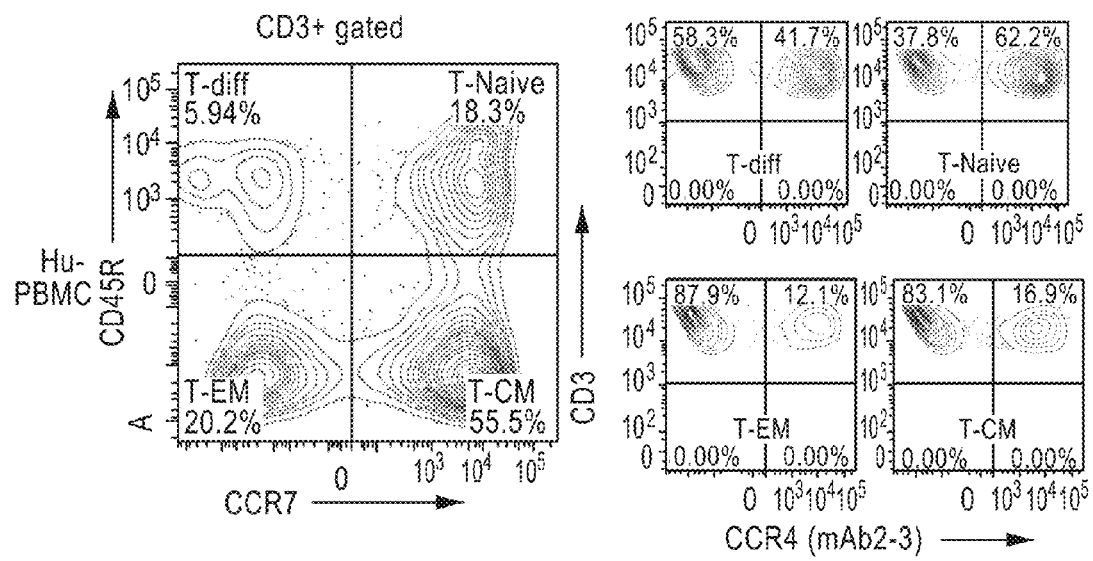
Figure 19B:
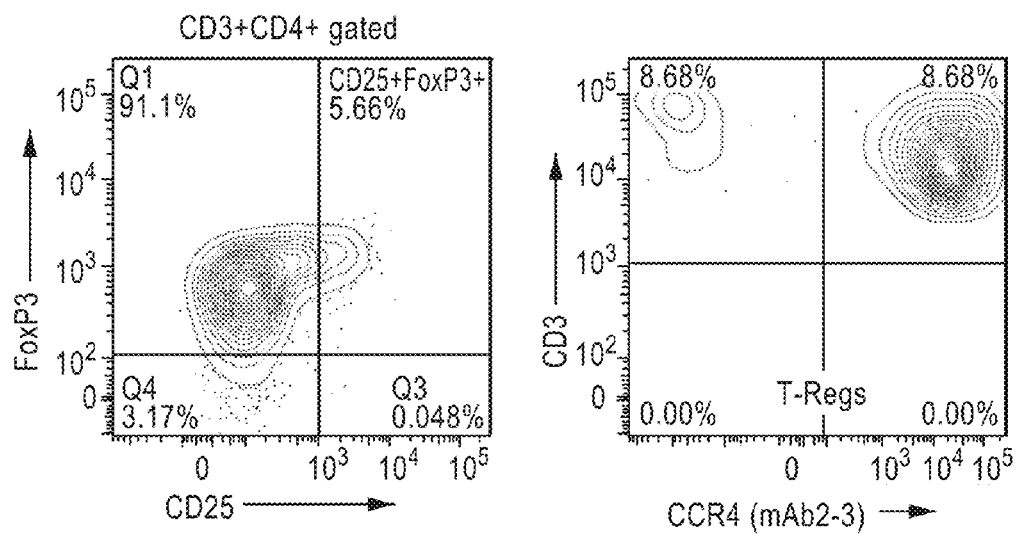
Figure 19C:
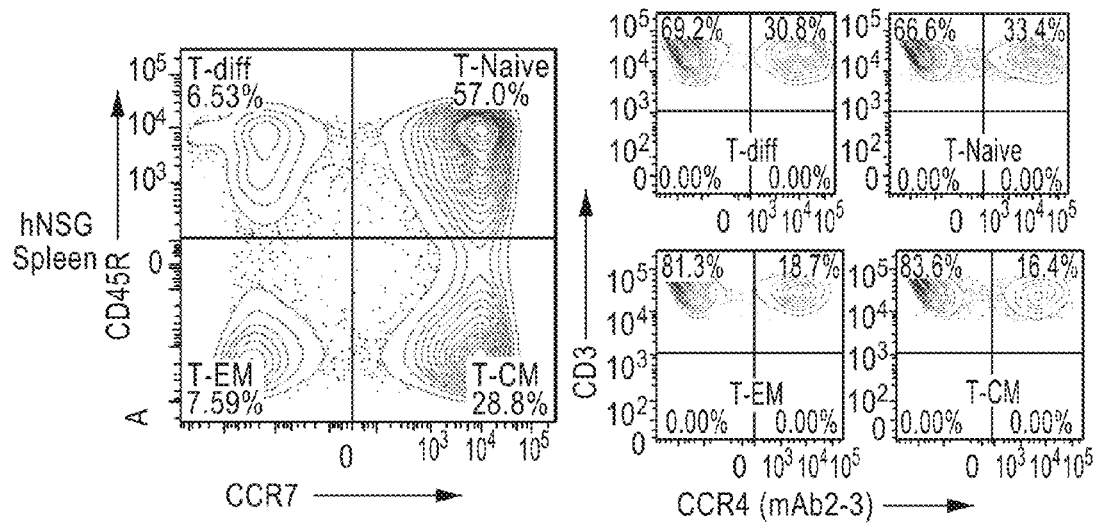
Figure 19D:
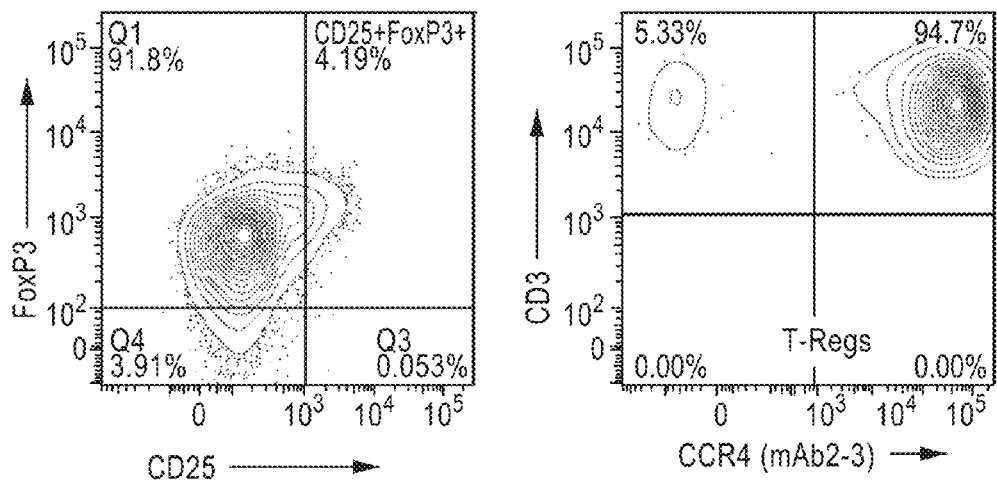

Teffs can be defined as four subpopulations based on their CD45RA and CCR7 expression profiles, T-different types (T-diff), T-naïve, central memory T (Tcm) and effector memory T (Tem) cells. The CCR4 expression profile on each distinct Teff subpopulation was examined further. Interestingly, CCR4$^+$ cells could be found in T-naïve (62.2%), Tcm (16.9%) and Tem (12.1%) subpopulations (FIG. 19A). To elucidate the mechanism(s) by which mAb2-3 acts through CCR4 on these cells to exercise proliferative effect, it will be important to perform additional studies. It was further determined whether mAb2-3 could induce cytokine production by CD4$^+$CD25$^-$ Teffs. An ELISPOT assay was used to detect and analyze the production and secretion of IFN-γ by CD4$^+$CD25$^-$ T cell response in the presence or absence of mAb2-3. By ELISPOT, IFN-γ was significantly produced and secreted following mAb2-3 stimulation of CD4$^+$CD25$^-$ T cells in a dose dependent manner.

Example 16

Comparison of mAb2-3 Binding Properties to Other Anti-CCR4 Antibodies

The binding properties of mAb2-3 were compared to the properties and effects of two different anti-CCR4 antibodies: KM2760 (mouse anti-CCR4 antibody) and KW0761 (humanized KM2760).

Figure 20A:
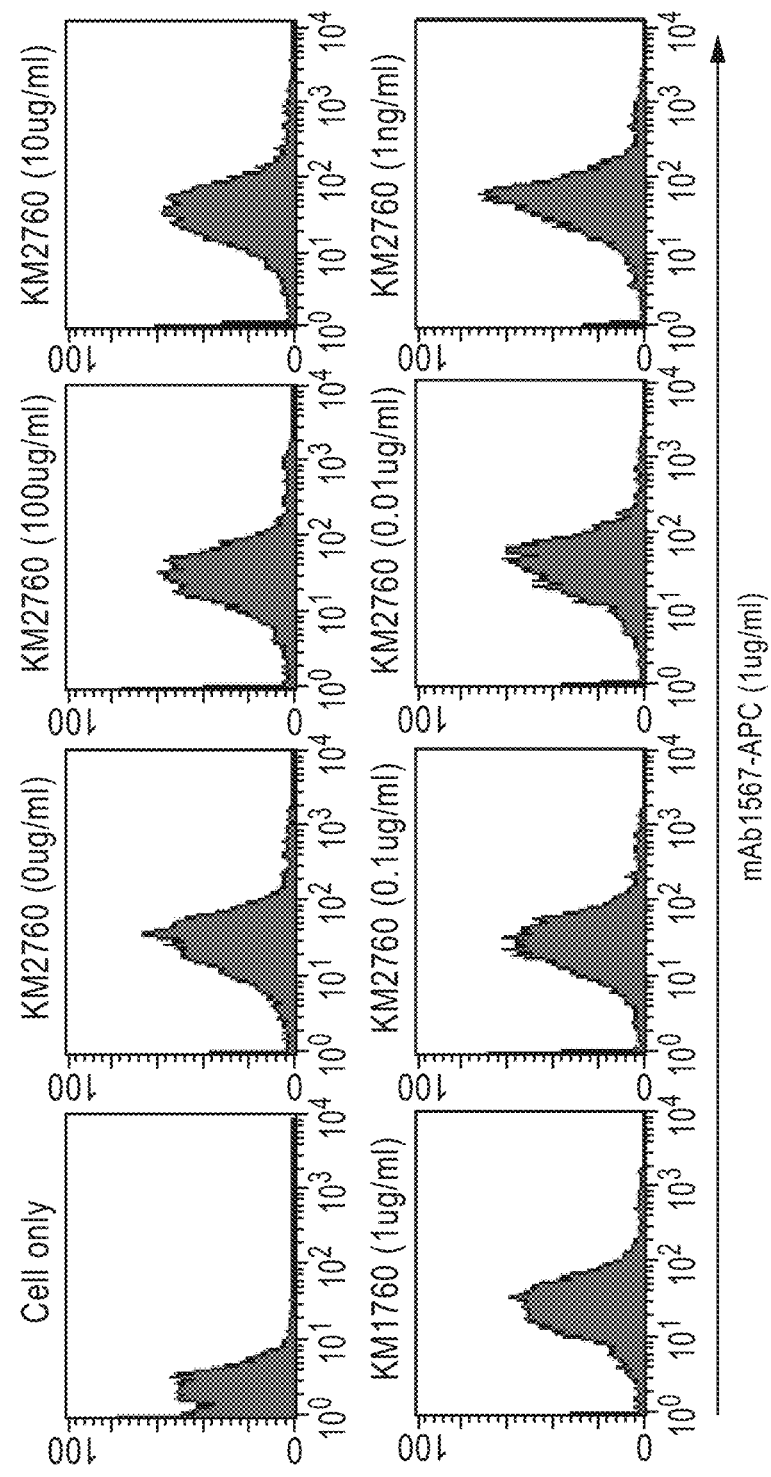

CCR4-Cf2 cells (Cf2 cells transiently expressing exogenous CCR4) were incubated with different concentrations of anti-CCR4 antibody KM2760. Cells were then stained with APC-labeled mAb2-3 (FIG. 20A). Results from the competition assay showed that mAb2-3 has a different binding motif than KM2760. Additional experiments to compare the binding motif of mAb2-3 to h1567 were also performed (FIG. 14). Results indicate that h1567, mAb1567 and mAb2-3 bind to the same motif of CCR4.

Figure 20B:
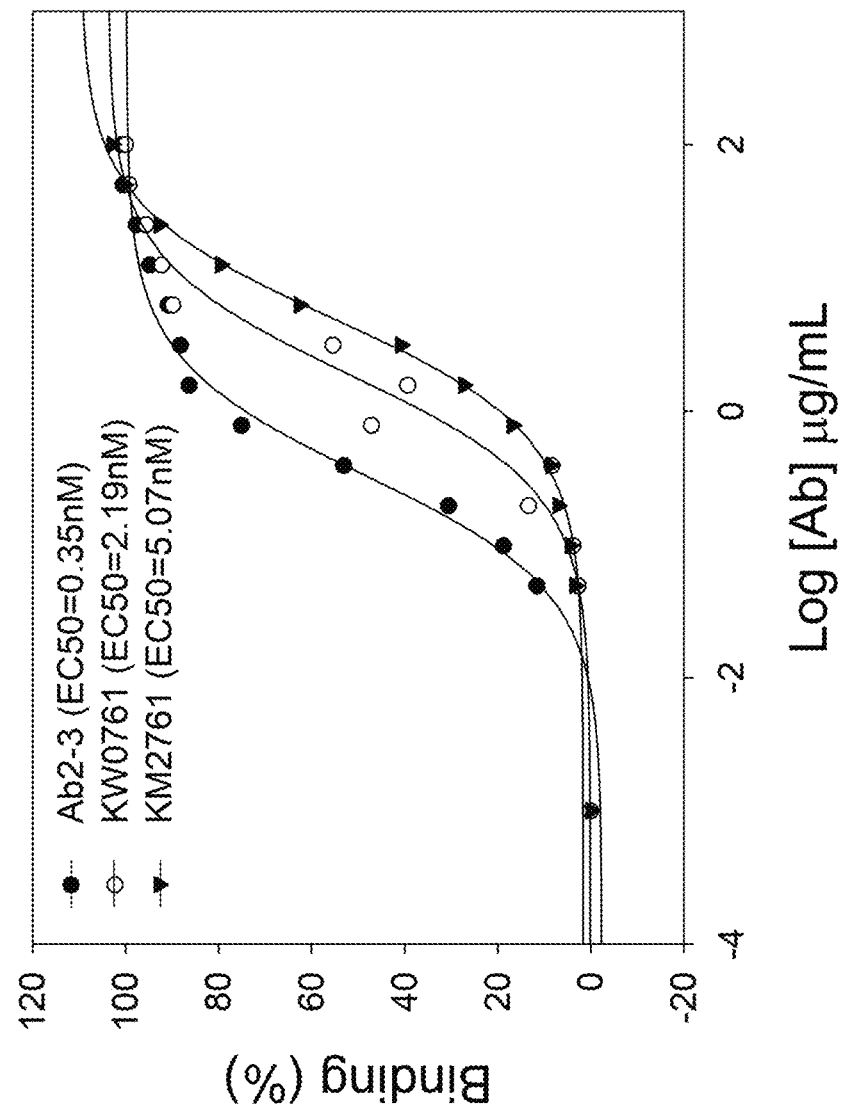

The binding affinities of mAb2-3, KM2760 and KW0761 (humanized KM2760) were determined. FIG. 20B shows that mAb2-3 (EC50=0.35 nM) has a higher binding affinity than KW0761 (EC50=2.19 nM) and KM2760 (EC50=5.07 nM).

Example 17 mAb2-3 Stimulates of T Cell Proliferation

Figure 20C:
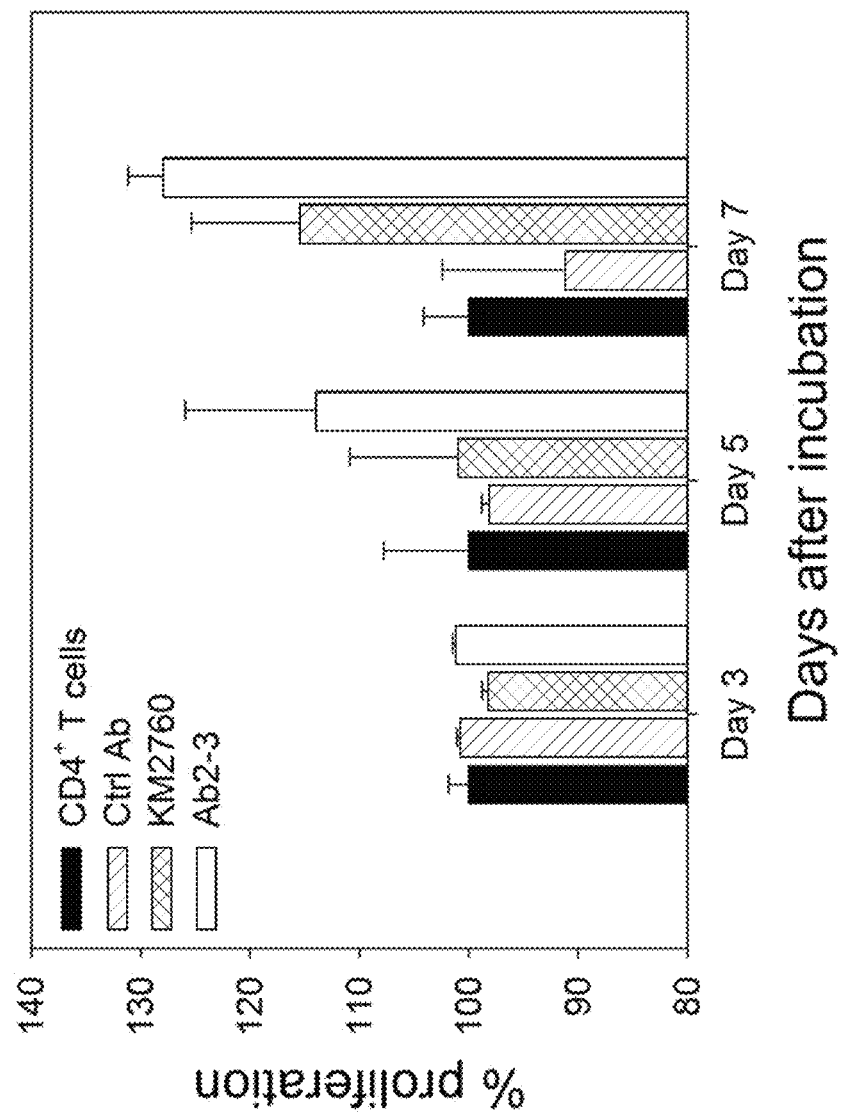

The ability of mAb2-3 and KM2760 to stimulate Teff proliferation was also assessed. CD4$^+$CD25$^-$ T effector cells were CFSE-labeled, incubated with anti-CCR antibodies mAb2-3 or KM2760 or control antibody and harvested at Day 3, 5, and 7. Proliferation was assessed by flow-cytometry. The percentage of cells was calculated from the fluorescence of CD4$^+$CD25$^-$ T cells. The percent proliferation was normalized to CD4$^+$CD25$^-$ T effector cells at Day 3. Treatment with mAb2-3 stimulated Teff proliferation earlier (at Day 5 in comparison to Day 7 for KM2760) and stimulated more proliferation than KM2760 (FIG. 20C).

Example 18 mAb2-3 Stimulates Cyotkine Release

Figure 21A:
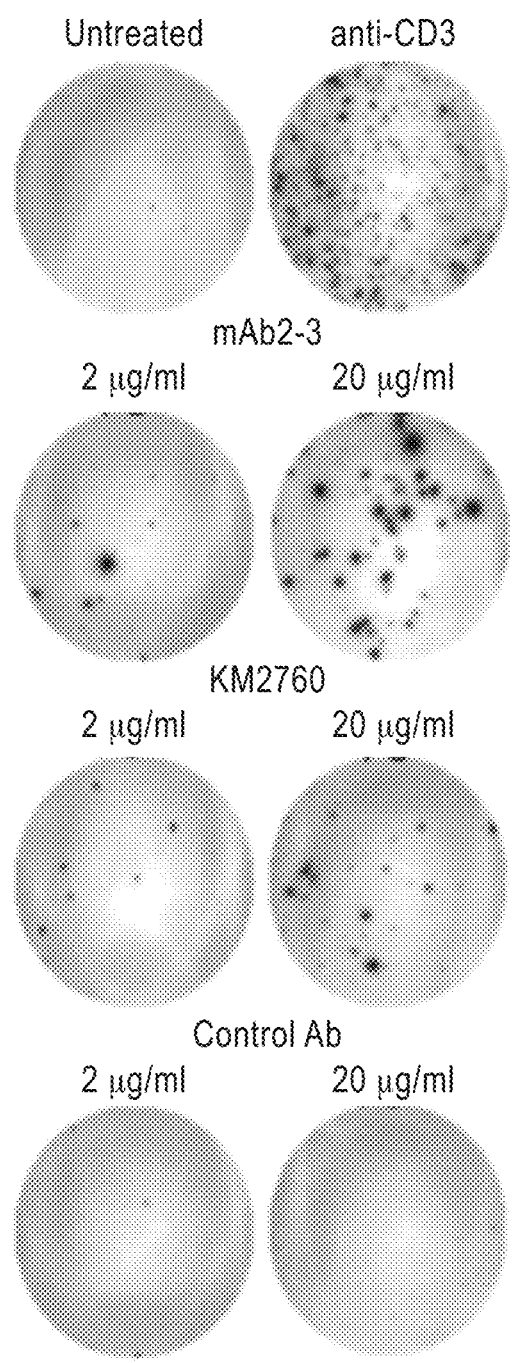

To test the stimulation function in different populations of T cells, an ELISpot assay was used to determine IFN gamma release from CD4$^+$CD25$^-$ T cells in response to mAb2-3 and KM2760. CD4+CD25− T cells were analyzed in an IFN-γ ELISpot assay according to manufacturer's recommendations (Mabtech). Positive control was incubated with anti-CD3 antibody. Negative controls were incubated with medium with 10 unit/ml IL-2 or control antibody. Spots were counted by computer assisted image analysis. Both anti-CCR4 antibodies, mAb2-3 and KM2760, stimulated IFN-γ release at low (2 µg/ml) and high (20 µg/ml) concentrations, compared to control antibody. In multiple experiments, mAb2-3 stimulated more IFN-γ spots than T cells treated with KM2760 (FIGS. 21A and 21B).

Figure 22A:
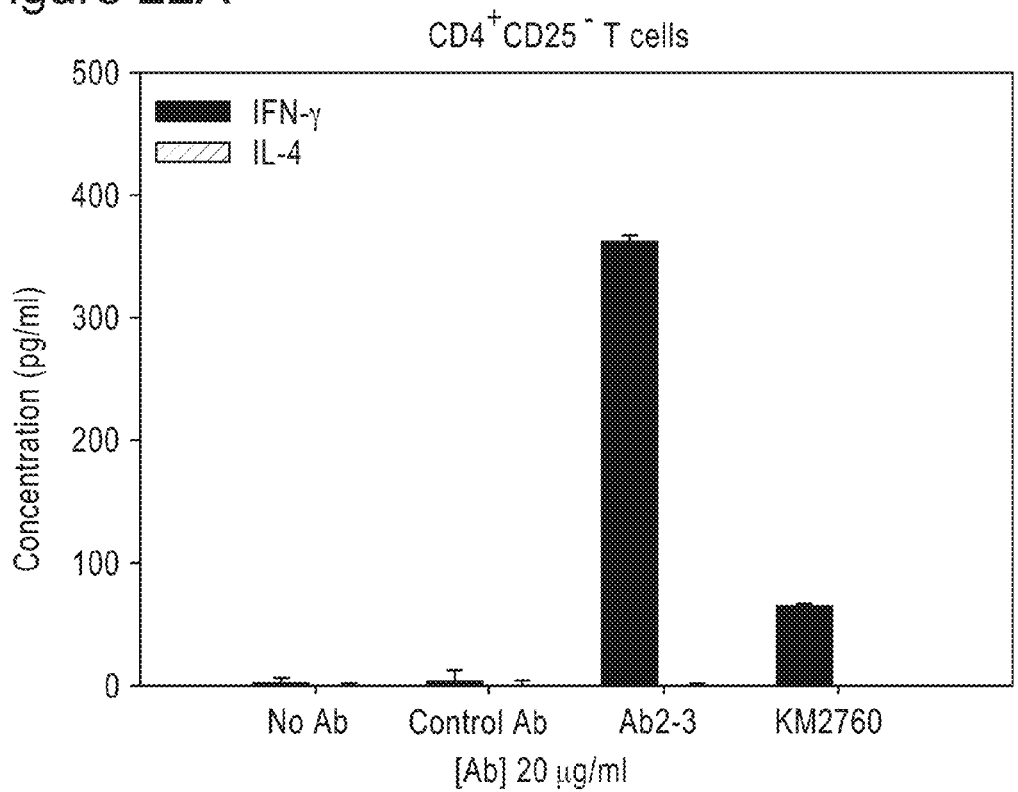
Figure 22B:
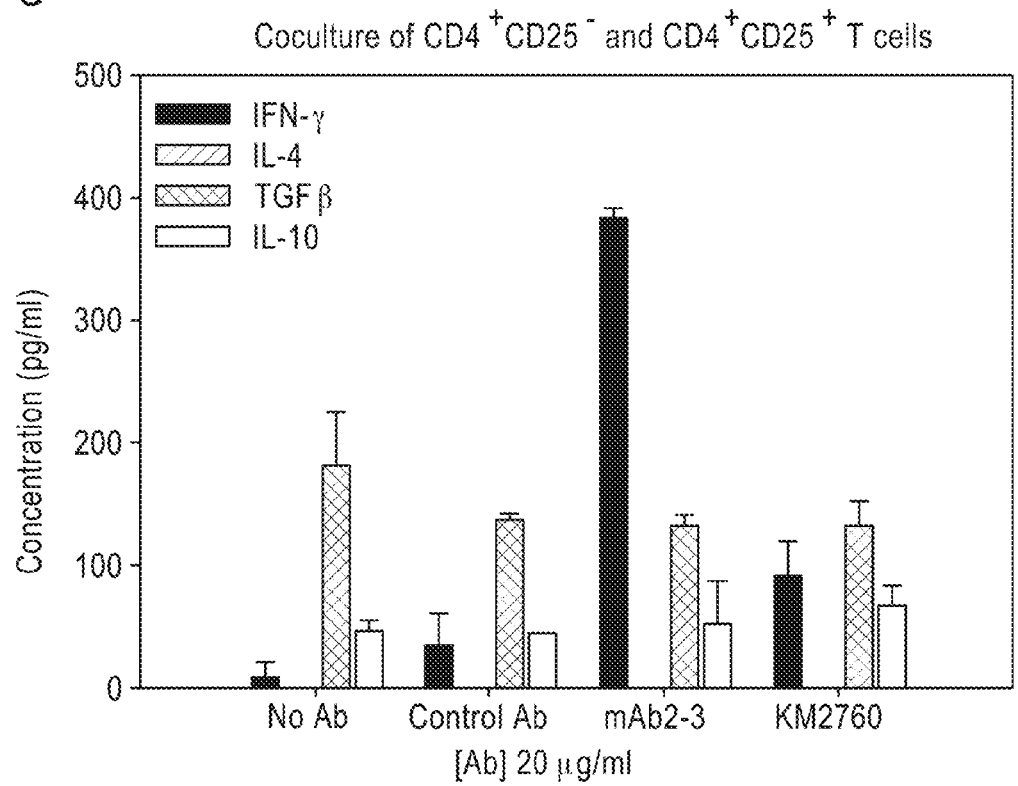

To further examine the cytokine releasing profiles in response to CCR4 antibodies, the release of four cytokines, IFN-γ, IL-4, TGFβ, and IL-10, was examined (FIG. 22). IFN-g production is associated with Th1 cells, IL-4 production is associated with Th2 and TGF-beta and IL-10 cytokine release is associated with Treg cells. Simultaneous measurement of the cytokines were conducted with a sandwich ELISA assay using supernatant mixtures from the cells following exposure to anti-CCR4 antibodies (mAb2-3 and KM2760) or control antibody for 48 hours of stimulation. Levels of IL-4 and IL-10 release were relatively unchanged after stimulation by anti-CCR4 antibodies. TGF-beta release was slightly reduced in cells incubated with anti-CCR4 antibodies compared to negative no antibody control (FIG. 22B). IFN-gamma release was increased after treatment with either mAb2-3 or KM2760 (FIGS. 22A and B).

Figure 23D:
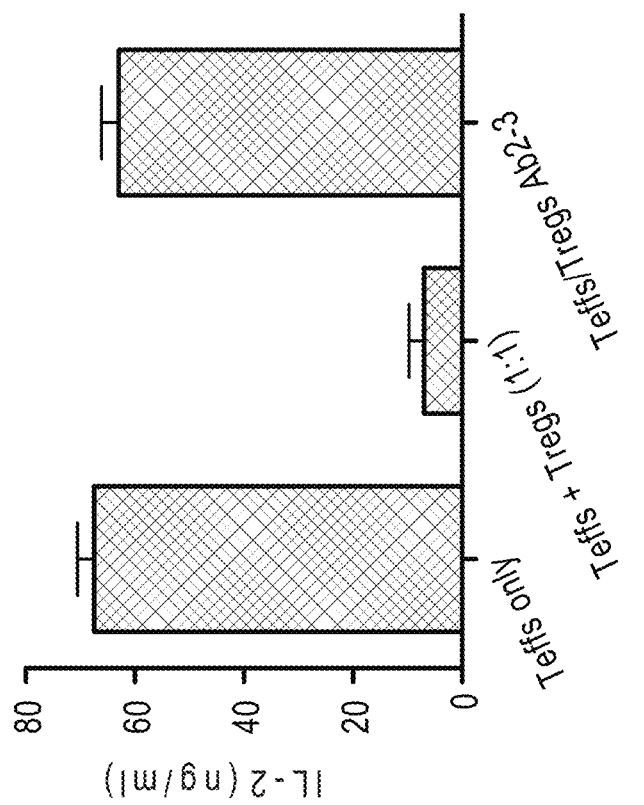
Figure 23C:
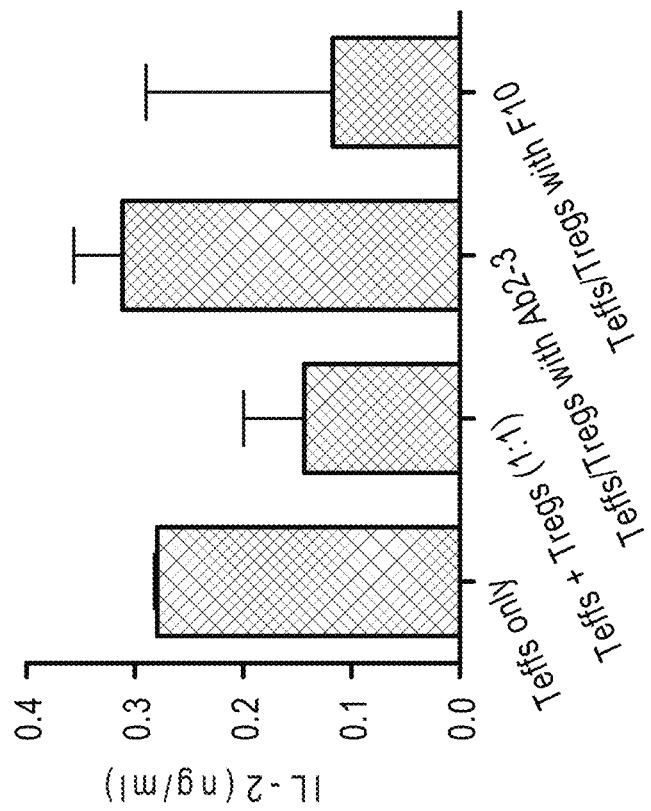

Further analysis of IL-2 cytokine release in CD4$^+$CD25$^-$ T cells in the absence of CD4$^+$CD25$^+$ regulatory T cells was performed. Tregs were isolated using negative selection of CD4+CD127dimCD49d− EasySep kit. T regs (3000/reaction) cultures were incubated in the absence of exogenous 6 ng/ml (10IU) IL-2, and the concentration of IL-2 produced in the supernatant of the cultures were measured by ELISA (FIGS. 23A, 23B and 23C). In some experiments, T regs were co-incubated with T effs, for example at a 1:1 ratio, and the concentration of IL-2 produced in the supernatant of the cultures were measured (FIGS. 23 C and D). In FIG. 23D, exogenous IL-2 was added to the cell cultures (Teffs only and Teffs+ T regs) and treated with mAb2-3 antibody.

Example 19 mAb2-3 Treatment and Proliferation of T Cells

The effect of mAb2-3 treatment on the proliferation of CD4+ T cells was assessed by CFSE staining and FACS analysis. FACs profiles over 5 days of stimulation by mAb2-3 and control antibodies and CD3/28 beads are shown in FIG. 24. In FIG. 25, the four subpopulations of CD4+CD25− T eff cells (T-diff, T naïve, T em, and T cm cells, sorted by CD45 and CCR7 status) were separately measured after 3 days of incubation with varying concentrations of mAb2-3, a negative control antibody, and KM2760 (anti-CCR4 monoclonal antibody). Proliferation was measured and statistical significance was determined, with p-value<0.05.

Example 20 mAb2-3 INHIBITS Chemoattraction of Human Lymphocytes

Figure 26A:
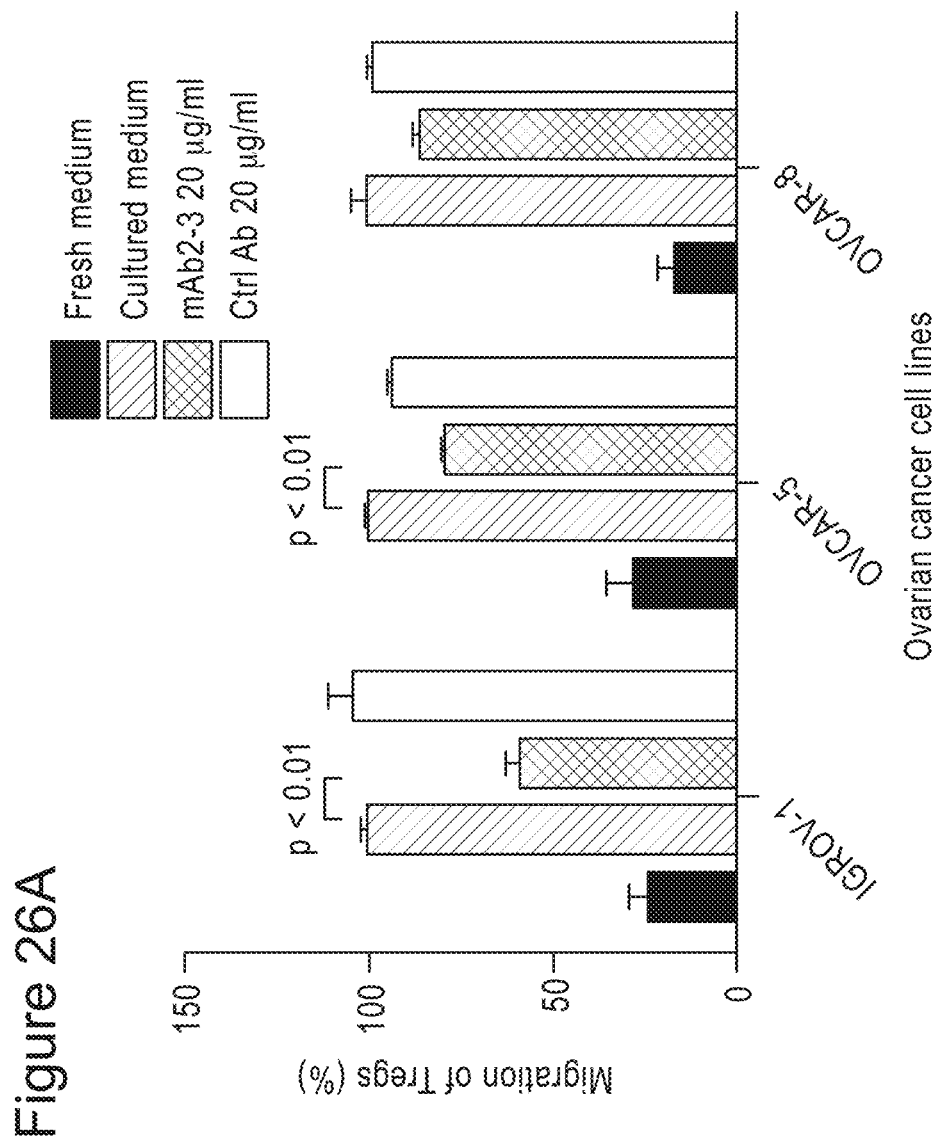

The effects in vitro chemotaxis of CD4$^+$CD25$^+$ T cells induced by CCL22-expressing ovarian cancer cell supernatant after treatment with mAb2-3 were examined. In vitro chemotaxis was inhibited by mAb2-3, but not by control antibody (Ab 20). Results were expressed as means±SD and student's t-test (FIG. 26A).

Figure 26B:
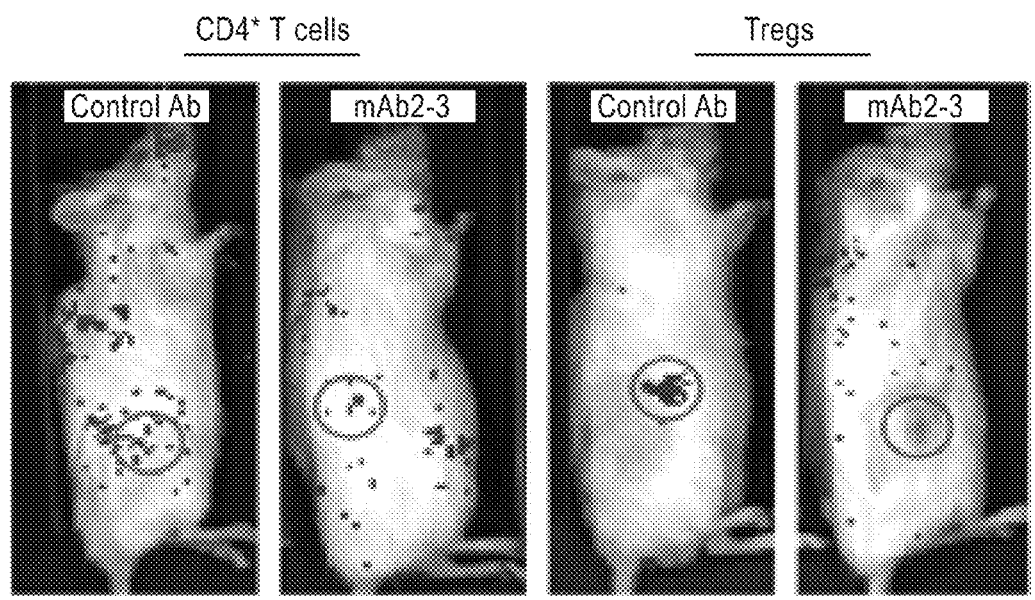
Figure 26C:
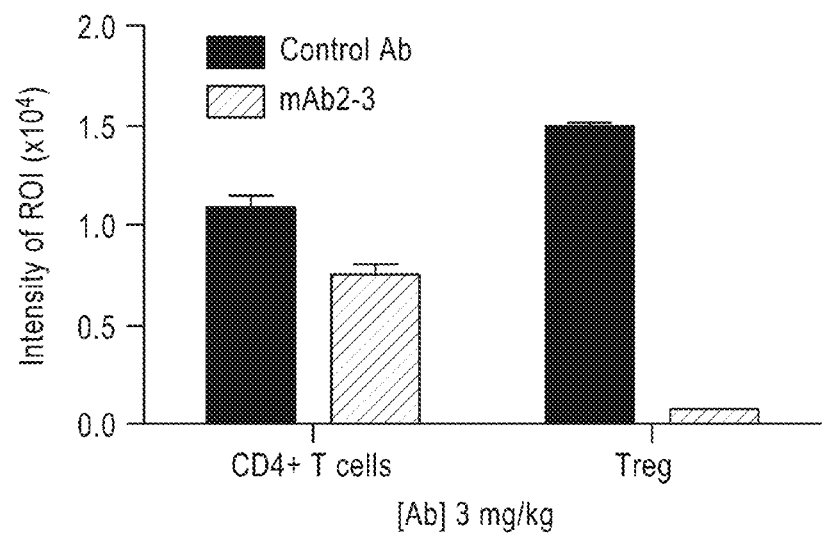

The effects of in vivo chemotaxis were observed using ovarian cancer xenograft mouse models were injected with luciferized CD4+ T cells. At 48 hours post-injection of the luciferized CD4$^+$ T cells, the in vivo bioluminescence was measured (FIG. 26B). Tumor tissues had strong bioluminescence accumulation after injection CD4$^+$ T cells in the presence of control antibody as shown in the circle in the panels of FIG. 26B. However, the intensity of luminescence signal was dramatically reduced by co-injection with mAb2-3. Quantification of bioluminescence intensity of tumor-infiltrating CD4$^+$ T cells and Tregs by the region of interest (ROI as specified by the circle in FIG. 26B) analysis was performed using the IVIS imaging system (FIG. 26C).

Example 21

Generation of Bi-Specific Antibodies

Bi-specific antibodies that recognize CCR4 and CAIX were generated using two independent vectors. The mAb-23 vector was used to produce full anti-CCR4 antibodies. A vector producing full anti-CAIX antibodies (G119) was used. Glutathione (GSH) was added to each antibody to disrupt the di-sulfide bridging of the full antibody, to produce populations of single heavy-light chain fragments of anti-CCR4 and anti-CAIX antibodies (monomers). SDS-PAGE protein electrophoresis of samples incubated with increasing concentrations of GSH show the increased amount of monomers, and decreased amount of full antibodies (FIG. 27A). Anti-CCR4 monomers were then conjugated with anti-CAIX monomers in solution with glutathione disulfide (GSSG). Upon addition of GSSG, conjugates containing anti-CCR4 and anti-CAIX monomers were generated, as shown by the protein gel in FIG. 27B.

Functionality of the anti-CCR4 and anti-CAIX bispecific antibody was assessed using flow cytometry analysis. SKCRC-52 cells and Mac-1 cells were stained with full anti-CAIX or anti-CCR4 antibodies, control antibodies, and the bispecific antibodies (FIG. 27B).

OTHER EMBODIMENTS

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

REFERENCES

1. Wood, K. J. & Sakaguchi, S. Regulatory T cells in transplantation tolerance. *Nat Rev Immunol* 3, 199-210 (2003).
2. Levings, M. K., Sangregorio, R. & Roncarolo, M. G. Human cd25(+)cd4(+) t regulatory cells suppress naive and memory T cell proliferation and can be expanded in vitro without loss of function. *J Exp Med* 193, 1295-1302 (2001).
3. Curiel, T. J., et al. Specific recruitment of regulatory T cells in ovarian carcinoma fosters immune privilege and predicts reduced survival. *Nat Med* 10, 942-949 (2004).
4. Iellem, A., et al. Unique chemotactic response profile and specific expression of chemokine receptors CCR4 and CCR8 by CD4(+)CD25(+) regulatory T cells. *J Exp Med* 194, 847-853 (2001).
5. Chang, D. K., et al. Humanization of an anti-CCR4 antibody that kills Cutaneous T Cell Lymphoma cells and abrogates suppression by T regulatory cells. *Mol Cancer Ther* (2012).
6. Han, T., et al. Human Anti-CCR4 Minibody Gene Transfer for the Treatment of Cutaneous T-Cell Lymphoma. *PLoS One* 7, e44455 (2012).
7. Imai, T., et al. Selective recruitment of CCR4-bearing Th2 cells toward antigen-presenting cells by the CC chemokines thymus and activation-regulated chemokine and macrophage-derived chemokine. *Int Immunol* 11, 81-88 (1999).
8. Wagsater, D., Dienus, O., Lofgren, S., Hugander, A. & Dimberg, J. Quantification of the chemokines CCL17 and CCL22 in human colorectal adenocarcinomas. *Mol Med Report* 1, 211-217 (2008).
9. Niens, M., et al. Serum chemokine levels in Hodgkin lymphoma patients: highly increased levels of CCL17 and CCL22. *Br J Haematol* 140, 527-536 (2008).
10. Jacobs, J. F., et al. Prognostic significance and mechanism of Treg infiltration in human brain tumors. *J Neuroimmunol* 225, 195-199 (2010).
11. Hiraoka, N., Onozato, K., Kosuge, T. & Hirohashi, S. Prevalence of FOXP3+ regulatory T cells increases during the progression of pancreatic ductal adenocarcinoma and its premalignant lesions. *Clin Cancer Res* 12, 5423-5434 (2006).
12. Woo, E. Y., et al. Regulatory CD4(+)CD25(+) T cells in tumors from patients with early-stage non-small cell lung cancer and late-stage ovarian cancer. *Cancer Res* 61, 4766-4772 (2001).
13. Zou, W. Regulatory T cells, tumour immunity and immunotherapy. *Nat Rev Immunol* 6, 295-307 (2006).
14. Yu, P., et al. Intratumor depletion of CD4+ cells unmasks tumor immunogenicity leading to the rejection of late-stage tumors. *J Exp Med* 201, 779-791 (2005).
15. Mahnke, K., et al. Depletion of CD4+CD25+ human regulatory T cells in vivo:

kinetics of Treg depletion and alterations in immune functions in vivo and in vitro. *Int J Cancer* 120, 2723-2733 (2007).
16. Roncarolo, M. G. & Battaglia, M. Regulatory T-cell immunotherapy for tolerance to self antigens and alloantigens in humans. *Nat Rev Immunol* 7, 585-598 (2007).
17. Sakaguchi, S., Yamaguchi, T., Nomura, T. & Ono, M. Regulatory T cells and immune tolerance. *Cell* 133, 775-787 (2008).
18. Kohm, A. P., et al. Cutting Edge: Anti-CD25 monoclonal antibody injection results in the functional inactivation, not depletion, of CD4+CD25+ T regulatory cells. *J Immunol* 176, 3301-3305 (2006).
19. Baatar, D., et al. Human peripheral blood T regulatory cells (Tregs), functionally primed CCR4+ Tregs and unprimed CCR4− Tregs, regulate effector T cells using FasL. *J Immunol* 178, 4891-4900 (2007).
20. Mizukami, Y., et al. CCL17 and CCL22 chemokines within tumor microenvironment are related to accumulation of Foxp3+ regulatory T cells in gastric cancer. *Int J Cancer* 122, 2286-2293 (2008).
21. Gobert, M., et al. Regulatory T cells recruited through CCL22/CCR4 are selectively activated in lymphoid infiltrates surrounding primary breast tumors and lead to an adverse clinical outcome. *Cancer Res* 69, 2000-2009 (2009).
22. Faget, J., et al. Early detection of tumor cells by innate immune cells leads to T(reg) recruitment through CCL22 production by tumor cells. *Cancer Res* 71, 6143-6152 (2011).

We claim:

1. A pharmaceutical composition comprising an isolated humanized affinity-matured monoclonal antibody capable of binding human CCR4 having
   a. a heavy chain with three CDRs comprising a CDR 1 comprising amino acid sequence GYTFASQW (SEQ ID NO:22), a CDR 2 comprising amino acid sequence INPGNVNT (SEQ ID NO:27), and a CDR 3 comprising amino sequence STWYRPLDY (SEQ ID NO:30) and a light chain with three CDRs comprising a CDR 1 comprising amino acid sequence QSILYSSNQKNY (SEQ ID NO:26), a CDR 2 comprising amino acid sequence WASTRE (SEQ ID NO:28), and a CDR 3 comprising amino acid sequence HQYISSYT (SEQ ID NO:35);
   b. a heavy chain with three CDRs comprising a CDR 1 comprising amino acid sequence GYTFASSW (SEQ ID NO:23), a CDR 2 comprising amino acid sequence INPGNVNT (SEQ ID NO:27), and a CDR 3 comprising amino sequence STWYRPNDY (SEQ ID NO:31) and a light chain with three CDRs comprising a CDR 1 comprising amino acid sequence QSILYSSNQKNY (SEQ ID NO:26), a CDR 2 comprising amino acid sequence WASTRE (SEQ ID NO:28), and a CDR 3 comprising amino sequence HQYKSSYT (SEQ ID NO:36);
   c. a heavy chain with three CDRs comprising a CDR 1 comprising amino acid sequence GYTFASSW (SEQ ID NO:23), a CDR 2 comprising amino acid sequence INPGNVNT (SEQ ID NO:27), and a CDR 3 comprising amino sequence TTRYRPLDY (SEQ ID NO:32) and a light chain with three CDRs comprising a CDR 1 comprising amino acid sequence QSILYSSNQKNY (SEQ ID NO:26), a CDR 2 comprising amino acid sequence WASTRE (SEQ ID NO:28), and a CDR 3 comprising amino sequence HQYRSSYT (SEQ ID NO:37);
   d. a heavy chain with three CDRs comprising a CDR 1 comprising amino acid sequence GYTFASQY (SEQ ID NO:24), a CDR 2 comprising amino acid sequence INPGNVNT (SEQ ID NO:27), and a CDR 3 comprising amino acid sequence LTYYRPPDY (SEQ ID NO:33) and a light chain with three CDRs comprising a CDR 1 comprising amino acid sequence QSILYSSNQKNY (SEQ ID NO:26), a CDR 2 comprising amino acid sequence WASTRE (SEQ ID NO:28), and a CDR 3 comprising amino acid sequence HQYYSSYT (SEQ ID NO:38); or
   e. a heavy chain with three CDRs comprising a CDR 1 comprising amino acid sequence GYTFASAW (SEQ ID NO:25), a CDR 2 comprising amino acid sequence INPGNVNT (SEQ ID NO:27), and a CDR 3 comprising amino acid sequence STYYRPLDY (SEQ ID NO:29) and a light chain with three CDRs comprising a CDR 1 comprising amino acid sequence QSILYSSNQKNY (SEQ ID NO:26), a CDR 2 comprising amino acid sequence WASTRE (SEQ ID NO:28), and a CDR 3 comprising amino acid sequence HQYMSSYT (SEQ ID NO:39).

2. The pharmaceutical composition of claim 1, wherein the monoclonal antibody has an equilibrium dissociation constant (KD) for CCR4 of less than or equal to about 2.5 nM.

3. The pharmaceutical composition of claim 1, wherein the monoclonal antibody has an equilibrium dissociation constant (KD) for CCR4 of about 1.5 nM or less.

4. The pharmaceutical composition of claim 1, wherein the monoclonal antibody is present in the composition in an amount effective to reduce primary tumor growth in a human subject to whom the composition is administered.

5. The pharmaceutical composition of claim 1, wherein the monoclonal antibody is monovalent, bivalent, or a single chain antibody.

6. The pharmaceutical composition of claim 1, wherein the monoclonal antibody is a bi-specific antibody that also immunospecifically binds to a second antigen.

* * * * *

SEQUENCE LISTING

<160> NUMBER OF SEQ ID NOS: 42

<210> SEQ ID NO 1
<211> LENGTH: 354
<212> TYPE: DNA
<213> ORGANISM: Artificial Sequence
<220> FEATURE:
<223> OTHER INFORMATION: Variable heavy chain

<400> SEQUENCE: 1

```
caggtgcagc tggtgcagag cggagccgag gtgaagaagc ctggagcttc cgtcaaggtg      60
tcctgcaagg ccagcggcta caccttcgcc agccaatgga tgcactggat gcggcaggca     120
cctggacagg gcctcgaatg gatcggctgg atcaaccccg gcaacgtgaa caccaagtac     180
aacgagaagt tcaagggcag ggccaccctg accgtggaca ccagcaccaa caccgcctac     240
atggaactga gcagcctgcg gagcgaggac accgccgtgt actactgcgc cagaagcacc     300
tggtaccggc cgctggacta ctggggccag ggcaccctgg tgaccgtgag cagc           354
```

<210> SEQ ID NO 2
<211> LENGTH: 118
<212> TYPE: PRT
<213> ORGANISM: Artificial Sequence
<220> FEATURE:
<223> OTHER INFORMATION: Variable heavy chain

<400> SEQUENCE: 2

```
Gln Val Gln Leu Val Gln Ser Gly Ala Glu Val Lys Lys Pro Gly Ala
1               5                  10                  15

Ser Val Lys Val Ser Cys Lys Ala Ser Gly Tyr Thr Phe Ala Ser Gln
            20                  25                  30

Trp Met His Trp Met Arg Gln Ala Pro Gly Gln Gly Leu Glu Trp Ile
        35                  40                  45

Gly Trp Ile Asn Pro Gly Asn Val Asn Thr Lys Tyr Asn Glu Lys Phe
    50                  55                  60

Lys Gly Arg Ala Thr Leu Thr Val Asp Thr Ser Thr Asn Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Thr Trp Tyr Arg Pro Leu Asp Tyr Trp Gly Gln Gly Thr
            100                 105                 110

Leu Val Thr Val Ser Ser
        115
```

<210> SEQ ID NO 3
<211> LENGTH: 336
<212> TYPE: DNA
<213> ORGANISM: Artificial Sequence
<220> FEATURE:
<223> OTHER INFORMATION: Variable light chain

<400> SEQUENCE: 3

```
gacatcgtga tgacccagag ccccgacagc ctggccgtga gcctgggcga gcgggccacc      60
atcaactgca agagcagcca gagcatcctg tacagcagca accagaagaa ctacctggcc     120
tggtatcagc agaagcccgg ccagagcccc aagctgctga tctactgggc cagcacccgg     180
gagagcggcg tgcccgaccg gtttagcggc agcggctccg gcaccgactt cacccctgacc     240
atcagcagcc tgcaggccga ggacgtggcc gtgtactact gccaccagta catcagcagc     300
tacaccttcg gccagggcac aaagctggaa atcaag                               336
```

<210> SEQ ID NO 4
<211> LENGTH: 112
<212> TYPE: PRT
<213> ORGANISM: Artificial Sequence
<220> FEATURE:
<223> OTHER INFORMATION: Variable light chain

<400> SEQUENCE: 4

```
Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Ile Leu Tyr Ser
            20                  25                  30

Ser Asn Gln Lys Asn Tyr Leu Ala Trp Tyr Gln Gln Lys Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys His Gln
                85                  90                  95

Tyr Ile Ser Ser Tyr Thr Phe Gly Gln Gly Thr Lys Leu Glu Ile Lys
            100                 105                 110
```

<210> SEQ ID NO 5
<211> LENGTH: 354
<212> TYPE: DNA
<213> ORGANISM: Artificial Sequence
<220> FEATURE:
<223> OTHER INFORMATION: Variable heavy chain

<400> SEQUENCE: 5

```
caggtgcagc tggtgcagag cggagccgag gtgaagaagc ctggagcttc cgtcaaggtg    60
tcctgcaagg ccagcggcta caccttcgcc agcagctgga tgcactggat gcggcaggca   120
cctggacagg gcctcgaatg gatcggctgg atcaaccccg gcaacgtgaa caccaagtac   180
aacgagaagt tcaagggcag ggccaccctg accgtggaca ccagcaccaa caccgcctac   240
atggaactga gcagcctgcg gagcgaggac accgccgtgt actactgcgc cagaagcacg   300
tggtatcggc cgaatgacta ctggggccag ggcaccctgg tgaccgtgag cagc          354
```

<210> SEQ ID NO 6
<211> LENGTH: 118
<212> TYPE: PRT
<213> ORGANISM: Artificial Sequence
<220> FEATURE:
<223> OTHER INFORMATION: Variable heavy chain

<400> SEQUENCE: 6

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Ala Ser Ser
            20                  25                  30

Trp Met His Trp Met Arg Gln Ala Pro Gly Gln Gly Leu Glu Trp Ile
        35                  40                  45

Gly Trp Ile Asn Pro Gly Asn Val Asn Thr Lys Tyr Asn Glu Lys Phe
    50                  55                  60

Lys Gly Arg Ala Thr Leu Thr Val Asp Thr Ser Thr Asn Thr Ala Tyr
65                  70                  75                  80
```

```
Met Glu Leu Ser Ser Leu Arg Ser Glu Asp Thr Ala Val Tyr Tyr Cys
            85                  90                  95

Ala Arg Ser Thr Trp Tyr Arg Pro Asn Asp Tyr Trp Gly Gln Gly Thr
            100                 105                 110

Leu Val Thr Val Ser Ser
            115

<210> SEQ ID NO 7
<211> LENGTH: 336
<212> TYPE: DNA
<213> ORGANISM: Artificial Sequence
<220> FEATURE:
<223> OTHER INFORMATION: Variable light chain

<400> SEQUENCE: 7
gacatcgtga tgacccagag ccccgacagc ctggccgtga gcctgggcga gcgggccacc      60
atcaactgca agagcagcca gagcatcctg tacagcagca ccagaagaa ctacctggcc      120 tggtatcagc agaagcccgg ccagagcccc aagctgctga tctactgggc cagcacccgg     180
gagagcggcg tgcccgaccg gtttagcggc agcggctccg gcaccgactt caccctgacc     240
atcagcagcc tgcaggccga ggacgtggcc gtgtactact gccaccagta caaaagcagc     300
tacaccttcg gccagggcac aaagctggaa atcaag                               336

<210> SEQ ID NO 8
<211> LENGTH: 112
<212> TYPE: PRT
<213> ORGANISM: Artificial Sequence
<220> FEATURE:
<223> OTHER INFORMATION: Variable light chain

<400> SEQUENCE: 8

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Ile Leu Tyr Ser
            20                  25                  30

Ser Asn Gln Lys Asn Tyr Leu Ala Trp Tyr Gln Gln Lys Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys His Gln
            85                  90                  95

Tyr Lys Ser Ser Tyr Thr Phe Gly Gln Gly Thr Lys Leu Glu Ile Lys
            100                 105                 110

<210> SEQ ID NO 9
<211> LENGTH: 354
<212> TYPE: DNA
<213> ORGANISM: Artificial Sequence
<220> FEATURE:
<223> OTHER INFORMATION: Variable heavy chain

<400> SEQUENCE: 9
caggtgcagc tggtgcagag cggagccgag gtgaagaagc tggagcttc cgtcaaggtg       60 tcctgcaagg ccagcggcta caccttcgcc agcagctgga tgcactggat gcggcaggca     120
cctggacagg gcctcgaatg gatcggctgg atcaaccccg gcaacgtgaa caccaagtac     180
aacgagaagt tcaagggcag ggccaccctg accgtggaca ccagcaccaa caccgcctac     240
```

```
atggaactga gcagcctgcg gagcgaggac accgccgtgt actactgcgc cagaaccacc    300
cgttatcggc ccctggacta ctggggccag ggcaccctgg tgaccgtgag cagc           354
```

<210> SEQ ID NO 10
<211> LENGTH: 118
<212> TYPE: PRT
<213> ORGANISM: Artificial Sequence
<220> FEATURE:
<223> OTHER INFORMATION: Variable heavy chain

<400> SEQUENCE: 10

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Ala Ser Ser
            20                  25                  30

Trp Met His Trp Met Arg Gln Ala Pro Gly Gln Gly Leu Glu Trp Ile
        35                  40                  45

Gly Trp Ile Asn Pro Gly Asn Val Asn Thr Lys Tyr Asn Glu Lys Phe
    50                  55                  60

Lys Gly Arg Ala Thr Leu Thr Val Asp Thr Ser Thr Asn Thr Ala Tyr
65                  70                  75                  80

Met Glu Leu Ser Ser Leu Arg Ser Glu Asp Thr Ala Val Tyr Tyr Cys
                85                  90                  95

Ala Arg Thr Thr Arg Tyr Arg Pro Leu Asp Tyr Trp Gly Gln Gly Thr
            100                 105                 110

Leu Val Thr Val Ser Ser
        115
```

<210> SEQ ID NO 11
<211> LENGTH: 336
<212> TYPE: PRT
<213> ORGANISM: Artificial Sequence
<220> FEATURE:
<223> OTHER INFORMATION: Variable light chain

<400> SEQUENCE: 11

```
Gly Ala Cys Ala Thr Cys Gly Thr Gly Ala Thr Gly Ala Cys Cys Cys
1               5                   10                  15

Ala Gly Ala Gly Cys Cys Cys Cys Gly Ala Cys Ala Gly Cys Cys Thr
            20                  25                  30

Gly Gly Cys Cys Gly Thr Gly Ala Gly Cys Cys Thr Gly Gly Gly Cys
        35                  40                  45

Gly Ala Gly Cys Gly Gly Gly Cys Cys Ala Cys Ala Thr Cys Ala
    50                  55                  60

Ala Cys Thr Gly Cys Ala Ala Gly Ala Gly Cys Ala Gly Cys Cys Ala
65                  70                  75                  80

Gly Ala Gly Cys Ala Thr Cys Cys Thr Gly Thr Ala Cys Ala Gly Cys
                85                  90                  95

Ala Gly Cys Ala Ala Cys Ala Gly Ala Ala Gly Ala Ala Cys Thr
            100                 105                 110

Ala Cys Cys Thr Gly Gly Cys Cys Thr Gly Gly Thr Ala Thr Cys Ala
        115                 120                 125

Gly Cys Ala Gly Ala Ala Gly Cys Cys Cys Gly Gly Cys Cys Ala Gly
    130                 135                 140

Ala Gly Cys Cys Cys Cys Ala Gly Cys Thr Gly Cys Thr Gly Ala
145                 150                 155                 160
```

```
Thr Cys Thr Ala Cys Thr Gly Gly Cys Ala Gly Cys Ala Cys
            165                 170                 175

Cys Cys Gly Gly Gly Ala Gly Ala Gly Cys Gly Gly Cys Gly Thr Gly
        180                 185                 190

Cys Cys Cys Gly Ala Cys Gly Gly Thr Thr Ala Gly Cys Gly
        195                 200                 205

Gly Cys Ala Gly Cys Gly Gly Cys Thr Cys Gly Gly Cys Ala Cys
        210                 215                 220

Cys Gly Ala Cys Thr Thr Cys Ala Cys Cys Thr Gly Ala Cys Cys
225                 230                 235                 240

Ala Thr Cys Ala Gly Cys Ala Gly Cys Thr Gly Cys Ala Gly Gly
            245                 250                 255

Cys Cys Gly Ala Gly Gly Ala Cys Gly Thr Gly Gly Cys Cys Gly Thr
        260                 265                 270

Gly Thr Ala Cys Thr Ala Cys Thr Gly Cys Cys Ala Cys Cys Ala Gly
            275                 280                 285

Thr Ala Cys Cys Gly Thr Ala Gly Cys Ala Gly Cys Thr Ala Cys Ala
        290                 295                 300

Cys Cys Thr Thr Cys Gly Gly Cys Cys Ala Gly Gly Gly Cys Ala Cys
305                 310                 315                 320

Ala Ala Ala Gly Cys Thr Gly Gly Ala Ala Thr Cys Ala Ala Gly
            325                 330                 335

<210> SEQ ID NO 12
<211> LENGTH: 112
<212> TYPE: PRT
<213> ORGANISM: Artificial Sequence
<220> FEATURE:
<223> OTHER INFORMATION: Variable light chain

<400> SEQUENCE: 12

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Ile Leu Tyr Ser
            20                  25                  30

Ser Asn Gln Lys Asn Tyr Leu Ala Trp Tyr Gln Lys Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys His Gln
                85                  90                  95

Tyr Arg Ser Ser Tyr Thr Phe Gly Gln Gly Thr Lys Leu Glu Ile Lys
            100                 105                 110

<210> SEQ ID NO 13
<211> LENGTH: 354
<212> TYPE: DNA
<213> ORGANISM: Artificial Sequence
<220> FEATURE:
<223> OTHER INFORMATION: Variable heavy chain

<400> SEQUENCE: 13
caggtgcagc tggtgcagag cggagccgag gtgaagaagc ctggagcttc cgtcaaggtg    60
tcctgcaagg ccagcggcta caccttcgcc agccaatata tgcactggat gcggcaggca   120
cctggacagg gcctcgaatg gatcggctgg atcaacccg gcaacgtgaa caccaagtac   180
```

```
aacgagaagt tcaagggcag ggccaccctg accgtggaca ccagcaccaa caccgcctac    240
atggaactga gcagcctgcg gagcgaggac accgccgtgt actactgcgc cagactgacc    300
tattatcggc cgccggacta ctggggccag ggcaccctgg tgaccgtgag cagc          354
```

<210> SEQ ID NO 14
<211> LENGTH: 118
<212> TYPE: PRT
<213> ORGANISM: Artificial Sequence
<220> FEATURE:
<223> OTHER INFORMATION: Variable heavy chain

<400> SEQUENCE: 14

```
Gln Val Gln Leu Val Gln Ser Gly Ala Glu Val Lys Lys Pro Gly Ala
1               5                  10                  15

Ser Val Lys Val Ser Cys Lys Ala Ser Gly Tyr Thr Phe Ala Ser Gln
            20                  25                  30

Tyr Met His Trp Met Arg Gln Ala Pro Gly Gln Gly Leu Glu Trp Ile
        35                  40                  45

Gly Trp Ile Asn Pro Gly Asn Val Asn Thr Lys Tyr Asn Glu Lys Phe
    50                  55                  60

Lys Gly Arg Ala Thr Leu Thr Val Asp Thr Ser Thr Asn Thr Ala Tyr
65                  70                  75                  80

Met Glu Leu Ser Ser Leu Arg Ser Glu Asp Thr Ala Val Tyr Tyr Cys
                85                  90                  95

Ala Arg Leu Thr Tyr Tyr Arg Pro Pro Asp Tyr Trp Gly Gln Gly Thr
            100                 105                 110

Leu Val Thr Val Ser Ser
        115
```

<210> SEQ ID NO 15
<211> LENGTH: 336
<212> TYPE: DNA
<213> ORGANISM: Artificial Sequence
<220> FEATURE:
<223> OTHER INFORMATION: Variable light chain

<400> SEQUENCE: 15

```
gacatcgtga tgacccagag ccccgacagc ctggccgtga gcctgggcga gcgggccacc    60
atcaactgca agagcagcca gagcatcctg tacagcagca ccagaagaa ctacctggcc    120 tggtatcagc agaagcccgg ccagagcccc aagctgctga tctactgggc cagcacccgg    180
gagagcggcg tgcccgaccg gtttagcggc agcggctccg gcaccgactt caccctgacc    240
atcagcagcc tgcaggccga ggacgtggcc gtgtactact gccaccagta ctatagcagc    300
tacaccttcg gccagggcac aaagctggaa atcaag                               336
```

<210> SEQ ID NO 16
<211> LENGTH: 112
<212> TYPE: PRT
<213> ORGANISM: Artificial Sequence
<220> FEATURE:
<223> OTHER INFORMATION: Variable light chain

<400> SEQUENCE: 16

```
Asp Ile Val Met Thr Gln Ser Pro Asp Ser Leu Ala Val Ser Leu Gly
1               5                  10                  15

Glu Arg Ala Thr Ile Asn Cys Lys Ser Ser Gln Ser Ile Leu Tyr Ser
            20                  25                  30
```

```
Ser Asn Gln Lys Asn Tyr Leu Ala Trp Tyr Gln Gln Lys Pro Gly Gln
            35                  40                  45

Ser Pro Lys Leu Leu Ile Tyr Trp Ala Ser Thr Arg Glu Ser Gly Val
 50                  55                  60

Pro Asp Arg Phe Ser Gly Ser Gly Ser Gly Thr Asp Phe Thr Leu Thr
 65                  70                  75                  80

Ile Ser Ser Leu Gln Ala Glu Asp Val Ala Val Tyr Tyr Cys His Gln
                    85                  90                  95

Tyr Tyr Ser Ser Tyr Thr Phe Gly Gln Gly Thr Lys Leu Glu Ile Lys
                100                 105                 110

<210> SEQ ID NO 17
<211> LENGTH: 354
<212> TYPE: DNA
<213> ORGANISM: Artificial Sequence
<220> FEATURE:
<223> OTHER INFORMATION: Variable heavy chain

<400> SEQUENCE: 17
caggtgcagc tggtgcagag cggagccgag gtgaagaagc ctggagcttc cgtcaaggtg      60
tcctgcaagg ccagcggcta caccttcgcc agcgcgtgga tgcactggat gcggcaggca     120
cctggacagg gcctcgaatg gatcggctgg atcaaccccg gcaacgtgaa caccaagtac     180
aacgagaagt tcaagggcag ggccaccctg accgtggaca ccagcaccaa caccgcctac     240
atggaactga gcagcctgcg gagcgaggac accgccgtgt actactgcgc cagaagcacg     300
tattaccggc cgctggacta ctggggccag ggcaccctgg tgaccgtgag cagc           354

<210> SEQ ID NO 18
<211> LENGTH: 118
<212> TYPE: PRT
<213> ORGANISM: Artificial Sequence
<220> FEATURE:
<223> OTHER INFORMATION: Variable heavy chain

<400> SEQUENCE: 18

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Ala Ser Ala
                20                  25                  30

Trp Met His Trp Met Arg Gln Ala Pro Gly Gln Gly Leu Glu Trp Ile
            35                  40                  45

Gly Trp Ile Asn Pro Gly Asn Val Asn Thr Lys Tyr Asn Glu Lys Phe
 50                  55                  60

Lys Gly Arg Ala Thr Leu Thr Val Asp Thr Ser Thr Asn Thr Ala Tyr
 65                  70                  75                  80

Met Glu Leu Ser Ser Leu Arg Ser Glu Asp Thr Ala Val Tyr Tyr Cys
                85                  90                  95

Ala Arg Ser Thr Tyr Tyr Arg Pro Leu Asp Tyr Trp Gly Gln Gly Thr
                100                 105                 110

Leu Val Thr Val Ser Ser
        115

<210> SEQ ID NO 19
<211> LENGTH: 336
<212> TYPE: DNA
<213> ORGANISM: Artificial Sequence
<220> FEATURE:
<223> OTHER INFORMATION: Variable light chain
```

-continued

<400> SEQUENCE: 19

```
gacatcgtga tgacccagag ccccgacagc ctggccgtga gcctgggcga gcgggccacc      60
atcaactgca agagcagcca gagcatcctg tacagcagca accagaagaa ctacctggcc     120
tggtatcagc agaagcccgg ccagagcccc aagctgctga tctactgggc cagcacccgg     180
gagagcggcg tgcccgaccg gtttagcggc agcggctccg gcaccgactt caccctgacc     240
atcagcagcc tgcaggccga ggacgtggcc gtgtactact gccaccagta catgagcagc     300
tacaccttcg gccagggcac aaagctggaa atcaag                               336
```

<210> SEQ ID NO 20
<211> LENGTH: 112
<212> TYPE: PRT
<213> ORGANISM: Artificial Sequence
<220> FEATURE:
<223> OTHER INFORMATION: Variable light chain

<400> SEQUENCE: 20

```
Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Ile Leu Tyr Ser
            20                  25                  30

Ser Asn Gln Lys Asn Tyr Leu Ala Trp Tyr Gln Gln Lys Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys His Gln
                85                  90                  95

Tyr Met Ser Ser Tyr Thr Phe Gly Gln Gly Thr Lys Leu Glu Ile Lys
            100                 105                 110
```

<210> SEQ ID NO 21
<211> LENGTH: 8
<212> TYPE: PRT
<213> ORGANISM: Artificial Sequence
<220> FEATURE:
<223> OTHER INFORMATION: Variable heavy chain, CDR1

<400> SEQUENCE: 21

```
Gly Tyr Thr Phe Ala Ser Tyr Tyr
1               5
```

<210> SEQ ID NO 22
<211> LENGTH: 8
<212> TYPE: PRT
<213> ORGANISM: Artificial Sequence
<220> FEATURE:
<223> OTHER INFORMATION: Variable heavy chain, CDR1

<400> SEQUENCE: 22

```
Gly Tyr Thr Phe Ala Ser Gln Trp
1               5
```

<210> SEQ ID NO 23
<211> LENGTH: 8
<212> TYPE: PRT
<213> ORGANISM: Artificial Sequence
<220> FEATURE:
<223> OTHER INFORMATION: Variable heavy chain, CDR1

```
<400> SEQUENCE: 23

Gly Tyr Thr Phe Ala Ser Ser Trp
1               5

<210> SEQ ID NO 24
<211> LENGTH: 8
<212> TYPE: PRT
<213> ORGANISM: Artificial Sequence
<220> FEATURE:
<223> OTHER INFORMATION: Variable heavy chain, CDR1

<400> SEQUENCE: 24

Gly Tyr Thr Phe Ala Ser Gln Tyr
1               5

<210> SEQ ID NO 25
<211> LENGTH: 8
<212> TYPE: PRT
<213> ORGANISM: Artificial Sequence
<220> FEATURE:
<223> OTHER INFORMATION: Variable heavy chain, CDR1

<400> SEQUENCE: 25

Gly Tyr Thr Phe Ala Ser Ala Trp
1               5

<210> SEQ ID NO 26
<211> LENGTH: 12
<212> TYPE: PRT
<213> ORGANISM: Artificial Sequence
<220> FEATURE:
<223> OTHER INFORMATION: Variable light chain, CDR1

<400> SEQUENCE: 26

Gln Ser Ile Leu Tyr Ser Ser Asn Gln Lys Asn Tyr
1               5                   10

<210> SEQ ID NO 27
<211> LENGTH: 8
<212> TYPE: PRT
<213> ORGANISM: Artificial Sequence
<220> FEATURE:
<223> OTHER INFORMATION: Variable heavy chain, CDR2

<400> SEQUENCE: 27

Ile Asn Pro Gly Asn Val Asn Thr
1               5

<210> SEQ ID NO 28
<211> LENGTH: 6
<212> TYPE: PRT
<213> ORGANISM: Artificial Sequence
<220> FEATURE:
<223> OTHER INFORMATION: Variable light chain, CDR2

<400> SEQUENCE: 28

Trp Ala Ser Thr Arg Glu
1               5

<210> SEQ ID NO 29
<211> LENGTH: 9
<212> TYPE: PRT
<213> ORGANISM: Artificial Sequence
<220> FEATURE:
<223> OTHER INFORMATION: Variable heavy chain, CDR3

<400> SEQUENCE: 29
```

```
Ser Thr Tyr Tyr Arg Pro Leu Asp Tyr
1               5
```

<210> SEQ ID NO 30
<211> LENGTH: 9
<212> TYPE: PRT
<213> ORGANISM: Artificial Sequence
<220> FEATURE:
<223> OTHER INFORMATION: Variable heavy chain, CDR3

<400> SEQUENCE: 30

```
Ser Thr Trp Tyr Arg Pro Leu Asp Tyr
1               5
```

<210> SEQ ID NO 31
<211> LENGTH: 9
<212> TYPE: PRT
<213> ORGANISM: Artificial Sequence
<220> FEATURE:
<223> OTHER INFORMATION: Variable heavy chain, CDR3

<400> SEQUENCE: 31

```
Ser Thr Trp Tyr Arg Pro Asn Asp Tyr
1               5
```

<210> SEQ ID NO 32
<211> LENGTH: 9
<212> TYPE: PRT
<213> ORGANISM: Artificial Sequence
<220> FEATURE:
<223> OTHER INFORMATION: Variable heavy chain, CDR3

<400> SEQUENCE: 32

```
Thr Thr Arg Tyr Arg Pro Leu Asp Tyr
1               5
```

<210> SEQ ID NO 33
<211> LENGTH: 9
<212> TYPE: PRT
<213> ORGANISM: Artificial Sequence
<220> FEATURE:
<223> OTHER INFORMATION: Variable heavy chain, CDR3

<400> SEQUENCE: 33

```
Leu Thr Tyr Tyr Arg Pro Pro Asp Tyr
1               5
```

<210> SEQ ID NO 34
<211> LENGTH: 8
<212> TYPE: PRT
<213> ORGANISM: Artificial Sequence
<220> FEATURE:
<223> OTHER INFORMATION: Variable light chain, CDR3

<400> SEQUENCE: 34

```
His Gln Tyr Leu Ser Ser Tyr Thr
1               5
```

<210> SEQ ID NO 35
<211> LENGTH: 8
<212> TYPE: PRT
<213> ORGANISM: Artificial Sequence
<220> FEATURE:
<223> OTHER INFORMATION: Variable light chain, CDR3

<400> SEQUENCE: 35

His Gln Tyr Ile Ser Ser Tyr Thr
1               5

<210> SEQ ID NO 36
<211> LENGTH: 8
<212> TYPE: PRT
<213> ORGANISM: Artificial Sequence
<220> FEATURE:
<223> OTHER INFORMATION: Variable light chain, CDR3

<400> SEQUENCE: 36

His Gln Tyr Lys Ser Ser Tyr Thr
1               5

<210> SEQ ID NO 37
<211> LENGTH: 8
<212> TYPE: PRT
<213> ORGANISM: Artificial Sequence
<220> FEATURE:
<223> OTHER INFORMATION: Variable light chain, CDR3

<400> SEQUENCE: 37

His Gln Tyr Arg Ser Ser Tyr Thr
1               5

<210> SEQ ID NO 38
<211> LENGTH: 8
<212> TYPE: PRT
<213> ORGANISM: Artificial Sequence
<220> FEATURE:
<223> OTHER INFORMATION: Variable light chain, CDR3

<400> SEQUENCE: 38

His Gln Tyr Tyr Ser Ser Tyr Thr
1               5

<210> SEQ ID NO 39
<211> LENGTH: 8
<212> TYPE: PRT
<213> ORGANISM: Artificial Sequence
<220> FEATURE:
<223> OTHER INFORMATION: Variable light chain, CDR3

<400> SEQUENCE: 39

His Gln Tyr Met Ser Ser Tyr Thr
1               5

<210> SEQ ID NO 40
<211> LENGTH: 27
<212> TYPE: DNA
<213> ORGANISM: Artificial Sequence
<220> FEATURE:
<223> OTHER INFORMATION: Chemically synthesized primer

<400> SEQUENCE: 40
tctgagtagg tgtcattcta ttctggg                                       27

<210> SEQ ID NO 41
<211> LENGTH: 25
<212> TYPE: DNA
<213> ORGANISM: Artificial Sequence
<220> FEATURE:
<223> OTHER INFORMATION: Chemically synthesized primer

<400> SEQUENCE: 41
cactaggggt tcctagatct ctccc                                         25

```
<210> SEQ ID NO 42
<211> LENGTH: 26
<212> TYPE: PRT
<213> ORGANISM: Artificial Sequence
<220> FEATURE:
<223> OTHER INFORMATION: Chemically synthesized probe

<400> SEQUENCE: 42

Thr Cys Thr Thr Cys Cys Cys Ala Ala Thr Cys Cys Thr Cys Cys Cys
1               5                   10                  15

Cys Cys Thr Thr Gly Cys Thr Gly Thr Cys
            20                  25
```